US011913005B2

(12) United States Patent
Graham

(10) Patent No.: US 11,913,005 B2
(45) Date of Patent: Feb. 27, 2024

(54) OPTIMIZED CRISPR-CAS NUCLEASES AND BASE EDITORS AND METHODS OF USE THEREOF

(71) Applicant: Pairwise Plants Services, Inc., Durham, NC (US)

(72) Inventor: Nathaniel Graham, Durham, NC (US)

(73) Assignee: Pairwise Plants Services, Inc., Durham, NC (US)

(*) Notice: Subject to any disclaimer, the term of this patent is extended or adjusted under 35 U.S.C. 154(b) by 29 days.

(21) Appl. No.: 18/048,236

(22) Filed: Oct. 20, 2022

(65) Prior Publication Data

US 2023/0114342 A1    Apr. 13, 2023

Related U.S. Application Data

(62) Division of application No. 17/078,576, filed on Oct. 23, 2020, now Pat. No. 11,591,607.

(60) Provisional application No. 62/925,422, filed on Oct. 24, 2019.

(51) Int. Cl.
  *C12N 15/82* (2006.01)
  *C12N 9/22* (2006.01)
  *C12N 15/113* (2010.01)

(52) U.S. Cl.
  CPC .......... *C12N 15/8218* (2013.01); *C12N 9/22* (2013.01); *C12N 15/113* (2013.01); *C12N 2310/20* (2017.05)

(58) Field of Classification Search
  None
  See application file for complete search history.

(56) References Cited

U.S. PATENT DOCUMENTS

| | | |
|---|---|---|
| 2014/0283200 A1 | 9/2014 | Chittoor et al. |
| 2015/0191721 A1 | 7/2015 | Kelker et al. |
| 2016/0068864 A1 | 3/2016 | Doudna et al. |
| 2017/0218384 A1 | 8/2017 | Abbitt et al. |
| 2018/0073012 A1 | 3/2018 | Liu et al. |
| 2018/0327784 A1 | 11/2018 | Jin et al. |
| 2019/0292553 A1 | 9/2019 | Gao et al. |
| 2020/0080090 A1* | 3/2020 | Cereseto ................. A61P 43/00 |

FOREIGN PATENT DOCUMENTS

WO    2019067910 A1    4/2019

OTHER PUBLICATIONS

International Search Report and the Written Opinion of the International Searching Authority corresponding to International Patent Application No. PCT/US20/56963 (13 pages) (dated Mar. 3, 2021).
Christensen, et al., "Ubiquitin promoter-based vectors for high-level expression of selectable and/or screenable marker genes in monocotyledonous plants", Transgenic Research, 5, 1996, 213-218.
Endo, et al., "Genome editing in plants by engineered CRISPR-Cas9 recognizing NG PAM", Nature Plants 5, 2019, 14-17.
Genbank, "Cas9D10A nickase [Cloning vector pVIR-Nick]", GenBank: AWD73737.1; Retrieved from: https://www.ncbi.nlm.nih.gov/protein/AWD73737.1/, 2018, (1 page).
Hua, et al., "Expanding the base editing scope in rice by using Cas9 variants", Plant Biotechnology Journal 17(2), 2019, 499-504.
Jin, et al., "Cytosine, but not adenine, base editors induce genome-wide off-target mutations in rice", Science 364 (6437), 2019, 292-295.
Komor, et al., "Programmable editing of a target base in genomic DNA without double-stranded DNA cleavage", Nature, 533, 2016, 420-424.
Li, et al., "Generation of Targeted Point Mutations in Rice by a Modified CRISPR/Cas9 System", Molecular Plant: Letter to the Editor 10(3), 2016, 526-529.
Lu, et al., "Precise Editing of a Target Base in the Rice Genome Using a Modified CRISPR/Cas9 System", Molecular Plant: Letter to the Editor 10 (3), 2017, 523-525.
Mauro, et al., "A critical analysis of codon optimization in human therapeutics", Trends in Molecular Medicine, 20(11), 2014, 604-613.
Xue, et al., "Manipulating mRNA splicing by base editing in plants", Science China Life Sciences 61(11), 2018, 1293-1300.
Zong, et al., "Precise base editing in rice, wheat and maize with a Cas9-cytidine deaminase fusion", Nature Biotechnology 35(5), 2017, 438-440.

\* cited by examiner

*Primary Examiner* — Weihua Fan
(74) *Attorney, Agent, or Firm* — Myers Bigel, P.A.

(57) ABSTRACT

This invention relates to CRISPR-Cas nucleases codon optimized for expression in plants and nucleic acid constructs encoding base editors comprising a CRISPR-Cas nuclease and a deaminase domain, wherein the nucleic acid constructs are optimized for expression in a plant. The invention further relates to methods of modifying nucleic acids using the nucleic acid constructs.

8 Claims, 3 Drawing Sheets

Specification includes a Sequence Listing.

500

SEQUENCE LISTING

```
Sequence total quantity: 76
SEQ ID NO: 1              moltype = DNA  length = 4101
FEATURE                   Location/Qualifiers
misc_feature              1..4101
                          note = Cas9 polynucleotide
source                    1..4101
                          mol_type = other DNA
                          organism = synthetic construct
SEQUENCE: 1
gacaagaagt acagcatcgg gctggcgatc gggaccaact ccgtcggctg ggctgtgatt    60
accgacgagt acaaggtgcc atccaagaag ttcaaggtcc tcggcaacac tgaccggcac   120
agcattaaga agaacctgat tggggcgctg ctgttcgatt cgggggagac tgcggaggcg   180
accaggctga agcggactgc gcgccggagg tacaccagga ggaagaatcg gatctgctac   240
ctccaggaga tttttctcgaa tgagatggcc aaggtggacg attccttctt ccatcgcctg   300
gaggagtcgt tcctcgttga ggaggacaag aagcatgaga ggcatcccat tttcgggaat   360
atcgttgacg aggtggctta ccatgagaag tacccgacca tctaccatct gcggaagaag   420
ctcgtcgatt cgaccgataa ggccgacctg cggctgatct acctggccct cgcgcacatg   480
attaagttcc ggggccattt cctcatcgag ggcgacctca acccggacaa ctcggacgtg   540
gataagctct tcattcagct cgtgcagaca tacaaccagc tcttcgagga gaatcccatt   600
aacgcctcgg gggtcgacgc taaggctatt ctctcggctc ggctgtcgaa gtgcgccagg   660
ctggagaatc tcattgccca gctcccaggc gagaagaaga acggcctctt cggcaacctg   720
attgccctgt cgctggggct cacaccgaat ttcaagtcga acttcgacct cgccgaggac   780
gctaagctcc agctcagcaa ggatacttac gatgatgacc tcgataacct gctcgcccag   840
attgggggatc agtacgcgga tctgttcctc gcggccaaga atctcagcga tgctattctc   900
ctgtcggaca ttctccgcgt caacacagag attactaagg ccccactgtc ggcgagcatg   960
attaagaggt acgatgagca tcatcaggac ctgacactgc tcaaggcgct ggtccggcag  1020
cagctccccg agaagtacaa ggagattttc ttcgatcagt caaagaatgg gtacgcgggc  1080
tacattgatg gcggcgcgtc ccaggaggag ttctacaagt tcattaagcc catcctggag  1140
aagatggacg gaccgagga gctgctggtg aagctcaatc gggaggacct gctccggaac  1200
cagcgcacat tcgacaatgg ctcgattcct caccagattc acctgggcga gctgcacgcc  1260
attctccgca ggcaggagga cttctacccg ttcctcaagg acaaccgcga gaagatcgag  1320
aagatcctga ccttccggat tccatactac gtggggccgc tcgcgcgggg gaactcccgg  1380
ttcgcgtgga tgactcgcaa gtccgaagaa acgattacac cgtggaattt cgaggaggtc  1440
gtcgacaagg gcgctagtgc gcagtcattc attgagagga tgaccaattt cgataagaac  1500
ctgcctaacg agaaggtgct gccgaagcat tcgctgctct acgagtactt caccgtttac  1560
aatgagctga ccaaggtgaa gtatgtgact gagggcatga ggaagccagc gttcctgagc  1620
ggcgagcaga agaaggctat cgtggacctg ctcttcaaga ctaaccggaa ggtgactgtc  1680
aagcagctca aggaggacta cttcaagaag attgagtgct tcgattccgt tgagattagc  1740
ggggtggagg atcggttcaa tgcttcgctc gggacatacc acgatctcct gaagatcatt  1800
aaggataagg acttcctcga caacgaggag aacgaggaca ttctcgaaga tattgtcctg  1860
accctcaccc tcttcgagga tcgggagatg atcgaggaga ggctcaagac atacgctcat  1920
ctgttcgatg ataaggtcat gaagcagctg aagcgcaggc ggtacacagg gtgggggcgg  1980
ctgagccgga agctgatcaa cgggattcgg gataagcagt ccgggaagac aattctcgac  2040
ttcctcaagt ccgacgggtt cgctaaccgg aacttcatgc agctcattca tgatgactcg  2100
ctgacattca aggaggatat tcagaaggcg caggtttcgg ggcagggcga ctcgctccac  2160
gagcatattg cgaatctggc gggctccccc gcgattaaga ggggcattct gcaaaccgtc  2220
aaggtggttg atgagctggt caaggtcatg gggcggcata agccagagaa tattgtcatc  2280
gagatggcgc gggagaatca gaccacacag aaggggcaga agaactcacg ggagcggatg  2340
aagcgcatcg aggagggcat caaggagctg gggtcgcaga tcctgaagga gcatcccgtg  2400
gagaacactc agctgcaaaa tgaagagctg tacctctact acctccagaa cgggagggac  2460
atgtatgtgg atcaggagct ggatattaat aggctgagcg attacgatgt cgaccacatt  2520
gtcccacagt cgttcctgaa ggacgacagc attgacaaca aggtgctgac ccgctcggat  2580
aagaacaggg gcaagagcga taatgttcca agcgaggagg ttgtgaagaa gatgaagaac  2640
tactggcggc agctcctgaa cgcgaagctc atcacacagc ggaagttcga caacctcacc  2700
aaggctgagc gcggggggcct gagcgagctg gacaaggcgg ggttcattaa gaggcagctc  2760
gtcgagacac ggcagattac aaagcatgtt gcgcagattc tcgattcccg gatgaacacc  2820
aagtacgatg agaacgataa gctgattcgg gaggtcaagg taattaccct gaagtccaag  2880
ctggtgtccg acttcaggaa ggacttccag ttctacaagg ttcgggagat caacaactac  2940
caccacgcgc atgatgccta cctcaacgcg gtcgtgggga ccgctctcat caagaagtac  3000
```

-continued

```
ccaaagctgg agtcagagtt cgtctacggg gattacaagg tttacgacgt gcggaagatg   3060
atcgctaaga gcgagcagga gattggcaag gctaccgcta agtacttctt ctactccaac   3120
atcatgaact tcttcaagac agagattacc ctcgcgaatg gcgagatccg gaagaggccc   3180
ctcatcgaga caaatgggga gacagggag attgtctggg ataaggggcg ggatttcgcg    3240
accgtccgga aggtcctgtc gatgccccag gttaatattg tcaagaagac tgaggtccga   3300
actggcggct tctcaaagga gtcgattctc ccaaagagga actccgataa gctcattgct   3360
cggaagaagg attgggaccc caagaagtac gggggattcg actcccccac tgttgcttac   3420
tctgttctgg ttgttgctaa ggtggagaag gggaagtcga agaagctgaa gagcgtgaag   3480
gagctgctcg ggattacaat tatggagagg tcatccttcg agaagaatcc catcgacttc   3540
ctggaggcca agggctacaa ggaggtgaag aaggacctga ttattaagct gcccaagtac   3600
tcgctcttcg agctggagaa tgggcggaag cggatgctgg cgtccgcggg ggagctgcaa   3660
aaggggaacg agctggcgct cccctccaag tatgtgaact tcctctacct ggcgtcgcac   3720
tacgagaagc tgaaggggtc cccagaggat aatgagcaga agcagctctt cgtcgagcag   3780
cataagcact acctggacga gattatcgag cagattacga agttctcgaa gcgggtcatc   3840
ctcgcggatg cgaacctgga taaggtgctc agccgcctaca ataagcaccg ggacaagccg   3900
attcgggagc aggcggagaa tattattcac ctcttcacac tcaccaacct cggggcacca   3960
gctgcgttca agtacttcga cactactatc gaccggaagc ggtacacctc gacgaaggag   4020
gtgctcgacg ccaccctcat tcaccagtcg atcacaggc tgtacgagac acggattgac    4080
ctgtcccagc tcggggcga c                                              4101

SEQ ID NO: 2        moltype = DNA  length = 4101
FEATURE             Location/Qualifiers
misc_feature        1..4101
                    note = Cas9 polynucleotide
source              1..4101
                    mol_type = other DNA
                    organism = synthetic construct
SEQUENCE: 2
gacaagaagt actccattgg cctggcgatt gggacaaact cggtggggtg ggccgtgatt   60
acggatgagt acaaggttcc aagcaagaag ttcaaggtc tcgggaacac agatcggcat   120
tcgattaaga agaatctcat tgggcgcctc ctcttcgact cggggagac agccggaggct   180
accaggctca gcggacagc caggcggcgg tacacaaggc ggaagaatcg catctgctac   240
ctccaggaga tttttctcgaa tgagatggcg aaggtggacg acagcttctt ccatcggctg   300
gaggagtcct tcctggtgga ggaggataag aagcacgaga ggcatccaat tttcgggaac   360
atcgtggacg aggttgcgta ccatgagaag taccctacaa tctaccatct gcggaagaag   420
ctggttgact ccacagacaa ggcggacctg aggctgatct acctcgctct ggcccacatg   480
attaagttcc gcgggcattt cctgatcgag ggggacctga tcccgacaa ttcggatgtg   540
gacaagctct tcatccagct ggtgcagacc tacaaccagc tgttcgagga gaatcccatc   600
aatgcgtcgg gcgttgacgc taaggccatt ctgtccgcta ggctgtcgaa gagcaggagg   660
ctggagaacc tgatcgccca gctgccaggc gagaagaaga atgggctctt cgggaatctg   720
attgcgctct ccctggggct gacaccgaac ttcaagagca atttcgatct ggctgaggac   780
gcgaagctcc agctctcgaa ggacacttac gacgatgacc tcgataacct cctcgcgcag   840
atcgggagcc agtacgctga tctcttcctc gccgctaaga acctctcgga tgctatccfg   900
ctctccgaca ttctccgggt taataccgag attacaaagg ccccactgtc ggcgtccatg   960
atcaagcggt acgatgagca tcatcaggat ctcaccctgc tcaaggccct cgtgcggcag   1020
cagctgcccg agagtacaa ggagattttt tcgaccaga gcaagaatgg gtacgctggc   1080
tacattgacg gcggggcctc acaggaggag ttctacaagt tcatcaagcc aatcctggag   1140
aagatggatg gcacagagga gctgctggtg aagctcaacc gggaggatct gctcaggaag   1200
cagcggacgt tcgacaacgg gtcgattccc atcagatcc acctgggga gctgcacgcg   1260
atcctgcgcc ggcaggagga tttctaccct ttcctgaagg ataatcggga gaagatcgag   1320
aagattctca cccttccggat tccctactac gtcgggccac tcgcgcgggg caatagcagg   1380
ttcgcctgga tgacacggaa gagcgaggag acaatcaccc cctgaacttc gaggaggtt   1440
gtcgacaagg gggcgtccgc ccagtcattc attgagcgga tgaccaattt cgacaagaat   1500
ctgccaaatg agaaggttct cccaaagcat agcctcctct acgagtactt cactgtttac   1560
aacgagctga ccaaggtgaa gtatgtgacc gagggcatgc ggaagcccgc gttcctgtcc   1620
ggcgagcaga agaaggccat tgtggacctc ctgttcaaga ccaatcgcaa ggtcacagtc   1680
aagcagctca ggaggatta cttcaagaag atcgagtgct tcgactcggt tgagattagc   1740
ggggtggagg atcggttcaa cgcgagcctc ggcacttacc acgacctcct gaagatcatc   1800
aaggataagg acttcctcga caacgaggag aacgaggata ttctgaggga catcgtgctc   1860
accctgacgc tgttcgagga tcgggagatg atcgaggagc gcctgaagac ctacgctcat   1920
ctcttcgatg ataaggtcat gaagcagctg aagaggaggc ggtacaccgg gtggggccgc   1980
ctgagcagga agctcattaa cgggatcagg gacaagcaga gcggcaagac catcctggac   2040
ttcctcaaga gcgatggctt cgccaaccgg aatttcatgc agctcatcca cgacgactcc   2100
ctcaccttca aggaggacat tcagaaggct caggtcagc gccaggcgga ctcgctgcat   2160
gagcacatcg ctaacctggc gggcagccca gccatcaaga gggcatcct ccagacagtg   2220
aaggtcgtgg atgagctggt gaaggtcatg ggccggcata gcccgagaa atttgtgatt   2280
gagatggcgc gggagaatca gaccactcag aagggccaga gaactcgcg ggagcgcatg   2340
aagaggatcg aggaggggat taaggagctg gcagcagaa ttctcaagga gcaccccgtg   2400
agaataccc agctccagaa cgagaagctg tacctctact acctccagaa tggggggac   2460
atgtatgttg atcaggagct ggacatcaat cgcctctcgg attacgacgt ggaccacatc   2520
gtgccccaga gcttcctgaa ggatgatagc atcgacaata aggtcctgac ccgctccgac   2580
aagaatcgcg gcaagagcga caacgtgccg agcgaggagg tcgtgaagaa gatgaagaac   2640
tactggcggc agctgctgaa cgcgaagctc attacacagc ggaagttcga taacctgacg   2700
aaggcggaga ggggcggcct ctccgagctg gacaaggcgg gcttcattaa gaggcagctc   2760
gtggagactc gccagatcac caagcacgtg gctcagatcc tcgatagccg gatgaatacg   2820
aagtacgatg agaatgacaa gctcatccgg gaggtgaagg taatcaccct gaagtccaaa   2880
ctcgttagcg atttccggaa ggacttccag ttctacaagg tgcgggagat taacaactac   2940
catcatgcgc acgatgcgta cctcaatgcg gtggtgggca cagccctgat taagaagtac   3000
cccaagctgg agagcgagtt cgtctacggg gactacaagg tgtacgatgt tcggaagatg   3060
```

-continued

```
atcgccaaga gcgagcagga gattgggaag gccaccgcta agtacttctt ctactcgaat   3120
attatgaatt tcttcaagac cgagatcaca ctcgctaatg gggagattcg gaagcggccc   3180
ctcatcgaga ctaacgggga gactggcgag attgtgtggg acaaggggcg cgacttcgct   3240
accgtgcgca aggtcctctc gatgcccag gttaatattg ttaagaagac agaggtgcag    3300
acgggcgggt tctccaagga gtctatcctg ccgaagcgga actcggacaa gctgatcgcc   3360
cgcaagaagg attgggaccc caagaagtac gggggattcg atagcccaac cgtggcttac   3420
agcgtcctgg tggtcgccaa ggttgagaag gggaagtcga agaagctcaa gagcgttaag   3480
gagctgctgg gcatcaccat catggagcgg tccagcttcg agaagaatcc tatcgacttc   3540
ctggaggcta aggggtacaa ggaggtcaag aaggacctga tcattaagct gcccaagtac   3600
tctctgttcg agctggagaa cgggaggaag cggatgctgg cgtctgctgg cgagctacag   3660
aagggcaatg agctggcgct ccctcgaag tatgtcaact tcctctacct ggcttcccat    3720
tacgagaagc tgaagggctc gcccgaggat aatgagcaga agcagctctt cgtggagcag   3780
cacaagcact acctcgacga gatcattgag cagatttcgg agttctcgaa gcgggtcatt   3840
ctcgcggacg cgaacctcga caaggtcctc tcggcgtaca acaagcaccg ggacaagcct   3900
atccggggag aggccgagaa cattatccac ctcttcacac tgaccaacct cggcgctccc   3960
gccgcgttca agtacttcga caccaccatt gaccgcaaga gatacacatc caccaaggag   4020
gtgctggacg cgaccctcat ccaccagagc atcacaggcc tctacgagac acggatcgac   4080
ctctcgcagc tcggggggcga t                                            4101

SEQ ID NO: 3           moltype = DNA   length = 4092
FEATURE                Location/Qualifiers
misc_feature           1..4092
                       note = Cas9 polynucleotide
source                 1..4092
                       mol_type = other DNA
                       organism = synthetic construct
SEQUENCE: 3
gacaagaagt actcgatcgg cctggcgatt ggcacaaaca gcgtggggtg ggctgtgatc   60
actgatgagt acaaggtgcc atcgaagaag ttcaaggtgc tggggaatac agaccggcat   120
tcgatcaaga agaatctcat tggcgctctc ctcttcgatt ccggcgagac tgctgaggcg   180
acccgcctga agcgcaccgc ccggcggcgc tacactcggc ggaagaatag gatttgctac   240
ctccaggaga ttttctcgaa tgagatggcc aaggtggatg acagcttctt ccaccgcctg   300
gaggagtcgt tcctggtcga ggaggacaag aagcatgagc ggcaccctat cttcgggaat   360
atcgttggac aggtcgccta ccacgagaag taccccacta tctaccatct cgcaagaag    420
ctcgtggaca gcacagataa ggccgacctc cgcctgatct acctcgccct cgcgcacatg   480
attaagttcc gggggcactt cctcattgag ggggatctga atcccgataa ctccgacgtg   540
gacaagctgt tcatccagct ggtgcagaca taaaccagc tgttcgagga gaatcccatc    600
aacgcgagcg gcgtggacgc taaggccatt ctgtcggcta ggctctcgaa gtcgaggcgg   660
ctggagaacc tgattgcgca gctccccggc gagaagaaga acgggctgtt cgggaatctc   720
atcgccctct ccctcggcct cacaccaaac ttcaagagca atttcgacct ggctgaggac   780
gctaagctgc aactctcaaa ggatacatac gatgacgacc tggacaatct cctggctcag   840
atcggcgacc agtacgctga cctgttcctc gcggccaaga tctgtcgga cgcgattctc   900
ctcagcgaca tcctgcgcgt caataccgag attacgaagg ctccactgtc tgcgtcaatg   960
attaagcggt acgatgagca tcaccaggat ctgaccctcc tgaaggcgct cgtgcggcag   1020
cagctgcccg agaagtacaa ggagatttc ttcgatcaga gcaagaatgg ctacgccggc   1080
tacatcgacg ggggcgcgag ccaggaggag ttctacaagt catcaagcc catcctggag    1140
aagatgcacg gcaccgagga gctactcgtg aagctcaatc gggaggatct cctccggaag   1200
cagcggacat cgataacgg gtctatccca caccagatcc acctcggcga gctgcatgcg    1260
attctgcggc ggcaggagga tttctaccct ttcctgaagg acaacgggga agatcgag     1320
aagatcctca cattccggat tccatactac gtcgcccccc tggcgagggg caatagccgg   1380
ttcgcgtgga tgcaaggaa gtccgaggag actattaccc cgtggaattt cgaggaggtg    1440
gttgacaagg gcgcttccgc gcagagcttc attgagcgga tgacaaactt cgacaagaat   1500
ctccccaacg agaaggtcct gccgaagcat agcctcctgt acgagtactt caccgtctac   1560
aatgagctaa ctaaggtcaa gtatgtgaca gagggcatga ggaagccagc cttcctctca   1620
ggcgagcaga agaaggccat tgtggacctc tgttcaaga caaaccgcaa ggtgacagtg   1680
aagcagctga aggaggatta cttcaagaag attgagtgct tcgactcagt ggagatttca   1740
ggcgtggagg atcggttcaa cgcgagcctg gggacttacc acgacctgct gaagattatt   1800
aaggacaagg acttcctgga taacgaggag aatgaggaca tcctggagga tattgtgctc   1860
acccctcaccc tgttcgagga cagggagatg attgaggaga ggctcaagac ctacgcgcac   1920
ctgttcgatg acaaggtcat gaagcagctg aagaggcggc gctcactctg gtggggccgc   1980
ctgtcgcgga gctgatcaa cggcattcgg ataagcagt ccgggaagac cattctggat     2040
ttcctgaagt cggacggctt cgccaacagg aatttcatgc agctgatcca cgacgactcc   2100
ctcaccttca aggaggacat tcagaaggcc caggttagcg gccaggggga ctcactccac   2160
gagcatattg ccaatctggc cggctctcca gctatcaagt aggatcct gcaaacagtt    2220
aaggttgttg acgagctggt taaggtcatg ggccggcata agcccgagaa cattgtcatc   2280
gagatggctc gggagaacca gacaactcag aaggcgccaga agaactccag ggagcgcatg  2340
aagcggattg aggagggcat taaggagctg gggtccccaga tcctcaagga gcaccctgtc  2400
gagaacactc agctgcaaaa cgagaagctc tacctgtact acctccagaa cggcgggat   2460
atgtatgtgg atcaggagct ggacatcaac aggctctccg ctacgacgt ggatcacatt    2520
gtcccacagt cttttcctcaa ggatgattcc atcgacaaca aggtgctgac gcgcagcgac  2580
aagaataggg ggaagtcgga caacgttccg agcgaggagg tcgtgaagaa gatgaagaat   2640
tactggaggc agctcctgaa tgcgaagctg atcactcaga ggaagttcga caatctgaca   2700
aaggcggaga ggggcgggct ctcggagctg gataagcggg gcttcatcaa gcggcagctc   2760
gttgaaaccc gacagatcac caagcatgtc gcccagataa agatagccg catgaaccc    2820
aagtacgatg agaacgacaa gctcattcgg gaggttaagg tcattacgct gaagtccaag   2880
ctcgtcagcg acttcaggaa ggattccag ttctacaagg ttcggagat taacaactac    2940
caccacgcgc atgatgcgta cctgaacgct gttgtcggca ctgctctcat caagaagtac   3000
ccaaagctgg agtccgagtt cgtctacggg gactacaagg tctacgatgt ccggaagatg   3060
atcgccaagt cggagcagga gatcgggaag gctactgcga agtacttctt ctacagcaac   3120
```

-continued

```
attatgaatt tcttcaagac ggagattacg ctggcgaacg gggagattag gaagaggccc 3180
ctcattgaga ctaatgggga gacaggcgag attgtttggg acaagggccg cgacttcgcg 3240
actgtgcgga aggtcctgtc catgccacag gtgaatattg ttaagaagac agaggtgcag 3300
actgggggct tctcgaagga gagcattctc ccaaagcgga acagcgataa gctcatcgcg 3360
cgcaagaagg attgggaccc taagaagtac ggcggctcg attctcccac tgtggcctac 3420
tccgttctcg tggttgccaa ggttgagaag gggaagtcga agaagctgaa gtcggtcaag 3480
gagctgctcg ggattacaat catggagcgg agcagcttcg agaagaaccc tattgatttc 3540
ctggaggcca agggctacaa ggaggttaag aaggatctca ttatcaagct ccctaagtac 3600
tctctgttcg agctggagaa tggccggaag aggatgctgg cctcggctgg cgagctacag 3660
aagggaatg agctggccct cccgtcgaag tatgtgaatt tcctgtacct cgcgtcgcac 3720
tacgagaagc tcaagggcag cccggaggat aatgagcaga agcagctctt cgtggagcag 3780
cataagcact acctggacga gatcattgag cagatcagcg agttctcgaa gcgggttatt 3840
ctggctgatg ctaacctgga caaggttctg agcgcctaca ataagcatcg cgacaagccg 3900
attcgcgagc aggcggagaa tattatccac ctgttcaccc tcactaacct cggggctccc 3960
gcggccttca agtacttcga taccacaata gataggaagc ggtacacctc gacgaaggag 4020
gtcctcgacg ccacactcat ccatcagtcg attacaggcc tgtacgagac acggattgac 4080
ctctcgcagc tg                                                    4092

SEQ ID NO: 4         moltype = DNA   length = 4101
FEATURE              Location/Qualifiers
misc_feature         1..4101
                     note = Cas9 polynucleotide
source               1..4101
                     mol_type = other DNA
                     organism = synthetic construct
SEQUENCE: 4
gacaagaagt attccatagg cctggctatc ggcaccaaca gcgtgggctg ggccgtcatc 60
accgacgagt acaaagtgcc gagtaaaaag ttcaaagtgc tcgcaacac cgaccgccac 120
tccataaaga aaaacctgat cggggcgctc ctgttcgaca cgggcgagac ggcggaggcc 180
acccgcttga aacgcacggc ccgacgcgc tacacggga caagaaccg gatctgttac 240
ctacaggaga tttctctaa cgagatggcg aagtggacg actcgttctt tcaccgcctc 300
gaagagtcct tcctcgtgga ggaggacaag aaacacgagc gccacccgat cttcggcaac 360
atcgtggacg aggtggccta ccacgagaag taccccgacc tctaccacct ccggaagaaa 420
ctcgtggaca gcacggacaa ggccgacctg cggctcatct acctcgccct ggcgcacatg 480
attaagttcc ggggccactt cctgatcgag cgcgacctga acccggacaa cagcgacgtg 540
gacaagctgt tcatccagct agtccagacc tacaaccagc ttttcgagga aaaccccatc 600
aacgccagcg gggtggacgc gaaggcgatc ctgtccgccc ggctgagcaa gtccggcgg 660
ctggagaacc tcatcgcgca gttgcccggc gagaagaaga cgggctgtt cgggaacctg 720
atcgccctct cccttgggct caccccgaac ttcaagtcca acttcgacct cgccgaggac 780
gccaaactac agctgagcaa ggacacctac gacgacgacc tcgacaacct gctggccag 840
atcggggacc agtacgcaga cctgttcctc gccgccaaga acctctccga cgccatcctg 900
ctgtcggaca tcctgcgggt gaacacggag atcacgaagg cccgctctc ggcctcgatg 960
attaaacgct acgacgagca ccaccaggac gtgaccctcc tcaaggcgct ggtccgcag 1020
cagcttcccg agaagtacaa ggaaatcttt ttcgatcaga gcaagaacgg gtacgccggg 1080
tacatcgacg gcggggcgtc ccaggaggag ttctacaagt tcatcaagcc catcctggag 1140
aaaatggacg ggaccgagga gctgctcgtg aagctcaacc gcgaagattt gctccgcaag 1200
cagcgcacgt tcgacaacgg gtcgatcccg caccagatcc actggggcga gctgcacgcg 1260
atcctcaggc gtcaggaaga cttctacccc ttcctcaagg acaaccgcga gaagatagag 1320
aagattctga ccttcagaat tccttattac gtgggcccgc tggctcgggg caactcgcgc 1380
ttcgcctgga tgacgcgcaa gtccgaggag accatcaccc cgtggaactt cgaggaggtg 1440
gtggataagg gtgcctcggc ccagtccttc atcgagcgga tgaccaactt cgacaagaac 1500
ctgccgaacg agaaggtgct ccccaagcac agcctgctct acgaatattt cacggtgtac 1560
aacgagctga cgaaggtcaa gtacgtgacc gagggaatga ggaaacctgc attcctctcc 1620
ggggagcaga agaaagccat agtcgacctc ctgttcaaga ccaaccggaa ggtcaccgtc 1680
aagcagctca aggaggacta cttcaagaag atcgagtgct tcgattcagt ggagatcagc 1740
ggcgtcgagg accggttcaa cgccagcctg ggcacctacc acgacctgct caagatcatc 1800
aaggacaagg acttcctcga caacgaggag aacgaggaca tcctggagga catcgtgctg 1860
accctgacgc tcttcgagga ccgcgagatg atcgaggagc gcctcaagac ctacgcccac 1920
ctgttcgacg acaaggtgat gaagcagctc aagcggcgga gatatactgg gtgggccgc 1980
ctctcccgga agctcattaa cggtatcagg gataagcagt ccgggaagac gatcctcgac 2040
ttcctcaagt cggacgggtt cgccaaccgc aacttcatgc agctcatcca cgacgactcc 2100
ctgacgttca aggaggacat ccagaaggcc aagtgtctg gtcaaggtga ctcgctccac 2160
gagcacatcg ccaacctcgc gggcagcccg gccatcaaga agggaatact ccagaccgtc 2220
aaggtggtgg acgagctggt gaaggtcatg ggccgcagca gccggagaa catcgtcatc 2280
gagatggcgc gggagaacca gaccacgcag aagggccaga aaaatagccg tgagcgcatg 2340
aagcgcatcg aggaggggat taaggagttg gcagccagaa tcctcaagga gcaccctgtg 2400
gagaacacgc agttgcaaaa cgagaagctc tacctgtact acctccagaa cgggagggat 2460
atgtacgtgg accaagaact ggacatcaac cgcctgtccg actacgacgt ggaccacatc 2520
gtgccgcaga gcttcctcaa ggacgacagc atcgacaaca aggtgctcac ccggtccgac 2580
aagaatcggg gcaagtccga caacgtgccc agcgaggagg tcgtcaaaaa gatgaaaaac 2640
tactggcgac aactactgaa cgccaagctc atcccgcagc gcaagttcga caacctcaca 2700
aaagccgagc gcggcgggtt gagcgagctg acaaggccg ggttcatcaa cgccagctc 2760
gtcgagacgc gccagatcac gaagcacgtc gcgcagatac tcgacagccg gatgaacacc 2820
aagtacgacg aagaacgacaa gctcatccgg gaggtgaagg tcatcacct caagtcgaag 2880
ctcgtgagcg acttccgcaa ggacttccag ttctacaagg tccggagagt aacaactac 2940
caccacgccc acgatgctta tcttaacgcc gtggtgggga cggccctcat taagaaatac 3000
ccgaagctgg agtcggagtt cgtgtacggc gactacaagg tgtacgacgt caggaagatg 3060
atcgccaagt ccgaacagga gatcgggaag gccacggcga atacttctt ctacagcaac 3120
atcatgaact tcttcaagac cgagatcacc ctcgccaacg gcgagatccg caagcgcccg 3180
```

```
ctcatcgaga cgaacgggga gaccggcgag atcgtctggg acaaggggcg cgacttcgcc   3240
actgtgcgga aggtgctgtc gatgcccag gtcaacatcg tcaagaagac ggaggtccag   3300
acgggcgggt tcagcaagga gagcatcctg ccgaagcgca acagcgacaa gctgatcgcc   3360
cgcaaaaagg actgggatcc aaaaaagtac ggcggcttcg acagcccac cgtcgcctac   3420
agcgtcctcg tcgtcgctaa agtcgagaag ggcaagtcca aaaagctcaa gagcgtcaag   3480
gagctgctcg ggatcaccat catggagcgg tccagcttcg agaagaaccc aattgatttc   3540
ctggagcga agggctacaa ggaggtcaag aaagacctca tcataaagct gccgaagtac   3600
tcactcttcg agctggagaa cgggcgcaag cggatgctgg cgtcggccgg agagctccaa   3660
aagggcaacg agctggcgct gccgagcaag tacgtgaact tcctctacct ggcgtccac   3720
tacgagaagc tcaagggcag tccagaggat aacgagcaga agcagctatt cgtggagcag   3780
cacaagcact acctggacga gatcatcgag cagatcagcg agttctccaa gcgcgtcatc   3840
ctggcggacg ccaacctgga caaggtgctg tccgcgtaca caagcaccg cgacaagccg   3900
atccgcgagc aagccgagaa catcatccac ctgttcaccc tcacgaacct cggggcaccc   3960
gccgccttca aatatttcga cacgaccatc gaccgcaagc gctacaccag cacgaaggag   4020
gtgctcgacg ccaccctgat ccaccagagc atcaccgggc tgtacgagac ccgcatcgac   4080
ctctcgcagc tcggcgggga c                                            4101

SEQ ID NO: 5                moltype = DNA    length = 4101
FEATURE                     Location/Qualifiers
misc_feature                1..4101
                            note = Cas9 polynucleotide
source                      1..4101
                            mol_type = other DNA
                            organism = synthetic construct
SEQUENCE: 5
gacaagaagt acagtattgg attggccatc gggacgaaca gcgtgggctg ggccgtcatc    60
accgacgagt acaaggtgcc atccaagaag tttaaggttc tggggaatac cgaccgccac   120
tcgatcaaga aaaatctcat cggggcgctg cttttcgaca cgggcgagac ggcggaagcg   180
acgcggctca agcggacggc tcgtcgccgt tacacccgc gtaagaaccg catctgttac   240
ctccaggaga tattcagcaa cgagatggcg aaggtgacag actcctttt ccaccgtctt   300
gaggagtcct tcctggtcga ggaggacaag aagcacgagc gccacccgat cttcgggaac   360
atcgtggacg aggtggccta ccacgagaag taccccacga tctaccacct ccgcaaaaaa   420
ctcgtggact caactgacaa ggccgatttg aggcttatct acctcgccct cgcccacatg   480
attaagttcc gtgggcactt cctaatcgag ggtgacctca accccgacaa ctctgacgtg   540
gacaagctgt tcatccagct tgtgcagacc tacaatcagc tctttgagga gaatccgatc   600
aacgcatctg tgtggacgc aaaggccatc ctcagcgcgc ggctgagcaa gtctaggcgg   660
ttggagaacc tgatcgccca actgcccggc gagaagaaaa atggcctctt cggcaacctg   720
atcgccctgt cgctggggct cacgccgaac ttcaagagta actttgacct ggcggaggac   780
gctaagctcc agctatctaa ggacacatac gacgacgacc tggacaacct cctggcccag   840
atcggcgacc agtacgccga cctcttccta gccgccaaga acctgtccga cgccatcctc   900
ctcagcgaca tcctgcgcgt gaacacggag atcacgaagg ctccgctcag cgcctccatg   960
attaagcggt acgacgagca ccaccaagac ctaactttac tcaaagccct cgtgcggcag  1020
cagcttcccg agaagtacaa agagatattt tttgatcagt ccaagaacgg ttatgcgggc  1080
tacatcgacg gcggcgcgag ccaggaggag ttctacaagt tcatcaagcc catcctggag  1140
aagatggacg gcacggagga gctgctcgtg aagctcaacc gtgaagacct cctgcgaaag  1200
cagcgaacct tcgacaacgg ttcgatcccg caccagatcc acctcgggga gctgcacgcc  1260
atcctgaggc gacaggagga cttctaccct ttcctaaagg acaaccgcga agattgaa   1320
aaaatcctga cgtttcgcat accctactac gtcggcccgc tggcgcgcgg caactcccgg  1380
ttcgcctgga tgaccgtaa gagcgaggag acgatcaccc cgtggaactt cgaggaggtc  1440
gtggacaagg cgcgagcgc gcagagcttc atcgagcgca tgaccaactt cgacaagaac  1500
ctcccgaacg agaaggtgct cccaaagcac tccctcctgt acgagtattt caccgtgtcc  1560
aacgagttga caaaggtgaa gtacgtgacg gagggaatgc ggaagcctgc gttcctctcg  1620
ggcgagcaga agaaggcaat cgtggacctg ctcttcaaga ccaacggaaa ggtgacggtg  1680
aagcagctca aggaggacta cttcaaaaaa atcgagtgct tcgactccgt ggagataagc  1740
ggcgtggaga accgattcaa cgcctccctc ggcacctacc acgaccttcct taagatcatc  1800
aaggacaagg acttcctgga caacgaggag aacgaggaca tcctggagga catcgtgctc  1860
accctgaccc tcttcgagga ccgggagatg atcgaggagc gcctcaagac gtacgccac  1920
ttgttcgacg acaaggtgat gaagcagctc aagcggcggc gatacaccgg tgtggggccgc  1980
ctatcccgca aacttatcaa cggcatccgc gacaagcagt ccggcaagac gatcctggat  2040
ttcctcaagt cggacgggtt cgccaaccgg aacttcatgc agctcatcca cgacgacagc  2100
ctcacgttca aggaggacat ccagaaggcc aagtgagcg gtcaagggga cagcctccac  2160
gagcacattg cgaaccttgc tgggagccct gcgatcaaga agggggatat tgcaaaccgtg  2220
aaggtcgtgg acgagttggt gaaggtcatg ggcgacaca gcccgagaa catcgtgatc  2280
gagatgcca gggaaaatca gaccacgcag aagggccaaa aaaacagccg gactcggtac  2340
aagcggatcc aggagggcat caaggagctg gggtcgcaga tcctcaagga gcacccggtg  2400
gagaacacgc agctccagaa cgagaagctg tacctctatt acctacgaa cgggcgggat  2460
atgtacgtgg accaggagct agacatcaac cgcctgtccg actacgacgt ggaccatatc  2520
gtcccgcagt cgttcttgaa ggacgacagc atcgacaaca aggtgctcac aagatcggat  2580
aagaatcgag gcaagtccga caacgtgccc tcggaatgga ggtcaagaa aatgaaaaac  2640
tactggcggc agttgctgaa cgccaagctc attacgcagc ggaagttcga caacctgacg  2700
aaggctgaac gtggtgggct cagcgagcta gacaagcgg ggttcatcaa gcggcagctc  2760
gtcgagaccc ggcagatcac caagcacgtg gcgcagatcc tggactcgcg catgaacacc  2820
aagtacgacg agaacgacaa gctcatccgt gaggtgaagg tcatcccct taagtctaag  2880
ctggtcgatg acttccggca ggacttccag ttctcggagt tccggagat caacaactac  2940
caccacgcgc acgacgccta cctcaacgcg gtgtgggga cggcgcttat taagaaatat  3000
cccaagctgg aaagcgagtt cgtttacggc gactacaagg tgtacgacgt ccgcaagatg  3060
atcgcaaagt cggaacagga aatcggaaag gcgacggcca atatttctt ttactccaac  3120
atcatgaatt ttttaagac ggagatcacc ctggcgaacg gggagatccg caagcggccc  3180
ctcatcgaga ccaacgggga gacgggcgag atcgtctggg acaaggggcg ggacttcgcc  3240
```

```
accgtgcgga aggtgctttc tatgcctcaa gtcaatatcg tcaaaaagac agaggtgcag  3300
accggcgggt tcagcaagga gtctatcctg ccgaagcgca actcggacaa gctcatcgcg  3360
cgcaagaaag actgggaccc caaaaaatat ggcgggttcg actcgccgac cgtcgcctac  3420
agcgtcctcg tggtggctaa ggtcgagaag ggcaagagca aaaagctaaa gtcggtgaag  3480
gagctgctgg gcatcaccat catggagcgc tcgtctttcg agaagaatcc aatcgacttc  3540
ctagaggcga aggggtacaa ggaggtcaaa aaggatctta tcatcaaact gccgaagtac  3600
agtctgttcg agctggagaa cgggcggaag cggatgctgg ctagtgcggg cgagttgcag  3660
aagggcaacg agttggcact gccctccaag tacgtgaact tcctgtacct ggcctcccac  3720
tacgagaagc tcaagggggag ccccgaggac aacgagcaga cagcagctatt cgtcgagcag  3780
cacaagcact acctggacga gatcatcgag cagatcagtg agttctccaa gcgggtcatc  3840
ctcgcggacg ccaacctgga caaggtgctg agcgcgtaca caagcacag ggacaagcca  3900
atcagggaac aggccgagaa catcatccac ctgttcaccc tgaccaacct gggtgcaccg  3960
gctgccttca gtactttga cacgaccatc gaccggaagc gctacacctc cacgaaggag  4020
gtgctggacg ccacgctgat ccaccagagc atcaccgggc tctacgagac acggatcgac  4080
ctgagccagc ttggcgggga c                                              4101

SEQ ID NO: 6       moltype = DNA  length = 4092
FEATURE            Location/Qualifiers
misc_feature       1..4092
                   note = Cas9 polynucleotide
source             1..4092
                   mol_type = other DNA
                   organism = synthetic construct
SEQUENCE: 6
gacaaaaagt attccattgg actcgctatc ggcacgaaca gcgtcgggtg ggcggtcatc    60
actgacgagt acaaggtgcc gagcaagaag tttaaggtgc tgggaaacac cgacaggcac   120
tcgatcaaga aaatcttat cggggcccta ctcttcgact ccggagaaac cgccgaggcc    180
acccggttga agcgcacggc ccgccgtcgc tacaccaggc gcaagaaccg gatctgctac   240
ctccaggaga tattcagcaa tgagatggcg aaggtgacg actcgttttt tcacaggcta    300
gaggagtctt tcctcgtgga ggaggacaag aaacacgagc gccaccccat cttcggcaac   360
atcgtggatg aggtggcata tcacgagaag tacccaacca tctaccacct ccgcaaaaag   420
ctcgtggact ctaccgacaa ggccgacctc cgtctgatct acctcgcgct ggcccacatg   480
attaagttcc gaggacactt tctgatcgag ggcgacctga acccagacaa cagcgacgtg   540
gacagctgt tcatccaact tgtccagacc tacaatcagc tcttcgagga aaccctatc    600
aacgcctcgg gcgtgacgc gaaggccatc ctgtccgcgc cctgagcaa gtcgcggcgg   660
ctggagaacc tgatcgccca gctccccggc gaaaaaaaga acggcctctt cggcaacctc   720
atcgcgttgt cgctggggct cacccccaac ttcaagtcca acttcgacct ggccgaggac   780
gctaaactcc agctctcgaa ggatacctac gacgacgacc tcgacaacct gctggcccag   840
atcggcgacc agtacgcgga ccttttcctg gcggccaaga acctgagcga cgcgatcctc   900
cttagcgaca tactccgtgt gaacaccgag atcacgaagg cccgctctc cgcgtccatg   960
attaagcgct acgacgagca ccaccaagac cttaccctgc ttaaggcgct ggtcaggcag  1020
cagttaccgg agaagtacaa ggagatcttt tttgatcaat ctaagaacgg ttacgccggg  1080
tacatcgacg gcggcgcgtc ccaggaggag ttctacaagt tcatcaagcc gatcttggag  1140
aaaatggacg gaaccgagga gctgctcgtg aagctcaacc gcgaagacct cctccgcaag  1200
cagcgcacct tcgacaacgg gagcatcccc caccagatcc acctgggaga gctgcacgcg  1260
atcctgcgga gacaagagga cttctacccc ttcctcaagg acaaccggga gaagattgaa  1320
aaaatactta cttttcgtat cccgtactac gtcggggccg ttgcgaggga caactccaga  1380
ttcgcgtgga tgacccgcaa gtccgaggag accatcaccc cgtggaactt cgaggaggtg  1440
gtggacaagg gcgcgtcggc ccagtcgttc atcgagcgca tgaccaactt cgacaagaac  1500
cttccgaacg agaaggtgct cccgaagcac agcctgctct acgaatatt tactgtgtac  1560
aacgagtcga cgaaggtcaa gtacgttacg gaggggatga ggaagccgc cttcctccgc  1620
ggcgagcaga agaaagccat tgtggatctc ctgttcaaga ccaaccgcaa ggtgacggtg  1680
aaacagctca agaggacta cttcaagaag atcgagtgct tcgactccgt agagatcagc  1740
ggggtcgagg accgcttcaa cgcctcgctg ggcacgtacc acgacctgct aaagattatc  1800
aaggacaaag acttcctaga caatgaggag aacgaggaca tttctggagga catcgtgctg  1860
actctgacgc tgttcgaaga ccgcgagatg atcgaggagc ggcttaagac gtacgcccac  1920
ctgttcgacg acaaggtgat gaagcagttg aacggcggc gctacaccgg gtggggccgc  1980
ctctcccgca gctcatcaa cggcatccgc gacaagcagt cggggaagac gatcctggac  2040
ttcctcaaga gcgacggctt cgccaaccga aacttcatgc agctaatcca cgacgacagc  2100
ctgacgttca aggaggacat ccagaaggcc caagtgacgc gccagggaga ctcgctacac  2160
gagcatatcg ccaacctggc tggcagcccg cgattaagga aaggaatcct ccaaaccgtc  2220
aaagtggtgg acgagctggt gaaggtgatg ggccgccaca gcccgagaa cattgtgatc  2280
gagatggcgc gggagaacca gacgacgcag aagggccaaa aaaatagcag ggaaaggatg  2340
aagcgaatag aggaggggat caaggagctg gggagcctgg ttctcaaaga gcaccgggtc  2400
gagaacacac agctccagaa cgagaagctg tacctctact acctccaaaa cggccgcgat  2460
atgtacgtgg accaggaact agacatcaac cggctgagcg actatgacgt ggaccacatc  2520
gtgccgcagt ccttcctcaa ggacgactcg attgacaaca agtgctcac tagatccgac  2580
aagaacagag gcaagagcga taacgtcccg tcggaggagg tcgtcaagaa aatgaaaaac  2640
tactgccgga gctcctaaa cgccaagctc atcacgcagc gtaagttcga caacctgacg  2700
aaggcggagc ggggcgggct gagcgagctg gacaaagcgg ggttcatcaa gcggcagctc  2760
gttgagacgc ggcagatcac aaagcacgtc gcgcaaatcc tcgactcccg catgaacacc  2820
aagtacgacg agaacgacaa gctcatccgg gaggtgaagg tcattaccct taaatcgaag  2880
ctcgtcagcg acttcgtaa ggacttccag ttctacaagg tcagagagat caacaactac  2940
caccacgccc acgacgccta tctgaacgcc gtggtgggca ccgcgcttat taagaagtac  3000
cccaagctgg agtccgagtt cgtgtacggc gactacaagg tttatgacgt caggaagatg  3060
atcgccaagt cggaacagga gatcggaaaa gctaccgcca aatatttctt ctatagcaac  3120
atcatgaact tcttcaaaac cgagatcacc ctcgccaacg gcgagatccg gaagcgcccg  3180
ctcatcgaga ccaacgggga gaccggggag atcgtctggg acaaggggcg ggacttcgct  3240
actgtccgaa aggtgctctc catgccacaa gtgaatatcg tcaagaaaac agaggtgcag  3300
```

```
accggagggt tcagtaagga gtccatcctg cccaagcgga actccgacaa gctaattgct  3360
cgcaaaaagg attgggatcc taaaaaatat ggcggcttcg actcgcccac ggtcgcctac  3420
tctgtgctgg tcgtggcgaa ggtggagaag ggcaagtcca agaagctcaa gagcgtcaag  3480
gagctgctgg gatcacgat catggagcgt agttcgtttg agaagaatcc catcgacttc  3540
ctggaggcta agggctacaa ggaggtcaaa aaggacctca tcattaagct gccgaagtac  3600
agcctcttcg agctggagaa cgggcggaag cgtatgctcg cctccgctgg ggagttacaa  3660
aaggggaacg agctggcgct gccgtctaag tacgtcaact tcctgtacct ggcctcccac  3720
tacgagaagc tcaaggggtc gccggaggac aacgagcaga agcagctctt cgtagagcag  3780
cacaagcact acctggacga gatcatcgag cagatttcag agttctcaaa gcgggtcatc  3840
ctcgccgacg ccaacctgga caaggtgctc tcggcctaca acaagcaccg ggacaagccg  3900
atccgcgaac aggccgaaaa catcatccac ctgttcacgc tcaccaacct cggtgccccg  3960
gcggccttca agtactttga cacgaccatc gaccggaagc gctatacctc gacgaaggag  4020
gtgctggacg ccaccctgat ccaccagtcc atcaccgggc tttacgagac ccggatcgac  4080
ctctcgcagc ta                                                      4092

SEQ ID NO: 7          moltype = DNA   length = 4101
FEATURE               Location/Qualifiers
misc_feature          1..4101
                      note = Cas9 polynucleotide
source                1..4101
                      mol_type = other DNA
                      organism = synthetic construct
SEQUENCE: 7
gacaagaagt atagtattgg actcgccatc ggaaccaact ctgtggggtg ggctgttatt  60
acagatgaat ataaggtgcc atccaaaaag tttaaagttc tgggcaatac tgatagacac  120
tcaatcaaga gaatctgat aggtgcactt ctgtttgata gtggagagac tgccgaggca  180
accagactta aaaggactgc aagaagaaga tataccagaa gaaagaatag gatttgctat  240
ttgcaggaaa tcttcagcaa cgaaatggcc aaggttgatg actcattttt ccataggttg  300
gaggagagtt ttcttgtgga ggaagataag aagcacgaaa gacacccaat tttcgggaat  360
atagtggacg aggtggctta tcatgagaag tatcccacta tctaccacct gagaaagaaa  420
cttgtggact caaccgataa ggctgatctt aggcttatat acttggccct tgcacatatg  480
atcaaattca ggggccattt tcttatcgaa ggcgatctta atcccgataa ctcagatgtg  540
gacaagctgt ttatacaact tgtgcaaacc tacaatcaac tcttcgagga aatcccatt  600
aacgcctccg gcgtggatgc aaaagccata ctgtcagcca gactgagcaa aagtaggaga  660
ctggagaatc ttatagccca actgcccggt gaaaagaaga atgggctctt cggaaatctc  720
atcgctcttt cattggggtt gacacccaac tttaagagta actttgactt ggcagaagat  780
gcaaagttgc agctcagtaa agacacatat gacgatgacc ttgacaatct cttggcacaa  840
ataggggatc aatacgctga ccttttcctc gctgccaaga acctcagcga cgctatactg  900
ttgtccgaca ttcttagggt taataccgaa attacaaagg ccctcttag tgcaagtatg  960
atcaaaaggt atgatgagca tcaccaagac cttacactgc tgaaggctct ggttagacag  1020
caactccctg aaaagtataa ggaaatattc ttcgaccaaa gtaagaacgg gtacgccggt  1080
tatattgatg ggggcgcaag tcaagaagaa ttttacaat tcatcaagcc aattcttgaa  1140
aagatggacg ggactgagga attgctggtg aaactgagag agaggacct tcttagaaaa  1200
cagaggacat tgacaatgg gtccatccca caccagattc atctggggga actccacgca  1260
atattgagga gacaagaaga cttttaccca ttccttaagg ataatagaga gaaaatcgaa  1320
aaaatcctga ctttcaggat tccttactat gttgggccac tggccagggg gaactcaaga  1380
ttcgcttgga tgacaaggaa gtcagaagaa accataaacc cttggaattt tgaagaggtg  1440
gttgataagg gggcatcagc ccagtctttc atagagagga tgaccaactt tgataaaaat  1500
cttccaaatg agaaggtttt gccaaaacat agtctttgt acgagtactt tactgtttat  1560
aacgaattga ccaaggtgaa gtatgtgacc gagggaatga ggaagccagc attttttgtcc  1620
ggggacaaa agaaagcaat cgttgatctt ctcttcaaga ccaacagaaa agtgaccgtg  1680
aaacaactga aggaagacta cttcaaaaag atagaatgtt tcgattcagt ggaaattagc  1740
ggtgttgaag acaggttcaa tgccttcattg ggtacttacc acgacctgtt gaagataatc  1800
aaagacaagg actttctcga taatgaggag aacgaagaca tcttggaaga cattgtgctt  1860
acactcactt tgtttgagga cagggaaatg attgaggaaa gactcaaaac ttacgctcat  1920
ttgtttgatg ataaggttat gaaacaacta aaaagaagaa ggtacaccgg ctggggaaga  1980
ttgagtagga aactgatcaa cggtattaga gataaacaat ccggaaagac tatcctcgat  2040
ttccttaaga gtgatggctt tgcaaatagg aattttatgc agctgattca tgacgactca  2100
cttaccttca aagaagacat ccaaaaagct caggtgtctg ggcaaggcca cagtctgcat  2160
gaacatatag ctaacttggc tgggagtccc gccatcaaga aggggatact tcaaacagtt  2220
aaagttgtgg acgaattggt gaaggtaatg ggaaggcaca gcctgaaaa tatagtgata  2280
gaaatggcaa gggaaaatca aaacccag aagggacaga gaacagtag ggaaggatg  2340
aaaaggatag aagaggggat caaagagctt ggtgtagcaga tcctcaagga catccagtg  2400
gagaataccc aacttcaaaa cgagaaactc tatttgtact acttgcagaa cggaagagat  2460
atgtatgtgg accaagagct tgatattaac aggctgagcg attatgacgt tgaccacata  2520
gtgccccaat cattcctcaa ggatgactct attgataata aggtgctgac aaggagtgac  2580
aagaatagag ggaaatccga caacgttcca tccgaggaag ttgtgaagaa gatgaagaac  2640
tactggaggc agttgctgaa cgctaagctc attacccaga ggaaattcga taacctgacc  2700
aaagcagaga gaggcgggct gagcgaactc gataaagcag gtttcatcaa gagacaactc  2760
gtggagacta ggcaaattac taagcacgtg gctcaaatac tcgacagcag gatgaacaca  2820
aagtacgacg agaacgacaa gctcattaga gaggttaagg ttattactct gaaaagtaaa  2880
ttggttagcg atttcagaaa ggatttccaa ttctataagg ttagagagat caacaattat  2940
catcatgcac atgatgccta tctgaatgct gtggttggta cagcccttat caagaagtac  3000
cctaagctag agagcagtt tgtgtacgga gattataagg tgtatgatgt gaggaaaatg  3060
atcgctaaaa gtgagcaaga gattggaaag gctaccgcca atacttctt ttattccaat  3120
attatgaatt tcttcaagac agaaatcacc ctggctaacg gcgagataag gaagaggccg  3180
cttatcgaaa ctaatgggga gacaggcgaa atagtgtggg acaaagggag ggattttgca  3240
actgtgagga aggttttgag catgcctcag gtgaatatcg ttaagaaaac cgaagttcaa  3300
actggagggt ctctaaggaa aagcattctc cccaagagga ctccgacaa gctgattgct  3360
```

| | | | | |
|---|---|---|---|---|
| agaaagaaag | actgggaccc | caagaagtat | ggcggattcg | actcacccac tgtggcatat 3420 |
| agcgttctcg | tggtggcaaa | ggttgaaaag | ggtaaatcca | aaaaactcaa atccgtgaag 3480 |
| gaactccttg | gcataactat | tatggaaagg | agtagctttg | aaaagaatcc catcgacttt 3540 |
| ctcgaagcta | agggctataa | ggaagttaag | aaggacctta | taatcaaact tccaaaatac 3600 |
| tcccttttg | agttggaaaa | cggcagaaag | agaatgttgg | ccagtgccgg ggagcttcaa 3660 |
| aagggcaacg | aactggctct | gcctagcaaa | tatgtgaact | ttttgtatct ggcatcacac 3720 |
| tacgagaaac | ttaaaggctc | tcctgaggac | aacgagcaaa | aacagctctt tgttgaacag 3780 |
| cataagcact | acctcgacga | gattattgag | cagatcagcg | agttctcaaa gagagttatt 3840 |
| ctggctgacg | ctaatcttga | caaggttttg | tccgcttaca | acaaacacag ggataagcca 3900 |
| atcagggagc | aggcagaaaa | cataatccat | ctctttaccc | tgacaaacct cggtgccccc 3960 |
| gctgctttca | agtatttga | tactaccatt | gacaggaaga | gatatacttc cactaaggaa 4020 |
| gtgctcgacg | caaccctcat | acaccaaagt | atcacaggcc | tctatgaaac taggatagat 4080 |
| ttgtctcaac | ttgggggcga | t | | 4101 |

```
SEQ ID NO: 8           moltype = DNA  length = 4101
FEATURE                Location/Qualifiers
misc_feature           1..4101
                       note = Cas9 polynucleotide
source                 1..4101
                       mol_type = other DNA
                       organism = synthetic construct
SEQUENCE: 8
```

| | | | | |
|---|---|---|---|---|
| gacaaaagt | attccatcgg | gcttgctatc | ggaaccaact | ctgtggggtg ggcagttatt 60 |
| accgacgaat | acaaggtgcc | cagcaagaag | tttaaggttc | tggggaacac agatagacat 120 |
| agcataaaga | aaaacctgat | aggcgcactg | ttgttcgact | ccggggaaac agccgaagct 180 |
| accaggctga | agagaactgc | aaagaagaag | tacaccagaa | gaaaaacga aatatgttat 240 |
| ctccaagaga | tttctctaa | cgagatggcc | aagtggacg | actcattctt tcacagactg 300 |
| gaagaatctt | tccttgtgga | agaagataag | aaacacgaga | ggcacctat tttggcaat 360 |
| atcgtggatg | aggtggctta | ccacgaaaaa | taccctacaa | tataccacct caggaaaaaa 420 |
| ttggttgata | gtacagacaa | ggccgacctc | aggctcatct | atttggccct ggccccatg 480 |
| attaaattca | gggggcactt | tctcatcgag | ggagatttga | accccgacaa cagtgatgtt 540 |
| gataagctct | ttattcagct | cgtgcagact | acaatcagt | tgtttgagga aaaccccatt 600 |
| aatgcttccg | ggtggacgc | caaggcaatc | ctttctgcaa | gactctcaaa gtcaaggaga 660 |
| ctcgaaaatc | tgatagcaca | gcttccagga | gagaagaaga | acgggctctt tggaaacctg 720 |
| atcgctctgt | cactcggact | cacacccaat | ttcaaaagca | atttgatt ggcagaggac 780 |
| gctaagctgc | aactcagtaa | ggatacctac | gacgatgact | tggataatct gctcgcacaa 840 |
| attggggacc | agtatgcaga | cctgttctc | gcagctaaga | acttgagtga cgccatattg 900 |
| ctcagtgaca | tcctcagggt | taataccgag | attacaaaag | ctccactctc tgcaagcatg 960 |
| atcaagaggt | atgacgagca | ccatcaagac | ctaaggcgt | ttaaggcgtt ggttaggcag 1020 |
| caacttcctg | aaaagtataa | ggaaatcttc | ttcgatcaaa | gcaaaaacgg ctacgccggc 1080 |
| tatatagacg | ggggagcatc | ccaagaagaa | ttttataagt | tcataaaacc tatattggag 1140 |
| aagatgacg | ggacagagga | attgctcgtg | aaactgaaca | gggaggatct cctcaggaag 1200 |
| caaaggacct | tcgacaatgg | ctccatccca | catcagattc | acctcggcga actgcacgca 1260 |
| atactgagaa | gacaagagga | cttttatcct | ttcctgaagg | acaacaggga gaaaatcgag 1320 |
| aaaatcttga | cattcagaat | cccatactac | gttgggcctc | tggccagagg taacagtagg 1380 |
| ttcgcctgga | tgactaggaa | atcagaggag | actattacac | cctggaactt tgaagaagtt 1440 |
| gttgataagg | gagcttcagc | acaatcattc | atcgaaagat | tgacaaactt cgacaaaaat 1500 |
| ctgcctaatg | agaaagtgct | cccaaaacat | tccctgctgt | atgagtattt taccgttat 1560 |
| aacgagctta | ccaaggtgaa | atacgttact | gaaggtatga | gaaagccagc ttttctttca 1620 |
| ggggagcaaa | agaaggctat | cgtggatctt | ctctttaaga | ccaacagaaa ggttaccgtg 1680 |
| aagcagctta | aggaagacta | cttaaaaag | atcgagtgtt | ttgactcagt ggaaataagc 1740 |
| ggtgttgaag | atagattcaa | cgcatccttg | ggaacttatc | atgatcttct taagataatc 1800 |
| aaggataaag | actttctcga | caacgaggaa | aacgaagata | tactgagga catagttctg 1860 |
| acacttactt | tgttcgagga | tagggagatg | atcgaggaaa | gactgaaaac atatgctcac 1920 |
| cttttcgacg | acaaagttat | gaaacaactc | aagagaagaa | gatatacagg gtggggagaa 1980 |
| ttgagcagga | aactgattaa | tggtatcaga | gacaaacagt | caggaaaaac aatactcgac 2040 |
| ttttgaaat | cagacgggtt | cgcaaatagg | aatttcatgc | agcttataca cgacgattca 2100 |
| cttacttta | aagaggacat | tcaaaaggct | caagttagtg | gacaaggtga ctccctccac 2160 |
| gaacacatcg | caaatctcgc | tggcagccct | gcaattaaga | agggtatact ccagacagtt 2220 |
| aaggttgttg | acgagctggt | taaagtgatg | ggaagacaca | aacccgagaa catagtgata 2280 |
| gagatggcca | gggaaaacca | aaccactcaa | aaagggcaga | aaatccag agagaggatg 2340 |
| aaaaggatta | agaagggtat | caaggagctg | ggtagccaaa | ttctgaaaga acatcctgtg 2400 |
| gaaacactc | aactccagaa | tgagaaactc | tatctgtact | atctgcaaaa tgggagagat 2460 |
| atgtatgtgg | accaggaact | ggacataaac | aggctctcg | attacgatgt ggatcatatc 2520 |
| gtgccacagt | cctttcttaa | ggatgatagc | atcgacaata | aggtgcttac caggtccgac 2580 |
| aagaacaggg | gaaagtcaga | taacgtgcct | tctgaagaag | ttgttaaaaa gatgaagaac 2640 |
| tactggagac | agctgcttaa | cgctaagctc | ataacacaga | ggaagtttga acttgacc 2700 |
| aaggccgaga | gaggcggact | ctcagaattg | gataaggcag | ggttcataaa aaggcagctg 2760 |
| gtgaaacaa | ggcagataac | taaacatgtg | gctcagatcc | tcgatagtag gatgaataca 2820 |
| aaatacgatg | agaacgacaa | gctcataagg | gaggttaaag | tgataactct gaaatccaaa 2880 |
| ctggttagcg | attttaggaa | ggatttccag | ttttacaaag | ttaggagat caacaattat 2940 |
| catcacgccc | acgatgccta | cttgaacgca | gttgtgggta | ctgcacttat caaaaagtac 3000 |
| cctaagctgg | aatccgagtt | tgtttatgga | gactataagg | tgtacgacgt tagaaaaatg 3060 |
| attgcaaagt | cagagcagaa | gatagggaaa | gccactgcaa | aatttctt tatagcaat 3120 |
| atcatgaatt | tctttaagac | agaaatcaca | ctggccaatg | ggaaataag gaagaggccc 3180 |
| ctgatcgaaa | ctaatggcga | gacagggag | attgtgtggg | ataaaggtag ggactttgca 3240 |
| acagtgagga | aagtgctgag | catgcccaa | gttaatatcg | ttaaaagac cgaggttcaa 3300 |
| acaggggct | ttagtaagga | aagcatttg | cccaagagga | atagtgacaa attgattgct 3360 |
| aggaaaaag | attgggaccc | caaaaagtat | ggcggatttg | atagccccac tgttgcttac 3420 |

```
tccgtgctcg tggttgcaaa ggtggagaag ggaaagagca agaaactgaa gtcagttaag   3480
gaactccttg gtatcactat catggaagaa agctcctttg agaagaaccc tattgacttc   3540
ctggaggcta aagggtacaa agaggttaag aaagacctta tcattaaatt gcccaaatat   3600
agtcttttcg agcttgaaaa cggaagaaag aggatgcttg catccgctgg cgaattgcaa   3660
aagggcaatg agcttgctct cccttccaag tatgtgaact tcctttatct tgcctcacac   3720
tatgaaaaac tcaaaggttc acccgaagac aacgaacaaa agcaactatt tgtggaacaa   3780
cacaagcact acctggacga aatcattgag caaatttctg agttttcaaa aagggtaatc   3840
ttggctgacg caaatctcga caaagttttg tcagcttaca caaacatag  agataagcca   3900
attagagagc aagctgagaa tatcatccat ctgtttaccc tgactaacct tggagcgcct   3960
gctgctttta aatatttcga caccacaatc gacaggaaga ggtacactag cactaaggaa   4020
gttctcgacg ccaccctcat ccaccagagt attacaggcc tgtacgagac aagaattgat   4080
ctttctcaac ttggtggtga c                                             4101

SEQ ID NO: 9           moltype = DNA   length = 4101
FEATURE                Location/Qualifiers
misc_feature           1..4101
                       note = Cas9 polynucleotide
source                 1..4101
                       mol_type = other DNA
                       organism = synthetic construct
SEQUENCE: 9
gataagaagt actcaatcgg tctggcaatc ggaaccaact ctgtgggttg ggcagtgatt   60
acagatgagt ataaggtgcc aagcaaaaaa ttcaaggtgc tgggtaatac cgacagacac   120
agcattaaga gaattgat tggagcactc ctctttgact caggggaaac agcagaggca   180
acaaggctga gaggacagc aaggcggagg tacacaaggc ggaaaaacag gatatgctac   240
ctccaggaaa tctttagcaa cgagatggct aaagtgatg atagcttttt ccatagactc   300
gaagaatcct ttcttgttga agaggacaaa aagcatgaaa ggcatcccat cttcggcaat   360
atagttgatg aggttgcata ccatgagaag taccccacaa tctaccacct cagaaagaaa   420
cttgtggact ccacagataa agcagacctg aggctcatat acctcgcact cgcacacatg   480
atcaagttca gagggcactt tctcatcgaa ggtgacctga atccagataa ttcagatgtg   540
gataaactgt ttatacagct ggtgcaaaca tacaaccaac ttttcgagga aaacccaatc   600
aatgcctccg tgttgatgc aaaggccatc ctgtcagcaa gactcagcaa aagcaggcgg   660
ctcgaaaacc tcatcgccca gcttcccggt gaaaagaaga cgggctctt tggtaatctc   720
atcgcattga gccttggtct tactccaaac ttcaagagca attttgatct ggcagaggat   780
gctaaactgc aactctcaaa ggacacatat gacgatgacc ttgacaatct gttggcccag   840
atcggggacc aatatgcaga cctcttcctg gccgcaaaga atctgtcaga tgcaatcctc   900
ttgtccgaca tactgagagt taacactgag atcacaaagg cacctctgtc cgcctccatg   960
attaagagat acgatgagca tcaccaggat ctgactttgc tcaaagccct cgttagacag   1020
cagttgccag aaaagtacaa agaaatattc tttgatcaat caaaaacgg atatgcaggg   1080
tacatcgacg gtggggcaag ccaggaagag ttctacaaat tcatcaaacc tatcctggaa   1140
aagatggatg gacagaaga gctgctggtt aagctgaata gggaagacct cctcagaaag   1200
cagaggacat ttgataacgg gagcatccct catcaaatcc acctcggtga actccatgct   1260
atcctgagaa ggcaggaaga ctttttatcc ttttgagga acaataggga gaaatcgaa   1320
aaaatcctga cattcagaat cccatactac gttggtcctc tggcaagagg taacagtagg   1380
ttcgcatgga tgacaaggaa aagcgaggag acaatcacac cctggaattt tgaggaagtt   1440
gttgacaagg gtgccagcgc acaatccttt atcgaaagaa tgacaaattt cgacaagaat   1500
ctgcctaacg aaaaggttct cccaaagcat tcactcctgt acgaatattt tacagtttat   1560
aacgaactga ctaaagttaa atacgttacc gagggtatga ggaagccagc attcctttcc   1620
ggggaacaga agaaagctat tgtggaccte ctgttcaaga caaatagaaa agtgacagtt   1680
aagcaactca agaggatta cttcaaaaag atcgaatgtt ttgactctgt ggagatcagc   1740
ggggtgagaa atagattcaa cgccagcctg gtacatatc atgatctcct gaaaatcatt   1800
aaagacaagg acttccttga caacgaggag aacgaggaca ttctggaaga cattgttctg   1860
accctcacac tctttgagga tagggagatg attgaggaaa gactgaagac ctacgcccac   1920
ctctttgacg ataagtgat gaaacagctc aagagaagaa ggtatacagg ttgggggaga   1980
ctgagcagga agttgatcaa tgggattagg gacaaacagt ccgggaaaac aatcctcgat   2040
tttctgaagt cagacggttt cgcaaacaga aattttatgc agctcattca cgatgacagc   2100
ttgacattca aggaagacat ccaaaaggct caagtgagcg gccaagggga tagcctccac   2160
gagcatattg caaatctggc aggttcacca gccatcaaaa agggcatact tcagacagtg   2220
aaggttgtgg acgaattggt taaagtttatg ggcaggcata gccagagaa tatcgttatc   2280
gaaatggcaa gggagaacca aacaactcaa aaagggcaga aaatagcag agagaggatg   2340
aaagaatcg aggaagggat caaggaactt gggtcccaaa tcctcaagga gcacccagtt   2400
gaaaatactc aactgcaaaa cgagaagctc tatctctact atctccaaaa cgggagggat   2460
atgtatgttg ccaggagct ggatattaac agactgtcag attatgatgt tgatcatatc   2520
gtgccccagt cattcctgaa ggacgattcc atcgacaaca aagttctcac aaggtccgat   2580
aaaaacaggg gcaagtccga taacgttcca agcgaagtgg tggtgaaaaa gatgaaaaac   2640
tattggagac aacttctgaa tgcaaagttg attactcaga gaagtttga caacctcaca   2700
aaagcagaaa gaggcgggct tagcgaactc gataaggcag ggtttatcaa agacagctg   2760
gttgagacaa ggcagatcac aaaacatgtg gcacagatcc ttgactcaag gatgaataca   2820
aagtatgatg agaatgataa gttgatcagg gaggttaaag ttatcacact caaatccaaa   2880
ctggtgtcag acttcaggaa agactttcaa ttttataagg tgagggagat caataactac   2940
caccatgcac atgacgccta cctgaacgca gtggtgggta cagcattgat taaaaaatac   3000
cctaagctgg agtctgagtt tgtgtacggg gactacaagg tgtacgacgt gaggaaaatg   3060
atagccaagt ccgagcagga gatcgggaaa gcaacagcta gtatttctt ttacagtaat   3120
atcatgaatt tctttaaaac tgagattact ctggcaaacg gtgagatcag gaaagaccc   3180
ctcatcgaga ctaatggtga aacaggtgag atcgttggg acaaggggag ggattttgct   3240
actgttagaa aagttctgag tatgccacaa gtgaatattg tgaaaagac agaagttcag   3300
acaggtgggt tctccaaaga atccatcctg cccaagagaa attcagacaa gctcatcgca   3360
agaaagaagg actgggaccc taagaagtac ggaggatttg acagccccac cgtggcctat   3420
tccgtgcttg ttgtggcaaa ggtggagaaa gggaagagca aaaaactgaa atccgtgaaa   3480
```

```
gaactgctgg gaattaccat catggaaaga agctcctttg agaagaaccc aatcgacttc  3540
ctggaagcaa aaggatataa ggaagtgaaa aaggacctca ttatcaagct cccaaaatac  3600
tcactttcg agttggagaa cggtagaaag aggatgctgg caagcgcagg gaacttcag    3660
aaaggcaatg agctggcatt gccatcaaag tatgtgaact tcctctactt ggccagccat  3720
tacgagaaac ttaaaggtag cccagaagat aacgagcaaa aacagctctt tgtggaacag  3780
cataagcatt atctggatga gatcatagaa caaatctcag agttttccaa gagagttatc  3840
ctcgcagatg caaacctgga taaggttctc tcagcctata ataagcatag agacaagcca  3900
attagagagc aagcagagaa cattatccac ttgttcactc ttacaaacct gggggcacca  3960
gccgccttca aatatttcga tacaacaata gacagaaaga ggtataccag caccaaagaa  4020
gttctcgacg ccacactgat ccatcaatca atcacaggcc tttacgaaac taggatcgac  4080
ttgtcacaac tgggtgggga t                                            4101

SEQ ID NO: 10          moltype = DNA  length = 3307
FEATURE                Location/Qualifiers
misc_feature           1..3307
                       note = Cas9 polynucleotide
source                 1..3307
                       mol_type = other DNA
                       organism = synthetic construct SEQUENCE: 10
gagcaaggac acctcgacg acgacttgga caacctattg gcccagatag gtgaccagta   60
tgcagacctc ttccttgcgg ccaagaactt gagtgacgct atactgctca gtgacatcct  120
gagggtgaaa actgagatca ctaaggcccc tctctctgcc tcaatgatta agcgttacga  180
cgagcatcac caggatctca ccctgcttaa ggcccttgtt cggcagcagc tccctgagaa  240
gtacaaggag atatttttg accagtctaa gaacggctac gccggttaca ttgacggtgg   300
ggcaaggcag gaggagttct acaagttcat caagccgatc cttgagaaga tggacggcac  360
cgaggagcta cttgtcaagt tgaaccggga agacctgctc cggaaacagc gtacattcga  420
caacggcagc atccctcacc agatccacct gggcgaacta cacgccatcc tccgacgtca  480
ggaggacttc tatccattct tgaaagataa cagggaaaaa atcgaaaaaa tacttacgtt  540
tcgaatacct tactacgtgg ggccccttgc tcggggaaac tccagattcg catggatgac  600
caggaagtca gaggagacca tcacccctg gaactttgag gaggtggttg acaaaggtgc   660
ttctgcccag tccttcattg agcggatgac taacttcgac aagaacctgc caacgagaa   720
ggtgctgcca agcacagcc tgctctacga atacttact gtgtacaatg agctgacgaa    780
ggtgaagtac gtgacagagg ggatgcgaaa gcccgctttc ctgacgcggcg agcaaaaaaa  840
agcaatcgtg gacctactgt tcaagaccaa ccgaaaggtg acagtgaagc agctcaagga  900
ggactacttc aaaaaaatcg agtgcttcga ctctgttgag ataagcggcg tggaggaccg  960
attcaacgcc tcattgggaa cctatcacga cctgctcaag atcattaagg acaaggactt  1020
cctggataat gaggagaatg aggacatcct ggaggatatt gtgctgaccc ttactctatt  1080
cgaggacagg gagatgatcg aggagcgact caagacctac gctcacctgt tcgacgacaa  1140
ggttatgaag caattgaagc gtaggcgata cacggggtgg ggaagactct cccgaaaact  1200
gataaacggc atcagggaca agcagtcagg gaagacgatc ttggacttcc tgaaatccga  1260
cgggttcgc aaccgcaact tcatgcagct cattcacgac gactcactaa cgttcaaaga   1320
ggacattcag aaggctcaag tcagtggaca aggcgactc tgcacgagc acattgcaaa   1380
ccttgcgggc tccccggcga ttaaaaaggg cattctccaa acggttaagg tggtggacga  1440
gctggtgaag gtgatgggcc gacacaagcc tgagaacatc gtgatcgaga tggccaggga  1500
gaaccagact acccagaagg gtcagaagaa ctctcgggaa cgtatgaagc gtattgagga  1560
gggattaag gagttgggct ctcaaatcct caaggagcac cctgtggaga acactcagct   1620
ccaaaacgag aagctgtacc tgtactacct gcaaaacggg cgcgatatgt acgtggatca  1680
ggagttggac atcaacaggc ttagcgatta cgacgtggac cacatcgtgc cacagtcatt  1740
cttaaaggac gacagcatcg acaacaaggt tctgacgagg agcgacaaga atcgaggaa   1800
aagtgacaat gttccatccg aggaggtggt caagaaaatg aagaactatt ggcgtcagct  1860
tctgaacgcc aagctcatca cccagcggaa attcgacaac ctgactaagg ctgagcgagg  1920
cggactctcc gagcttgaca aggctggctt catcaagcgg cagttggtcg aaacccgaca  1980
gataacgaag cacgttgccc agatacttga ctcccgtatg aacaccaagt acgacgagaa  2040
cgacaagctc atcagggagg tgaaggtcat tacccttaag tccaaactcg tcagcgactt  2100
tcgtaaggac ttccagttct acaaggtgcg cgagatcaat aactaccacc acgcacacga  2160
cgcctacctg aacgcagtgg ttggaaccgc gttgattaaa aagtacccca gttggagtc   2220
ggagttcgtt tacgggact acaaggtgta cgacgttcgg aagatgatcg ccaagtctga  2280
acaggagatc gggaaagcaa ccgccaagta ttttcttcta t agcaacatca tgaacttctt  2340
taaaaccgag atcacacttg ccaatggcga gatccgtaag aggccgctga tcgagacaaa  2400
tggggagact ggcgagatcg tgtgggacaa gggccgcgac ttcgcaaccg ttcggaaagt  2460
cttgtccatg cctcaagtca acatcgtcaa gaagactgag gtgcaaacag gcgggttctc  2520
gaaggagtcc atactgccca gaggaactc agacaagctc atagcacgca aaaaagactg   2580
ggatccaaag aaatacggcg ggttcgactc gccgacagtc gcatactccg tgttagtggt  2640
ggctaaagtg gaaaggggaa agtccaagaa gctcaagtcc gtcaaggagt gctctcggat   2700
caccattatg gaacggtcct cattcgagaa gaatcccatt gacttcctag aggcgaaggg  2760
ctacaaagag gtcaaaaagg acctaattat taagctcccc aagtattcac tcttcgaact  2820
tgaaaatggt cgtaagcgga tgttggcaag cgctggagag cttcagaagg ggaacgagct  2880
tgcactgcct tccaagtacg tgaacttcct gtacctcgcc tctcattacg agagttgaa   2940
gggctcaccg gaggacaacg agcagaagca gttgttcgtg gagcagcaca agcactacct  3000
cgacgagatc attgagcaga taagtgagtt cagcaaacgg gtgatccttg ccgacgctaa  3060
cctggacaag gtgctgagcg cctacaacaa gcacagagac aagccgatcc gagagcaagc  3120
ggagaacatc atacacctgt tcaccctcac gaacctcggg gctcccgcag ccttcaaata   3180
ttttgacacg accatcgacc gtaaacgcta cactagcacg aaggaggtgc tggacgctac  3240
ccttatccac cagtccatca ccggcctgta cgagacgaga atcgacttgt cgcagctcgg  3300
tggtgac                                                            3307

SEQ ID NO: 11          moltype = DNA  length = 4101
FEATURE                Location/Qualifiers
```

| misc_feature | 1..4101 |
| | note = Cas9 polynucleotide |
| source | 1..4101 |
| | mol_type = other DNA |
| | organism = synthetic construct |

SEQUENCE: 11

```
gacaaaaaat actcaattgg tctggcaatt gggaccaaca gtgtcggatg ggccgtgatt    60
accgacgagt acaaggtgcc gtccaaaaaa ttcaaggtgc ttgggaacac cgaccgccac   120
tcgatcaaga aaaacctaat cggtgcgttg cttttcgaca gtgggagac cgccgaggca   180
acacgcttaa aacgcacagc taggaggaga tatacacggc gcaagaaccg aatatgctac   240
ttacaggaga tattctccaa tgagatggcg aaggtggacg actctttctt ccatcggctt   300
gaggaatcct tcctggtcga ggaggacaag aagcacgagc gacacccgat attcgggaac   360
atcgttgatg aggtggcgta ccacgagaag tacccaacga tataccactt acgcaagaag   420
ctcgtggact ctacggacaa ggccgacttg cgccttatct acttggcact ggccacatg   480
attaagttcc gaggccactt ccttatcgag ggtgacctga ccccgataa ctccgacgtg   540
gacaagctct tcatccaact cgtccagaca tacaaccagc tattcgagga gaatcctatc   600
aacgcctctg ggtggacgc taaagctatc ctctcagccc gcctgtcaaa gtcgaggagg   660
ttggagaacc taatcgccca gcttccaggc gagaagaaaa atgggctgtt cggaaacctt   720
atcgcactct cactgggcct aaccccgaac ttcaagtcca acttcgacct ggcagaggac   780
gcgaaattgc agttgtcgaa agacacctat gacgatgacc tggacaacct gttggccag   840
ataggggacc agtacgccga cctgttccta gcggccaaga acctgtccga cgccatcttg   900
ctgtcgggata tactgcgggt gaacaccgag atcactaaag cacctctctc cgccagcatg   960
attaagcgtt acgacgagca ccaccaagat ttgaccctgc taaaggcact tgtacgcag  1020
cagcttcccg agaagtacaa ggagatcttt ttcgaccaaa gcaagaacgg ctacgccggg  1080
tacatcgacg gaggtgccag ccaggaggag ttctacaagt tcattaagcc catcctggag  1140
aagatggacg gactgagga actacttgtg aagctgaacc gggaagactt actacggaag  1200
cagcgtacct tcgacaacgg ttctatccca catcagatcc atcttgggga gttgcacgcg  1260
atcctgcgac gccaggagga cttttacccc ttcctgaaag acaaccgcga gaaaatcgag  1320
aagatactga ccttcagaat accttactac gtcggacccc ttgcgcgagg caactcaaga  1380
ttcgcgtgga tgaccaggaa atcagaggag accatcacac cctggaattt cgaggaggtg  1440
gttgacaagg gtgcctccgc ccagtccttt atcgaacgaa tgaccaactt cgacaagaac  1500
ttgcccaacg agaaggtgct ccccaaaaca agcctcctct acgaatattt cacagtgtac  1560
aacgagctta ctaaagttaa gtatgttact gagggcatga ggaaacccgc cttcctgtca  1620
ggcgagcaga agaaagctat tgtggacctc cttttcaaga ccaaccggaa ggtgacagtg  1680
aagcagctca aggaggacta cttcaagaag atagagtgct tcgacagcgt gggagatcagc  1740
ggggtggagg acagattcaa tgcctctctc ggaacatacc acgacttgct taagatcatc  1800
aaggacaagg acttcctcga caacgaggaa acgaggata ttctggagga tattgttctg  1860
actcttaccc tgttcgagga ccgggagatg atcgaggagc gtctcaagac ctacgcccac  1920
ctgttcgacg acaaagttat gaagcagctc aagcgtcgga gatataccgg atggggccgt  1980
ctgtctcgga agctcatcaa cgggatcagg gacaagcagt cagggaagc gatcttagac  2040
ttccttaagt ctgacggctt cgccaacagg aacttcatgc agttgatcca cgacgacagc  2100
cttaccttca aggaggacat ccagaaggcc caagtgagtg gccagggtga cagcctccac  2160
gagcatattg ctaatcttgc gggttcccca gcgattaaaa aggatgcatct tcaaaccgtt  2220
aaggtggtgg acgagcttgt caaggtgatg gggcgacaca gcccgagaa catcgtgatc  2280
gagatggcca gggagaacca gaccacccag aagggggcaga agaatagccg agaacgcatg  2340
aagcgcatcg aggaggggat taaggagcta gggagccaga tcctcaagga catccccgtc  2400
gagaacaccc agctccagaa cgagaagcta tacctctact acttgcaaaa cggggagggat  2460
atgtacgtgg atcaggagtt ggacattaac cgcctaagcg actacgacgt agatcacatc  2520
gtgcctcagt cattcctcaa agacgacagc attgacaaca agtcttgac ccgatccgac  2580
aagaaccgag aaaatccga caatgtgccc tcagaggagg tcgtcaagaa atgaagaac  2640
tattggaggc agctacttaa cgccaaactc ataacccagc ggaagttcga caacctgaca  2700
aaggctgagc ggggtgggct cagcgagctt gacaaggctg gcttcatcaa gcggcagttg  2760
gtggagacaa gacagataac gaagcacgtg gctcagatcc tggactctcg catgaacacg  2820
aagtacgacg agaacgacaa attgatccgc gaggtcaagg ttattacgct caagagcaaa  2880
cttgtcagcg atttccgcaa ggacttccag ttctacaagg tgagggagat taacaactac  2940
caccatgcac atgatgccta cttgaacgca gtggtgggaa ccgcgcttat taaaagtac  3000
cctaagttgg agtcagagtt cgtttatggg gactacaagg tgtacgacgt ccggaagatg  3060
attgcaaagt ctgaacagga aatcgggaag gccaccgcca atatttctt ctacagtaac  3120
attatgaatt ttttttaagac tgaaattact ctcgcaaacg gcgagatcag gaagcgtccc  3180
ctcatcgaga caaacgggga gaccgggag atagtctgag acaaggggcg ggacttcgct  3240
acggtgagga aggtgctctc gatgccacaa gtgaacatcg tcaaaaagac agaggtgcag  3300
accggtggct tctcaaagga gtcaatcctg ccaaaacgta acagcgacaa gctcatcgcc  3360
cgcaagaaag actgggaccc taagaagtat ggtgggttcg actcaccgac ggtcgcatac  3420
tccgttctgg tcgtggcaaa ggtggaaaag ggcaagtcca aaaactgaa atccgtgaag  3480
gagttgcttg gcattaccat catggaacgc agcagcttcg agaagaaccc cattgacttc  3540
ctggaggcta aagggtacaa ggaggtcaag aaagatttaa ttattaagct acctaagtac  3600
agcttgttcg agctggagaa cggccgaaaa cgaatgctcg catccgccgg gaacttcaa  3660
aagggcaacg agctcgcgct gccctccaag tacgtgaact tcctgtactt ggcatcccac  3720
tacgagaaac tcaagggtag cccagaggac aacgagcaga gcagctatt cggtggagcg  3780
cacaagcact acctcgacga gataatcgag cagatcagtg agttcagtaa gcgggtgata  3840
ctcgcggacg ccaacttgga caaggtgctt agtgcctaca caagcaccg tgacaagccc  3900
atccgagaac aggctgagaa catcatccac cttttcactc tgacaaacct cggtgctccc  3960
gccgccttca aatacttcga cactaccatc gacaggaagc gctacacatc tacgaaggaa  4020
gttcttgacg ctacgcttat tcatcagtct atcacagggc tgtacgagac aaggatcgac  4080
cttagccaac tcggcgggga t                                            4101
```

| SEQ ID NO: 12 | moltype = DNA length = 5499 |
| FEATURE | Location/Qualifiers |
| misc_feature | 1..5499 |

```
                        note = base editor
source                  1..5499
                        mol_type = other DNA
                        organism = synthetic construct
SEQUENCE: 12
ggttcgaaga agagaagaat taaacaagat tcttcggaga caggccccgt tgccgttgac    60
cccacgctgc ggaggcggat tgagccccac gagttcgagg ttttcttcga cccaagggag   120
ctgaggaaag agacatgcct cctctacgag atcaactggg gcgggcggca cagcatctgg   180
aggcatacct cgcagaacac caacaagcat gtggaggtta atttcattga gaagttcaca   240
actgagaggt acttctgccc caacactagg tgctcgatta cttggttcct gagctggagc   300
ccatgcgggg agtgcagccg cgcgatcaca gagttcctgt cccgctaccc ccacgtgacg   360
ctcttcatct acattgcccg gctgtaccat catgccgatc cacggaatag gcaggggctg   420
cgggatctga tcagcagcgg ggtgacgatt cagatcatga ccgagcagga gtcggggtac   480
tgctggcgga acttcgtgaa ttactccccc tccaacgagg cgcactggcc caggtatcca   540
catctctggg tccggctgta tgtgctggag ctgtactgca tcatcctcgg cctgccccca   600
tgcctcaaca tcctcaggcg gaagcagccc cagctgacgt tcttcacgat cgctctgcaa   660
tcgtgccact accagaggct gccccctcat atcctctggg ctaccggcct caagtcggga   720
ggctcttccg gcggggagca cggctcggaa acgccaggta cctcggagtc ggctacacca   780
gagagttccg gcgggtccag cgggggcagc gacaagaagt acagcatcgg gctggcgatc   840
gggaccaact ccgtcggctg ggctgtgatt accgacgagt caaggtgcc atccaagaag   900
ttcaaggtcc tcggcaacac tgaccggcac agcattaaga agaacctgat tggggcgctg   960
ctgttcgatt cggggggagac tgcggaggcg accaggctga agcggactgc ggcgcggagg  1020
tacaccagga ggaagaatcg gatctgctac ctccaggaga ttttctcgaa tgagatggcc  1080
aaggtggacg attccttctt ccatcgcctg gaggagtcgt tcctcgttga ggaggacaag  1140
aagcatgaga ggcatcccat tttcgggaat atcgttgacg aggtggctta ccatgagaag  1200
taccgaccac tctaccattc gcggaagaag ctcgtcgatt cgaccgataa ggccgacctg  1260
cggctgatct acctggccct cgcgcacatg attaagttcc ggggccattt cctcatcgag  1320
ggcgacctca acccggacaa ctcggacgtg ataagctct tcattcagct cgtgcagaca  1380
tacaaccagc tcttcgagga gaatcccatt aacgcctcgg gggtcgacgc taaggctatt  1440
ctctcggctc ggctgtcgaa gtcgcgccgg ctggagaatc tcattgccca gctcccaggc  1500
gagaagaaga acggcctctt cggcaacctg attgccctgt cgctggggct cacaccgaat  1560
ttcaagtcga acttcgacct cgccgaggac gctaagctcc agctcagcaa ggatacttac  1620
gatgatgacc tcgataacct gctcgcccag attggggatc agtacgcgga tctgttcctc  1680
gcggccaaga atctcagcga tgctattctc cgtcggaca ttctccgcgt caacacagg  1740
attactaagg cccccactgt cggcgagcat gattaagagg acgatgagca tcatcaggac  1800
ctgacactgc tcaaggcgct ggtccggcag cagctccccg agaagtacaa ggagattttc  1860
ttcgatcagt caaagaatgg gtacgcgggc tacattgatg gcggcgcgtc ccaggaggag  1920
ttctacaagt tcattaagcc catcctggag aagatggacg ggaccgagga gctgctggtg  1980
aagctcaatc ggggaggacct gctccggaag cagcgcacat tcgacaatgg ctcgattcct  2040
caccagattc acctgggcga gctgcacgcc attctccgca ggcaggagga cttctacccg  2100
ttcctcaagg acaaccgcga gaagatcgag aagatcctga ccttccggat tccatactac  2160
gtggggccgc tcgcgcgggg gaactcccgg ttcgcgtgga tgactcgcaa gtccgaagaa  2220
acgattacac cgtggaattt cgaggaggtc gtcgacaagg gcgtagtgc gcagtcattc  2280
attgagagga tgaccaatttt cgataagaac ctgcctaacg agaaggtgct gccgaagcat  2340
tcgctgctct acgagtactt caccgtttac aatgagctga ccaaggtgaa gtatgtgact  2400
gagggcatga ggaagccagc gttcctgagc ggcgagcaga agaaggctat cgtggacctg  2460
ctcttcaaga ctaaccggaa ggtgactgtg aagcagctca agaggacta cttcaagaag  2520
attgagtgct tcgattccgt tgagattagc ggggtggagg atcggttcaa tgcttcgctc  2580
gggacatacc acgatctcct gaagatcatt aaggataagg acttcctcga caacgaggag  2640
aacgaggaca ttctcgaaga tattgtcctg accctcaccc tcttgaggga tcgggagatg  2700
atcgaggaga ggctcaagac atacgctcat ctgttcgatg ataaggtcat gaagcagctg  2760
aagcgcaggc ggtacacagg gtgggggcgg ctgagccgga agctgatcaa cgggattcgg  2820
gataagcagt ccgggaagac aatttctcgac ttcctcaagt ccgacgggtt cgctaaccgg  2880
aacttcatgc agctcattca tgatgactcg ctgacattca aggaggatat tcagaaggcg  2940
caggtttcgg ggcagggcga ctcgctccac gagcatattg cgaatctggc gggctcccc  3000
gcgattaaga agggcattct gcaaaccgtc aaggtggttg atgagctgtt caaggtcatg  3060
gggcggcata agcagagaa tattgtcatc gagatggcgc gggagaatca gaccacacag  3120
aagggcaga gaactcacg ggagcggatg aagcgcatcg aggagggcat caaggagctg  3180
gggtcgcaga tcctgaagga gcatcccgtg gagaacactc agctgcaaaa tgagaagctg  3240
tacctctact acctccagaa cgggagggac atgtatgtgg atcaggagct ggatattaat  3300
aggctgagcg attacgatgt cgaccacatt gtcccacagt cgttcctgaa ggacgacagc  3360
attgacaaca aggtgctgac ccgctcggat aagaacaggg gcaagagcga taatgttcca  3420
agcgaggagg ttgtgaagaa gatgaagaac tactggcggc agctcctgaa cgcgaagctc  3480
atcacacagc ggaagttcga caacctcacc aaggctgagc cctgggagtc gagcggtctg  3540
gacaaggcgg ggttcattaa gaggcagctg gtcgagacac ggcagattac aaagcatgtt  3600
gcgcagattc tcgattcccg gatgaacacc aagtacgatg agaacgataa gctgattcgg  3660
gaggtcaagg taattaccct gaagtccaag ctggtgtccg acttcaggaa ggacttccag  3720
ttctacaagg ttcgggagat caacaactac caccacgcgc atgatgccta cctcaacgcg  3780
gtcgtgggga ccgctctcat caagaagtac ccaaagctgg agtcagagtt cgtctacggg  3840
gattacaagg tttacgacgt gcggaagatg atcgctaaga gcgagcagga gattggcaag  3900
gctaccgcta agtacttctt ctactccaac atcatgaact tcttcaagac agagattacc  3960
ctcgcgaatg gcgagatccg gaagaggccc tcatcgaga caaatgggga gacagggag  4020
attgtctggg ataaggggcg ggatttcgcg ccgtccggaa aggtcctgtc gatgcccag  4080
gttaatattg tcaagaagac tgaggtccga ctggccggtt ctcaaagga gtcgattctc  4140
ccaaagagga actccgataa gctcattgct cggaagaagg attgggaccc caagaagtac  4200
ggggatttcg actcccccac tgttgcttac tctgttctgg ttgttgctaa ggtgagaag  4260
gggagtcga agagctgaa gagcgtgaag gagctgctcg gattacaat tatggagagg  4320
tcatccttcg agaagaatcc catcgacttc ctggaggcca ggggctacaa ggaggtgaag  4380
aaggacctga ttattaagct gcccaagtac tcgctcttcg agctggagaa tgggcggaag  4440
```

```
cggatgctgg cgtccgcggg ggagctgcaa aaggggaacg agctggcgct cccctccaag 4500
tatgtgaact tcctctacct ggcgtcgcac tacgagaagc tgaaggggtc cccagaggat 4560
aatgagcaga agcagctctt cgtcgagcag cataagcact acctggacga gattatcgag 4620
cagattagcg agttctcgaa gcgggtcatc ctcgcggatg cgaacctgga taaggtgctc 4680
agcgcctaca ataagcaccg ggacaagccg attcgggagg aggcggagaa tattattcac 4740
ctcttcacac tcaccaacct cggggcacca gctgcgttca agtacttcga cactactatc 4800
gaccggaagc ggtacacctc gacgaaggag gtgctcgacg ccaccctcat tcaccagtcg 4860
atcacaggcc tgtacgagac acggattgac ctgtcccagc tcgggggcga cagcggcggg 4920
tcgggcgggt cgggcggctc aaccaacctg tcggatatta ttgagaagga gacaggcaag 4980
cagctggtta ttcaggagtc gatcctgatg ctccccggagg aggtggagga ggtcatcggg 5040
aacaagccag agtcggatat tctcgtgcac accgcgtacg acgagtcgac agacgagaac 5100
gttatgctgc tcacatcgga cgcgccagag tacaagccct gggcgctggt aattcaggat 5160
tcaaatggcg agaacaagat caagatgctg tccggggggca gcggcgggtc cggggggctcg 5220
accaacctct ccgatataat tgagaaggaa accggcaagc agctcgttat tcaggagtcg 5280
attctgatgc tccccgagga ggtcgaggag gtaattggga ataagccgga gtcggatatt 5340
ctggtgcaca ctgcttacga tgagagcaca gacgagaatg ttatgctgct gaccagcgac 5400
gctcctgagt acaagccgtg ggcgctggtt attcaggatt ccaatgggga gaacaagatt 5460
aagatgctgg gatctaagaa gagaagaatt aaacaagat 5499

SEQ ID NO: 13          moltype = DNA   length = 5499
FEATURE                Location/Qualifiers
misc_feature           1..5499
                       note = base editor
source                 1..5499
                       mol_type = other DNA
                       organism = synthetic construct
SEQUENCE: 13
ggttcgaaga agagaagaat taaacaagat tcttctgaga ctggcccgt tgctgttgac 60
cccacgctcc gccgccgcat tgagcccac gagttcgagg ttttcttcga cccacgcgag 120
ctgcggaagg agacatgcct cctgtacgag attaattggg gagggcggca ttcgatttgg 180
cggcacacct cgcagaatac aaacaagcac gttgaggtga acttcatcga gaagttcaca 240
accgagcggt acttctgccc caatacgcgg tgctcaatta cttggttcct gtcctggagc 300
ccctgcgggg agtgctccag ggcgatcaca gagttcctgt cccggtatcc acacgtcacc 360
ctcttcatct acatcgatcg gctctaccac catgctgatc cgcaaccg ccaggggctc 420
cgcgacctca tttcgtcaag cgtgaccatc cagatcatga cggagcagga gagcggctac 480
tgctggcgca atttcgtcaa ctactcaccc tccaacgagg ctcactgcc tcggtatccc 540
cacctctggg tgcggctcta cgtgctggag ctgtactgca ttattctggg cctcccacca 600
tgcctcaata tcctccgccg gaagcagcca cagctcacct tcttcaccat tgctctccag 660
tcctgccatt accagcggct ccctcccaca atcctctggc ccactggcct caagtccggc 720
gggtcgagcg gcgggtcgag cggctcagag acacccggta cctcggagtc ggccacacca 780
gagtcgtccg gcggcagcag cggcggctca gacaagaagt actccattgg cctggcgatt 840
gggacaaact cggtggggtg ggccgtgatt acggatgagt acaaggttcc aagcaagaag 900
ttcaaggtcc tcgggaacac agatctgcat tcgattaaga gaatctcat tggggcgctc 960
ctcttcgact cggggggagac agcggaggct accaggctca agcggacagc caggcggcgg 1020
tacacaaggc ggaagaatcg catctgctac ctccaggaga ttttctcgaa tgagatggcg 1080
aaggtggacg acagcttctt ccatcggctg gaggagtcct tcctggtgga ggaggataag 1140
aagcacgaga ggcatccaat tttcgggaac atcgtggaca aggttgctga ccatgagaag 1200
taccctacaa tctaccatct gcggaagaag ctggttgact ccacagacaa ggcggacctg 1260
aggctgatct acctcgctct ggcccacatg attaagttcc gcgggcattt cctgatcgag 1320
ggggacctga atcccgacaa ttcggatgtg gacaagctct catccagct ggtgcagacc 1380
tacaaccagc tgttcgagga gaatcccatc aatgcgtcga cgtttgacgc taaggccatt 1440
ctgtccgcta ggctgtcgaa gagcaggagg ctggagaacc tgatcgccca gctgccaggc 1500
gagaagaaga atgggctctt cgggaatctg attgcgctct ccctggggct gacaccgaac 1560
ttcaagagca atttcgatct ggctgaggac gcgaagctcc agctctcgaa ggacacttac 1620
gacgatgacc tcgataacct cctcgcgcag atcggggacc agtacgctga tctcttcctc 1680
gccgctaaga acctctcgga tgctatcctg ctctccgaca ttctccgggt taataccgag 1740
attacaaagg ccccactgtc ggcgtccatg atcaagcggt acgatgagca tcatcaggat 1800
ctcaccctgc tcaaggccct cgtgcggcag cagctgcccg agaagtacaa ggagattttc 1860
ttcgaccaga gcaagaatgg gtacgctggc tacattgacg gcggggccga cagggaggag 1920
ttctacaagt tcatcaagcc aatcctggag aagatggatg gacagagca gctgctggtg 1980
aagctcaacc gggaggatct gctcaggaag cagcggacgt tcgacaacgg gtcgattccc 2040
catcagatcc acctggggga gctgcacgcg atcctgcgcc ggcaggagga tttctaccct 2100
ttcctgaagg ataatcggga aagatcgag aagattctca ccttccggat tcctactac 2160
gtcgggccac tcgcgcgggg caatagcagg ttcgcctgga tgacacggaa gagcgaggag 2220
acaatcaccc cctggaactt cgaggaggtt gtcgacaagg gggcgtccgc ccagtcattc 2280
attgagcgga tgaccaattt cgacaagaat ctgccaaatg agaaggttct cccaaagcat 2340
agcctcctct acgagtactt cactgtttac aacgagctga ccaaggtgaa gtatgtgacc 2400
gagggcatgc ggaagcccgc gttcctgtcc ggcgagcaga agaaggccat tgtggacctc 2460
ctgttcaaga ccaatcgcaa ggtcacagtc aagcagctca aggaggatta cttcaagaag 2520
atcgagtgct tcgactcggt tgagattagc ggggtggagg atcggttcaa cgcgagcctc 2580
ggcacttacc acgacctcct gaagatcatc aaggataagg acttcctcga caacgaggag 2640
aacgaggata ttctggagga catcgtgctc accctgacgc tgttcgagga tcgggagatg 2700
atcgaggagc gcctgaagac ctacgctcat ctcttcgatg ataaggtcat gaagcagctg 2760
aagagggggg gtacacggg gtgggggccgc ctgagcagga agctcattaa cgggatcagg 2820
gacaagcaga gcggcaagac catcctggac ttcctcaaga gcgatggctt cgccaaccgg 2880
aatttcatgc agctcatcca cgacgactcc ctcaccttca aggaggacat tcagaaggct 2940
caggtcagcg gccagggcga ctcgctgcat gagcacatcg ctaacctggc gggcagccca 3000
gccatcaaga aagggcatcct ccagacagtg aaggtcgtgg atgagctggt gaaggtcatg 3060
ggccggcata agcccgagaa tattgtgatt gagatggcgc gggagaatca gaccactcag 3120
```

```
aagggccaga agaactcgcg ggagcgcatg aagaggatcg aggagggat taaggagctg    3180
ggcagccaga ttctcaagga gcaccccgtg gagaataccc agctccagaa cgagaagctg    3240
tacctctact acctccagaa tgggcgggac atgtatgttg atcaggagct ggacatcaat    3300
cgcctctcgg attacgacgt ggaccacatc gtgcccaga gcttcctgaa ggatgatagc    3360
atcgacaata aggtcctgac ccgctccgac aagaatccga caagagcga caacgtgccg    3420
agcgaggagg tcgtgaagaa gatgaagaac tactggcggc agctgctgaa cgcgaagctc    3480
attacacagc ggaagttcga taacctgacg aaggcggaga ggggcggcct ctccgagctg    3540
gacaaggcgg gcttcattaa gaggcagctc gtggagactc gccagatcac caagcacgtg    3600
gctcagatcc tcgatagccg gatgaatacg aagtacgatg agaatgacaa gctcatccgg    3660
gaggtgaagg taatcaccct gaagtcaaag ctcgttagcg atttccggaa ggacttccag    3720
ttctacaagg tgcgggagat taacaactac catcatgcgc acgatgcgta cctcaatgcg    3780
gtggtgggca cagccctgat taagaagtac cccaagctgg agagcgagtt cgtctacggg    3840
gactacaagg tgtacgatgt tcggaagatg atcgccaaga gcgagcagga gattgggaag    3900
gccaccgcta agtacttctt ctactcgaat attatgaatt tcttcaagac cgagatccaa    3960
ctcgctaatg gggagattcg gaagcggccc ctcatcgaga ctaacgggga gactggcgag    4020
attgtgtggg acaaggggcg cgacttcgct accgtgcgca aggtcctctc gatgcccag    4080
gttaatattg ttaagaagac agaggtgcag acgggcgggt tctccaagga gtctatcctg    4140
ccgaagcgga actcggacaa gctgatcgcc cgcaagaagg attgggaccc caagaagtac    4200
ggggattcg atagcccaac cgtgcgttac agcgtcctgg tggtcgccaa ggttgagaag    4260
ggggaagtcga agaagctcaa gagcgttaag gagctgctgg gcatcaccat catggagcgg    4320
tccagcttcg agaagaatcc tatcgacttc ctggaggcta aggggtacaa ggaggtcaag    4380
aaggacctga tcattaagct gcccaagtac tctctgttcg agctgagaga cggaggaag    4440
cggatgctgg cgtctgctgg cgagctacag aagggcaatg agctggcgct cccctcgaag    4500
tatgtcaact tcctctacct ggcttccat tacgagaagc tgaagggctc gcccgaggat    4560
aatgagcaga agcagctctt cgtggagcag cacaagcact acctcgacga gatcattgag    4620
cagatttcgg agttctcgaa gcgggtcatt ctcgcggacg cgaacctgca caagttcctc    4680
tcggcgtaca acaagcaccg ggacaagccc atccgggagc aggccgagaa cattatccac    4740
ctcttcacac tgaccaacct cggcgctccc gccgcgttca agtacttcga caccaccatt    4800
gaccgcaaga gatacacatc caccaaggag gtgctggacg cgaccctcat ccaccagagc    4860
atcacaggcc tctacgagac acggatcgac ctctcggaca ctcggggcga tagcggcggg    4920
tctgggggct ccggcgggtc gacaaacctc agcgatatta tcgagaagga gactgggaag    4980
cagctggtaa ttcaggagtc aatcctcatg ctcccagagg aggtgggag ggttatcggg    5040
aacaagccgg agtcggacat tctcgtgcac acggcgtacg atgagtccac tgacgagaat    5100
gtgatgctcc tcacctccga tgcgcccgag tacaagcgct gggcgctcgt gattcaggac    5160
tccaacggcg agaataagat caagatgctc agcgggggct ccggcggcag cggcggctcg    5220
acaaacctga gcgatattat tgagaaggag acagggaagc agctggtaat ccaggagagc    5280
attctcatgc tccccgagga ggtcgaggag gtaattggga ataagcccga gagcgatatt    5340
ctcgtgcata cagcgtacga tgagtcgaca gatgagaacg tgatgctcct cacatccgac    5400
gctccagagt acaagccgtg ggcgctcgtt attcaggatt ccaatgggga gaacaagatt    5460
aagatgctcg gatctaagaa gagaagaatt aaacaagat                        5499

SEQ ID NO: 14          moltype = DNA  length = 5499
FEATURE                Location/Qualifiers
misc_feature           1..5499
                       note = base editor
source                 1..5499
                       mol_type = other DNA
                       organism = synthetic construct
SEQUENCE: 14
ggttcgaaga agagaagaat taaacaagat agcagcgaga caggcccagt tgccgtggac      60
cctactctga ggaggcgcat tgagcccctg gagttcgagg tgttcttcga ccccccgcag     120
ctaaggaagg agacatgcct cctctacaga atcaactggg gcgggcggca ttcgatctgc     180
cggcatacaa gccagaacac caataagcac gtggaggtca acttcatcga gaagttcacc     240
accgagaggt acttctgccc aaacacgcgg tgctctatca catggttcct gtcgtggtcg     300
ccatgcgggg agtgctcgcg ggcgattact gagttcctgt cgcgctaccc acacgtcacc     360
ctgttcatct acattgcgcg cctgtaccat catgctgacc ccaggaatag gcaggggctc     420
cgggacctga tttcctctgg ggtcacaatt cagatcatga ccgagcagga gtcggggtac     480
tgctggcgga acttcgttaa ctacagccca tccaacgagg cgcactggcc acggtatcca     540
cacctgtggg ttcggctcta cgtcctggag ctgtactgca tcatcctcgg gctgccacca     600
tgcctgaaca ttctgcggcg gaagcgaccg cagctcacgt tcttcactat tgctctccag     660
agctgccact accagaggct gccacccac attctgtggg cgaccgggct gaagtccggc     720
ggctccagcg gcgggtcgtc aggctcagag acaccaggta cctccgagtc agccaccccc     780
gagtcgtcgc gcggcagctc gggcggctcg gacaagaagt actcgatcgg cctggcgatt     840
ggcacaaaca gcgtgggggtg ggctgtgatc actgatgagt acaaggtgcc atcgaagaag     900
ttcaaggtgc tggggaatac agaccggcat tcgatcaaga agaatctcat tggcgctctc     960
ctcttcgatt ccggcgagac tgctgaggcg acccgcctga gcgcaccgc ccggcggcgc    1020
tacactcggc ggaagaatag gatttgctac ctccaggaga ttttctcgaa tgagatggcc    1080
aaggtggatg acagcttctt ccaccgcctg gaggagtcgt tcctggtcga ggaggacaag    1140
aagcatgagc ggcaccccat cttcgggaat atcgttgatg aggtcgccta ccacgagaag    1200
taccccacta tctaccatct ccgcaagaag ctcgtggaca gcacagataa ggccgacctc    1260
cgcctgatct acctcgccct cgcgcacatg attaagttcc gggggcactt cctcattgag    1320
ggggatctga atcccgataa ctccgacgtg acaagctgt tcatccagct ggtgcagaca    1380
tacaaccagc tgttcgagga gaatcccatc aacgcgagcg gcgtggacgc taaggccatt    1440
ctgtcggcta ggctctccaa gtcgaggcgg ctggaaaacc tgattgcgca gctccccgga    1500
gagaagaaga acgggctgtt cgggaatctc atcgccctct cctcggcct cacaccaaac    1560
ttcaagagca atttcgacct ggctgaggac gctaagctgc aactctcaaa ggatacatac    1620
gatgacgacc tggacaatct cctggctcag atcggcgacc agtacgctga cctgttcctc    1680
gcggccaaga atctgtcgga cgcgattctc ctcagcgaca tcctgcgcgt caataccgag    1740
attacgaagg ctccactgtc tgcgtcaatg attaagcggt acgatgagca tcaccaggat    1800
```

-continued

```
ctgaccctcc tgaaggcgct cgtgcggcag cagctgcccg agaagtacaa ggagattttc   1860
ttcgatcaga gcaagaatgg ctacgccggc tacatcgacg ggggcgcgag ccaggaggag   1920
ttctacaagt tcatcaagcc catcctggag aagatggacg gcaccgagga gctactcgtg   1980
aagctcaatc gggaggatct cctccggaag cagcggacat tcgataacgg gtctatccca   2040
caccagatcc acctcggcga gctgcatgcg attctgcggc ggcaggagga tttctaccct   2100
ttcctgaagg acaaccggga gaagatcgag aagatcctca cattccggat tccatactac   2160
gtcggccccc tggcgagggg caatagccgg ttcgcgtgga tgacaaggaa gtccgaggag   2220
actattaccc cgtggaattt cgaggaggtg gttgacaagg gcgcttccgc gcagagcttc   2280
attgagcgga tgacaaactt cgacaagaat ctccccaacg agaaggtcct gccgaagcat   2340
agcctcctgt acgagtactt caccgtctac aatgagctaa ctaaggtcaa gtatgtgaca   2400
gagggcatga ggaagccagc cttcctctca ggcgagcaga agaggccat tgtggacctc    2460
ctgttcaaga caaaccgcaa ggtgacagtg aagcagctga aggaggatta cttcaagaag   2520
attgagtgct cgactcagt ggagatttca ggcgtggagg atcggttcaa cgcgagcctg    2580
gggacttacc acgacctgct gaagattatt aaggacaagg acttcctgga taacgaggag   2640
aatgaggaca tcctggagga tattgtgctc accctcaccc tgttcgagga cagggagatg   2700
attgaggaga ggctcaagac ctacgcgcac ctgttcgatg acaaggtcat gaagcagctg   2760
aagaggcggc gctacactgg gtggggccgc ctgtcgcgga agctgatcaa cggcattcgg   2820
gataagcagt ccgggaagac cattctggat ttcctgaagt cggacggctt cgccaacagg   2880
aatttcatgc agctgatcca cgacgactcc ctcaccttca aggaggacat tcagaaggcc   2940
caggttagcg gccaggggga ctcactccac gagcatattg ccaatctggc cggctctcca   3000
gctatcaaga agggcatcct gcaaacagtt aaggttgttg acgagctggt taaggtcatg   3060
gggcgcata agcccgagaa cattgtcatc gagatggctc gggagaacca gacaactcag    3120
aagggccaga agaactccag ggagcgcatg aagcggattg aggagggcat taaggagctg   3180
gggtcccaga tcctcaagga gcaccctgtc gagaacactc agctgcaaaa cgagaagctc   3240
tacctgtact acctccagaa cgggcgggat atgtatgtgg atcaggagct ggacatcaac   3300
aggctctccg actacgacgt ggatcacatt gtcccacagt cttcctcaa ggatgattcc    3360
atcgacaaca aggtgctgac gcgcagcgac aagaataggg ggaagtcgga caacgttccg   3420
agcgaggagg tcgtgaagaa gatgaagaat tactggaggc agctcctgaa tgcgaagctg   3480
atcactcaga ggaagttcga caatctgaca aaggcggaga ggggcgggct ctcggagctg   3540
gataaggcgg gcttcatcaa gcggcagctc gttgaaaccc ggcagatcac caagcatgtc   3600
gcccagatcc tcgatagccg catgaacacc aagtacgatg agaacgacaa gctcattcgg   3660
gaggttaagg tcattacgct gaagtccaag ctcgtcagcg acttcaggaa ggatttccag   3720
ttctacaagg ttcgggagat taacaactac caccacgcgc atgatgcgta cctgaacgct   3780
gttgtcggca ctgctctcat caagaagtac ccaaagctgg agtccgagtt cgtctacggg   3840
gactacaagg tctacgatgt ccggaagatg atcgccaagt cggagcagga gatcgggaag   3900
gctactgcga agtacttctt ctacagcaac attatgaatt tcttcaagac ggagattacg   3960
ctggcgaacg gggagattag gaagaggccc ctcattgaga ctaatgggga gacaggcgag   4020
attgtttggg acaaggggcc gacttcgcg actgtgcgga aggtcctgtc catgccacag    4080
gtgaatattg ttaagaagac agaggtgcag actgggggct tctcgaagga gagcattctc   4140
ccaaagcgga acagcgataa gctcatcgcg cgcaagaagg attgggaccc taagaagtac   4200
ggcggcttcg attctcccac tgtggcctac tccgttctcg tggttgccaa ggttgagaag   4260
gggaagtcga agaagctgaa gtcggtcaag gagctgctcg ggattacaat catggagcgg   4320
agcagcttcg agaagaaccc tattgatttc ctggaggcca agggctacaa ggagggttaag  4380
aaggatctca ttatcaagct ccctaagtac tctctgttcg agctggagaa tggccggaag   4440
aggatgctgg cctcggctgg cgagctcaga aaggggaatg agctgccct cccgtcgaag    4500
tatgtgaatt tcctgtacct cgcgtcgcac tacgagaagc tcaagggcag cccggaggat   4560
aatgagcaga agcagctctt cgtggagcag cataagcacc acctggacga gatcattgag   4620
cagatcagcg agttctcgaa gcgggttatt ctggctgatg ctaacctgga caaggttctg   4680
agcgcctaca ataagcatcg cgacaagccg attcgcgagc aggcggagaa tattatccac   4740
ctgttcaccc tcactaacct cggggctccc gcggccttca gtacttcga taccacaata    4800
gataggaagc ggtacacctc gacgaaggag gtcctcgacg ccacactcat ccatcagtcg   4860
attacaggcc tgtacgagac acggattgac ctctcgcagc tgggcggcga tagcggcggg   4920
tccggcggga gcgggggctc gaccaatctg tcggacatca ttgagaagga aaccgggaag   4980
cagctggtta tccaggagtc catcctcatg ctcccggagg aggttgagga ggtaatcggg   5040
aataagccag agtctgacat cctcgtccac acagcgtacg atgagtcgac agacgagaat   5100
gtcatgctcc tcactagcga tgcgcccgag tacaagcctt gggcgctggt cattcaggat   5160
agcaacggcg agaataagat taagatgctg agcggcgggt cgggaggctc tggcgggtcc   5220
acgaacctgt ctgacatcat cgagaaggag acaggcaagc agctcgtgat ccaggagagc   5280
attctgatgc tgccggagga ggtggaggag gtaattggca ataagcccga gtctgatatt   5340
ctggtgcaca cagcgtacga cgagagcacg gatgagaatg tcatgctcct gacatccgat   5400
gctcctgagt acaagccgtg ggcgctcgtg attcaggact caaatgggga gaacaagatt   5460
aagatgctcg gatctaagaa gagaagaatt aaacaagat                          5499
```

| SEQ ID NO: 15 | moltype = DNA length = 5499 |
|---|---|
| FEATURE | Location/Qualifiers |
| misc_feature | 1..5499 |
| | note = base editor |
| source | 1..5499 |
| | mol_type = other DNA |
| | organism = synthetic construct |

SEQUENCE: 15

```
ggttcgaaga agagaagaat taaacaagat tcctcggaga ccggcccgt ggcggtggac      60
ccgacgctca ggaggcgcat cgagccgcac gagttcgagg tgttttttcga cccgcgcag   120
ttgcgcaagg aaacctgcct gctctacgag atcaactggg gcggccgaca ttcgatctgg   180
cggcacacca gccagaacac caacaagcac gtggaggtca acttcatcga gaagttcacc   240
accgagcgct acttctgccc gaacacgcgg tgctcgatca cgtggttcct ctcctggtcg   300
ccctgcggca gtgctcgcg ggccatcacc gagttcctgt cccgctaccc gcacgtcacg    360
ctcttcatct acatcgcccg gctgtaccac cacgccgacc ccggaaccg ccaggggctg    420
cgggatctca tctcctcggg cgtcacgatc cagatcatga ccgaacagga gtcgggctac   480
```

```
tgctggcgga acttcgtgaa ctactcgccg agcaacgagg cccactggcc gcgctacccg    540
cacctgtggg tccggctgta cgtgctggag ctgtactgca tcatcctcgg cctaccgccg    600
tgcctcaaca tcctccgccg gaagcagccg cagctcacat tcttcaccat cgcccttcag    660
agctgccact accagcgcct gccgccgcac atcctgtggg ccaccgggct caagagcggc    720
ggttccagcg gcggctcgtc tggctccgag actcccggca ccagcgagag cgcgacgccc    780
gagtcgagcg gcggttcatc tggcgggagc gacaagaagt attccatagg cctggctatc    840
ggcaccaaca gcgtgggctg ggccgtcatc accgacgagt acaaagtgcc gagtaaaaag    900
ttcaaagtgc tcggcaacac cgaccgccac tccataaaga aaaacctgat cggggcgctc    960
ctgttcgaca gcggcgagac ggcggaggcc acccgcttga aacgcacggc ccgacggcgc   1020
tacacgcggc gcaagaaccg gatctgttac ctacaggaga ttttctctaa cgagatggcg   1080
aaggtggacg actcgttctt tcaccgcctc gaagagtcct tcctcgtgga ggaggacaag   1140
aaacacgagc gccacccgat cttcggcaac atcgtggacg aggtggccta ccacgagaag   1200
tacccgacca tctaccacct ccggaagaaa ctcgtggaca gcacggacaa ggccgacctg   1260
aggctcatct acctcgccct ggcgcacatg attaagttcc ggggccactt cctgatcgag   1320
ggcgacctga acccggacaa cagcgacgtg gacaagctgt tcatccagct agtccgacc    1380
tacaaccagc ttttcgagga aaaccccatc aacgccagcg gggtgacgc gaaggcgatc    1440
ctgtccgccc ggctgagcaa gtcccggcgg ctggagaacc tcatcgcgca gttgcccggc    1500
gagaagaaga acgggctgtt cgggaacctg atcgccctct ccctggggct caccccgaac    1560
ttcaagtcca acttcgacct cgccgaggac gccaaactac agctgagcaa ggacacctac    1620
gacgacgacc tcgacaacct gctggcccag atcgggacc agtacgcaga cctgttcctc    1680
gccgccaaga acctctccga cgccatcctg ctgtcggaca tcctgcgggt gaacacggag    1740
atcacgaagg cccccgctctc ggcctcgatg attaaacgct acgacgagca ccaccaggac    1800
ttgaccctcc tcaaggcgct ggtccgccaa cagcttcccg agaagtacaa ggaaatcttt    1860
ttcgatcaga gcaagaacgg gtacgccggg tacatcgacg gcggggcgtc ccaggaggag    1920
ttctacaagt tcatcaagcc catcctggag aaaatggacg gaccgagga gctgctcgtg    1980
aagctcaacc gcgaagattt gctccgcaag cagcgcacgt tcgacaacga gtcgatccgc    2040
caccagatcc acctgggcga gctgcacgcg atcctcaggc gtcaggaaga cttctacccc    2100
ttcctcaagg acaaccgcga gaagatagag aagattctga ccttcagaat tccttattac    2160
gtgggccgc tggctcgggg caactcgcgc ttcgcctgga tgacgcgcaa gtccgaggag    2220
accatcaccc cgtggaactt cgaggaggtg gtggataagg tgcctcggc ccagtccttc    2280
atcgagcgga tgaccaactt cgacaagaac ctgccgaacg agaaggtgct ccccaagcac    2340
agcctgctct acgaatattt cacggtgtac aacgagctga cgaaggtcaa gtacgtgacc    2400
gagggaatga ggaaacctgc attcctctcc ggggagcaga agaaagccat agtcgacctc    2460
ctgttcaaga ccaaccggaa ggtcaccgtc aagcagtcca aggagacta cttcaagaag    2520
atcgagtgct tcgattcagt ggagatcagc ggcgtcgagg accggttcaa cgccagcctg    2580
ggcacctacc acgacctgct caagatcatc aaggacaagg acttcctcga caacgaggag    2640
aacgaggaca tcctggagga catcgtgctg accctgacgc tcttgaggga ccgcgagatg    2700
atcgaggagc gcctcaagac ctacgcccac ctgttcgacg acaaggtgat gaagcagctc    2760
aagcggcgga gatatactgg gtgggccgc ctctcccgga agctcattaa cggtatcagg    2820
gataagcagt ccgggaagac gatcctcgac ttcctcaagt cggacgggtt cgccaaccgg    2880
aacttcatgc agctcatcca cgacgactcc ctgacgttca aggaggacat ccagaaggcc    2940
caagtgtctg gtcaaggtga ctcgctccac gagcacatcg ccaacctcgc gggcagcccg    3000
gccatcaaga agggaatact ccagaccgtc aaggtggtgg acgagctggt gaaggtcatg    3060
ggccgccaca agccgagaa catcgtcatc gagatggcgc gggagaacca gaccacgcag    3120
aaggggcaga aaaatagccg tgagcgcatg aagcgcatcg aggagggat taaggagttg    3180
ggcagccaga tcctcaagga gcaccctgtg agaacacgc agttgcaaaa cgagaagctc    3240
tacctgtact acctccagaa cgggagggat atgtacgtgg accaagaact ggacatcaac    3300
cgcctgtccg actacgacgt ggaccacatc gtgccgcaga gcttcctcaa ggacgacagc    3360
atcgacaaca aggtgctcac ccggtccgac aagaatcggg gcaagtccga caacgtgccc    3420
agcgaggagg tcgtcaaaaa gatgaaaaac tactggcgac aactactgaa cgccaagctc    3480
atcacccagc gcaagttcga caacctcaca aaagccgagc gcgggcgggtt gagcgagctg    3540
gacaaggccg ggttcatcaa gcgccagctc gtcgagacgc gccagatcac gaagcacgtc    3600
gcgcagatac tcgacagccg gatgaacacc aagtacgacg agaacgacaa gctcatccgg    3660
gaggtgaagg tcatcacccct caagtcgaag ctcgtgagcg acttccgcaa ggacttccag    3720
ttctacaagg tccgggagat caacaactac caccacgcc acgatgctta tcttaacgcg    3780
gtggtgggga cggccctcat taagaaatac ccgaagctgg agtcggagtt cgtgtacgcg    3840
gactacaagg tgtacgacgt caggaagatg atcgccaagt ccgaacagga gatcgggaag    3900
gccacgcgca atacttctt ctacagcaac atcatgaact tcttcaagac cgagatcacc    3960
ctcgccaacg gcgagatccg caagccgccc ctcatcgaga cgaacgggga gaccggcgag    4020
atcgtctggg acaaggggcg cgacttcgcc actgtgcgga aggtgctgtc gatgccccag    4080
gtcaacatcg tcaagaagac ggaggtccag acgggcgggt tcagcaagga gagcatcctg    4140
ccgaagcgca acagcgacaa gctgatcgcc cgcaaaaagg actgggatcc aaaaaagtac    4200
ggcggcttcg acagccccac cgtcgcctac agcgtcctcg tcgtcgctaa agtcgagaag    4260
ggcaagtcca aaaagctcaa gagcgtcaag gagctgctcg ggatcaccat catggagcgg    4320
tccagcttcg agaagaaccc aattgatttc ctggaggcga agggctacaa ggaggtcaag    4380
aaagacctca tcataaagct gccgaagtac tcactcttcg agctggagaa cgggcgcaag    4440
cggatgctga cgtcggccgg agagctccaa aagggcaacg agctggcgct gccgagcaag    4500
tacgtgaact tcctctacct ggcgtcccac tacgagaagc tcaagggcag tccaggaggat    4560
aacagcagca agcagctatt cgtggagcag cacaagcact acctgacga gatcatcgag    4620
cagatcagcg agttctccaa gcgcgtcatc ctggcggacg ccaacctgga caaggtgctg    4680
tccgcgtaca acaagcaccg cgacaagccg atccgcgagc aagccgagaa catcatccac    4740
ctgttcaccc tcacgaacct cggggcaccc gccgccttca atatttcga cacgaccatc    4800
gaccgcaagc gctacaccag cacgaaggag gtgctcgacg ccaccctgat ccaccagagc    4860
atcaccggca tgtacgagac ccgcatcgac ctccgcgacg tccggcggga cggggttggc    4920
tcggccgggct cggcgggag caccaacctg agcgacatca tcgagaagga cacgggcaag    4980
cagctcgtga tccaggagtc catcctcatg ctcccggagg aggtcgagga ggtgatcgc    5040
aacaagccag agtcggacat cctggtgcac accgcgtacg acgagtccac cgacgagaac    5100
gtcatgctgc tcaccagcga cgccccgagt acaagcccct gggccctggt catacaggac    5160
tcgaacgggg agaacaagat caagatgctc tctggcggca gcggcgggag cggcggctcg    5220
```

```
accaacctca gcgacatcat cgagaaggag accggcaagc agttggtgat ccaggagagc    5280
atactgatgc tccccgagga ggtggaggag gtgatcggca acaagccgga gtcggacatc    5340
ctggtgcaca cggcgtacga cgagagcacg gacgagaacg tgatgctgct gacgtctgat    5400
gcgcccgagt acaagccctg ggccctggtg atccaggaca gcaacgggga gaacaagatc    5460
aagatgctgg gatctaagaa gagaagaatt aaacaagat                           5499
```

```
SEQ ID NO: 16           moltype = DNA   length = 5499
FEATURE                 Location/Qualifiers
misc_feature            1..5499
                        note = base editor
source                  1..5499
                        mol_type = other DNA
                        organism = synthetic construct
SEQUENCE: 16
ggttcgaaga agagaagaat taaacaagat tcgtccgaga ccggcccgt ggctgtggac      60
ccgacccttc gcagacgtat cgagcccac gagttcgagg tgttctttga cccgagggaa    120
ctccggaagg agacgtgcct gctctacgag atcaactggg gaggaagaca ctccatctgg    180
cggcacacct cgcagaacac gaacaagcac gtggaggtca acttcatcga gaagttcacg    240
actgagcggt acttctgtcc gaacacgcgg tgctcgatca catggttcct gtcttggagc    300
ccgtgcgggg agtgctctcg ggccattacc gagttcctct cccgctaccc gcacgtcacg    360
ctgttcatct acattgcgcg gctataccac cacgccgatc cacggaaccg ccagggcctc    420
cgcgaccta tcagctccgg cgtgacgatc cagatcatga cgcagcaaga gtccgggtac    480
tgctggcgca acttcgtcaa ctactcaccg tccaacgagg cgcactggcc gcgttaccct    540
catctctggg tccggctgta cgtgctggag ctgtactgca taatcctggg cctgccgcct    600
tgcctgaaca tcctcaggcg gaagcagccc caacttacat ttttcaccat tgcgctccag    660
tcctgccact accagcgtct gccgcccac atcctgtggg caccggctt gaagtccggt      720
ggctcgtccg gcggctccag cgggagcgag acgccgggca ccagcgagtc cgccacgcct    780
gagtccagcg gcggctccag cggcggttcg gacaagaagt acagtattgg attggccatc    840
gggacgaaca gcgtgggctg ggccgtcatc ccgacgagt acaaggtgcc atccaagaag    900
tttaaggttc tggggaatac cgaccgccac tcgatcaaga aaatctcat cggggcgctg   960
cttttcgaca gcggcgagac ggcggaagcg acgcggctca agcggacggc tcgtcgccgt   1020
tacaccgggc gtaagaaccg catctgttac ctccaggaga tattcagcaa cgagatggcg   1080
aaggtggacg actcctttt ccaccgtctt gaggagtcct tcctggtcga ggaggacaag   1140
aagcacgagc gccacccgat cttcgggaac atcgtggacg aggtggccta ccacgagaag   1200
taccccacga tctaccacct gcgcaaaaaa tcgtcggact caactgacaa ggccgatttg  1260
aggcttatct acctgcccct cgcccacatg attaagttcc gtgggcactt cctaatcgag   1320
ggtgacctca accccgacaa ctctgacgtg gacaagctgt tcatccagct tgtgcagacc   1380
tacaatcagc tctttgagga gaatccgatc aacgcatctg gtgtggacgc aaaggccatc   1440
ctcagcgcgc ggctgagcaa gtctaggcgg ttggagaacc tgatcgccca actgcccggc   1500
gagaagaaaa atggcctctt cggcaacctg atcgccctgt cgctggggct cacgccgaac   1560
ttcaagagta cttttgacct ggcggaggac gctaagctcc agctatctaa ggacacatac   1620
gacgacgacc tggacaacct gctggcccag atcgcgacc agtacgccga cctcttccta   1680
gccgccaaga acctgtccga cgccatcctc ctcagcgaca tcctgcgcgt gaacacggag   1740
atcacgaagg ctccgctcag cgcctccatg attaagcggt acgacgagca ccaccaagac   1800
ctaactttac tcaaagccct cgtgcggcag cagcttcccg agaagtacaa agagatattt   1860
tttgatcagt ccaagaacgg ttatgcgggc tacatcgacg gcgcgcgag ccaggaggag   1920
ttctacaagt tcatcaagcc catcctggag aagatggacg gcaccgagga gctgctcgtg   1980
aagctcaacc gtgaagacct cctgcgaaag cagcgaacct tcgacaacgg ttcgatcccg   2040
caccagatcc acctcgggga gctgcacgcc atcctgagc gacaggagga cttctaccct   2100
ttcctaaagg acaaccgcga gaagattgaa aaaatcctga cgtttcgcat accctactac   2160
gtcggcccgc tggcgcgcgg caactcccgg ttcgcctgga tgacccgtaa gagcgaggag   2220
acgatcaccc cgtggaactt cgaggaggtc gtggacaagg cgcgagcgc gcagagcttc   2280
atcgagcgca tgaccaactt cgacaagaac ctcccgaacg agaaggtgct cccaaagcac   2340
tccctcctgt acgagtattt caccgtgtac aacgagttga caaggtgaa gtacgtgacg   2400
gagggaatgc ggaagcctgc gttcctctcg ggcgagcaga agaaggcaat cgtggacctg   2460
ctcttcaaga ccaaccggaa ggtgacggtg aagcagctca aggaggacta cttcaaaaaa   2520
atcgagtgct tcgactccgt ggagataagc ggcgtggagg accgattcaa cgcctccctc   2580
ggcacctacc acgacctcct taagatcatc aaggacaagg acttcctgga caacgaggag   2640
aacgaggaca tcctggagga catcgtgctc acccctgaccc tcttcgagga cccgggagatg   2700
atcgaggagc gcctcaagac gtacgcccgc ttgttcgacg acaaggtgat gaagcagctc   2760
aagcggcggc gatacaccgg gtgggggccgc ctatcccgca aacttatcaa cggcatccgc   2820
gacaagcagt ccggcaagac gatcctggat ttcctcaagt cggacgggtt cgccaaccgg   2880
aacttcatgc agctcatcca cgacgacagc ctcacgttca aggaggacat ccagaaggcc   2940
caagtgagcg gtcaagggga cagcctccac gagcacattg cgaaccttgc tgggagccct   3000
gcgatcaaga ggggatatt gcaaaccgtg aaggtcgtgg acgagttggt gaaggtcatg   3060
gggcgacaca gcccgagaa catcgtgatc gagatggcca ggaaaatca gaccacgcag   3120
aagggccaaa aaacagccg cgagcggatg aagcggatcg aggagggcat caaggagctg   3180
gggtcgcaga tcctcaagga gcaccgggtg gagaacacgc agctccagaa cgagaagctg   3240
tacctctatt acctacagaa cgggcgggat atgtacgtgg accaggagct agacatcaac   3300
cgcctgtccg actacgacgt ggaccatatc gtcccgcagt cgttcttgaa ggacgacagc   3360
atcgacaaca aggtgctcac aagatcggat aagaatcgag gcaagtccga caacgtgccc   3420
tcggaggagg tggtcaagaa aatgaaaaac tactggcggc agttgctgaa cgccaagctc   3480
attacgcagc ggaagttcga caacctgacg aaggctgaac tggtgggct cagcgagcta   3540
gacaaggtcg ggtttcatca agcgctcatc gtcgagacc cagcatgacc caacacgtg   3600
gcgcagatcc tggactcgcg catgaacacc aagtacgacg agaacgacaa gctcatccgt   3660
gaggtgaagg tcatcaccct taagtctaag ctggtcagtg acttccgcaa ggacttccag   3720
ttctacaagg tccgggagat caacaactac caccacgcgc acgacgccta cctcaacgcg   3780
gtggtgggga cggcgcttat taagaaatat cccaagctgg aaagcgagtt cgtttacggc   3840
gactacaagg tgtacgacgt ccgcaagatg atcgcaaagt cggaacagga aatcggaaag   3900
```

```
gcgacggcca aatatttctt ttactccaac atcatgaatt tttttaagac ggagatcacc   3960
ctggcgaacg gggagatccg caagcggccc ctcatcgaga ccaacgggga cgggcgag    4020
atcgtctggg acaagggccg ggacttcgcc accgtgcgga aggtgctttc tatgcctcaa   4080
gtcaatatcg tcaaaagac agaggtgcag accggcgggt tcagcaagga gtctatcctg    4140
ccgacgaca actcggacaa gctcatcgcg cgcaagaaag actgggaccc caaaaaatat   4200
ggcgggttcg actcgccgac cgtcgcctac agcgtcctcg tggtggctaa ggtcagaaag    4260
ggcaagagca aaaagctaaa gtcggtgaag gagctgctgg gcatcaccat catgagcgc   4320
tcgtctttcg agaagaatcc aatcgacttc ctagaggcga aggggtacaa ggaggtcaaa    4380
aaggatctta tcatcaaact gccgaagtac agtctgttcg agctggagaa cgggcggaga   4440
cggatgctgg ctagtgcggg cgagttgcag aagggcaacg agttggcact gccctccaag    4500
tacgtgaact tcctgtacct ggcctccac tacgagaagc tcaaggggag ccccgaggac    4560
aacgagcaga agcagctatt cgtcgagcag cacaagcact acctggacga gatcatcgag   4620
cagatcagtg agttctccaa gcgggtcatc ctcgcggacg ccaacctgga caaggtgctg    4680
agcgcgtaca acaagcacag ggacaagcca atcagggaac aggccgagaa catcatccac    4740
ctgttcaccc tgaccaacct gggtgcaccg gctgccttca agtactttga cacgaccatc   4800
gaccggaagc gctacacctc cacgaaggag gtgctggacg ccacgctgat ccaccagagc    4860
atcaccgggc tctacgagac acggatcgac ctgagccagc ttggcgggga ctcgggcggc    4920
agcggcggta gcggcgggta caccaacctc tccgacatca tcgagaagga cgcgggaag    4980
cagtggtga tccaggagag catcctcatg ctgccggagg aggtcgagga ggtgatcggg    5040
aacaagccgg agtcggacat tctcgtgcac acagcctacg acgagtccac cgacgagaac   5100
gtcatgctcc tgacctcgga cgccccgag tacaagcct gggcgctggt gatccaggac    5160
agcaacggcg agaacaagat caagatgctg tccggccgga ccggtgggca cggcggagc    5220
accaacctga gcgacatcat cgagaaggac acaggcaagc agctcgtgat ccaggagtcg    5280
atactgatgc tccccgagga ggtcgaggag gtcatcggga acaagcccga gtcagacatc    5340
ctcgtgcaca ccgcctacga cgagagcacg gacgagaacg tgatgctcct gacctccgac    5400
gcaccggagt acaagccctg ggccctggtc atccaggaca gcaacggcga gaacaagatc    5460
aagatgctcg gatctaagaa gagaagaatt aaacaagat                            5499

SEQ ID NO: 17          moltype = DNA   length = 5499
FEATURE                Location/Qualifiers
misc_feature           1..5499
                       note = base editor
source                 1..5499
                       mol_type = other DNA
                       organism = synthetic construct
SEQUENCE: 17
ggttcgaaga agagaagaat taaacaagat tcatccgaga cggggcccgt cgccgtggac     60
cccacgctca gacgccggat cgagcccac gagttcgagg tctttttcga cccgagagag    120
ctacgaaagg agacctgcct gctgtgtacg atcaactggc ggggcggca ttcgatctgg    180
cggcacacga gccagaacac gaacaagcac gtggaggtca acttcatcga gaagttcacg    240
acggagcggt acttctgccc caacaccgc tgctctatca cctggttcct gtcgtggagc    300
ccgtgcggcg agtgcagccg cgccatcacg gagttcctca ccgctatcc gcacgtgacc    360
ctgttcatct acatcgcgcg gctctaccac cacgccgacc cacgcaaccg ccagggcgtg    420
cgcgacttaa tcagctccgg ggtcacgatc cagatcatga cggaacaaga gtccggctat    480
tgctggcgca acttcgtcaa ctacagcccg agtaacgagg cccactggcc gcgctacccg    540
cacctctggg tccggctgta cgtcctggag ctgtactgca tcatattggg gctcccgccg    600
tgtctcaaca tcctccgcg gaagcagccc cagctccat tctttactat agccttgcag    660
tcgtgccact accagcgcct cccgccgcac atcctctggg cgaccgggct taagagcggt    720
ggctccagcg gcgtagcag cggcagcgag acgcccggca cgagcgagtc tgccactcca    780
gaatcatctg gcggctccag cggcggttcc gacaaaaagt attccattgg gactcgctat    840
ggcacgaaca gcgtcgggtg ggcggtcatc actgacgagt acaaggtgcc gagcaagaag    900
tttaaggtgc tgggaaacac cgacaggcac tcgatcaaga aaaatcttat cggggccta    960
ctcttcgact ccggagaaac cgccgaggcc accggttga agcgcacggc ccgccgtcgc   1020
tacaccaggc gcaagaaccg gatctgctac ctccaggaga tattcagcaa tgagatggcg   1080
aaggtggacg actcgttttt tcacaggcta gaggagtctt cctcgtgga ggaggacaag   1140
aaacacgagc gccaccccat cttcggcaac atcgtggatg aggtggcata tcacgagaag   1200
taccaaccca tctaccacct ccgcaaaaag ctcgtggact ctaccgacaa ggccgacctc   1260
cgtctgatct acctcgcgct ggcccacatg attaagttcc gaggacactt tctgatcgag   1320
ggcgacctga acccagacaa cagcgacgtg gacaagctgt tcatccaact tgtccagacc   1380
tacaatcagc tcttcgagga gaaccctatc aacgcctcgg gcgtggacgc gaaggcatc   1440
ctgtccgccc gcctgagcaa gtcgcggcgg ctggagaacc tgatcgccca gctccccggc   1500
gaaaaaaga acgcctcttt cggcaacctc atcgcgttgt cgctgggct caccccgaac   1560
ttcaagtcca acttcgacct ggcgaggac gctaaactcc agctctcgaa ggatacctac   1620
gacgacgaca tcgacaaacct gctgccccag atcgcgaca agtacgcgga cctttttctg   1680
gcggccaaga acctgagcga cgcgatcctc cttagcgaca tactccgtgt gaacaccgag   1740
atcacgaagg ccccgctctc cgcgtccatg attaagcgct acgacgagca ccaccaagac   1800
cttaccctgc ttaaggcgct ggtcaggcag cagttaccgg agaagtacaa ggagatctttt   1860
tttgatcaat ctaagaacgg ttacgccggg tacatcgacg gcggcgcgtc ccaggaggag   1920
ttctacaagt tcatcaagcc gatcttggag aaaatggacg gaaccgagga gctgctcgtg   1980
aagctcaacc gcgaagacct cctccgcaag cagcgcacct tcgacaacgg gagcatcccg   2040
caccagatcc acctgggaga gctgcacgcg atcctgcgga acaagagga cttctacccc   2100
ttcctcaagg acaaccggga gaagattgaa aaatacttac ttttcgtat cccgtactac   2160
gtcgggcccc ttgcgagggg caactccaga ttcgcgtgga tgacccgcaa gtccgaggag   2220
accatcaccc cgtggaactt cgaggaggtg gtggacaagg gccagtcgttc   2280
atcgagcgca tgaccaactt cgacaagaac cttccgaacg agaaggtgct cccgaagcac   2340
agcctgctct acgaatattt tactgtgtac aacgagctga cgaaggtcaa gtacgttacg   2400
gaggggatga ggaagcccgc cttcctctcc ggcgagcaga gaaagccat tgtggatctc   2460
ctgttcaaga ccaaccgcaa ggtgacggtg aaacagctca agaggacta cttcaagaag   2520
atcgagtgct tcgactccgt agagatcagc ggggtcgagg accgcttcaa cgcctcgctg   2580
```

```
ggcacgtacc acgacctgct aaagattatc aaggacaaag acttcctaga caatgaggag   2640
aacgaggaca ttctggagga catcgtgctg actctgacgc tgttcgaaga ccgcgagatg   2700
atcgaggagc ggcttaagac gtacgcccac ctgttcgacg acaaggtgat gaagcagttg   2760
aaacggcggc gctacaccgg gtggggccgc ctctcccgca agctcatcaa cggcatccgc   2820
gacaagcagt cggggaagac gatcctggac ttcctgaaga gcgacggctt cgccaaccga   2880
aacttcatgc agctaatcca cgacgacagc ctgacgttca aggaggacat ccagaaggcc   2940
caagtgagcg gccagggaga ctcgctacac gagcatatcg ccaacctggc tggcagcccg   3000
gcgattaaga aaggaatcct ccaaaccgtc aaagtggtgg acgagctggt gaaggtgatg   3060
ggccgccaca agcccgagaa cattgtgatc gagatggcgc gggagaacca gacgacgcag   3120
aaggcccaaa aaatagcag gaaaggatg aagcgaatag aggaggggat caaggagctg   3180
gggagccaga ttctcaaaga gcacccggtc gagaacacac agctccagaa cgagaagctg   3240
tacctctact acctccaaaa cggccgcgat atgtacgtgg accaggaact agacatcaac   3300
cggctgagcg actatgacgt ggaccacatc gtgccgcagt ccttcctcaa ggacgactcg   3360
attgacaaca aagtgctcac tagatccgac aagaacagag gcaagagcga taacgtccgg   3420
tcggaggagg tcgtcaagaa aatgaaaaac tactggcggc agctcctaaa cgccaagctc   3480
atcacgcagc gtaagttcga caacctgacg aaggcggagc ggggcgggct gagcgagctg   3540
gacaaagcgg ggttcatcaa gcggcagctc gttgagacgc ggcagatcac aaagcacgtc   3600
gcgcaaatcc tcgactcccg catgaacacc aagtacgacg agaacgacaa gctcatccgg   3660
gaggtgaagg tcattaccct taaatcgaag ctcgtcagcg actttcgtaa ggacttccag   3720
ttctacaagg tcagagagat caacaactac caccacgccc acgacgccta tctgaacgcc   3780
gtggtgggca ccgcgcttat taagaagtac cccaagctgg agtccgagtt cgtgtacggc   3840
gactacaagg tttatgacgt caggaagtcg atcgccaagt cggaacagga gatcggaaaa   3900
gctaccgcca aatatttctt ctatagcaac atcatgaact tcttcaaaac cgagatcacc   3960
ctcgccaacg gcgagatccg gaagcgcccc ctcatcgaga ccaacgggga gaccggggag   4020
atcgtctggg acaaggggcg ggacttcgct actgtccgaa aggtgctctc catgccacaa   4080
gtgaatatcg tcaagaaaac agaggtgcag accggagggt tcagtaagga gtccatcctg   4140
cccaagcgga actccgacaa gctaattgct cgcaaaaagg attgggatcc taaaaaatat   4200
ggcggcttcg actcgcccac ggtcgcctac tctgtgctgg tcgtggcgaa ggtggagaag   4260
ggcaagtcca gaagctcaa gagcgtcaag gagctgctgg gatcacgat catggagcgt   4320
agttcgtttg agaagaatcc catcgacttc ctggaggcta agggctacaa ggaggtcaaa   4380
aaggacctca tcattaagct gccgaagtac agcctcttcg agctggagaa cgggcggaag   4440
cgtatgctcg cctccgctgg ggagttacaa aaggggaacg agctggcgct gccgtctaag   4500
tacgtcaact tcctgtacct ggcctccac tacgagaagc tcaaggggtc gccggaggac   4560
aacgagcaga agcagctctt cgtagagcag cacaagcact acctggacga gatcatcgag   4620
cagatttcag agttctcaaa gcgggtcatc ctcgccgacg ccaacctgga caaggtgctc   4680
tcggcctaca acaagcaccg ggacaagccg atccgcgaac aggccgaaaa catcatccac   4740
ctgttcacgc tcaccaacct cggtgccccg gcggccttca gtactttga cacgaccatc   4800
gaccggaagc gctatacctc gacgaaggag gtgctggacg ccaccctgat ccaccagtcc   4860
atcaccgggc tttacgagac ccggatcgac ctctcgcagc taggcgggga cctcgggcgc   4920
tcgggcggct ccggcgggag caccaacctg tccgacatca tcgagaagga gacggggaag   4980
cagctcgtca tccaggagtc gatcctcatg ctccccgagg aggtcgagga ggtgatcggc   5040
aacaagccgg agtccgacat cctggtccac acggcgtacg acgagagcac ggacgagaac   5100
gtgatgctcc tgacctccga cgcccccgag tacaagccct gggcgctgtc catccaggac   5160
agcaacggcg agaacaagat caagatgctc tccggcggct ccgcggcag cggagggagc   5220
acgaacctca gcgacatcat cgagaaggag accggcaagc agctcgtgat ccaggagtcc   5280
atcctcatgc tgccggagga ggtggaggag gtgatcggca caagccgga gtcggacata   5340
ctcgtgcaca ccgcgtatga cgagagcacc gacgagaacg tgatgctgct gacaagcgac   5400
gcgccagagt acaagccctg ggccctcgtg atccaggact ccaacggcga gaacaagatt   5460
aagatgctgg gatctaagaa gagaagaatt aaacaagat                         5499

SEQ ID NO: 18            moltype = DNA  length = 5499
FEATURE                  Location/Qualifiers
misc_feature             1..5499
                         note = base editor
source                   1..5499
                         mol_type = other DNA
                         organism = synthetic construct
SEQUENCE: 18
ggatctaaga agagaagaat taaacaagat tcatcagaga caggaccagt tgccgttgac     60
cccaccctta ggagaagaat agaaccccac gagtttgaag tgttttttcga cccaagagaa   120
ttgaggaagg aaacatgtct tctgtatgag ataaattggg gaggtaggca cagcatttgg   180
agacatacca gccagaatac aaacaagcat gttgaggtga atttttattga aaagttcact   240
accgaaagat atttttgtcc aaacactaga tgtagtataa cctggtttct cagttggagc   300
ccatgtgggg aatgtagcag ggcaatcacc gagtttctct caagataccc tcacgtgacc   360
ttgtttatct acatagccag actttatcat cacgcagacc caagaaacag acaaggtctg   420
agagatttga tttcttcagg agtgactatt cagatcatga ccgaacaaga gagcggttac   480
tgctggagaa actttgttaa ttattcacct agtaacgaag cacattggcc tagataccct   540
cacctgtggg ttaggctcta cgtgttggaa ctctattgta ttattcttgg cttgcctccc   600
tgcctgaaca tactgagaag gaagcagccc caactcacat tcttcactat agctcctgaa   660
agttgtcact accagaggct ccctcctcac atcctgtggg ccacaggttt gaagtcaggg   720
ggctccagtg gaggtagttc aggctccgag actccaggaa cttccgagtc agctacaccc   780
gaatccagcg gtggtagttc tggcggcagt gacaagaagt atagtattgg actcgccatc   840
ggaaccaact ctgtggggtg ggctgttatt acagatgaat ataaggtgcc atccaaaaag   900
tttaaagttc tgggcaatac tgatagacac tcaatcaaga agaatctgat aggtgcactt   960
ctgtttgata gtgagagac tgccgaggca accagactta aaggactgc aagaagaaga  1020
tataccagaa gaagaatag gatttgctat ttgcaggaaa tcttcagcaa cgaaatggcc  1080
aaggttgatg actcattttt ccataggttg gaggagagtt ttcttgtgga ggaagataag  1140
aagcacgaaa gacacccaat tttcgggaat atagtggacg aggtggctta tcatgagaag  1200
tatcccacta tctaccacct gagaaagaaa cttgtggact caaccgataa ggctgatctt  1260
```

```
aggcttatat acttggccct tgcacatatg atcaaattca ggggccattt tcttatcgaa 1320
ggcgatctta atcccgataa ctcagatgtg gacaagctgt ttatacaact tgtgcaaacc 1380
tacaatcaac tcttcgagga gaatcccatt aacgcctccg gcgtggatgc aaaagccata 1440
ctgtcagcca gactgagcaa aagtaggaga ctggagaatc ttatagccca actgccggt 1500
gaaaagaaga atgggctctt cggaaatctg atcgctcttt cattggggtt gacacccaac 1560
tttaagagta actttgactt ggcagaagat gcaaagttgc agctcagtaa agacacatat 1620
gacgatgacc ttgacaatct cttggcacaa ataggggatc aatacgctga ccttttcctc 1680
gctgccaaga acctcagcga cgctatactg ttgtccgaca ttcttagggt taataccgaa 1740
attacaaagg cccctcttag tgcaagtatg atcaaaaggt atgatgagca tcaccaagac 1800
cttacactgc tgaaggctct ggttagacag caactccctg aaaagtataa ggaaatattc 1860
ttcgaccaaa gtaagaacgg gtacgccggt tatattgatg ggggcgcaag tcaagaagaa 1920
ttttacaaat tcatcaagcc aattcttgaa aagatgacg ggactgagga attgctggtg 1980
aaactgaata gagaggacct tcttagaaaa cagaggacat tgacaatgg gtccatccca 2040
caccagattc atctggggga actccacgca atattgagga gacaagaaga ctttaccca 2100
ttccttaagg ataatagaga gaaatcgaa aaaatcctga ctttcaggat tccttactat 2160
gttgggccac tggccagggg gaactcaaga ttcgcttgga tgacaaggaa gtcagaagaa 2220
accataaccc cttggaattt tgaagaggtg gttgataagg gggcatcagc ccagtctttc 2280
atagagagga tgaccaactt tgataaaaat cttccaaatg agaaggtttt gccaaaacat 2340
agtcttttgt acgagtactt tactgtttat aacgaattga ccaaggtgaa gtatgtgacc 2400
gagggaatga ggaagccagc attttgtcc ggggagcaaa agaaagcaat cgttgatctt 2460
ctcttcaaga ccaacagaaa agtgaccgtg aaacaactga aggaagacta cttcaaaaag 2520
atagaatgtt tcgattcagt tggaaattagc ggtgttgaaa acaggttcaa tgcttcattg 2580
ggtacttacc acgacctgtt gaagataatc aaagacaagg actttctcga taatgaggag 2640
aacgaagaca tcttggaaga cattgtgctt acactcactt tgtttgagga cagggaaatg 2700
attgaggaaa gactcaaaac ttacgctcat tgttttgatg ataagttat gaaacaacta 2760
aaaagaagaa ggtacaccgg ctggggaaga ttgagtagaa aactgatcaa cggtattaga 2820
gataaacaat ccggaaagac tatcctcgat ttccttaaga gtgatggctt tgcaaatagg 2880
aattttatgc agctgattca tgacgactca cttaccttca aagaagacat ccaaaaagct 2940
caggtgtctg gcaaggcgac cagtctgcat gaacatatag ctaacttggc tgggagtccc 3000
gccatcaaga aggggatact tcaaacagtt aaagttgtgg acgaattgt gaaggtaatg 3060
ggaaggcaca agcctgaaaa tatagtgata gaaatggcaa gggaaaatca aacaacccag 3120
aagggacaga agaacagtag ggaaaggatg aaaaggatag agaggggat caaagagctt 3180
ggtagccaga tcctcaagga acatccagtg agaataccc aacttcaaaa cgagaaactc 3240
tatttgtact acttgcagaa cggaagagat atgtatgtgg accaagagct tgatattaac 3300
aggctgagcg attatgacgt tgaccacata gtgcccaat cattcctcaa ggatgactct 3360
attgataata aggtgctgac aaggagtgac aagaatagag ggaatccga caacgttcca 3420
tccgaggaag ttgtgaagaa gatgaagaac tactggaggc agttgctgaa cgctaagctc 3480
attcccagag gaaattcga taacctgacc aaagcagaga gaggcgggct gagcgaactc 3540
gataaagcag gtttcatcaa gagacaactc gtggagacta ggcaaattac taagcacgtg 3600
gctcaaatac tcgacagcag gatgaacaca aagtacgacg agaacgacaa gctcattaga 3660
gaggttaagg ttattactct gaaaagtaaa ttggttagcg atttcagaaa ggatttccaa 3720
ttctataagg ttagagagat caacaattat catcatgcac atgatgccta tctgaatgct 3780
gtggttggta cagcccttat caagaagtac cctaagctag gcgagagtt tgtgtacgga 3840
gattataagg tgtatgatgt gaggaaaatg atcgctaaaa gtgagcaaga gattggaaag 3900
gctaccgcca aatacttctt ttattccaat attatgaatt tcttcaagac agaaatcacc 3960
ctggctaacg gcgagataag gaagaggccg cttatcgaaa ctaatgggga gacaggcgaa 4020
atagtgtggg acaaagggag ggatttcgca actgtgagga aggttttgg catgcctcag 4080
gtgaatatcg ttaagaaaac cgaagttcaa actggagggt tctctaagga aagcattctc 4140
cccaagagga actccgacaa gctgattgct agaaagaaag actgggaccc caagaagtat 4200
ggcggattca actcacccac tgtggcatat agcgttctcg tggtggcaaa ggttgaaag 4260
ggtaaatcca aaaactcaa atccgtgaag gaactccttg gcataactat tatggaaagg 4320
agtagctttg aaaagaatcc catcgacttt ctcgaagcta agggtataaa ggaagttaag 4380
aaggaccta taatcaaact tccaaaatac tccttttg agttggaaaa cggcagaaag 4440
agaatgttg ccagtgccgg ggagcttcaa aagggcaacg aactggctct gcctagcaaa 4500
tatgtgaact ttttgtatct ggcatcacac tacgagaaac ttaaaggctc tcctgaggac 4560
aacgagcaaa aacagctctt tgttgaacag cataagcact acctcgacga gattattgag 4620
cagatcagcg agttctcaaa gagagttatt ctggctgacg ctaatcttga caaggttttg 4680
tccgcttaca acaaacacag ggataagcca atcagggagc aggcagaaaa cataatccat 4740
ctctttaccc tgacaaacct cggtgccccc gctgctttca gtattttga tactaccatt 4800
gacaggaaga gatatacttc cactaaggaa gtgctcgacg caaccctcat acaccaaagt 4860
atcacaggcc tctatgaaac taggatagat ttgtctcaac ttgggggcga ttccggaggt 4920
tctggggct ccgagggag tactaatctg agtgatataa ttgaaaagga aaccggaaag 4980
caactcgtta tccaggaatc catacttatg ttgcccgaag aggtggaaga ggttattggt 5040
aataagcctg aaagtgatat tttggttcac actgcctacg acgaatccac tgacgagcaa 5100
gtgatgctgc tgacctctga cgctcccgag tataagcctt gggctctggt aattcaagac 5160
tccaacggag aaaataagat caaaatgctt tcagggggaa gtggtggttc cggcggtagt 5220
actaacctca gcgatattat tgagaaggaa accggcaagc aactagttat acaagagagt 5280
attctcatgc tgcctgagga agttgaagag gttataggaa acaagcccga gtctgatatt 5340
ctggttcaca ctgcctatga cgaaagtaca gacgaaacg tgatgcttct tacatccgac 5400
gcacccgaat acaaaccctg ggcactcgtg attcaagact ctaacgggga aaacaagatt 5460
aaaatgctcg gatctaagga gagaagaatt aaacaagat 5499
```

SEQ ID NO: 19           moltype = DNA    length = 5499
FEATURE                 Location/Qualifiers
misc_feature            1..5499
                        note = base editor
source                  1..5499
                        mol_type = other DNA
                        organism = synthetic construct

SEQUENCE: 19

```
ggatctaaga agagaagaat taaacaagat tcttccgaga ctggaccegt tgctgtggac    60
cctacactga ggagaaggat agagccccat gagtttgagg ttttctttga ccctagagaa   120
cttaggaagg agacatgcct gttgtacgag attaattggg gcggcaggca cagcatatgg   180
agacacacca gtcagaacac aaataagcac gtggaggtga acttcatcga gaaattcacc   240
accgagagat attttttgccc aaacaccaga tgttcaataa cttggttcct ttccttggagc   300
ccctgtggag agtgttccag ggcaattaca gagttcctca gtaggtatcc acacgttacc   360
cttttatct atatcgccag gctttatcac cacgctgacc caaggaatag acagggcctt   420
agggacctca tatctagcgg tgttacaatt cagataatga ctgagcaaga atctggttac   480
tgttggagaa attttgtgaa ttactccecct agcaacgagg cacactggcc aagatacccca   540
cacctctggg ttaggcttta tgttctggaa ctttactgca tcatacttgg tctacctccc   600
tgtcttaaca tcctcaggag aaagcaacct caactcacat ttttcaccat gcccttcaa    660
agctgccact atcagaggtt gccaccacat attctctggg ccactgggct gaagagtgga   720
ggctcctcag ggggaagttc tggcagcgaa acaccaggta ctagcgaaag cgccacccccc   780
gaaagcagtg gaggcctcc cggcggtagc gacaaaaagt attccatcgg gcttgctatc   840
ggaaccaact ctgtggggtg ggcagttatt accgacgaat acaaggtgcc cagcaagaag   900
tttaaggttc tggggaacac agatagacat agcataaaga aaaacctgat aggcgcactg   960
ttgttcgact ccggggaaac agccgaagct accaggctga agaactgc aagaagaagg   1020
tacaccagaa gaaaaaacag aatatgttat ctccaagaga ttttctctaa cgagatggcc   1080
aaggtggacg actcattctt tcacagactg gaagaatctt tccttgtgga agaagataag   1140
aaacacgaga ggcaccctat ttttggcaat atcgtggatg aggtggctta ccacgaaaaa   1200
taccctacaa tataccacct caggaaaaaa ttggttgata gtacagacaa ggccgacctc   1260
aggctcatct atttggccct ggcccatatg attaaattca ggggggcactt tctcatcgag   1320
ggagatttga accccgacaa cagtgatgtt gataagctct ttattcagct cgtgcagact   1380
tacaatcagt tgtttgagga aacccccatt aatgcttccg ggtggacgc caaggcaatc   1440
ctttctgcaa gactctcaaa gtcaaggaga ctcgaaaatc tgatagcaca gcttccagga   1500
gagaagaaga acgggctctt tggaaacctg atcgctctgt cactcggact cacacccaat   1560
ttcaaaagca atttttgattt ggcagaggac gctaagctgc aactcagtaa ggatacctac   1620
gacgatgact tggataatct gctcgcacaa attggggacc agtatgcaga cctgtttctc   1680
gcagctagaa acttgagtga cgccatattg ctcagtgaca tcctcaggggt taataccgag   1740
attacaaaag ctccactctc tgcaagcatg atcaagaggt atgacgagca ccatcaagac   1800
ctgacactcc ttaaggcgtt ggtaggcag caacttcctg aaaagtataa ggaaatcttc   1860
ttcgatcaaa gcaaaaacgg ctacgccggc tatatagacg gggagcatc ccaagaagaa   1920
ttttataagt tcataaaacc tatattggag aagatgacgg ggacagagga attgctcgtg   1980
aaactgaaca gggaggatct cctcaggaag caaaggacct tcgacaatgg ctccatccca   2040
catcagattc acctcggcga actgcacgca atactgagaa gacaagagga cttttatcct   2100
ttcctgaagg acaacaggga gaaaatcgag aaaatcttga cattcagaat cccatactac   2160
gttgggcctc tggccagagg taacagtagg ttcgcctgga tgactaggaa atcagaggag   2220
actattacac cctggaactt tgaagaagtt gttgataagg gacttcagc acaatcattc   2280
atcgaaagaa tgacaaactt tgacaaaaat ctgcctaatg agaaagtgct cccaaaacat   2340
tccctgctgt atgagtattt taccgtttat aacgagctta ccaaggtgaa atacgttact   2400
gaaggtatga gaaagccagc ttttctttca ggggagcaaa agaaggctat cgtggatctt   2460
ctcttttaaga ccaacagaaa ggttaccgtg aagcagctta acgatgcagc cttaaaaag   2520
atcgagtgtt tgactcagt ggaaataagc ggtgttgaag atagattcaa cgcatccttg   2580
ggaacttatc atgatcttct taagataatc aaggataag actttctcga caacgaggaa   2640
aacgaagata tactggagga catagttctg acacttactt tgttcgagga tagggagatg   2700
atcgaggaca gactgaaaac atatgctcac cttttcgacg acaaagttat gaaacaactc   2760
aagagaagga gatatacagg gtggggagaa ttgagcagga aactgattaa tggtatcaga   2820
gacaaacagt caggaaaaac aatactcgac tttttgaaat cagacgggtt cgcaaatagg   2880
aatttcatgc agcttataca cgacgattca cttactttta aagaggacat tcaaaaggct   2940
caagttagtg gacaaggtga ctccctccac gaacacatca caaatctcgc tggcagccgt   3000
gcaattaaga agggtatact ccagacagtt aaggttgttg acgagctggt taaagtgatg   3060
ggaagacaca aaccagagaa catagtgata gagatggcca gggaaaaacca aaccactcaa   3120
aaagggcaga aaaattccag agagaggatg aaaaggattg agaaggtat caaggagctg   3180
ggtagccaaa ttctgaaaga aactcctgtg gaaaacactc aactccagaa tgagaaactc   3240
tatctgtact atctgcaaaa tggggagagat atgtatgtgg accaggaact ggacataaac   3300
aggctctcag attacgatgt ggatcatatc gtgccacagt cctttcttaa ggatgatagc   3360
atcgacaata aggtgcttac caggtccgac aagaacaggg gaaagtcaga taacgtgcct   3420
tctgaagaag ttgttaaaaa gatgaagaac tactggagac agctgcttaa cgctaagctc   3480
ataacacaga ggaagtttga caacttgacc aaggccgaga gaggcggact ctcagaattg   3540
gataaggcag ggttcataaa aaggcagctg gtggaaacaa ggcagataac taaacatgtg   3600
gctcagatcc tcgatagtag gatgaataca aaatacgatg agaacgacaa gctcataagg   3660
gaggttaaag tgataactct gaaatccaaa ctggttagcg atttttaggaa ggatttccag   3720
ttttacaaag ttagggagat caacaattat catcacgccg acgatgccta cttgaacgca   3780
gttgtgggta ctgcacttat caaaaagtac cctaagctgg aatccgagtt tgtttatgga   3840
gactataagg tgtacgacgt tagaaaaatg attgcaaagt cagacagga gatagggaaa   3900
gccactgcaa aatatttctt ttatagcaat atcatgaatt tctttaagac agaaatcaca   3960
ctggccaatg gggaaataag gaagaggccc ctgatcgaaa ctaatggcga gacaggggag   4020
attgtgtggg ataaaggtag ggactttgca acagtgagga agtgctgag catgcecccaa   4080
gttaatatcg ttaaaaagac cgaggttcaa acagggggct ttagtaagga aagcatttg   4140
cccaagagga atagtgacaa attgattgct aggaaaaaag attgggaccc caaaagtat   4200
ggcggatttg atagccccac tgttgcttac tccgtgctcg tggttgcaaa ggtggagaag   4260
ggaaagagca agaaactgaa gtcagttaag gaactccttg gtatcactat catggaaaga   4320
agctcctttg agaagaaccc tattgacttc ctggaggcta gaggttacga aaggttaag   4380
aaagaccta tcattaaatt gcccaaatat agtctttttcg agcttgaaaa cggaagaaag   4440
aggatgcttg catccgctgg cgaattgcaa aagggcaatg agcttgctct ccccttccaag   4500
tatgtgaact tcctttatct tgcctcacac atgaaaaac tcaaaggttc acccgaagac   4560
aacgaacaaa agcaactatt tgtggaacaa cacaagcact acctgacga aatcattgag   4620
caatttctg agttttcaaa aagggtaatc ttggctgacg caaatctcga caaagttttg   4680
```

```
tcagcttaca acaaacatag agataagcca attagagagc aagctgagaa tatcatccat   4740
ctgtttaccc tgactaacct tggagcgcct gctgctttta aatatttcga caccacaatc   4800
gacaggaaga ggtacactag cactaaggaa gttctcgacg ccaccctcat ccaccagagt   4860
attacaggcc tgtacgagac aagaattgat ctttctcaac ttggtggtga cagcggcggt   4920
agtggggggt caggggggcag tactaacctc agcgatataa ttgaaaagga aaccgggaaa   4980
cagcttgtta ttcaagagtc tatcctcatg ctgcccgaag aagtggagga agtgattggt   5040
aacaaacccg aatccgacat tctggttcat acagcatacg acgagtctac cgatgagaac   5100
gttatgcttc tcaccagtga tgcccctgag tacaagcctt gggccttggt aattcaagac   5160
tccaacgggg agaacaagat caagatgctt agcggtggca gtgggggaag cggcggtagt   5220
acaaatctgt ccgacatcat agaaaaggag actgggaaac aactcgtgat acaagagtct   5280
attcttatgc ttcctgaaga agttgaagaa gtgatcggta ataagcccga atcagacata   5340
ctcgttcata ccgcatacga cgaatctacc gatgagaacg tgatgctcct cacatccgat   5400
gctcccgagt acaaaccttg ggctctcgtg atacaggact ctaatgggga aaataagata   5460
aaaatgcttg gatctaagaa gagaagaatt aaacaagat                          5499

SEQ ID NO: 20         moltype = DNA   length = 5499
FEATURE               Location/Qualifiers
misc_feature          1..5499
                      note = base editor
source                1..5499
                      mol_type = other DNA
                      organism = synthetic construct
SEQUENCE: 20
ggatctaaga agagaagaat taaacaagat agcagcgaga caggaccagt tgccgttgac     60
cctacattga gaagaagaat tgaacccac gagtttgaag tgtttttcga tcccaggaa      120
ctcagaaaag agacttgcct cctgtatgag atcaactggg gtggggaggca cagcatctgg   180
aggcacacct cacagaacac taacaaaac gttgaagtga atttcattga gaagttcact    240
accgagaggt acttctgccc aaatacaagg tgttccatca cttggtttct ttcctggagc    300
ccatgtggtg aatgttcaag gcaatcaca gagttttttgt caagatacccc acacgttacc   360
ctctttatat atatcgaag actgtaccac cacgccgatc caaggaatag acaagggctt    420
agggacctta tatcctccgg ggttactatc cagattatga ctgaacagga aagcgggtac    480
tgttggagga atttcgtgaa ttattcccca tcaaacgaag cacactggcc aagatacccca  540
cacctgtggg tgaggcttta tgtgttggag ctatactgca tcatcctggg gctcccacct   600
tgtcttaata ttttgagaag aaaacaacca caactcctt ttttcacaat cgctctccag    660
agctgccatt atcaaaggct gccccctcac atcttgtggg ctactgggct gaaatccggg   720
ggtagctccg ggggttccag tgggtccgaa acacctggga cttcagaatc cgcaacacct   780
gagagcagcg ggggcagcag cggcggaagt gataagaagt actcaatcgg tctggcaatc   840
ggaaccaact ctgtggggttg ggcagtgatt acagatgagt ataaggtgcc aagcaaaaaa   900
ttcaaggtgc tgggtaatac cgacagacac agcattaaga agaatttgat tggagcactc   960
ctctttgact caggggaaac agcagaggca acaaggctga aggacacagc aaggcggagg   1020
tacacaaggc ggaaaaacag gatatgctac ctccaggaaa tctttagcaa cgagatggct   1080
aaagtggatg atagctttt ccatagactc gaagaatcct tcttgttgga gaggacaaa    1140
aagcatgaaa ggcatcccat cttcggcaat atagtggatc cagata atgtgctcta       1200
taccccacaa tctaccacct cagaaagaaa cttgtggact ccacagataa agcagcctg    1260
aggctcatat acctcgcact cgcacacatg atcaagttca gagggcactt tctcatcgaa   1320
ggtgacctga atccagataa ttcagatgtg gataaactgt ttatacagct ggtgcaaaca   1380
tacaaccaac ttttcgagga aaacccaatc aatgcctcg tgtttgatgc aaaggccatc    1440
ctgtcagcaa gactcagcaa aagcaggcgg ctcgaaaaacc tcatcgccca gcttcccggt   1500
gaaaagaaga acgggctctt tggtaatctc atcgcattga gccttggtct tactccaaac   1560
ttcaagagca attttgatct ggcagaggat gctaaactgc aactctcaaa ggacacatat   1620
gacgatgacc ttgacaatct gttgcccag atcggggacc aatatgcaga cctcttcctg   1680
gccgcaaaga atctgtcaga tgcaatcctc ttgtccgaca tactgagagt taacactgag   1740
atcacaaagg cacctctgtc cgcctccatg attaagagat acgatgagca tcaccaggat   1800
ctgactttgc tcaagcctct cgttagacag cagttgccag aaagtacaa agaaatattc    1860
tttgatcaat caaaaacgg atatgcaggg tacatcgcgt gtgggcaag ccaggaagag     1920
ttctacaaat tcatcaaacc tatcctggaa aagatgatgg ggacagaaga gctgctggtt    1980
aagctgaata gggaagacct cctcagaaag cagaggacat tgataacgg gagcatccct    2040
catcaaatcc acctcggtga actccatgct atcctgagaa ggcaggaaga ctttatcca    2100
tttttgaagg acaataggga gaaaatcgaa aaaatcctga cattcagaat cccataatac   2160
gttggtcctc tggcaagagg taacagtagg ttcgcatgga tgacaaggaa aagcgaggag    2220
acaatcacac cctggaattt tgaggaagtt gttgacaagg gtgccagcgc acaatccttt    2280
atcgaaagaa tgacaaattt cgacaagaat ctgcctaacg aaaaggttct cccaaagcat   2340
tcactcctgt acgaatattt tacagtttat aacgaactga ctaaagttaa atacgttacc    2400
gagggtatga ggaagccagc attccttttcc ggggaaccaa agaaagctat tgtggacctc   2460
ctgttcaaga caaatagaaa agtgacagtt aagcaactca aagaggatta cttcaaaaag    2520
atcgaatgtt ttgactctgt ggagatcagc ggggtggagg atagattcaa cgccagcctg    2580
ggtacatatc atgatctcct gaaaatcatt aaagacaagg acttccttga caacgaggag    2640
aacgaggaca ttctggaaga cattgttctg accctcacac tctttgagga taggagagta    2700
attgaggaaa gactgaagac ctacgcccac ctctttgacg ataaagtgat gaaacagctc   2760
aagagaagaa ggtatacagg ttgggggaga ctgagcagga agttgatcaa tgggattagg    2820
gacaaacagt ccgggaaaac aatcctcgat tttctgaagt cagacggttt cgcaacagaa    2880
aattttatgc agctcattca cgatgacagc ttgacattca aggaagacat ccaaaaggct    2940
caagtgagcg gccaagggga tagcctccac gagcatattg caaatctggc aggttccacca    3000
gccatcaaaa agggtatact tcagacagtt aaggttgtgg acgaattggt taaagttatg    3060
ggcaggcata agcccagaga tatcgttatc gaaatggcaa gggagaacca aacaactcaa    3120
aaagggcaga aaaatagcag agagaggatg aaaagaatcg aggaagggat caaggaactt    3180
gggtcccaaa tcctcaagga gcacccagtt gaaaatactc aactgcaaaa cgagaagctc    3240
tatctctact atctccaaaa cgggagggat atgtatgttg accaggagct ggatattaac    3300
agactgtcag attatgatgt tgatcatatc gtgccccagt cattcctgaa ggacgattcc    3360
```

```
atcgacaaca aagttctcac aaggtccgat aaaaacaggg gcaagtccga taacgttcca 3420
agcgaagaag tggtgaaaaa gatgaaaaac tattggagac aacttctgaa tgcaaagttg 3480
attactcaga gaaagtttga caacctcaca aaagcagaaa gaggcgggct tagcgaactc 3540
gataaggcag ggtttatcaa aagacagctg gttgagacaa ggcagatcac aaaacatgtg 3600
gcacagatcc ttgactcaag gatgaatacc aagtatgatg agaatgataa gttgatcagg 3660
gaggttaaag ttatcacact caaatccaaa ctggtgtcag acttcaggaa agactttcaa 3720
ttttataagg tgagggagat caataactac caccatgcac atgacgccta cctgaacgca 3780
gtggtgggta cagcattgat taaaaaatac cctaagctgg agtctgagtt tgtgtacggg 3840
gactacaagg tgtacgacgt gaggaaaatg atagccaagt ccgagcagga gatcgggaaa 3900
gcaacagcta gtatttctt ttacagtaat atcatgaatt tctttaaaac tgagattact 3960
ctggcaaacg gggagatcag gaaaagaccc ctcatcgaga ctaatggtga aacaggtgag 4020
atcgtttggg acaaggggag ggattttgct actgttagaa aagttctgag tatgccacaa 4080
gtgaatattg tgaaaaagac agaagttcag acaggtgggt tctccaaaga atccatcctg 4140
cccaagagaa attcagacaa gctcatcgca agaaagaagg actgggacc taagaagtac 4200
ggaggatttg acagccccac cgtggcctat tccgtgcttg ttgtggcaaa ggtggagaaa 4260
gggaagagca aaaaactgaa atccgtgaaa gaactgctgg gaattaccat catggaaaga 4320
agctcctttg agaagaaccc aatcgacttc ctggaagcaa aaggatataa ggaagtgaaa 4380
aaggacctca ttatcaagct cccaaaatac tcacttttcg agttggagaa cggtagaaag 4440
aggatgctgg caagcgcagg ggaacttcag aaaggcaatg agctggcatt gccatcaaag 4500
tatgtgaact tcctctactt ggccagccat acgagaaac ttaaaggtag cccagaagat 4560
aacgagcaaa aacagctctt tgtggaacag cataagcatt atctggatga gatcatagaa 4620
caaatctcag agttttccaa gagagttatc ctcgcagatg caaacctgga taaggttctc 4680
tcagcctata ataagcatag agacaagcca attagagagc aagcagaaca cattatccac 4740
ttgttcactc ttacaaacct gggggcacca gccgccttca aatatttcga tacaacaata 4800
gacagaaaga ggtataccag caccaaagaa gttctcgacg ccacactgat ccatcaatca 4860
atcacaggcc tttacgaaac taggatcgac ttgtcacaac tgggtgggga tagcggtgaa 4920
tcaggggggct ccggtggttc aacaaatctc tccgacataa tcgaaaaaga gactggcaaa 4980
cagctcgtga tccaagagag catcctgatg ctgccagaag aggtggaaga agtgatcggt 5040
aacaaaccag agagtgacat actggttcac actgcttacg atgagagcac agatgagaac 5100
gtgatgctgc ttacaagcga tgcacctgag tacaaaccct gggctctggt tatccaagac 5160
tccaacggag agaacaagat taaatgctga agcggtggta gcgggggtag cggcggaagc 5220
actaacctca gcgacataat cgagaaagag acaggtaaac agctcgtgat tcaggaatcc 5280
atcctcatgc tcccagagga agtggaggaa gttatcggca caaaccaga atcagacatc 5340
ctggttcata cagcctatga cgagagcact gacgaaaatg tgatgctgct caccagcgac 5400
gcacccgagt acaaaaccttg gcactcgtg atacaggatt caaatggcga aaataagatt 5460
aagatgctgg gatctaagaa gagaagaatt aaacaagat                         5499
```

| SEQ ID NO: 21 | moltype = DNA  length = 5469 |
|---|---|
| FEATURE | Location/Qualifiers |
| misc_feature | 1..5469 |
|  | note = base editor |
| source | 1..5469 |
|  | mol_type = other DNA |
|  | organism = synthetic construct |

SEQUENCE: 21

```
ggatctaaga agagaagaat taaacaagat tcaagtgaga cgggcccggt cgcggtggac  60
cccacgctcc gacggcgtat cgagccccac gagttcgagg tgttttttga cccgcgcgag 120
cttcgtaagg agacctgctt gctttacgag atcaactggg gaggacggca ctccatctgt 180
cggcacacct cgcagaacac caacaagcac gtcgaggtca actttatcga gaaattcaca 240
accgagcgct acttctgccc caacacacgg tgttcaatca catggttcct gagctggtcg 300
ccttgcggag agtgctcacg cgccatcacg gagttcctgt ctcgctaccc gcacgtcacg 360
ctctttatct atatcgcacg cctctaccac cacgccgatc cgcgtaatcg ccaggggttg 420
cgcgacctaa tctcatccgg cgtaaccatt cagatcatga ccgaacaaga atctggttac 480
tgctggagga atttcgtaaa ctactccccg tcgaacgagg cccactggcc ccgctatccc 540
cacctttggg tgcgcctta cgtgctggag ctgtactgca tcatactcgg tcttcctcct 600
tgcctgaaca tccttcggcg aaagcagccg cagttgactt tcttcaccat tgcacttcaa 660
agctgccact accagcgtct ccctccacat attctctggg cgaccggctt gaagtctggt 720
ggttcaagcg gaggctcatc tggcagcgaa actccgggca cttccgagtc agctactcct 780
gagtctagcg gcgggtcgtc aggagggtct gacaagaaat acagtattgg ccttgcaatt 840
gggactaact ctgtgggatg ggccgtgatt acagacgagt acaaggtgcc gagcaagaag 900
tttaaggtgc ttgggaacac cgaccggcac tcgattaaga gaacctaat aggggcactt 960
ctgttcgact ccgagaaac cgcagaggcc accgcctta acgcaccgc acgacgacga 1020
tacccggcc gtaagaaccg gatctgctat ctacaggaaa tcttcagtaa tgagatggca 1080
aaggtggatg acagtttttt tcacaggctt gaggagtcgt tcctagttga gggagacaaa 1140
aagcacgaac gccatcccat cttcgggaac atcgtggatg aggtcgccta ccacgagaag 1200
tacccgacca tctaccacct ccgcaagaaa ctcgtggaca gcacagacaa ggctgacctg 1260
cgactgatct acttagccct ggcccacatg attaagttcc gggtcactt cctaatcgag 1320
ggagacctca accccgataa cagtgacgtg gacaagctct tcatccaact tgtgcagacc 1380
tacaaccagt tgttcgagga aaccctatc aacgccagcg gggtggacgc gaaagctatc 1440
ctgtccgcca ggctgtcgaa gtctaggcgt ctggagaacc taatcgctca gctaccgggc 1500
gaaaaaaaga tggactgtt cggcaacctc atagccctga gctggggct gacgcccaac 1560
ttcaaaagca acttcgacct ggccgaggac gccaagctcc aattgagcaa ggacacctac 1620
gacgcgact tggacaacct attggcccag ataggtgacc agtatgcaga cctcttcctt 1680
gcggccaaa acttgagtga cgctatactg ctgtcggacat tcctgaggct gaacactgga 1740
atcactaagg cccctctctc tgcctcaatg attaagcgtt acgacgagca tcaccaggat 1800
ctcacccctgc ttaaggccct tgttcggcag cagctccctg agaagtacaa ggagatattt 1860
tttgaccagt ctaagaacgg ctacgccggt tacattgacg gtggcgcaag ccaggaggag 1920
ttctacagt tcatcaagcc gatccttgag aagatggacg gcaccgagga gctacttgtc 1980
aagttgaacc gggaagacct gctccggaaa cagcgtacat cgacaacgg cagcatccct 2040
```

```
caccagatcc acctgggcga actcacgcc atcctccgac gtcaggagga cttctatcca    2100
ttcttgaaag ataacaggga aaaaatcgaa aaaatactta cgtttcgaat accttactac    2160
gtggggcccc ttgctcgggg aaactccaga ttcgcatgga tgaccaggaa gtcagaggag    2220
accatcacac cctggaactt tgaggaggtg gttgacaaag gtgcttctgc ccagtccttc    2280
attgacggga tgactaactt cgacaagaac ctgcccaacg agaaggtgct gccaaagcac    2340
agcctgctct acgaatactt tactgtgtac aatgagctga cgaaggtgaa gtacgtgaca    2400
gaggggatgc ggaagcccgc tttcctgagc ggcgagcaaa aaaagcaat cgtggaccta    2460
ctgttcaaga ccaaccgaaa ggtgacagtg aagcagctca aggaggacta cttcaaaaaa    2520
atcgagtgct tcgactctgt tgagataagc ggcgtggagg accgattcaa cgcctcattg    2580
ggaacctatc acgacctgct caagatcatt aaggacaagg acttcctgga taatgaggag    2640
aatgaggaca tcctggagga tattgtgctg acccttactc tattcgagga cagggagatg    2700
atcgaggagc gactcaagac ctacgctcac ctgttcgacg acaaggttat gaagcaattg    2760
aagcgtaggc gatacacggg gtggggaaga ctctcccgaa aactgataaa cggcatcagg    2820
gacaagcagt cagggaaatc gatcttggac ttcctgaaaa gcgacgggtt cgccaacgac    2880
aacttcatgc agctcattca cgacgactca ctaacgttca aagaggacat tcagaaggct    2940
caagtcagtg acaaggcga ctccctgcac gagcacattg caaaccttgc gggctccccg    3000
gcgattaaaa agggcattct ccaaacggtt aaggtggtgg acgagctggt gaaggtgatg    3060
ggccgacaca agcctgagaa catcgtgatc gagatgccga ggaagaacca gactacccag    3120
aagggtcaga agaactctcg ggaacgtatg aagcgtattg aggaggggat taaggagttg    3180
ggctctcaaa tcctcaagga gcaccctgtg gagaacactc agctccaaaa cgagaagctg    3240
tacctgtact acctgcaaaa cgggcgcgat atgtacgtgg atcaggagtt ggacatcaac    3300
aggcttagcg attacgacgt ggaccacatc gtgccacagt cattcttaaa ggacgacagc    3360
atcgacaaca aggttctgac gaggagcgac aagaatcgag ggaaaagtga caatgttcca    3420
tccgaggagg tggtcaagaa aatgaagaac tattggcgtc agcttctgaa cgccaagctc    3480
atcacccagc ggaaattcga caacctgact aaggctgagc gaggcggact ctccgagctt    3540
gacaaggctg gcttcatcaa gcggcagttg gtcgaaaccc gacagataac gaagcacgtt    3600
gcccagatac ttgactcccg tatgaacacc aagtacgacg agaacgacaa gctcatcagg    3660
gaggtgaagg tcattaccct taagtccaaa ctcgtcagcg actttcgtaa ggacttccag    3720
ttctacaagg tgcgcgagat caataactac caccacgcac acgacgccta cctgaacgca    3780
gtggttggaa ccgcgttgat taaaaagtac cccaagttgg agtcggagtt cgtttacggg    3840
gactacaagg tgtacgacgt tcggaagatg atcgccaagt ctgaacagga gatcgggaaa    3900
gcaaccgcca agtatttctt ctatagcaac atcatgaact tctttaaaac cgagatcaca    3960
cttgccaatg gcgagatccg taagaggccg ctgatcgaga caaatgggga gactggcgag    4020
atcgtgtggg acaagggccg cgacttcgca accgttcgga aagtcttgtc catgcctcaa    4080
gtcaacatcg tcaagaagac tgaggtgcaa acaggcgggt tctcgaagga gtccatactg    4140
cccaagagga actcagacaa gctcatagca cgcaaaaaag actgggatcc aaagaaatac    4200
ggcgggttcg actcgccgac agtcgcatac tccgtgttag tggtggctaa agtggaaaag    4260
gggaagtcca agagctcaa gtccgtcaag gagttgctcg ggatcaccat tatggaacgg    4320
tcctcattcg agaagaatcc cattgacttc ctagaggcga agggctacaa agaggtcaaa    4380
aaggacctaa ttattaagct ccccaagtat tcactcttcg aacttgaaaa tggtcgtaag    4440
cggatgttgg caagcgctgg agagcttcag aaggggaacg agcttgcact gccttccaag    4500
tacgtgaact tcctgtacct cgcctctcat tacgagaagt tgaagggctc accggaggac    4560
aacgagcaga agcagttgtt cgtggagcag cacaagccat acctcgacga gatcattgag    4620
cagataagtg agttcagcaa acgggtgatc cttgccgacg ctaacctgga caaggtgctg    4680
agcgcctaca acaagcacag agacaagccg atccgagagc aagcggagaa catcatacac    4740
ctgttcaccc tcacgaacct cggggctccc gcagccttca atatttga cacgaccatc    4800
gaccgtaaac gctacactag cacgaaggag gtgctggacg ctaccctta ccaccagtcc    4860
atcaccggcc tgtacgagac gagaatcgac ttgtcgcagc tcggtggtga ctctggcggt    4920
agtgaggaa gcgcgggag taccaacctc agcgacatta tcgagaagga gaccggcaag    4980
caactcgtga tccaggagag catactgatg ctccccgagg aggtcgagga ggtgattggc    5040
aataagccg agtccgatat actggttcat actgcgtatg acgaaagcac agacgagaac    5100
gtcatgctac ttaccagcga cgccccggag tacaagccct gggccctagt catccaagac    5160
agcaacggtg agaacaagat caagatgctt accaacctga gcgacatcat tgaaaaggag    5220
accggaaagc agcttgtgat ccaggagtcc atcctaatgt tgcccgagga ggtcgaggag    5280
gtcatcggaa acaagcccga gtcggacatc ctagtgcaca ccgcctacga cgaatcgacc    5340
gacgagaacg tgatgctcct cacctccgac gcacctgagt acaagccgtg ggccctcgtt    5400
atccaagact ctaatggtga gaacaagatc aagatgctcg gatctaagaa gagaagaatt    5460
aaacaagat                                                             5469

SEQ ID NO: 22        moltype = DNA   length = 5499
FEATURE              Location/Qualifiers
misc_feature         1..5499
                     note = base editor
source               1..5499
                     mol_type = other DNA
                     organism = synthetic construct
SEQUENCE: 22
ggatctaaga agagaagaat taaacaagat tcgtccgaga ccggcccgt cgccgttgac     60
ccgaccctcc gccgccgcat cgagcccat gagttcgagg tgttttttcga cccacgtgaa   120
ctccgcaagg aaacttgcct cctgtacgag atcaactggg gtggacgtca ctccatctgg   180
agacacacca gccagaacac gaacaagcac gtcgaggtca acttcatcga gaagttcacc   240
accgagcgct acttctgccc caacacgcgg tgctcgatca cgtggttcct gtcctggtcc   300
ccatgcgggg agtgcagccg cgccatcacc gagttcctct cccgatccc gcacgtcacc   360
ctcttcatct acattgcccg gctctaccac acgcagaccg acgaaaccg caggggctca   420
cgcgacctca tatcctccgg cgtgaccata cagatcatga ccgaacagga gtctggctac   480
tgctggcgca acttcgtgaa ctacagcccc tcgaacgagg cccactggcc gcgttaccc    540
cacttgtggg tgaggctgta cgtcctggag ttgtactgca tcatcctggg cctgcctccc   600
tgcctaaaca tcctccgccg gaagcagccc cagctcacgt tcttcacaat tgcgttgcaa   660
tcctgtcact accagcggct tccacctcac atcctctggg ctaccggcct caagagcggc   720
```

```
ggtagctccg gaggctcatc tgggagcgag acacccggca cttccgagtc tgcaaccccg    780
gagagtagtg gtggctcctc tggtggatct gacaaaaaat actcaattgg tctggcaatt    840
gggaccaaca gtgtcggatg ggccgtgatt accgacgagt acaaggtgcc gtccaaaaaa    900
ttcaaggtgc ttgggaacac cgaccgccac tcgatcaaga aaaacctaat cggtgcgttg    960
cttttcgaca gtggggagac cgccgaggca acacgcttta aacgcacagc taggaggaga   1020
tatacacggc gcaagaaccg aatatgctac ttacaggaga tattctccaa tgagatggca   1080
aaggtggacg actctttctt ccatcggctt gaggaatcct tcctggtcga ggaggacaag   1140
aagcacgagc gacacccgat attcgggaac atcgttgatg aggtggcgta ccacgagaag   1200
tacccaacga tataccactt acgcaagaag ctcgtggact ctacgacaa ggccgacttg    1260
cgccttatct acttggcact ggcccacatg attaagttcc gaggccactt ccttatcgag   1320
ggtgacctga accccgataa ctccgacgtg gacaagctct tcatccaact cgtccagaca   1380
tacaaccagc tattcgagga gaatcctatc aacgcctctg ggtggacgc taaagctatc    1440
ctctcagccc gcctgtcaaa gtcgaggagg ttggagaacc taatcgccca gcttccaggc   1500
gagaagaaaa atgggctgtt cggaaaactt atcgcactct cactgggcct aaccccgaac   1560
ttcaagtcca acttcgacct ggcagaggac gcgaaattgc agttgtcgaa agacacctat   1620
gacgatgacc tggacaacct gttggcccag ataggggacc agtacgccga cctgttccta   1680
gcggccaaga acctgtccga cgccatcttg ctgtcggata tactgcgggt gaacaccgag   1740
atcactaaag cacctctctc cgccagcatg attaagcgtt acgacgagca ccaccaagat   1800
ttgaccctgc taaaggcact tgtacggcag cagcttcccg agaagtacaa ggagatctt    1860
ttcgaccaaa gcaagaacgg ctacgccggg tacatcgacg gaggtgccag ccaggaggag   1920
ttctacaagt tcattaagcc catcctggag aagatggacg ggactgagga actacttgtg   1980
aagctgaacc gggaagactt actacggaag cagcgtaccc tcgacaacgg ttctatccca   2040
catcagatcc atcttgggga gttgcacgcg atcctgcgac gccaggagga cttttacccc   2100
ttcctgaaag acaaccgcga gaaaatcgag aagatactga ccttcagaat accttactac   2160
gtcggacccc ttgcgcgagg caactcaaga ttcgcgtgga tgaccaggaa atcagaggag   2220
accatcacac cctggaattt cgaggaggtg gttgacaagg gtgcctccga ccagtcctt    2280
atcgaacgaa tgaccaactt cgacaagaac ttgcccaacg agaaggtgct ccccaaaaca   2340
agcctcctct acgaatattt cacagtgtac aacgagctta ctaaagttaa gtatgttact   2400
gagggcatga ggaaacccgc cttcctgtca ggcgagcaga gaaagctat tgtgacctc     2460
cttttcaaga ccaaccggaa ggtgacagtg aagcagctca aggaggacta cttcaagaag   2520
atagagtgct tcgacagcgt ggagatcagc ggggtggagg acagattcaa tgcctctctc   2580
ggaacatacc acgacttgct taagatcatc aaggacaagg acttcctcga caacgaggaa   2640
aacgaggata ttctggagga tattgttctg actcttaccc tgttcgagga ccgggagatg   2700
atcgaggagc gtctcaagac ctacgcccac ctgttcgacg acaaagttat gaagcagctc   2760
aagcgtcgga gatataccgg atggggccgt ctgtctcgga agctcatcaa cgggatcagg   2820
gacaagcagt cagggaagac gatcttagac ttccttaagt ctgacggctt cgccaacagg   2880
aacttcatgc agttgatcca cgacgacagc cttaccttca aggaggacat ccagaaggcc   2940
caagtgagtg gccagggtga cagcctccac gagcatattg ctaatcttgc gggttcccca   3000
gcgattaaaa agggcatact tcaaaccgtt aaggtggtgg acgagcttgt caaggtgatg   3060
gggcgacaca gcccgagaa catcgtgatc gagatggcca gggaaccaga gaccacccag   3120
aaggggcaga agaatagccg agaacgcatg aagcgcatcg aggagggat taaggagcta   3180
gggagccaga tcctcaagga acatccgtc gagaacaccc agctcagaa cgagaagcta   3240
tacctctact acttgcaaaa cgggagggat atgtacgtgg ataccaggtg acagcattaac   3300
cgcctaagcg actacgacgt agatcacatc gtgcctcagt cattcctcaa agacgacagc   3360
attgacaaca aagtcttgac ccgatccgac aagaaccgag gaaaatccga caatgtgccc   3420
tcagaggagg tcgtcaagaa aatgaagaac tattggaggc agctacttaa cgccaaactc   3480
ataacccagc ggaagttcga caacctgaca aaggctgagc ggggtgggct ccgcgagctt   3540
gacaaggctg gcttcatcaa gcggcagttg gtggagacaa gacagataac gaagcacgtg   3600
gctcagatcc tggactctcg catgaacacg aagtacgacg agaacgacaa attgatccgc   3660
gaggtcaagg ttattacgct caagagcaaa cttgtcagcg atttccgcaa ggacttccag   3720
ttctacaagg tgagggagat taacaactac caccatgcac atgatgccta cttgaacgca   3780
gtggtgggga ccgcgcttat taaaaagtac cctaagttgg agtcagagtt cgtttatggg   3840
gactacaagg tgtacgacgt ccggaagatg attgcaaagt ctgaacagga aatcgggaag   3900
gccaccgcca aatatttctt ctacagtaac attatgaatt ttttaagac tgaaattact   3960
ctcgcacgga gcgagatcag gaagcgtccc ctcatcgaga caaacgggga gaccggggag   4020
atagtctggg acaaggggcg ggacttcgct acggtgagga aggtgctctc gatgccacaa   4080
gtgaacatcg tcaaaaagac agaggtgcag accgtggct tctcaaagga gtcaatcctg   4140
ccaaaacgta acagcgacaa gctcatcgcc cgcaagaaag actgggaccc taagaagtat   4200
ggtgggttcg actcaccgac ggtgcatac tccgttctgg tcgtggcaaa ggtggaaaag   4260
ggcaagtcca aaaactgaa atccgtgaag gagttgcttg gcattaccat catggaacgc   4320
agcagcttcg agaagaaccc cattgacttc ctggaggcta aagggtacaa ggaggtcaag   4380
aaaagatttaa ttattaagct acctaagtac agcttgttcg agctggagaa cggccgaaaa   4440
cgaatgctcg catccgccgg ggaacttcaa aagggcaacg agcttgcgct gccctccaag   4500
tacgtgaact tcctgtactt ggcatcccac tacgagaaac tcaagggtag cccagaggac   4560
aacgagcaga agcagctatt cgtggagcag cacaagcact acctcgacga gataatcgag   4620
cagatcagtg agttcagtaa gcgggtgata ctcgcggacg ccaacttgga caaggtgctt   4680
agtgcctaca acaagcaccg tgacaagccc atccgagaac aggctgagaa catcatccac   4740
cttttcactc tgacaaacct cggtgctccc gccgccttca aatacttcga cactaccatc   4800
gacaggaagc gctacacatc tacgaaggaa gttcttgacg ctacgcttat tcatcagtct   4860
atcacagggc tgtacgagac aaggatcgac cttagccaac tcggcgggga ttccggagga   4920
agcggcggct ccggtggttc tacaaacctg tccgacatca tcgagaagga aaccggcaag   4980
cagcttgtga tccaggagag catactcatg ctccccgagg aggtcgagga ggtgatcggc   5040
aacaagcccg agtcagacat tctggtccac acagcctacg acgagtcaac cgacgagaac   5100
gtgatgctcc tgacaagcga cgcgcccgag tacaagccca acatcgacaa gtttgatgct   5160
tcgaatgggg agaacaagat caagatgctt agtggaggct ctggagggag cggtggatca   5220
actaacctgt ctgacattat cgaaaaggag acgggcaagc agcttgtgat ccaagaatct   5280
atcctaatgt tgccggagga ggtcgaggag gtgattggaa caagccggaa agcgacatc    5340
ctcgtccaca ccgcctatga cgagagcacg gacgagaatg tgatgctcct gacatcagac   5400
gcgccggagt acaagccgtg ggccctggtc ataacaggaca gcaacgggga gaacaagatc   5460
```

SEQ ID NO: 23        moltype = DNA   length = 3987
FEATURE              Location/Qualifiers
misc_feature         1..3987
                     note = Cas12a polynucleotide
source               1..3987
                     mol_type = other DNA
                     organism = synthetic construct
SEQUENCE: 23
atggccggga gcaagaagcg ccggataaag caggacacgc agttcgaggg cttcaccaac     60
ctgtaccaag tctccaagac gctccggttc gagcttatcc cgcaagggaa gaccctgaaa    120
cacatccagg aacaaggttt catcgaggag gacaaggccc gcaacgacca ctacaaggag    180
ctcaagccca taatcgatcg gatctacaag acgtacgccg accagtgcct ccaactggtg    240
cagctcgact gggagaacct gagcgccgcc attgacagct accgcaagga aaagacggag    300
gagacgcgca acgcccttat tgaggagcaa gccacctacc gcaacgccat ccacgactac    360
ttcatcgggc gcaccgacaa cctgacggac gcgatcaaca agcgccacgc ggaaatctac    420
aagggccttt tcaaggccga gctcttcaac gggaaggtcc taaaacagct cgggactgtc    480
acgacaaccg agcatgagaa cgccctcctt cgcagcttcg acaagttcac cacatacttc    540
tcgggcttct accggaaccg caagaacgtt tcagcgccg aggacatctc caccgccatc    600
ccgcacagga tcgtccagga caacttcccc aagttcaagg agaactgcca catcttcacg    660
cgcctgatta cagccgtacc ttcacttcgt gagcacttcg agaacgtcaa aaaggccatc    720
gggatcttcg tctccacgtc catcgaggag gtattctctt tcccgttcta taaccagctc    780
ctgacccaga cgcagatcga cctctacaac cagctactgg gcggcatcag ccggaggcc    840
gggaccgaga aaataagggg cctcaacgaa gttctcaacc tggccatcca agaacgac     900
gagaccgcgc atatcatcgc atccctgccg catcgcttca ttcctttgtt caagcagata    960
ttgagcgacc ggaacaccct ctcgttcatc ctcgaagaat tcaagagcga cgaggaggtc   1020
attcagtctt tctgcaagta caagacgctc tacggaatgg agaatgtgct ggagaccgcg   1080
gaggcactct tcaatgagct gaactccatt gacctgaccc acatcttcat tagccacaag   1140
aaactggaga cgatctccag cgccctgtgc gaccactggg acactctccg caacgccctc   1200
tacgaacgcc ggatctccga acttaccggc aagataacta agtcggctaa ggagaaggtg   1260
caacggagcc tcaagcacga ggacatcaac cttcaggaaa tcatctcagc cgcgggcaag   1320
gagctgagcg aggcgtttaa gcagaaaaca tcggagatac tgagccacgc gcacgcggcc   1380
ctggatcaac cgctgccgac gactctcaag aagcaagagg agaaggaaat ccttaagtcc   1440
cagctcgact cgctgctcgg cctctatcac ttgctcgact ggttcgcggt tgatgagtcc   1500
aacgaggtgg accggagtt ctccgcgcgc tcacgggta ttaagctgga gatgagcca    1560
agcttaagct tctacaacaa ggccgcaac tacgcgacca aaaaaccgta ctcagtcgag    1620
aaattcaagc tgaatttcca gatgcctaca ttggcgaggg ggtgggacgt gaaccgcgag    1680
aagaacaatg gagccatcct gttcgtcaaa aatgggttgt actacctggg catcatgccc    1740
aagcagaagg gccgttacaa ggccctgtca ttcgagccta ccgagaagac ctcggagggc    1800
ttcgacaaga tgtactacga ctatttcccg gacgccgcca agatgatccc gaagtgctcc    1860
acgcagctca agccgtcac ggcccacttc cagacgcata ccacgccgat acttctgagc    1920
aacaacttca ttgagccgct agagatcacg aaggagatat acgacctaaa caaccccgaa    1980
aaggagccca agaagttcca gacagcctac gctaagaaga caggtgatca gaagggatat    2040
agggaggcac tctgcaagtg gatcgacttc acgcgcgact tcctgtcgaa atatacaaag    2100
acgaccagca ttgacctaag ttctctccgc ccatcctccc agtacaagga tctgggcgag    2160
tattatcgg agctgaaccc attgctgtac cacatccgct tccagaggat cgccgagaag    2220
gagattatgg acgcggtgga acgggaaaa ctataccgt tccaaatata taacaaggac    2280
ttcgctaaag ggcaccacgg gaagcccaac ctgcacacac tctactggac gggcttgttt    2340
tcgccagaaa atttggccaa gacttcgatc aagctcaacg ccaggcgga gttgttttac    2400
cgtccaagt ctcgcatgaa gcgcatggcg catcgcctcg gagagaaaat gcttaacaag    2460
aagctcaagg atcagaagac gcccatacct gatacgttgt accaggaatt gtacgactac    2520
gtgaaccacc gcctatcgca cgacctctca gacgaggccc gcgcctcct cccaaacgtg    2580
attactaagg aggtttccca tgaaataatc aaggaccgac ggttcaccag cgacaaattt    2640
ttttccacg tgcctatcac gctcaattac caggcggcca actccccatc gaagttcaac    2700
cagcgcgtga acgcctacct taaggagcac ccggagaccc aatcatcgg gatcgaccgt    2760
ggcgagcgga acctgatcta tattacggtg atcgatagca ccgggaagat cctggagcag    2820
cgctccctga acacaatcca gcagtttgac taccagaaga actcgacaa ccgggagaag    2880
gagcgcgtcg cagcccggca agcatggagt gtggtcggca ccataaagga cctgaaacag    2940
ggttacctaa gtcaagttat ccacgagatc gttgacctga tgatacacta tcaagccgta    3000
gtcgtgctgg agaacctcaa cttcgggttt aagtccaagc gcaccggcat cgcggagaag    3060
gcggtgtacc agcagttcga gaagatgctg atcgacaagc tgaactgcct ggtgctcaag    3120
gactaccctg cggagaaggt cggcgggtc ttgaacccgt accagctaac cgaccagttc    3180
acgagcttcg ccaaaatggg cacgcagtcc ggattcttgt tttatgtccc ggctccatat    3240
acaagtaaga tcgacccgct gacagggtt gttgaccat tcgtgtggaa gaccatcaag    3300
aaccacgaga gcaggaaaca cttcttgagg ggcttcgact tcctgcatta cgacgttaag    3360
acaggcgact tcatcctgca cttcaagatg aaccgcaacc tgtcgttcca gaggggcctg    3420
cccggcttca tgccgcctg gatatcgtc tttgagaaga tgacgca gttcgacgcg    3480
aagggggacgc cgttcatcgc tggaaagcgg atcgtgccgg tcatcgaaca ccacgcttc    3540
acgggtcgct accgagattt ataccccgcc aacgaactaa ttgcgctgct ggaggagaag    3600
gggatcgtgt tccgagatgg cagcaacatt ctcccgaagc tgctggagaa cgacgactcg    3660
cacgctattg acacgatggt cgccctcata cggagcgtgc ttcagatgcg gaacagtaac    3720
gctgccacgg gcgaggacta cattaactcc ccgtccgcg acctcaacgg ggtctgcttc    3780
gatgccgct tccagaactg ggagtggcct atggatgcgc acgcgaacgg gcctaccgac    3840
atcgccctca agggcaact cctgctcaac cacttgaagg aaagcaaaga cctcaaattg    3900
cagaatggca tcagtaacca ggactggctc gcgtacatcc aggaactgag aaacgggtcc    3960
aagaagcggc gtatcaagca agattga                                       3987

SEQ ID NO: 24        moltype = DNA   length = 3987

| FEATURE | Location/Qualifiers |
|---|---|
| misc_feature | 1..3987 |
| | note = Cas12a polynucleotide |
| source | 1..3987 |
| | mol_type = other DNA |
| | organism = synthetic construct |

SEQUENCE: 24

```
atggcgggaa gcaaaaagcg ccggattaag caagacacgc agttcgaggg cttcacgaac    60
ctctaccaag tcagcaagac cctccggttc gagctgatac cacaggaaa gacgctcaag    120
cacatccagg aacagggctt catcgaggag gacaaggcgc gcaacgacca ctacaaggag    180
ttgaaaccga tcatcgaccg catctacaag acgtacgccg accagtgcct ccagctcgtg    240
cagctcgact gggagaacct ctccgccgcc attgactcgt accggaagga gaagactgag    300
gagacccgca acgccctgat cgaggagcaa gcaacctacc ggaacgccat ccacgactac    360
ttcatcggcc gcaccgacaa cctcaccgac gcgatcaaca ggcgcacgc ggagatatac    420
aaagggctgt tcaaggcgga gctgttcaac ggcaaggtgc tcaagcagct agggacggtg    480
accacgaccg agcacgagaa cgcgctcctc cgcagcttcg acaagttcac cacctacttc    540
agcggcttct accggaaccg caagaatgtg ttcagcgcgg aggacatcag cacggccatc    600
ccgcaccgca tcgtccagga caacttcccg aagttcaagg agaactgcca catcttcacc    660
cgcctgataa ccgccgtccc ctccctgcgg gagcacttcg agaacgtcaa aaaggcaatt    720
gggatcttcg tctcgaccag cattgaggag tgttcagct tcccttcta caaccagctc    780
ctcacccaga cgcagatcga cctgtacaat cagttgctcg gcgggataag ccgcgaggcg    840
ggaacccgaaa aatcaaggg gctgaacgaa gtgttgaaca tcgccatcca gaagaacgac    900
gagaccgcgc acatcatcgc ctccctgccc caccggttca tcccgctgtt caagcagatc    960
ctctctgacc ggaacaccct gtccttcatt cttgaggagt tcaagtcgga cgaggaggtc    1020
atccagagct tctgcaagta caagacgctg ctacggaacg agaacgtgct ggagacggcg    1080
gaggcactgt tcaacgagct aaacagcatc gacctcacgc acatcttcat cagtcacaag    1140
aaactggaga ccatctcctc cgcgctgtgc gaccactggg acacgctcag gaacgcgctc    1200
tacgagcgcc gaatcagtga gctgacgggc aagatcacga agtccgcgaa ggagaaggtg    1260
cagcggtccc tcaagcacga ggacatcaac ctccaggaga tcatctcagc ggctgggaaa    1320
gagctgtccg aggcgttcaa gcagaaaacg agcgaaatcc tgtccacgc gcacgcggcc    1380
ctggatcagc ctctgccgac gaccctcaag aaacaagaag aaaaggaaat cctcaagtcg    1440
cagctcgact cgctgctggg cctgtaccat ctcctcgact ggttcgccgt ggacgagagc    1500
aacgaggtgg accccgagtt ctccgcgcgg cttacgggga tcaagctgga gatggagccc    1560
agcctgtcct tctacaacaa ggcgcgcaac tacgccacca agaagccca cagcgtggag    1620
aagttcaagc tcaacttcca gatgccacct ctcgcacgtg ggtgggacgt caaccgcgaa    1680
aaaaataatg gggcgatcct gttcgtcaag aacggcctgt actactgggg catcatgccg    1740
aaacagaagg gccgctacaa ggccctgagc ttcaaccga ccgagaaaac gagcgagggg    1800
ttcgacaaga tgtactacga ctacttcccc gacgccgcga agatgattcc aaagtgctcc    1860
acgcagctta aggccgtgac ggcccacttc cagacgcacg cgacccgat cctcctcagc    1920
aacaacttca tcgagcccct ggagatcacg aaggagatat acgacctgaa caacccggag    1980
aaggagccca gaaattcca gaccgcctac gccaagaaga caggcgacca aaagggttac    2040
agggaggccc tctgcaagtg gatcgacttc actagggact tcctgtccaa gtacaccaag    2100
actacctcta tcgacctgtc cagcctccgc ccgtcgtccc agtacaaaga tttgggcgag    2160
tattacgcgg agctgaaccc actgctctac cacatcagct tccagcgcat cgcggagaag    2220
gagatcatgg acgcagtgga cggggcaag ctataccta ttcagatata caacaaagac    2280
ttcgctaagg acaccacggg caagcctaac ctgcacaccc tctactggac ggggctcttc    2340
agcccggaga acctcgccaa gaccatcgatc aagctcaacg gccaggccga gctgttctac    2400
cggcccaagt cccgcatgaa gcggatggcc caccggctcg gggagaaaat gctcaacaag    2460
aaattgaagg accaaaaaac gccgatacc gacaccctat accaggagct gtacgactat    2520
gtgaaccacc gcctgagcca cgacctcagc gacgaggcgc gggcccctcc tgccgaacgtc    2580
atcacaaagg aggtcagcca cgagatcaatc aaggaccggc gcttcacctc cgacaagttt    2640
ttctttcacg tgcccatcac gctcaactac caggccgcca actcgccgtc caagttcaac    2700
cagcgcgtga acgcctacct caaggagcac cccgagaccc cgatcatcgg gattgaccga    2760
ggggagcgga acctcatcta catcaccgtc atcgacagca ccgggaagat ccttgaacag    2820
cggtcgtca acaccatcca gcagttcgac taccagaaga actcgacaa ccgggagaag    2880
gagagagtgg cggcccgcca ggcttggtcc gtcgtcggga cgattaagga cttgaaacaa    2940
ggttacctgt cgcaagtgat ccacgagatc gttgacctga tgatccacta ccaagccgtc    3000
gtggtcctgg agaacctcaa cttcggcttc aagagcaaac gaaccggcat cgcggagaag    3060
gccgtgtacc agcagttcga aaaaatgctg atcgacaagc tgaactcgct cgtgctcaag    3120
gactacccgg ctgagaaggt cggcggggtg ctgaaccgt accagctcac tgaccagttc    3180
accagcttcg caaagatggg cacccagtcc ggcttcctgt tctacgtgcc tgcgccatac    3240
acctcgaaga tcgaccgcct caccgggttc gtggacccct tcgtctggaa gaccatcaag    3300
aaccacgaga gccgcaagca cttcctggag ggcttcgact tcctccacta cgacgtcaag    3360
accggggact tcatcctgca cttcaagatg aaccgcaacc tcagtttcca gcggcctg    3420
ccgggggttca tgcccgcttg ggatatagtc ttcgagaaga atgagacgca gttcgacgcg    3480
aagggcaccc cgttcatcgc cgggaagcgc atcgtgccgg tcatcgagaa ccaccggttc    3540
accgggcgct accgcgacct ataccgcgg aacgagttga tcgccctcct ggaggagaag    3600
ggcatcgtgt tccgcgacgg ctccaacatc ctcccgaagc tgctcgaaaa cgacgactcc    3660
cacgccatcg acacgatggt gcgctgatc cggtcggtcg tccagatgcg gaactccaac    3720
gccgcgacgg gcgaggacta catcaacagt ccggtccgcg atctgaacgg cgtctgcttc    3780
gactccggt tccagaaccc cgagtggccg atgacgcgg acgcgaacgg cgcataccac    3840
atcgccctaa aagggcaatt gctgctcaac cacctcaagg aatccaaaga cctaaagctc    3900
cagaacggca tctccaacca ggactggctg gcgtacatcc aggaactgcg gaacgggagc    3960
aaaaaacgtc ggatcaagca agattga                                          3987
```

| SEQ ID NO: 25 | moltype = DNA length = 3987 |
|---|---|
| FEATURE | Location/Qualifiers |
| misc_feature | 1..3987 |
| | note = Cas12a polynucleotide |

|  |  |  |
|---|---|---|
| source | 1..3987 | |
| | mol_type = other DNA | |
| | organism = synthetic construct | |

SEQUENCE: 25

| | | | | | |
|---|---|---|---|---|---|
| atggcgggct | ccaagaaacg | ccggattaag | caagataccc | agttcgaggg | gttcacgaac | 60 |
| ctctaccaag | tgagcaagac | cctccgattc | gaactgattc | ctcagggaa | gaccctcaag | 120 |
| cacatccagg | agcaagggtt | catcgaggag | gacaaggcgc | ggaacgacca | ctacaaggaa | 180 |
| ctcaaaccca | tcatcgaccg | catctacaag | acctacgccg | atcagtgcct | ccagctcgtg | 240 |
| cagttggact | gggagaacct | cagcgcggcc | attgactcct | accggaagga | gaaaacggag | 300 |
| gagacgcgca | acgcgctcat | cgaggaacag | gcaacctatc | gcaacgccat | ccacgactac | 360 |
| ttcatcggga | ggactgacaa | cctcactgac | gcgattaaca | agcgcacgc | ggagatatac | 420 |
| aagggactct | tcaaagcgga | gctgtttaac | ggcaaggttc | tcaagcaact | cggcactgtg | 480 |
| accacgaccg | agcatgagaa | cgccctgctc | cgctccttcg | acaagttcac | cacctacttc | 540 |
| tccgggttct | accgcaaccg | caagaatgtc | ttcagcgcgg | aggacatcag | cacggccatt | 600 |
| ccacatcgaa | tcgtccaaga | taacttcccg | aagttcaagg | agaactgcca | catcttcacc | 660 |
| cgactcatta | ctgctgtacc | gtcgttacgc | gaacacttcg | agaacgtcaa | gaaggcaatt | 720 |
| ggaatcttcg | tctctacgtc | aatagaggag | gtgttcagct | tccctttcta | caaccagctc | 780 |
| cttacgcaga | cccagataga | cctgtacaat | cagctcctcg | gtgggatcga | ccgggaggcg | 840 |
| gggactgaga | agattaaagg | gctcaacgag | gtcttgaacc | tggccatcca | aaaaaacgat | 900 |
| gagacggcgc | acatcatcgc | ctcgctgccc | caccggttca | tcccgctgtt | caagcagatc | 960 |
| ctcagtgaca | ggaacacctt | gagctttatc | ctagaggagt | tcaagagcga | cgaggaggtg | 1020 |
| atccagagct | tctgcaagta | caaaaccctg | ctgaggaacg | agaacgtcct | ggagacgcgg | 1080 |
| gaggcgctgt | tcaacgagct | gaactctatc | gacttaactc | acatattcat | ctcgcacaag | 1140 |
| aagctggaga | ctattagctc | tgcactctgc | gaccactggg | acaccctccg | caacgcgctc | 1200 |
| tacgagcgcc | gcatctcgga | gctgaccggg | aagatcacca | aatccgcgaa | ggaaaaggtc | 1260 |
| cagcgttccc | tcaaacacga | ggatattaac | ttacaggaga | ttatctcagc | ggctgggaag | 1320 |
| gagttgtcag | aggcgttcaa | gcagaaaact | tccgagatcc | tgagccacgc | gcacgcagcg | 1380 |
| ctcgaccagc | ctctgcccac | caccctcaaa | aagcaggaag | aaaaagagat | cctcaagagc | 1440 |
| cagttggact | ccctgctggg | gctctatcac | cttctcgact | ggttcgccgt | cgatgagtcg | 1500 |
| aacgaggtgg | accccgagtt | ctccgcccgg | ctgaccggca | tcaagctaga | gatggagccg | 1560 |
| tccctcagct | tctacaataa | ggccgcaac | tacgcgacca | aaaaccccta | cagcgtggag | 1620 |
| aagttcaagc | tgaacttcca | gatgccgacc | ttagcacgcg | gttgggacgt | aaacagggag | 1680 |
| aagaacaatg | gagccatcct | gttcgtcaag | aacgggcttt | actacctcgg | gataatgccc | 1740 |
| aagcagaagg | gccgctacaa | ggcccttttcc | ttcgagccga | cggagaaaac | ctccgagggg | 1800 |
| ttcgacaatga | tgtactacga | ctacttcccc | gacgccgcca | agatgatccc | gaagtgctca | 1860 |
| acgcagctaa | aagccgtgac | cgcccacttc | cagacccaca | cgacgccgat | cctgctgagc | 1920 |
| aacaacttca | tcgagcccct | tgagatcact | aaggagatat | acgacctgaa | caaccccgag | 1980 |
| aaggagccca | agaagtttca | aaccgcctac | gccaaaaaaa | ctggcgacca | aaagggctac | 2040 |
| agggaggcgc | tgtgtaagtg | gatcgacttc | acacgcgact | tcctttcgaa | gtatacgaag | 2100 |
| acaacctcta | ttgacctgag | cagcctgcgt | cctagctccc | agtacaaaga | tttgggcgag | 2160 |
| tactacgcgg | agcttaatcc | actactctac | cacatctcat | tccagcgcat | cgctgagaag | 2220 |
| gaaatcatgg | acgcggtgga | gacaggcaaa | ctgtacctct | tccagatata | caacaaagac | 2280 |
| ttcgctaagg | ggcaccacgg | gaagcccaac | cttcatacgc | tctactggac | gggcctattc | 2340 |
| agccccgaaa | atctggccaa | gacctccatc | aagctgaacg | gccaagcgga | gctgttctac | 2400 |
| agacccaaga | gccggatgaa | gcggatggcc | cacaggctcg | gcgagaaaat | gcttaacaaa | 2460 |
| aagttgaagg | accagaaaac | ccctatcccc | gacaccctct | accaggaact | gtacgactac | 2520 |
| gtgaaccaca | ggctctcgca | cgacctttcc | gacgaggccc | gtgccctact | cccgaaccgt | 2580 |
| attaccaaag | aggtttcgca | cgagatcatc | aaggaccggc | ggttcacgag | cgacaagttt | 2640 |
| ttctttcacg | tccccatcac | ccttaactac | caggcggcca | actccccatc | caagttcaac | 2700 |
| cagcgtgtga | atgcctacct | caaggagcac | ccagagaccc | cgatcattgg | gatcgaccgg | 2760 |
| ggcgaggcga | acctgatcta | catcaccgtc | atcgactcga | cgggcaagat | tcttgagcag | 2820 |
| agatcgttga | ataccataca | gcagttcgac | taccagaaga | aactcgacaa | ccgcgagaag | 2880 |
| gagcgcgtgg | cggcccgcca | ggcgtggtcc | gtcgttggga | cgattaagga | cttgaaacaa | 2940 |
| ggttatctgt | cccaagtcat | ccacgagatc | gttgatctga | tgatccacta | tcaggcagtg | 3000 |
| gtggtgctgg | agaatctcaa | cttcggcttc | aagagtaagc | ggacgggaat | cgccgagaag | 3060 |
| gccgtgtacc | agcagttcga | gaagatgctg | atcgacaagc | tcaactgcct | tgtgctgaaa | 3120 |
| gactaccgg | ccgagaaggt | cggcggcgtc | tcaacccgt | accaacttac | cgaccagttc | 3180 |
| acctccttcg | ccaagatggg | cactcagtcc | gggttcttgt | tctacgtccc | cgcaccttac | 3240 |
| acctctaaga | tcgaccctct | gactggcttc | gtagatccat | tcgtgtggaa | gaccattaag | 3300 |
| aaccacgaga | gccgcaagca | cttcctggag | ggcttcgact | tcctgcacta | cgacgtgaag | 3360 |
| accggggact | tcatccttca | cttcaagatg | aaccggaacc | tcagcttcca | gcggggcctg | 3420 |
| ccggggttca | tgcccgcctg | ggacatcgtg | ttcgagaaga | acgagaccca | gttcgacgcg | 3480 |
| aagggcacgc | ccttcatcgc | cgggaagcgt | atcgtgccgg | tgatcgagaa | ccatcgtttc | 3540 |
| acgggtcgct | accgtgacct | ctacccggcg | aacgagctta | cctgcactcc | gagggagaag | 3600 |
| ggcatcgtct | tccgggacgg | ctccaacatc | ctcccgaaac | tgctggaaaa | cgacgactct | 3660 |
| cacgccatcg | acacgatggt | ggccctcatc | cggtccgtgc | tccaaatgcg | gaacagcaac | 3720 |
| gccgccaccg | tgaggacta | catcaacagc | ccggtccggg | atctgaacgg | ggtgtgcttc | 3780 |
| gattcgcggt | tccagaatcc | tgagtggccg | atggacgcgg | atgcaaacgg | ggcgtaccac | 3840 |
| atcgcgctca | agggccagtt | acttctgaac | caccttaagg | agtctaaaga | tttgaaactc | 3900 |
| cagaacggga | tctcgaacca | ggactgctg | gcctacatcc | aagagttgcg | gaacggcagc | 3960 |
| aagaagcggc | ggattaagca | agattag | | | 3987 |

| | |
|---|---|
| SEQ ID NO: 26 | moltype = AA length = 1228 |
| FEATURE | Location/Qualifiers |
| REGION | 1..1228 |
| | note = Lachnospiraceae bacterium |
| source | 1..1228 |
| | mol_type = protein |
| | organism = unidentified |

```
SEQUENCE: 26
MSKLEKFTNC YSLSKTLRFK AIPVGKTQEN IDNKRLLVED EKRAEDYKGV KKLLDRYYLS    60
FINDVLHSIK LKNLNNYISL FRKKTRTEKE NKELENLEIN LRKEIAKAFK GNEGYKSLFK   120
KDIIETILPE FLDDKDEIAL VNSFNGFTTA FTGFFDNREN MFSEEAKSTS IAFRCINENL   180
TRYISNMDIF EKVDAIFDKH EVQEIKEKIL NSDYDVEDFF EGEFFNFVLT QEGIDVYNAI   240
IGGFVTESGE KIKGLNEYIN LYNQKTKQKL PKFKPLYKQV LSDRESLSFY GEGYTSDEEV   300
LEVFRNTLNK NSEIFSSIKK LEKLFKNFDE YSSAGIFVKN GPAISTISKD IFGEWNVIRD   360
KWNAEYDDIH LKKKAVVTEK YEDDRRKSFK KIGSFSLEQL QEYADADLSV VEKLKEIIIQ   420
KVDEIYKVYG SSEKLFDADF VLEKSLKKND AVVAIMKDLL DSVKSFENYI KAFFGEGKET   480
NRDESFYGDF VLAYDILLKV DHIYDAIRNY VTQKPYSKDK FKLYFQNPQF MGGWDKDKET   540
DYRATILRYG SKYYLAIMDK KYAKCLQKID KDDVNGNYEK INYKLLPGPN KMLPKVFFSK   600
KWMAYYNPSE DIQKIYKNGT FKKGDMFNLN DCHKLIDFFK DSISRYPKWS NAYDFNFSET   660
EKYKDIAGFY REVEEQGYKV SFESASKKEV DKLVEEGKLY MFQIYNKDFS DKSHGTPNLH   720
TMYFKLLFDE NNHGQIRLSG GAELFMRRAS LKKEELVVHP ANSPIANKNP DNPKKTTTLS   780
YDVYKDKRFS EDQYELHIPI AINKCPKNIF KINTEVRVLL KHDDNPYVIG IDRGERNLLY   840
IVVVDGKGNI VEQYSLNEII NNFNGIRIKT DYHSLLDKKE KERFEARQNW TSIENIKELK   900
AGYISQVVHK ICELVEKYDA VIALEDLNSG FKNSRVKVEK QVYQKFEKML IDKLNYMVDK   960
KSNPCATGGA LKGYQITNKF ESFKSMSTQN GFIFYIPAWL TSKIDPSTGF VNLLKTKYTS  1020
IADSKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IAISNKEWLE YAQTSVKH                                    1228

SEQ ID NO: 27          moltype = AA  length = 1307
FEATURE                Location/Qualifiers
source                 1..1307
                       mol_type = protein
                       organism = Acidaminococcus sp.
SEQUENCE: 27
MTQFEGFTNL YQVSKTLRFE LIPQGKTLKH IQEQGFIEED KARNDHYKEL KPIIDRIYKT    60
YADQCLQLVQ LDWENLSAAI DSYRKEKTEE TRNALIEEQA TYRNAIHDYF IGRTDNLTDA   120
INKRHAEIYK GLFKAELFNG KVLKQLGTVT TTEHENALLR SFDKFTTYFS GFYENRKNVF   180
SAEDISTAIP HRIVQDNFPK FKENCHIFTR LITAVPSLRE HFENVKKAIG IFVSTSIEEV   240
FSFPFYNQLL TQTQIDLYNQ LLGGISREAG TEKIKGLNEV LNLAIQKNDE TAHIIASLPH   300
RFIPLFKQIL SDRNTLSFIL EEFKSDEEVI QSFCKYKTLL RNENVLETAE ALFNELNSID   360
LTHIFISHKK LETISSALCD HWDTLRNALY ERRISELTGK ITKSAKEKVQ RSLKHEDINL   420
QEIISAAGKE LSEAFKQKTS EILSHAHAAL DQPLPTTLKK QEEKEILKSQ LDSLLGLYHL   480
LDWFAVDESN EVDPEFSARL TGIKLEMEPS LSFYNKARNY ATKKPYSVEK FKLNFQMPTL   540
ASGWDVNKEK NNGAILFVKN GLYYLGIMPK QKGRYKALSF EPTEKTSEGF DKMYYDYFPD   600
AAKMIPKCST QLKAVTAHFQ THTTPILLSN NFIEPLEITK EIYDLNNPEK EPKKFQTAYA   660
KKTGDQKGYR EALCKWIDFT RDFLSKYTKT TSIDLSSLRP SSQYKDLGEY YAELNPLLYH   720
ISFQRIAEKE IMDAVETGKL YLFQIYNKDF AKGHHGKMLN KLKDQKTPIP TLYQELYDYV   780
LNGQAELFYR PKSRMKRMAH RLGEKMLNKK LKDQKTPIPF FHVPITLNYQ AANSPSKFNQ   840
EARALLPNVI TKEVSHEIIK DRRFTSDKFF FHVPITLNYQ AANSPSKFNQ RVNAYLKEHP   900
ETPIIGIDRG ERNLIYITVI DSTGKILEQR SLNTIQQFDY QKKLDNREKE RVAARQAWSV   960
VGTIKDLKQG YLSQVIHEIV DLMIHYQAVV VLENLNFGFK SKRTGIAEKA VYQQFEKMLI  1020
DKLNCLVLKD YPAEKVGGVL NPYQLTDQFT SFAKMGTQSG FLFYVPAPYT SKIDPLTGFV  1080
DPFVWKTIKN HESRKHFLEG FDFLHYDVKT GDFILHFKMN RNLSFQRGLP GFMPAWDIVF  1140
EKNETQFDAK GTPFIAGKRI VPVIENHRFT GRYRDLYPAN ELIALLEEKG IVFRDGSNIL  1200
PKLLENDDSH AIDTMVALIR SVLQMRNSNA ATGEDYINSP VRDLNGVCFD SRFQNPEWPM  1260
DADANGAYHI ALKGQLLLNH LKESKDLKLQ NGISNQDWLA YIQELRN               1307

SEQ ID NO: 28          moltype = AA  length = 1241
FEATURE                Location/Qualifiers
source                 1..1241
                       mol_type = protein
                       organism = Butyrivibrio proteoclasticus
SEQUENCE: 28
MLLYENYTKR NQITKSLRLE LRPQGKTLRN IKELNLLEQD KAIYALLERL KPVIDEGIKD    60
IARDTLKNCE LSFEKLYEHF LSGDKKAYAK ESERLKKEIV KTLIKNLPEG IGKISEINSA   120
KYLNGVLYDF IDKTHKDSEE KQNILSDILE TKGYLALFSK FLTSRITTLE QSMPKRVIEN   180
FEIYAANIPK MQDALERGAV SFAIEYESIC SVDYYNQILS QEDIDSYNRL ISGIMDEDGA   240
KEKGINQTIS EKNIKIKSEH LEEKPFRILK QLHKQILEER EKAFTIDHID SDEEVVQVTK   300
EAFEQTKEQW ENIKKINGFY AKDPGDITLF IVVGPNQTHV LSQLIYGEHD RIRLLLEEYE   360
KNTLEVLPRR TKSEDARYDK FVNAVPKKVA KESHTFDGLQ KMTGDDRLFI LYRDELARNY   420
MRIKEAYGTF ERDILKSRRG IKGNRDVQES LVSFYDELTK FRSALRIINS GNDEKADPIF   480
YNTFDGIFEK ANRTYKAENL CRNYVTKSPA DDARIMASCL GTPARLRTHW WNGEENFAIN   540
DVAMIRRGDE YYYFVLTPDV KPVDLKTKDE TDAQIFVQRK GAKSFLGLPK ALFKCILEPY   600
FESPEHKNDK NCVIEEYVSK PLTIDRRAYD IFKNGTFKKT NIGIDGLTEE KFKDDCRYLI   660
DVYKEFIAVY TRYSCFNMSG LKRADEYNDI GEFFSDVDTR LCTMEWIPVS FERINDMVDK   720
KEGLLFLVRS MFLYNRPRKP YERTFIQLFS DSNMEHTSML LNSRAMIQYR AASLPRRVTH   780
KKGSILVALR DSNGEHIPMH IREAIYKMKN NFDISSEDFI MAKAYLAEHD VAIKKANEDI   840
IRNRRYTEDK FFLSLSYTKN ADISARTLDY INDKVEEDTQ DSRMAVIVTR NLKDLTYVAV   900
VDEKNNVLEE KSLNEIDGVN YRELLKERTK IKYHDKTRLW QYDVSSKGLK EAYVELAVTQ   960
ISKLATKYNA VVVVESMSST FKDKFSFLDE QIFKAFEARL CARMSDLSFN TIKEGEAGSI  1020
SNPIQVSNNN GNSYQDGVIY FLNNAYTRTL CPDTGFVDVF DKTRLITMQS KRQFFAKMKD  1080
IRIDDGEMLF TFNLEEYPTK RLLDRKEWTV KIAGDGSYFD KDKGEYVYVN DIVREQIIPA  1140
LLEDKAVFDG NMAEKFLDKT AISGKSVELI YKWFANALYG IITKKDGEKI YRSPITGTEI  1200
DVSKNTTYNF GKKFMFKQEY RGDGDFLDAF LNYMQAQDIA V                     1241
```

```
SEQ ID NO: 29           moltype = AA  length = 1238
FEATURE                 Location/Qualifiers
source                  1..1238
                        mol_type = protein
                        organism = Candidatus Methanoplasma termitum
SEQUENCE: 29
MNNYDEFTKL YPIQKTIRFE LKPQGRTMEH LETFNFFEED RDRAEKYKIL KEAIDEYHKK    60
FIDEHLTNMS LDWNSLKQIS EKYYKSREEK DKKVFLSEQK RMRQEIVSEF KKDDRFKDLF   120
SKKLFSELLK EEIYKKGNHQ EIDALKSFDK FSGYFIGLHE NRKNMYSDGD EITAISNRIV   180
NENFPKFLDN LQKYQEARKK YPEWIIKAES ALVAHNIKMD IVFSLEYFNK VLNQEGIQRY   240
NLALGGYVTK SGEKMMGLND ALNLAHQSEK SSKGRIHMTP LFKQILSEKE SFSYIPDVFT   300
EDSQLLPSIG GFFAQIENDK DGNIFDRALE LISSYAEYDT ERIYIRQADI NRVSNVIFGE   360
WGTLGGLMRE YKADSINDIN LERTCKKVDK WLDSKEFALS DVLEAIDRTG NNDAFNEYIS   420
KMRTAREKID AARKEMKFIS EKISGDEESI HIIKTLLDSV QQFLHFFNLF KARQDIPLDG   480
AFYAEFDEVH SKLFAIVPLY NKVRNYLTKN NLNTKKIKLN FKNPTLANGW DQNKVYDYAS   540
LIFLRDGNYY LGIINPKRKK NIKFEQGSGN GPFYRKMVYK QIPGPNKNLR PVFLTSTKGK   600
KEYKPSKEII EGYEADKHIR GDKFDLDFCH KLIDFFKESI EKHKDWSKFN FYFSPTESYG   660
DISEFYLDVE KQGYRMHFEN ISAETIDEYV EKGDLFLFQI YNKDFVKAAT GKKDMHTIYW   720
NAAFSPENLQ DVVVKLNGEA ELFYRDKSDI KEIVHREGEI LVNRTYNGRT PVPDKIHKKL   780
TDYHNGRTKD LGEAKEYLDK VRYFKAHYDI TKDRRYLNDK IYFHVPLTLN FKANGKKNLN   840
KMVIEKFLSD EKAHIIGIDR GERNLLYYSI IDRSGKIIDQ QSLNVIDGFD YREKLNQREI   900
EMKDARQSWN AIGKIKDLKE GYLSKAVHEI TKMAIQYNAI VVMEELNYGF KRGRFKVEKQ   960
IYQKFENMLI DKMNYLVFKD APDESPGGVL NAYQLTNPLE SFAKLGKQTG ILFYVPAAYT  1020
SKIDPTTGFV NLFNTSSKTN AQERKEFLQK FESISYSAKD GGIFAFAFDY RKFGTSKTDH  1080
KNVWTAYTNG ERMRYIKEKK RNELFDPSKE IKEALTSSGI KDGGQNILP DILRSNNNGL  1140
IYTMYSSFIA AIQMRVYDGK EDYIISPIKN SKGEFFRTDP KRRELPIDAD ANGAYNIALR  1200
GELTMRAIAE KFDPDSEKMA KLELKHKDWF EFMQTRGD                          1238

SEQ ID NO: 30           moltype = AA  length = 1281
FEATURE                 Location/Qualifiers
source                  1..1281
                        mol_type = protein
                        organism = Eubacterium eligens
SEQUENCE: 30
MNGNRSIVYR EFVGVIPVAK TLRNELRPVG HTQEHIIQNG LIQEDELRQE KSTELKNIMD    60
DYYREYIDKS LSGVTDLDFT LLFELMNLVQ SSPSKDNKKA LEKEQSKMRE QICTHLQSDS   120
NYKNIFNAKL LKEILPDFIK NYNQYDVKDK AGKLETLALF NGFSTYFTDF FEKRKNVFTK   180
EAVSTSIAYR IVHENSLIFL ANMTSYKKIS EKALDEIEVI EKNNQDKMGD WELNQIFNPD   240
FYNMVLIQSG IDFYNEICGV VNAHMNLYCQ QTKNNYNLFK MRKLHKQILA YTSTSFEVPK   300
MFEDDMSVYN AVNAFIDETE KGNIIGKLKD IVNKYDELDE KRIYISKDFY ETLSCFMSGN   360
WNLITGCVEN FYDENIHAKG KSKEEKVKKA VKEDKYKSIN DVNDLVEKYI DEKERNEFKN   420
SNAKQYIREI SNIITDTETA HLEYDDHISL IESEEKADEM KKRLDMYMNM YHWAKAFIVD   480
EVLDRDEMFY SDIDDIYNIL ENIVPLYNRV RNYVTQKPYN SKKIKLNFQS PTLANGWSQS   540
KEFDNNAIIL IRDNKYYLAI FNAKNKPDKK IIQGNSDKKN DNDYKKMVYN LLPGANKMLP   600
KVFLSKKGIE TFKPSDYIIS GYNAHKHIKT SENFDISFCR DLIDYFKNSI EKHAEWRKYE   660
FKFSATDSYS DISEFYREVE MQGYRIDWTY ISEADINKLD EEGKIYLFQI YNKDFAENST   720
GKENLHTMYF KNIFSEENLD KIIKLNGQAE LFYRRASVKN PVKHKKDSVL VNKTYKNQLD   780
NGDVVRIPIP DDIYNEIYKM YNGYIKESDL SEAAKEYLDK VEVRTAQKDI VKDYRYTVDK   840
YFIHTPITIN YKVTARNNVN DMVVKYIAQN DDIHVIGIDR GERNLIYISV IDSHGNIVKQ   900
KSYNILNNYD YKKKLVEKEK TREYARKNWK SIGNIKELKE GYISGVVHEI AMLIVEYNAI   960
IAMEDLNYGF KRGRFKVERQ VYQKFESMLI NKLNYFASKE KSVDEPGGLL KGYQLTYVPD  1020
NIKNLGKQCG VIFYVPAAFT SKIDPSTGFI SAFNFKSIST NASRKQFFMQ FDEIRYCAEK  1080
DMFSFGFDYN NFDTYNITMG KTQWTVYTNG ERLQSEFNNA RRTGKTKSIN LTETIKLLLE  1140
DNEINYADGH DIRIDMEKMD EDKKSEFFAQ LLSLYKLTVQ MRNSYTEAEE QENGISYDKI  1200
ISPVINDEGE FFDSDNYKES DDKECKMPKD ADANGAYCIA LKGLYEVLKI KSEWTEDGFD  1260
RNCLKLPHAE WLDFIQNKRY E                                            1281

SEQ ID NO: 31           moltype = AA  length = 1300
FEATURE                 Location/Qualifiers
source                  1..1300
                        mol_type = protein
                        organism = Francisella novicida
SEQUENCE: 31
MSIYQEFVNK YSLSKTLRFE LIPQGKTLEN IKARGLILDD EKRAKDYKKA KQIIDKYHQF    60
FIEEILSSVC ISEDLLQNYS DVYFKLKKSD DDNLQKDFKS AKDTIKKQIS EYIKDSEKFK   120
NLFNQNLIDA KKGQESDLIL WLKQSKDNGI ELFKANSDIT DIDEALEIIK SFKGWTTYFK   180
GFHENRKNVY SSNDIPTSII YRIVDDNLPK FLENKAKYES IKDKAPEAIN KQIKKDLAE   240
ELTFDIDYKT SEVNQRVFSL DEVFEIANFN NYLNQSGITK FNTIIGGKFV NGENTKRKGI   300
NEYINLYSQQ INDKTLKKYK MSVLFKQILS DTESKSFVID KLEDDSDVVT TMQSFYEQIA   360
APKTVEEKSI KETLSLLFDD LKAQKLDLSK IYFKNDKSLT DLSQQVFDDY SVIGTAVLEY   420
ITQQIAPKNL DNPSKKEQEL IAKKTEKAKY LSLETIKLAL EEFNKHRDID KQCRFEEILA   480
NFAAIPMIFD EIAQNKDNLA QISIKYQNQG KKDLLQASAE DDVKAIKDLL DQTNNLLHKL   540
KIFHISQSED KANILDKDEH FYLVFEECYF ELANIVPLYN KIRNYITQKP YSDEKFKLNF   600
ENSTLANGWD KNKEPDNTAI LFIKDDKYYL GVMNKKNNKI FDDKAIKENK GEGYKKIVYK   660
LLPGANKMLP KVFFSAKSIK FYNPSEDILR IRNHSTHTKN GSPQKGYEKF EFNIEDCRKF   720
IDFYKQSISK HPEWKDFGFR FSDTQRYNSI DEFYREVENQ GYKLTFENIS ESYIDSVVNQ   780
GKLYLFQIYN KDFSAYSKGR PNLHTLYWKA LFDERNLQDV VYKLNGEAEL FYRKQSIPKK   840
ITHPAKEAIA NKNKDNPKKE SVFEYDLIKD KRFTEDKFFF HCPITINFKS SGANKFNDEI   900
```

```
NLLLKEKAND VHILSIDRGE RHLAYYTLVD GKGNIIKQDT FNIIGNDRMK TNYHDKLAAI      960
EKDRDSARKD WKKINNIKEM KEGYLSQVVH EIAKLVIEYN AIVVFEDLNF GFKRGRFKVE     1020
KQVYQKLEKM LIEKLNYLVF KDNEFDKTGG VLRAYQLTAP FETFKKMGKQ TGIIYYVPAG     1080
FTSKICPVTG FVNQLYPKYE SVSKSQEFFS KFDKICYNLD KGYFEFSFDY KNFGDKAAKG     1140
KWTIASFGSR LINFRNSDKN HNWDTREVYP TKELEKLLKD YSIEYGHGEC IKAAICGESD     1200
KKFFAKLTSV LNTILQMRNS KTGTELDYLI SPVADVNGNF FDSRQAPKNM PQDADANGAY     1260
HIGLKGLMLL GRIKNNQEGK KLNLVIKNEE YFEFVQNRNN                          1300

SEQ ID NO: 32          moltype = AA  length = 1206
FEATURE                Location/Qualifiers
REGION                 1..1206
                       note = Lachnospiraceae bacterium
source                 1..1206
                       mol_type = protein
                       organism = unidentified
SEQUENCE: 32
MYYESLTKQY PVSKTIRNEL IPIGKTLDNI RQNNILESDV KRKQNYEHVK GILDEYHKQL       60
INEALDNCTL PSLKIAAEIY LKNQKEVSDR EDFNKTQDLL RKEVVEKLKA HENFTKIGKK      120
DILDLLEKLP SISEDDYNAL ESFRNFYTYF TSYNKVRENL YSDKEKSSTV AYRLINENFP      180
KFLDNVKSYR FVKTAGILAD GLGEEEQDSL FIVETFNKTL TQDGIDTYNS QVGKINSSIN      240
LYNQKNQKAN GFRKIPKMKM LYKQILSDRE ESFIDEFQSD EVLIDNVESY GSVLIESLKS      300
SKVSAFFDAL RESKGKNVYV KNDLAKTAMS VIVFENWRTF DDLLNQEYDL ANENKKKDDK      360
YFEKRQKELK KNKSYSLEHL CNLSEDSCNL IENYIHQISD DIENIIINNE TFLRIVINEH      420
DRSRKLAKNR KAVKAIKDFL DSIKVLEREL KLINSSGQEL EKDLIVYSAH EELLVELKQV      480
DSLYNMTRNY LTKKPFSTEK VKLNFNRSTL LNGWDRNKET DNLGVLLLKD GKYYLGIMNT      540
SANKAFVNPP VAKTEKVFKK VDYKLLPVPN QMLPKVFFAK SNIDFYNPSS EIYSNYKKGT      600
HKKGNMFSLE DCHNLIDFFK ESISKHEDWS KFGFKFDTQA SYNDISEFYR EVEKQGYKLT      660
YTDIDETYIN DLIERNELYL FQIYNKDFSM YSKGKLNLHT LYFMMLFDQR NIDDVVYKLN      720
GEAEVFYRPA SISEDELIIH KAGEEIKNKN PNRARTKETS TFSYDIVKDK RYSKDKFTLH      780
IPITMNFGVD EVKRFNDAVN SAIRIDENVN VIGIDRGERN LLYVVVIDSK GNILEQISLN      840
SIINKEYDIE TDYHALLDER EGGRDKARKD WNTVENIRDL KAGLYLQVVN VVAKLVLKYN      900
AIICLEDLNF GFKRGRQKVE KQVYQKFEKM LIDKLNYLVI DKSREQTSPK ELGGALNALQ      960
LTSKFKSFKE LGKQSGVIYY VPAYLTSKID PTTGFANLFY MKCENVEKSK RFFDGFDFIR     1020
FNALENVFEF GFDYRSFTQR ACGINSKWTV CTNGERIIKY RNPDKNNMFD EKVVVVTDEM     1080
KNLFEQYKIP YEDGRNVKDM IISNEEAEFY RRLYRLLQQT LQMRNSTDG TRDYIISPVK      1140
NKREAYFNSE LSDGSVPKDA DANGAYNIAR KGLWVLEQIR QKSEGEKINL AMTNAEWLEY     1200
AQTHLL                                                               1206

SEQ ID NO: 33          moltype = AA  length = 1233
FEATURE                Location/Qualifiers
REGION                 1..1233
                       note = Lachnospiraceae bacterium
source                 1..1233
                       mol_type = protein
                       organism = unidentified
SEQUENCE: 33
MDYGNGQFER RAPLTKTITL RLKPIGETRE TIREQKLLEQ DAAFRKLVET VTPIVDDCIR       60
KIADNALCHF GTEYDFSCLG NAISKNDSKA IKKETEKVEK LLAKVLTENL PDGLRKVNDI      120
NSAAFIQDTL TSFVQDDADK RVLIQELKGK TVLMQRFLTT RITALTVWLP DRVFENFNIF      180
IENAEKMRIL LDSPLNEKIM KFDPDAEQYA SLEFYGQCLS QKDIDSYNLI ISGIYADDEV      240
KNPGINEIVK EYNQQIRGDK DESPLPKLKK LHKQILMPVE KAFFVRVLSN DSDARSILEK      300
ILKDTEMLPS KIIEAMKEAD AGDIAVYGSR LHELSHVIYG DHGKLSQIIY DKESKRISEL      360
METLSPKERK ESKKRLEGLE EHIRKSTYTF DELNRYAEKN VMAAYIAAVE ESCAEIMRKE      420
KDLRTLLSKE DVKIRGNRHN TLIVKNYFNA WTVFRNLIRI LRRKSEAEID SDFYDVLDDS      480
VEVLSLTYKG ENLCRSYITK KIGSDLKPEI ATYGSALRPN SRWWSPGEKF NVKFHTIVRR      540
DGRLYYFILP KGAKPVELED MDGDIECLQM RKIPNPTIFL PKLVFKDPEA FFRDNPEADE      600
FVFLSGMKAP VTITRETYEA YRYKLYTVGK LRDGEVSEEE YKRALLQVLT AYKEFLENRM      660
IYADLNFGFK DLEEYKDSSE FIKQVETHNT FMCWAKVSSS QLDDLVKSGN GLLFEIWSER      720
LESYYKYGNE KVLRGYEGVL LSILKDENLV SMRTLLNSRP MLVYRPKESS KPMVVHRDGS      780
RVVDRFDKDG KYIPPEVHDE LYRFFNNLLI KEKLGEKARK ILDNKKVKVK VLESERVKWS      840
KFYDEQFAVT FSVKKNADCL DTTKDLNAEV MEQYSESNRL ILIRNTTDIL YYLVLDKNGK      900
VLKQRSLNII NDGARDVDWK ERFRQVTKDR NEGYNEWDYS RTSNDLKEVY LNYALKEIAE      960
AVIEYNAILI IEKMSNAFKD KYSFLDDVTF KGFETKKLAK LSDLHFRGIK DGEPCSFTNP     1020
LQLCQNDSNK ILQDGVIFMV PNSMTRSLDP DTGFIFAIND HNIRTKKAKL NFLSKFDQLK     1080
VSSEGCLIMK YSGDSLPTHN TDNRVWNCCC NHPITNYDRE TKKVEFIEEP VEELSRVLEE     1140
NGIETDTELN KLNERENVPG KVVDAIYSLV LNYLRGTVSG VAGQRAVYYS PVTGKKYDIS     1200
FIQAMNLNRK CDYYRIGSKE RGEWTDFVAQ LIN                                 1233

SEQ ID NO: 34          moltype = AA  length = 1227
FEATURE                Location/Qualifiers
REGION                 1..1227
                       note = Lachnospiraceae bacterium
source                 1..1227
                       mol_type = protein
                       organism = unidentified
SEQUENCE: 34
MSKLEKFTNC YSLSKTLRFK AIPVGKTQEN IDNKRLLVED EKRAEDYKGV KKLLDRYYLS       60
FINDVLHSIK LKNLNNYISL FRKKTRTEKE NKELENLEIN LRKEIAKAFK GNEGYKSLFK      120
KDIIETILPE FLDDKDEIAL VNSFNGFTTA FTGFFDNREN MFSEEAKSTS IAFRCINENL      180
```

```
TRYISNMDIF EKVDAIFDKH EVQEIKEKIL NSDYDVEDFF EGEFFNFVLT QEGIDVYNAI    240
IGGFVTESGE KIKGLNEYIN LYNQKTKQKL PKFKPLYKQV LSDRESLSFY GEGYTSDEEV    300
LEVFRNTLNK NSEIFSSIKK LEKLFKNFDE YSSAGIFVKN GPAISTISKD IFGEWNVIRD    360
KWNAEYDDIH LKKKAVVTEK YEDDRRKSFK KIGSFSLEQL QEYADADLSV VEKLKEIIIQ    420
KVDEIYKVYG SSEKLFDADF VLEKSLKKND AVVAIMKDLL DSVKFSFENYI KAFFGEGKET   480
NRDESFYGDF VLAYDILLKV DHIYDAIRNY VTQKPYSKDK FKLYFQNPQF MGGWDKDKET    540
DYRATILRYG SKYYLAIMDK KYAKCLQKID KDDVNGNYEK INYKLLPGPN KMLPKVFFSK    600
KWMAYYNPSE DIQKIYKNGT FKKGDMFNLN DCHKLIDFFK DSISRYPKWS NAYDFNFSET    660
EKYKDIAGFY REVEEQGYKV SFESASKKEV DKLVEEGKLY MFQIYNKDFS DKSHGTPNLH    720
TMYFKLLFDE NNHGQIRLSG GAELFMRRAS LKKEELVVHP ANSPIANKNP DNPKKTTTLS    780
YDVYKDKRFS EDQYELHIPI ANINKCPKNI FKINTEVRVL LKHDDNPYVI GIDRGERNLL    840
YIVVVDGKGN IVEQYSLNEI INNFNGIRIK TDYHSLLDKK EKERFEARQN WTSIENIKEL    900
KAGYISQVVH KICELVEKYD AVIALEDLNS GFKNSRVKVE KQVYQKFEKM LIDKLNYMVD    960
KKSNPCATGG ALKGYQITNK FESFKSMSTQ NGFIFYIPAW LTSKIDPSTG FVNLLKTKYT   1020
SIADKKFISS FDRIMYVPEE DLFEFALDYK NFSRTDADYI KKWKLYSYGN RIRIFRNPKK   1080
NNVFDWEEVC LTSAYKELFN KYGINYQQGD IRALLCEQSD KAFYSSFMAL MSLMLQMRNS   1140
ITGRTDVDFL ISPVKNSDGI FYDSRNYEAQ ENAILPKNAD ANGAYNIARK VLWAIGQFKK   1200
AEDEKLDKVK IASNKEWLEY AQTSVKH                                      1227

SEQ ID NO: 35           moltype = AA  length = 1264
FEATURE                 Location/Qualifiers
source                  1..1264
                        mol_type = protein
                        organism = Leptospira inadai
SEQUENCE: 35
MEDYSGFVNI YSIQKTLRFE LKPVGKTLEH IEKKGFLKKD KIRAEDYKAV KKIIDKYHRA     60
YIEEVFDSVL HQKKKKDKTR FSTQFIKEIK EFSELYYKTE KNIPDKERLE ALSEKLRKML    120
VGAFKGEFSE EVAEKYNKNL FSKELIRNEI EKFCETDEER KQVSNFKSFT TYFTGFHSNR    180
QNIYSDEKKS TAIGYRIIHQ NLPKFLDNLK IIESIQRRFK DFPWSDLKKN LKKIDKNIKL    240
TEYFSIDGFV NVLNQKGIDA YNTILGGKSE ESGEKIQGLN EYINLYRQKN NIDRKNPLNV    300
KILFKQILGD RETKSFIPEA FPDDQSVLNS ITEFAKYLKL DKKKKSIIAE LKKFLSSFNR    360
YELDGIYLAN DNSLASISTF LFDDWSFIKK SVSPKYDESV GDPKKKIKSP LKYEKEKEKW    420
LKQKYYTISF LNDAIESYSK SQDEKRVKIR LEAYFAEFKS KDDAKKQFDL LERIEEAYAI    480
VEPLLGAEYP RDRNLKADKK EVGKIKDFLD SIKSLQFFID PLLSAEIFDE KDLGFYNQLE    540
GYYEEIDISG HLYNKVRNYL TGKIYSKEKF KLNFENSTLL KGWDENREVA NLCVIFREDQ    600
KYYLGVMDKE NNTILSDIPK VKPNELFYEK MVYKLIPTPH MQLPRIIFSS DNLSIYNPSK    660
SILKIREAKS FKEGKNFKLK DCHKFIDFYK ESISKNEDWS RFDFKFSKTS SYENISEFYR    720
EVERQGYNLD FKKVSKFYID SLVEDGKLYL FQIYNKDFSI FSKGKPNLHT IYFRSLFSKE    780
NLKDVCLKLN GEAEMFFRRK SINYDEKKKR EGHHPELFEK LKYPILKDKR YSEDKFQFHL    840
PISLNFKSKE RLNFNLKVNE FLKRNKDINI IGIDRGERNL LYLVMINQKG EILKQTLLDS    900
MQSGKGRPEI NYKEKLQEKE IERDKARKSW GTVENIKELK EGYLSIVIHQ ISKLMVENNA    960
IVVLEDLNIG FKRGRQKVER QVYQKFEKML IDKLNFLVFK ENKPTEPGGV LKAYQLTDEF   1020
QSFEKLSKQT GFLFYVPSWN TSKIDPRTGF IDFLHPAYEN IEKAKQWINK FDSIRFNSKM   1080
DWFEFTADTR KFSENLMLGK NRVWVICTTN VERYFTSKTA NSSIQYNSIQ ITEKLKELFV   1140
DIPFSNGQDL KPEILRKNDA VFFKSLLFYI KTTLSLRQNN GKKGEEEKDF ILSPVVDSKG   1200
RFFNSLEASD DEPKDADANG AYHIALKGLM NLLVLNETKE ENLSRPKWKI KNKDWLEFVW   1260
ERNR                                                               1264

SEQ ID NO: 36           moltype = AA  length = 1373
FEATURE                 Location/Qualifiers
source                  1..1373
                        mol_type = protein
                        organism = Moraxella bovoculi
SEQUENCE: 36
MLFQDFTHLY PLSKTVRFEL FIDRTLEHIH AKNFLSQDET MADMHQKVKV ILDDYHRDFI     60
ADMMGEVKLT KLAEFYDVYL KFRKNPKDDE LQKAQLKDLQ AVLRKEIVKP IGNGGKYKAG    120
YDRLFGAKLF KDGKELGDLA KFVIAQEGES SPKLAHLAHF EKFSTYFTGF HDNRKNMYSD    180
EDKHTAIAYR LIHENLPRFI DNLQILTTIK QKHSALYDQI INELTASGLD VSLASHLDGY    240
HKLLTQEGIT AYNTLLGGIS GEAGSPKIQG INELINSHHN QHCHKSERIA KLRPLHKQIL    300
SDGMSVSFLP SKFADDSEMC QAVNEFYRHY ADVFAKVQSL FDGFDDHQKD GIYVEHKNLN    360
ELSKQAFGDF ALLGRVLDGY YVDVVNPEFN ERFAKAKTDN AKAKLTKEKD KPIKGVHSLA    420
SLEQAIEHYT ARHDDESVQA GKLGQYFKHG LAGVDNPIQK IHNNHSTIKG FLERERPAGE    480
RALPKIKSGK NPEMTQLRQL KELLDNALNV AHFAKLLTTK TTLDNQDGNT YGEFGVLYDE    540
LAKIPTLYNK VRDYLSQKPF STEKYKLNFG NPTLLNGWDL NKEKDNFGVI LQKDGCYYLA    600
LLDKAHKKVF DNAPNTGKSI YQKMIYKYLE VRKQFPKVFF SKEAIAINYH PSKELVEIKD    660
KGRQRSDDER LKLYRFILEC LKIHPKYDKK FEGAIGDIQL FKKDKGREV PISEKDLFKD    720
INGIFSSKPK LEMEDFFIGE FKRYNPSQDL VDQYNIYKKI DSNDNRKKEN FYNNHPKFKK    780
DLVRYYYESM CKHEEWEESF EFSKKLQDIG CYVDVNELFT EIETRRLNYK ISFCNINADY    840
IDELVEGGQL YLFQIYNKDF SPKAHGKPNL HTLYFKALFS EDNLADPIYK LNGEAQIFYR    900
KASLDMNETT IHRAGEVLEN KNPDNPKKRQ FVYDIIKDKR YTQKDFMLHV PITMNFGVQG    960
MTIKEFNKKV NQSIQQYDEV NVIGIDRGER HLLYLTVINS KGEILEQCSL NDITTASANG   1020
TQMTTPYHKI LDKREIERLN ARVGWGEIET IKELKSGYLS HVVHQISQLM LKYNAIVULE   1080
DLNFGFKRGR FKVEKQIYQN FENALIKKLN HLVLKDKADE EIGSKYNALQ LTNNFTDLKS   1140
IGKQTGFLFY VPAWNTKEID PETGFVDLLK PRYENIQASQ AFFGKFDKIC YNADKDYFEF   1200
HIDYAKFTDK AKNSRQIWTI CSHGDKRYVY DKTANQNKGA AKGINVNDIL KSLFARHHIN   1260
EKQPNLVMDI CQNNDKEFHK SLMYLLKTLL ALRYSNASSD EDFILSPVAN DEGVFFNSAL   1320
ADDTQPQNAD ANGAYHIALK GLWLLNELKN SDDLNKVKLA IDNQTWLNFA QNR          1373

SEQ ID NO: 37           moltype = AA  length = 1352
```

```
FEATURE                 Location/Qualifiers
REGION                  1..1352
                        note = Parcubacteria bacterium
source                  1..1352
                        mol_type = protein
                        organism = unidentified
SEQUENCE: 37
MENIFDQFIG KYSLSKTLRF ELKPVGKTED FLKINKVFEK DQTIDDSYNQ AKFYFDSLHQ    60
KFIDAALASD KTSELSFQNF ADVLEKQNKI ILDKKREMGA LRKRDKNAVG IDRLQKEIND   120
AEDIIQKEKE KIYKDVRTLF DNEAESWKTY YQEREVDGKK ITESKADLKQ KGADFLTAAG   180
ILKVLKYEFP EEKEKEFQAK NQPSLFVEEK ENPGQKRYIF DSFPDKFAGYL TKFQQTKKNL   240
YAADGTSTAV ATRIADNFII FHQNTKVFRD KYKNNHTDLG FDEENIFEIE RYKNCLLQRE   300
IEHIKNENSY NKIIGRINKK IKEYRDQKAK DTKLTKSDFP FFKNLDKQIL GEVEKEKQLI   360
EKTREKTEED VLIERFKEFI ENNEERFTAA KKLMNAFCNG EFESEYEGIY LKNKAINTIS   420
RRWFVSDRDF ELKLPQQKSK NKSEKNEPKV KKFISIAEIK NAVEELDGDI FKAVFYDKKI   480
IAQGGSKLEQ FLVIWKYEFE YLFRDIEREN GEKLLGYDSC LKIAKQLGIF PQEKEAREKA   540
TAVIKNYADA GLGIFQMMKY FSLDDKDRKN TPGQLSTNFY AEYDGYYKDF EFIKYYNEFR   600
NFITKKPFDE DKIKLNFENG ALLKGWDENK EYDFMGVILK KEGRLYLGIM HKNHRKLFQS   660
MGNAKGDNAN RYQKMIYKQI ADASKDVPRL LLTSKKAMEK FKPSQEILRI KKEKTFKRES   720
KNFSLRDLHA LIEYYRNCIP QYSNWSFYDF QFQDTGKYQN IKEFTDDVQK YGYKISFRDI   780
DDEYINQALN EGKMYLFEVV NKDIYNTKNG SKNLHTLYFE HILSAENLND PVFKLSGMAE   840
IFQRQPSVNE REKITTQKNQ CILDKGDRAY KYRRYTEKKI MPHMSLVLNT GKGEIKQVQF   900
NKIINQRISS SDNEMRVNVI GIDRGEKNLL YYSVVKQNGE IIEQASLNEI NGVNYRDKLI   960
EREKERLKNR QSWKPVVKIK DLKKGYISHV IHKICQLIEK YSAIVVLEDL NMRFKQIRGG  1020
IERSVYQQFE KALIDKLGYL VFKDNRDLRA PGGVLNGYQL SAPFVSFEKM RKQTGILFYT  1080
QAEYTSKTDP ITGFRKNVYI SNSASLDKIK EAVKKFDAIG WDGKEQSYFF KYNPYNLADE  1140
KYKNSTVSKE WAIFASAPRI RRQKGEDGYW KYDRVKVNEE FEKLLKVWNF VNPKATDIKQ  1200
EIIKKIKAGD LQGEKELDGR LRNFWHSFIY LFNLVLELRN SFSLQIKIKA GEVIAVDEGV  1260
DFIASPVKPF FTTPNPYIPS NLCWLAVENA DANGAYNIAR KGVMILKKIR EHAKKDPEFK  1320
KLPNLFISNA EWDEAARDWG KYAGTTALNL DH                                1352

SEQ ID NO: 38           moltype = AA  length = 1260
FEATURE                 Location/Qualifiers
source                  1..1260
                        mol_type = protein
                        organism = Porphyromonas crevioricanis
SEQUENCE: 38
MDSLKDFTNL YPVSKTLRFE LKPVGKTLEN IEKAGILKED EHRAESYRRV KKIIDTYHKV    60
FIDSSLENMA KMGIENEIKA MLQSFCELYK KDHRTEGEDK ALDKIRAVLR GLIVGAFTGV   120
CGRRENTVQN EKEYESLFKEK LIKEILPDFV LSTEAESLPF SVEEATRSLK EFDSFTSYFA   180
GFYENRKNIY STKPQSTAIA YRLIHENLPK FIDNILVFQK IKEPIAKELE HIRADFSAGG   240
YIKKDERLED IFSLNYYIHV LSQAGIEKYN ALIGKIVTEG DGEMKGLNEH INLYNQQRGR   300
EDRLPLFRPL YKQILSDREQ LSYLPESFEK DEELLRALKE FYDHIAEDIL GRTQQLMTSI   360
SEYDLSRIYV RNDSQLTDIS KKMLGDWNAI YMARERAYDH EQAPKRITAK YERDRIKALK   420
GEESISLANL NSCIAFLDNV RDCRVDTYLS TLGQKEGPHG LSNLVENVFA SYHEAEQLLS   480
FPYPEENNLI QDKDNVVLIK NLLDNISDLQ RFLKPLWGMG DEPDKDERFY GEYNYIRGAL   540
DQVIPLYNKV RNYLTRKPYS TRKVKLNFGN SQLLSGWDRN KEKDNSCVIL RKGQNFYLAI   600
MNNRHKRSFE NKMLPEYKEG EPYFEKMDYK FLPDPNKMLP KVFLSKKGIE IYKPSPKLLE   660
QYGHGTHKKG DTFSMDDLHE LIDFFKHSIE AHEDWKQFGF KFSDTATYEN VSSFYREVED   720
QGYKLSFRVK SESYVYSLID QGKLYLFQIY NKDFSPCSKG TPNLHTLYWR MLFDERNLAD   780
VIYKLDGKAE IFFREKSLKN DHPTHPAGKP IKKKSRQKKG ELSEFEYDLV KDRRYTMDKF   840
QFHVPITMNF KCSAGSKVND MVNAHIREAK DMHVIGIDRG ERNLLYICVI DSRGTILDQI   900
SLNTINDIDY HDLLESRDKD RQQEHRNWQT IEGIKELKQG YLSQAVHRIA ELMVAYKAVV   960
ALEDLNMGFK RGRQKVESSV YQQFEKQLID KLNYLVDKKK RPEDIGGLLR AYQFTAPFKS  1020
FKEMGKQNGF LFYIPAWNTS NIDPTTGFVN LFHVQYENVD KAKSFFQKFD SISYNPKKDW  1080
FEFAFDYKNF TKKAEGSRSM WILCTHGSRI KNFRNSQKNG QWDSEEFALT EAFKSLFVRY  1140
EIDYTADLKT AIVDEKQKDF FVDLLKLFKL TVQMRNSWKE KDLDYLISPV AGADGRFFDT  1200
REGNKSLPKD ADANGAYNIA LKGLWALRQI RQTSEGGKLK LAISNKEWLQ FVQERSYEKD  1260

SEQ ID NO: 39           moltype = AA  length = 1324
FEATURE                 Location/Qualifiers
source                  1..1324
                        mol_type = protein
                        organism = Prevotella disiens
SEQUENCE: 39
MENYQEFTNL FQLNKTLRFE LKPIGKTCEL LEEGKIFASG SFLEKDKVRA DNVSYVKKEI    60
DKKHKIFIEE TLSSFSISND LLKQYFDCYN ELKAFKKDCK SDEEEVKKTA LRNKCTSIQR   120
AMREAISQAF LKSPQKKLLA IKNLIENVFK ADENVPFKIT FTSYFSGFET NRENFYSDEE   180
KSTSIAYRLV HDNLPIFIKN IYIFEKLKEQ FDAKTLSEIF ENYKLYVAGS SLDEVFSLEY   240
FNNTLTQKGI DNYNAVIGKI VKEDKQEIQG LNEHINLNYQ KHKDRRLPFF ISLKKQILSD   300
REALSWLPDM FKNDSEVIDA LKGFYIEDGF ENNVLTPLAT LLSSLDKYNL NGIFIRNNEA   360
LSSLSQNVYR NFSIDEAIDA QNAELQTFNN YELIANALRA KIKKETKQGR KSFEKYEEYI   420
DKKVKAIDSL SIQEINELVE NYVSEFNSNS GNMPRKVEDY FSLMRKGDFG SNDLIENIKT   480
KLSAAEKLLG TKYQETAKDI FKKDENSKLI KELLDATKQF QHFIKPLLGT GEEADRDLVF   540
YGDFLPLYEK FEELTLLYNK VRNRLTQKPY SKDKIRLCFN KPKLMTGWVD SKTEKSDNGT   600
QYGGYLFRKK NEIGEYDYFL GISSKAQLFK KNEAVIGDYE RLDYYQPKAN TIYGSAYEGE   660
NSYKEDKKRL NKVIIAYIEQ IKQTNIKKSI IESISKYPNI SDDDKVTPSS LLEKIKKVSI   720
DSYNGILSFK SFQSVNKEVI DNLLKTISPL KNKAEFLDLI NKDYQIFTEV QAVIDEICKQ   780
KTFIYFPISN VELEKEMGDK DKPLCLFQIS NKDLSFAKTF SANLRKKRGA ENLHTMLFKA   840
```

```
LMEGNQDNLD LGSGAIFYRA KSLDGNKPTH PANEAIKCRN VANKDKVSLF TYDIYKNRRY    900
MENKFLFHLS IVQNYKAAND SAQLNSSATE YIRKADDLHI IGIDRGERNL LYYSVIDMKG    960
NIVEQDSLNI IRNNDLETDY HDLLDKREKE RKANRQNWEA VEGIKDLKKG YLSQAVHQIA   1020
QLMLKYNAII ALEDLGQMFV TRGQKIEKAV YQQFEKSLVD KLSYLVDKKR PYNELGGILK   1080
AYQLASSITK NNSDKQNGFL FYVPAWNTSK IDPVTGFTDL LRPKAMTIKE AQDFFGAFDN   1140
ISYNDKGYFE FETNYDKFKI RMKSAQTRWT ICTFGNRIKR KKDKNYWNYE EVELTEEFKK   1200
LFKDSNIDYE NCNLKEEIQN KDNRKFFDDL IKLLQLTLQM RNSDDKGNDY IISPVANAEG   1260
QFFDSRNGDK KLPLDADANG AYNIARKGLW NIRQIKQTKN KDDLNLSISS TEWLDFVREK   1320
PYLK                                                                1324

SEQ ID NO: 40           moltype = AA  length = 1484
FEATURE                 Location/Qualifiers
REGION                  1..1484
                        note = Peregrinibacteria bacterium
SITE                    1073
                        note = misc_feature - Xaa can be any naturally occurring
                         amino acid
source                  1..1484
                        mol_type = protein
                        organism = unidentified
SEQUENCE: 40
MSNFFKNFTN LYELSKTLRF ELKPVGDTLT NMKDHLEYDE KLQTFLKDQN IDDAYQALKP     60
QFDEIHEEFI TDSLESKKAK EIDFSEYLDL FQEKKELNDS EKKLRNKIGE TFNKAGEKWK    120
KEKYPQYEWK KGSKIANGAD ILSCQDMLQF IKYKNPEDEK IKNYIDDTLK GFFTYFGGFN    180
QNRANYYETK KEASTAVATR IVHENLPKFC DNVIQFKHII KRKKDGTVEK TERKTEYLNA    240
YQYLKNNNKI TQIKDAETEK MIESTPIAEK IFDVYYFSSC LSQKQIEEYN RIIGHYNLLI    300
NLYNQAKRSE GKHLSANEKK YKDLPKFKTL YKQIGCGKKK DLFYTIKCDT EEEANKSRNE    360
GKESHSVEEI INKAQEAINK YFKSNNDCEN INTVPDFINY ILTKENYEGV YWSKAAMNTI    420
SDKYFANYHD LQDRLKEAKV FQKADKKSED DIKIPEAIEL SGLFGVLDSL ADWQTTLFKS    480
SILSNEKLKI ITDSQTPSEA LLKMIFNDIE KNMESFLKET NDIITLKKYK GNKEGTEKIK    540
QWFDYTLAIN RMLKYFLVKE NKIKGNSLDT NISEALKTLI YSDDAEWFKW YDALRNYLTQ    600
KPQDEAKENK LKLNFDNPSL AGGWDVNKEC SNFCVILKDK NEKKYLAMIK KGENTLFQKE    660
WTEGRGKNLT KKSNPLFEIN NCEILSKMEY DFWADVSKMI PKCSTQLKAV VNHFKQSDNE    720
FIFPIGYKVT SGEKFREECK ISKQDFELNN KVFNKNELSV TAMRYDLSST QEKQYIKAFQ    780
KEYWELLFKQ EKRDTKLTNN EIFNEWINFC NKKYSELLSW ERKYKDALTN WINFCKYFLS    840
KYPKTTLFNY SFKESENYNS LDEFYRDVDI CSYKLNINTT INKSILDRLV EEGKLYLFEI    900
KNQDSNDGKS IGHKNNLHTI YWNAIFENFD NRPKLNGEAE IFYRKAISKD KLGIVKGKKT    960
KNGTWIIKNY RFSKEKFILH VPITLNFCSN NEYVNDIVNT KFYNFSNLHF LGIDRGEKHL   1020
AYYSLVNKNG EIVDQGTLNL PFTDKDGNQR SIKKEKYFYN KQEDKWEAKE VDXWNYNDLL   1080
DAMASNRDMA RKNWQRIGTI KEAKNGYVSL VIRKIADLAV NNERPAFIVL EDLNTGFKRS   1140
RQKIDKSVYQ KFELALAKKL NFLVDKNAKR DEIGSPTKAL QLTPPVNNYG DIENKKQAGI   1200
MLYTRANYTS QTDPATGWRK TIYLKAGPEE TTYKKDGKIK NKSVKDQIIE TFTDIGFDGK   1260
DYYFEYDKGE FVDEKTGEIK PKKWRLYSGE NGKSLDRFRG EREKDKYEWK IDKIDIVKIL   1320
DDLFVNFDKN ISLLKQLKEG VELTRNNEHG TGESLRFAIN LIQQIRNTGN NERDNDFILS   1380
PVRDENGKHF DSREYWDKET KGEKISMPSS GDANGAFNIA RKGIIMNAHI LANSDSKDLS   1440
LFVSDEEWDL HLNNKTEWKK QLNIFSSRKA MAKRKKKRPA ATKK                   1484

SEQ ID NO: 41           moltype = AA  length = 1245
FEATURE                 Location/Qualifiers
source                  1..1245
                        mol_type = protein
                        organism = Porphyromonas macacae
SEQUENCE: 41
MKTQHFFEDF TSLYSLSKTI RFELKPIGKT LENIKKNGLI RRDEQRLDDY EKLKKVIDEY     60
HEDFIANILS SFSFSEEILQ SYIQNLSISE ARAKIEKTMR DTLAKAFSED ERYKSIFKKE    120
LVKKDIPVWC PAYKSLCKKF DNFTTSLVPF HENRKNLYTS NEITASIPYR IVHVNLPKFI    180
QNIEALCELQ KKMGADLYLE MMENLRNVWP SFVKTPDDLC NLKTYNHLMV QSSISEYNRF    240
VGGYSTEDGT KHQGINEWIN IYRQRNKEMR LPGLVFLHKQ ILAKVDSSSF ISDTLENDDQ    300
VFCVLRQFRK LFWNTVSSKE DDAASLKDLF CGLSGYDPEA IVSDAHLAT ISKNIFDRWN     360
YISDAIRRKT EVLMPRKKES VERYAEKISK QIKKRQSYSL AELDDLLAHY SEESLPAGFS    420
LLSYFTSLGG QKYLVSDGEV ILYEEGSNIW DEVLIAFRDL QVILDKDPTE KKLGKDEEAV    480
SVIKKALDSA LRLRKFFDLL SGTGAEIRRD SSFYALYTDR MDKLKGLLKM YDKVRNYLTK    540
KPYSIEKFKL HFDNPSLLSG WDKNKELNNL SVIFRQNGYY YLGIMTPKGK NLFKTLPKLG    600
AEEMFYEKME YKQIAEPMLM LPKVFFPKKT KPAFAPDQSV VDIYNKKTFK TGQKGFNKKD    660
LYRLIDFYKE ALTVHEWKLF NFSFSPTEQY RNIGEFFDEV REQAYKVSMV NVPASYIDEA    720
VENGKLYLFQ IYNKDFSPYS KGIPNLHTLY WKALFSEQNO SRVYKLCGGG ELFYRKASLH    780
MQDTTVHPKG ISIHKKNLNK KGETSLFNYD LVKDKRFTED KFFFHVPISI NYKNKKITNV    840
NQMVRDYIAQ NDDLQHGIDR GERNLLYISR IDTRGNLLEQ FSLNVIESDK GDLRTDYQKI    900
LGDREQERLR RRQEWKSIES IKDLKDGYMS QVVHKICNMV VEHKAIVVLE NLNLSFMKGR    960
KKVEKSVYEK FERMLVDKLN YLVVDKKNLS NEPGGLYAAY QLTNPLFSFE ELHRYPQSGI   1020
LFFVDPWNTS LTDPSTGFVN LLGRINYTNV GDARKFFDRF NAIRYDGKGN ILFDLDLSRF   1080
DVRVETQRKL WTLTTFGSRI AKSKKSGKWM VERIENLSLC FLELFEQFNI GYRVEKDLKK   1140
AILSQDRKEF YVRLIYLFNL MMQIRNSDGE EDYILSPALN EKNLQFDSRL IEAKDLPVDA   1200
DANGAYNVAR KGLMVVQRIK RGDHESIHRI GRAQWLRYVQ EGIVE                   1245

SEQ ID NO: 42           moltype = AA  length = 1250
FEATURE                 Location/Qualifiers
source                  1..1250
                        mol_type = protein
```

```
                         organism = Smithella sp.
SEQUENCE: 42
MQTLFENFTN QYPVSKTLRF ELIPQGKTKD FIEQKGLLKK DEDRAEKYKK VKNIIDEYHK   60
DFIEKSLNGL KLDGLEKYKT LYLKQEKDDK DKKAFDKEKE NLRKQIANAF RNNEKFKTLF  120
AKELIKNDLM SFACEEDKKN VKEFEAFTTY FTGFHQNRAN MYVADEKRTA IASRLIHENL  180
PKFIDNIKIF EKMKKEAPEL LSPFNQTLKD MKDVIKGTTL EEIFSLDYFN KTLTQSGIDI  240
YNSVIGGRTP EEGKTKIKGL NEYINTDFNQ KQTDKKKRQP KFKQLYKQIL SDRQSLSFIA  300
EAFKNDTEIL EAIEKFYVNE LLHFSNEGKS TNVLDAIKNA VSNLESFNLT KMYFRSGASL  360
TDVSRKVFGE WSIINRALDN YYATTYPIKP REKSEKYEER KEKWLKQDFN VSLIQTAIDE  420
YDNETVKGKN SGKVIADYFA KFCDDKETDL IQKVNEGYIA VKDLLNTPCP ENEKLGSNKD  480
QVKQIKAFMD SIMDIMHFVR PLSLKDTDKE KDETFYSLFT PLYDHLTQTI ALYNKVRNYL  540
TQKPYSTEKI KLNFENSTLL GGWDLNKETD NTAIILRKDN LYYLGIMDKR HNRIFRNVPK  600
ADKKDFCYEK MVYKLLPGAN KMLPKVFFSQ SRIQEFTPSA KLLENYANET HKKGDNFNLN  660
HCHKLIDFFK DSINKHEDWK NFDFRFSATS TYADLSGFYH EVEHQGYKIS FQSVADSFID  720
DLVNEGKLYL FQIYNKDFSP FSKGKPNLHT LYWKMLFDEN NLKDVVYKLN GEAEVFYRKK  780
SIAEKNTTIH KANESIINKN PDNPKATSTF NYDIVKDKRY TIDKFQFHIP ITMNFKAEGI  840
FNMNQRVNQF LKANPDINII GIDRGERHLL YYALINQKGK ILKQDTLNVI ANEKQKVDYH  900
NLLDKKEGDR ATARQEWGVI ETIKELKEGY LSQVIHKLTD LMIENNAIIV MEDLNFGFKR  960
GRQKVEKQVY QKFEKMLIDK LNYLVDKNKK ANELGGLLNA FQLANKFESF QKMGKQNGFI 1020
FYVPAWNTSK TDPATGFIDF LKPRYENLNQ AKDFFEKFDS IRLNSKADYF EFAFDFKNFT 1080
EKADGGRTKW TVCTTNEDRY QWNRALNNNR GSQEKYDITA ELKSLFDGKV DYKSGKDLKQ 1140
QIASQESADF FKALMKNLSI TLSLRHNNGE KGDNEQDYIL SPVADSKGRF FDSRKADDDM 1200
PKNADANGAY HIALKGLWCL EQISKTDDLK KVKLAISNKE WLEFVQTLKG           1250

SEQ ID NO: 43         moltype = AA  length = 166
FEATURE               Location/Qualifiers
source                1..166
                      mol_type = protein
                      organism = Escherichia coli
SEQUENCE: 43
SEVEFSHEYW MRHALTLAKR AWDEREVPVG AVLVHNNRVI GEGWNRPIGR HDPTAHAEIM   60
ALRQGGLVMQ NYRLIDATLY VTLEPCVMCA GAMIHSRIGR VVFGARDAKT GAAGSLMDVL  120
HHHPGMNHRVE ITEGILADEC AALLSDFFRM RRQEIKAQKK AQSSTD                166

SEQ ID NO: 44         moltype = AA  length = 166
FEATURE               Location/Qualifiers
REGION                1..166
                      note = adenosine deaminase
source                1..166
                      mol_type = protein
                      organism = synthetic construct
SEQUENCE: 44
SEVEFSHEYW MRHALTLAKR ARDEREVPVG AVLVLNNRVI GEGWNRAIGL HDPTAHAEIM   60
ALRQGGLVMQ NYRLIDATLY VTFEPCVMCA GAMIHSRIGR VVFGVRNAKT GAAGSLMDVL  120
HYPGMNHRVE ITEGILADEC AALLCYFFRM PRQVFNAQKK AQSSTD                 166

SEQ ID NO: 45         moltype = AA  length = 166
FEATURE               Location/Qualifiers
REGION                1..166
                      note = adenosine deaminase
source                1..166
                      mol_type = protein
                      organism = synthetic construct
SEQUENCE: 45
SEVEFSHEYW MRHALTLAKR AWDEREVPVG AVLVLNNRVI GEGWNRSIGL HDPTAHAEIM   60
ALRQGGLVMQ NYRLIDATLY VTFEPCVMCA GAMIHSRIGR VVFGVRNAKT GAAGSLMDVL  120
HYPGMNHRVE ITEGILADEC AALLCYFFRM RRQVFNAQKK AQSSTD                 166

SEQ ID NO: 46         moltype = AA  length = 166
FEATURE               Location/Qualifiers
REGION                1..166
                      note = adenosine deaminase
source                1..166
                      mol_type = protein
                      organism = synthetic construct
SEQUENCE: 46
SEVEFSHEYW MRHALTLAKR ALDEREVPVG AVLVLNNRVI GEGWNRAIGL HDPTAHAEIM   60
ALRQGGLVMQ NYRLIDATLY VTFEPCVMCA GAMIHSRIGR VVFGVRNAKT GAAGSLMDVL  120
HYPGMNHRVE ITEGILADEC NALLCYFFRM RRQVFNAQKK AQSSTD                 166

SEQ ID NO: 47         moltype = AA  length = 166
FEATURE               Location/Qualifiers
REGION                1..166
                      note = adenosine deaminase
source                1..166
                      mol_type = protein
                      organism = synthetic construct
SEQUENCE: 47
SEVEFSHEYW MRHALTLAKR ALDEREVPVG AVLVLNNRVI GEGWNRAIGL HDPTAHAEIM   60
```

```
ALRQGGLVMQ NYRLIDATLY VTFEPCVMCA GAMIHSRIGR VVFGVRNAKT GAAGSLMDVL   120
HYPGMNHRVE ITEGILADEC NALLCYFFRM PRQVFNAQKK AQSSTD                 166

SEQ ID NO: 48           moltype = AA  length = 167
FEATURE                 Location/Qualifiers
REGION                  1..167
                        note = adenine deaminase
source                  1..167
                        mol_type = protein
                        organism = synthetic construct
SEQUENCE: 48
MSEVEFSHEY WMRHALTLAK RARDEREVPV GAVLVLNNRV IGEGWNRAIG LHDPTAHAEI   60
MALRQGGLVM QNYRLYDATL YSTFEPCVMC AGAMIHSRIG RVVFGVRNAK TGAAGSLMDV   120
LHHPGMNHRV EITEGILADE CAALLCRFFR MPRRVFNAQK KAQSSTD                167

SEQ ID NO: 49           moltype = AA  length = 167
FEATURE                 Location/Qualifiers
REGION                  1..167
                        note = adenine deaminase
source                  1..167
                        mol_type = protein
                        organism = synthetic construct
SEQUENCE: 49
MSEVEFSHEY WMRHALTLAK RARDEREVPV GAVLVLNNRV IGEGWNRAIG LHDPTAHAEI   60
MALRQGGLVM QNYRLIDATL YVTFEPCVMC AGAMIHSRIG RVVFGVRNSK RGAAGSLMNV   120
LNYPGMNHRV EITEGILADE CAALLCDFYR MPRQVFNAQK KAQSSIN                167

SEQ ID NO: 50           moltype = AA  length = 228
FEATURE                 Location/Qualifiers
source                  1..228
                        mol_type = protein
                        organism = Rattus norvegicus
SEQUENCE: 50
SSETGPVAVD PTLRRRIEPH EFEVFFDPRE LRKETCLLYE INWGGRHSIW RHTSQNTNKH   60
VEVNFIEKFT TERYFCPNTR CSITWFLSWS PCGECSRAIT EFLSRYPHVT LFIYIARLYH   120
HADPRNRQGL RDLISSGVTI QIMTEQESGY CWRNFVNYSP SNEAHWPRYP HLWVRLYVLE   180
LYCIILGLPP CLNILRRKQP QLTFFTIALQ SCHYQRLPPH ILWATGLK                228

SEQ ID NO: 51           moltype = AA  length = 199
FEATURE                 Location/Qualifiers
source                  1..199
                        mol_type = protein
                        organism = Homo sapiens
SEQUENCE: 51
MEASPASGPR HLMDPHIFTS NFNNGIGRHK TYLCYEVERL DNGTSVKMDQ HRGFLHNQAK   60
NLLCGFYGRH AELRFLDLVP SLQLDPAQIY RVTWFISWSP CFSWGCAGEV RAFLQENTHV   120
RLRIFAARIY DYDPLYKEAL QMLRDAGAQV SIMTYDEFKH CWDTFVDHQG CPFQPWDGLD   180
EHSQALSGRL RAILQNQGN                                               199

SEQ ID NO: 52           moltype = DNA  length = 621
FEATURE                 Location/Qualifiers
source                  1..621
                        mol_type = other DNA
                        organism = Petromyzon marinus
SEQUENCE: 52
acagatgcag agtatgtgag aattcacgaa aagctggaca tctataccct caagaagcag   60
ttctttaaca ataagaagtc tgtgagccat aggtgctacg tgctgttcga gctgaagaga   120
aggggtgaaa gaagggcatg ttttggggg tatgctgtga acaagcccca gtctggaact    180
gagagaggca ttcacgccga aatttttcagc atcagaaagg tggaggaata cctgagggat   240
aaccctggac agtttacaat taattggtat tctagctggt ctccatgcgc tgactgtgcc   300
gagaagatcc tggaatggta caaccaggag ctgagaggaa atggccatac cctgaagatt   360
tgggcctgca agctgtacta tgaaaagaac gcaagaaatc agatcggact gtggaacctg   420
agggataatg gtgtggggct gaacgtgatg gtgtccgagc actatcagtg ctgtagaaag   480
attttcattc agtcctcaca taatcagctg aacgagaata gatggctgga aaagactctg   540
aagagggctg agaagagaag gtccgaactg tcaattatga tccaggtgaa gatcctgcac   600
accactaagt cacctgccgt g                                             621

SEQ ID NO: 53           moltype = AA  length = 160
FEATURE                 Location/Qualifiers
REGION                  1..160
                        note = cytosine deaminase
source                  1..160
                        mol_type = protein
                        organism = synthetic construct
SEQUENCE: 53
FERNYDPREL RKETYLLYEI KWGKSGKLWR HWCQNNRTQH AEVYFLENIF NARRFNPSTH   60
CSITWYLSWS PCAECSQKIV DFLKEHPNVL EIYVARLYYH EDERNRQGLR DLVNSGVTIR   120
IMDLPDYNYC WKTFVSDQGG DEDYWPGHFA PWIKQYSLKL                        160
```

| SEQ ID NO: 54 | moltype = AA   length = 207 |
| --- | --- |
| FEATURE | Location/Qualifiers |
| REGION | 1..207 |
|  | note = cytosine deaminase |
| source | 1..207 |
|  | mol_type = protein |
|  | organism = synthetic construct |

SEQUENCE: 54
```
TDAEYVRIHE KLDIYTFKKQ FSNNKKSVSH RCYVLFELKR RGERRACFWG YAVNKPQSGT  60
ERGIHAEIFS IRKVEEYLRD NPGQFTINWY SSWSPCADCA EKILEWYNQE LRGNGHTLKI 120
WVCKLYYEKN ARNQIGLWNL RDNGVGLNVM VSEHYQCCRK IFIQSSHNQL NENRWLEKTL 180
KRAEKRRSEL SIMFQVKILH TTKSPAV                                   207
```

| SEQ ID NO: 55 | moltype = AA   length = 228 |
| --- | --- |
| FEATURE | Location/Qualifiers |
| REGION | 1..228 |
|  | note = cytosine deaminase |
| source | 1..228 |
|  | mol_type = protein |
|  | organism = synthetic construct |

SEQUENCE: 55
```
SSKTGPVAVD PTLRRRIEPH EFEVFFDPRE LRKETCLLYE INWGGRHSIW RHTSQNTNKH  60
VEVNFIEKFT TERYFCPNTR CSITWFLSWS PCGECSRAIT EFLSRYPNVT LFIYIARLYH 120
LANPRNRQGL RDLISSGVTI QIMTEQESGY CWHNFVNYSP SNESHWPRYP HLWVRLYVLE 180
LYCIILGLPP CLNILRRKQS QLTSFTIALQ SCHYQRLPPH ILWATGLK             228
```

| SEQ ID NO: 56 | moltype = AA   length = 162 |
| --- | --- |
| FEATURE | Location/Qualifiers |
| REGION | 1..162 |
|  | note = cytosine deaminase |
| source | 1..162 |
|  | mol_type = protein |
|  | organism = synthetic construct |

SEQUENCE: 56
```
SFERNYDPRE LRKETYLLYE IKWGKSGKLW RHWCQNNRTQ HAEVYFLENI FNARRFNPST  60
HCSITWYLSW SPCAECSQKI VDFLKEHPNV NLEIYVARLY YPENERNRQG LRDLVNSGVT 120
IRIMDLPDYN YCWKTFVSDQ GGDEDYWPGH FAPWIKQYSL KL                  162
```

| SEQ ID NO: 57 | moltype = AA   length = 229 |
| --- | --- |
| FEATURE | Location/Qualifiers |
| source | 1..229 |
|  | mol_type = protein |
|  | organism = Rattus norvegicus |

SEQUENCE: 57
```
MSSETGPVAV DPTLRRRIEP HEFEVFFDPR ELRKETCLLY EINWGGRHSI WRHTSQNTNK  60
HVEVNFIEKF TTERYFCPNT RCSITWFLSW SPCGECSRAI TEFLSRYPHV TLFIYIARLY 120
HHADPRNRQG LRDLISSGVT IQIMTEQESG YCWRNFVNYS PSNEAHWPRY PHLWVRLYVL 180
ELYCIILGLP PCLNILRRKQ PQLTFFTIAL QSCHYQRLPP HILWATGLK            229
```

| SEQ ID NO: 58 | moltype = AA   length = 198 |
| --- | --- |
| FEATURE | Location/Qualifiers |
| source | 1..198 |
|  | mol_type = protein |
|  | organism = Homo sapiens |

SEQUENCE: 58
```
MDSLLMNRRK FLYQFKNVRW AKGRRETYLC YVVKRRDSAT SFSLDFGYLR NKNGCHVELL  60
FLRYISDWDL DPGRCYRVTW FTSWSPCYDC ARHVADFLRG NPNLSLRIFT ARLYFCEDRK 120
AEPEGLRRLH RAGVQIAIMT FKDYFYCWNT FVENHERTFK AWEGLHENSV RLSRQLRRIL 180
LPLYEVDDLR DAFRTLGL                                             198
```

| SEQ ID NO: 59 | moltype = AA   length = 197 |
| --- | --- |
| FEATURE | Location/Qualifiers |
| REGION | 1..197 |
|  | note = cytosine deaminase |
| source | 1..197 |
|  | mol_type = protein |
|  | organism = synthetic construct |

SEQUENCE: 59
```
MDSLLMNRRE FLYQFKNVRW AKGRRETYLC YVVKRRDSAT SFSLDFGYLR NKNGCHVELL  60
FLRYISDWDL DPGRCYRVTW FISWSPCYDC ARHVADFLRG NPNLSLRIFT ARLYFCEDRK 120
AEPEGLRRLH RAGVQIAIMT FKDYFYCWNT FVENHGRTFK AWEGLHENSV RLSRQLRRIL 180
LPLYEVDDLR DAFRTCT                                              197
```

| SEQ ID NO: 60 | moltype = AA   length = 83 |
| --- | --- |
| FEATURE | Location/Qualifiers |
| source | 1..83 |
|  | mol_type = protein |
|  | note = Bacillus phage |
|  | organism = unidentified |

SEQUENCE: 60
TNLSDIIEKE TGKQLVIQES ILMLPEEVEE VIGNKPESDI LVHTAYDEST DENVMLLTSD    60
APEYKPWALV IQDSNGENKI KML                                            83

SEQ ID NO: 61           moltype = DNA  length = 1592
FEATURE                 Location/Qualifiers
source                  1..1592
                        mol_type = other DNA
                        organism = Medicago truncatula
SEQUENCE: 61
actgttaata attttttaaac gtcagcgcac taaaaaaacg aaaagacgga cacgtgaaaa    60
taaaaaacac acactagttt atgacgcaat actattttac ttatgatttg ggtacattag   120
acaaaaccgt gaaagagatg tatcagctat gaaacctgta tacttcaata cagagactta   180
ctcatatcgg atacgtacgc acgaagtatc atattaatta tttttaatttt taataaatat   240
tttatcggat acttatgtga tactctacat atacacaagg atatttctaa gatactttat   300
agatacgtat cctagaaaaa catgaagagt aaaaaagtga gacaatgttg taaaaattca   360
ttataaaatgt atatgattca attttagata tgcatcagta taattgattc tcgatgaaac   420
acttaaaatt atatttcttg tggaagaacg tagcgagaga ggtgattcag ttagacaaca   480
ttaaataaaa ttaatgttaa gttctcttta tgatgtttct ctcaatatca catcatatga   540
aaatgtaata tgatttataa gaaaattttt aaaaaattta ttttaataat cacatgtact   600
atttttaaaa aattgtatct tttataataa tacaataata aagagtaatc agtgttaatt   660
tttctttcaaa tataagtttt attataaatc attgttaacg tatcataagt cattaccgta   720
tcgtatctta attttttttt aaaaaccgct aattcacgta cccgtattgt attgtacccg   780
cacctgtatc acaatcgatc ttagttagaa gaattgtctc gaggcggtgc aagacagcat   840
ataatagacg tggactctct tataccaaac gttgtcgtat cacaaagggt taggtaacaa   900
gtcacagttt gtccacgtgt cacgttttaa ttggaagagg tgccgttggc gtaatataac   960
agccaatcga tttttgctat aaaagcaaat caggtaaact aaacttcttc attcttttct  1020
tccccatcgc tacaaaaccg gttccttttgg aaaagagatt cattcaaacc tagcacccaa  1080
ttccgtttca aggtataatc tactttctat tcttcgatta ttttattatt attagctact  1140
atcgttttaat cgatcttttc ttttgatccg tcaaatttaa attcaattag ggttttgttc  1200
ttttctttca tctgattgaa atccttctga attgaaccgt ttacttgatt ttactgttta  1260
ttgtatgatt taatccttttg tttttcaaag acagtcttta gattgtgatt aggggttcat  1320
ataaattttt agatttggat ttttgtattg tatgattcaa aaaatacgtc ctttaattag  1380
attagtacat ggatattttt taccccgattt attgattgtc agggagaatt tgatgagcaa  1440
gtttttttga tgtctgttgt aaattgaatt gattataatt gctgatctgc tgcttccagt  1500
tttcataacc catattcttt taaccttgtt gtacacacaa tgaaaaattg gtgattgatt  1560
catttgtttt tctttgtttt ggattataca gg                               1592

SEQ ID NO: 62           moltype = DNA  length = 2000
FEATURE                 Location/Qualifiers
source                  1..2000
                        mol_type = other DNA
                        organism = Zea mays
SEQUENCE: 62
gtcgtgcccc tctctagaga taaagagcat tgcatgtcta aagtataaaa aattaccaca    60
tatttttttg tcacacttat ttgaagtgta gtttatctat ctctatacat atatttaaac   120
ttcactctac aaataaatata gtctataata ctaaaataat attagtgttt tagaggatca   180
tataaataaa ctgctagaca tggtctaaag gataattgaa tattttgaca atctacagtt   240
ttatcttttt agtgtgcatg tgatctctct gtttttttttg caaatagctt gacctatata   300
atacttcatc cattttatta gtacatccat ttaggattta gggttgatgg tttctataga   360
ctaattttta gtacatccat tttattcttt ttagtctcta aattttttaa aactaaaact   420
ctatttagt tttttatttta ataatttaga tataaaatga aataaaataa attgactaca   480
aataaaacaa atacccttta agaaataaaa aaactaagca aacatttttc ttgtttcgag   540
tagataatga caggctgttc aacgccgtcg acgagtctaa cggacaccaa ccagcgaacc   600
agcagcgtcg cgtcgggcca agcgaagcag acggcacggc atctctgtag ctgcctctgg   660
accccctctcg agagttccgc tccaccgttg gacttgctcc gctgtcggca tccagaaatt   720
gcgtggcgga gcgcagacg tgaggcggca cggcaggcgg cctcttcctc ctctcacggc   780
accggcagct acgggggatt cctttcccac cgctccttcg cttttccctc ctcgcccgcc   840
gtaataaata gacaccccct ccacaccctc tttcccaac ctcgtgttcg ttcggagcgc   900
acacacacgc aaccagatct cccccaaatc cagccgtcgg cacctccgct tcaaggtacg   960
ccgctcatcc tccccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaatttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaaatac tgtttcaaac tacctggtgg  1440
atttattaaa ggatctgtat gtatgtgcct acatctgtat agttacgagt ttaagatgat  1500
ggatggaaat atcgatctag gataggtata catgttgatg cgggttttac tgatgcatat  1560
acagagatgc ttttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgtcgcat  1800
ctattcatat gctctaacct tgagtaccta tctattataa taacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgtttg gtgatacttc                                              2000

```
SEQ ID NO: 63           moltype = DNA  length = 1594
FEATURE                 Location/Qualifiers
source                  1..1594
                        mol_type = other DNA
                        organism = Medicago truncatula
SEQUENCE: 63
actgttaata atttttaaac gtcagcgcac taaaaaaacg aaaagacgga cacgtgaaaa    60
taaaaaacac acactagttt atgacgcaat actattttac ttatgatttg ggtacattag   120
acaaaaccgt gaaagagatg tatcagctat gaaacctgta tacttcaata cagagactta   180
ctcatatcgg atacgtacgc acgaagtatc atattaatta ttttaatttt taataaatat   240
tttatcggat acttatgtga tactctacat atacacaagg atatttctaa gatactttat   300
agatacgtat cctagaaaaa catgaagagt aaaaagtga caatgttg taaaaattca      360
ttataaatgt atatgattca atttagata tgcatcagta taattgattc tcgatgaaac    420
acttaaaatt atatttcttg tggaagaacg tagcgagaga ggtgattcag ttagacaaca   480
ttaaataaaa ttaatgttaa gttcttttaa tgatgtttct ctcaatatca catcatatga   540
aaatgtaata tgatttataa gaaattttt aaaaaattta ttttaataat cacatgtact    600
atttttaaa aattgtatct tttataataa tacaataata aagagtaatc agtgttaatt    660
tttcttcaaa tataagtttt attataaatc attgttaacg tatcataagt cattaccgta   720
tcgtatctta atttttttt aaaaaccgct aattcacgta cccgtattgt attgtacccg    780
cacctgtatc acaatcgatc ttagttagaa gaattgtctc gaggcggtgc aagacagcat   840
ataatagacg tggactctct tataccaaac gttgtcgtat cacaagggg taggtaacaa    900
gtcacagttt gtcacgtgt cacgttttaa ttggaagagg tgccgttggc gtaatataac    960
agccaatcga ttttgctat aaaagcaaat caggtaaact aaacttcttc attcttttct    1020
tccccatcgc tacaaaaccg gttccttttgg aaaagagatt cattcaaacc tagcacccaa  1080
ttccgtttca aggtataatc tactttctat tcttcgatta tttattatt attagctact    1140
atcgttttaat cgatcttttc ttttgatccg tcaaatttaa attcaattag ggttttgttc  1200
ttttctttca tctgattgaa atccttctga attgaaccgt ttacttgatt ttactgttta   1260
ttgtatgatt taatccttg ttttttcaaag acagtcttta gattgtgatt aggggttcat   1320
ataaatttt agatttggat ttttgtattg tatgattcaa aaaatacgtc ctttaattag    1380
attagtacat ggatatttt tacccgattt attgattgtc agggagaatt tgatgagcaa    1440
gttttttgga tgtctgttgt aaattgaatt gattataatt gctgatcgc tgcttccagt    1500
tttcataacc catattcttt taaccttgtt gtacacacaa tgaaaattg gtgattgatt    1560
catttgtttt tctttgtttt ggattataca gggt                               1594

SEQ ID NO: 64           moltype =   length =
SEQUENCE: 64
000

SEQ ID NO: 65           moltype =   length =
SEQUENCE: 65
000

SEQ ID NO: 66           moltype =   length =
SEQUENCE: 66
000

SEQ ID NO: 67           moltype = AA  length = 1367
FEATURE                 Location/Qualifiers
REGION                  1..1367
                        note = Cas9 polypeptide
source                  1..1367
                        mol_type = protein
                        organism = synthetic construct
SEQUENCE: 67
DKKYSIGLAI GTNSVGWAVI TDEYKVPSKK FKVLGNTDRH SIKKNLIGAL LFDSGETAEA    60
TRLKRTARRR YTRRKNRICY LQEIFSNEMA KVDDSFFHRL EESFLVEEDK KHERHPIFGN   120
IVDEVAYHEK YPTIYHLRKK LVDSTDKADL RLIYLALAHM IKFRGHFLIE GDLNPDNSDV   180
DKLFIQLVQT YNQLFEENPI NASGVDAKAI LSARLSKSRR LENLIAQLPG EKKNGLFGNL   240
IALSLGLTPN FKSNFDLAED AKLQLSKDTY DDDLDNLLAQ IGDQYADLFL AAKNLSDAIL   300
LSDILRVNTE ITKAPLSASM IKRYDEHHQD LTLLKALVRQ QLPEKYKEIF FDQSKNGYAG   360
YIDGGASQEE FYKFIKPILE KMDGTEELLV KLNREDLLRK QRTFDNGSIP HQIHLGELHA   420
ILRRQEDFYP FLKDNREKIE KILTFRIPYY VGPLARGNSR FAWMTRKSEE TITPWNFEEV   480
VDKGASAQSF IERMTNFDKN LPNEKVLPKH SLLYEYFTVY NELTKVKYVT EGMRKPAFLS   540
GEQKKAIVDL LFKTNRKVTV KQLKEDYFKK IECFDSVEIS GVEDRFNASL GTYHDLLKII   600
KDKDFLDNEE NEDILEDIVL TLTLFEDREM IEERLKTYAH LFDDKVMKQL KRRRYTGWGR   660
LSRKLINGIR DKQSGKTILD FLKSDGFANR NFMQLIHDDS LTFKEDIQKA QVSGQGDSLH   720
EHIANLAGSP AIKKGILQTV KVVDELVKVM GRHKPENIVI EMARENQTTQ KGQKNSRERM   780
KRIEEGIKEL GSQILKEHPV ENTQLQNEKL YLYYLQNGRD MYVDQELDIN RLSDYDVDHI   840
VPQSFLKDDS IDNKVLTRSD KNRGKSDNVP SEEVVKKMKN YWRQLLNAKL ITQRKFDNLT   900
KAERGGLSEL DKAGFIKRQL VETRQITKHV AQILDSRMNT KYDENDKLIR EVKVITLKSK   960
LVSDFRKDFQ FYKVREINNY HHAHDAYLNA VVGTALIKKY PKLESEFVYG DYKVYDVRKM  1020
IAKSEQEIGK ATAKYFFYSN IMNFFKTEIT LANGEIRKRP LIETNGETGE IVWDKGRDFA  1080
TVRKVLSMPQ VNIVKKTEVQ TGGFSKESIL PKRNSDKLIA RKKDWDPKKY GGFDSPTVAY  1140
SVLVVAKVEK GKSKKLKSVK ELLGITIMER SSFEKNPIDF LEAKGYKEVK KDLIIKLPKY  1200
SLFELENGRK RMLASAGELQ KGNELALPSK YVNFLYLASH YEKLKGSPED NEQKQLFVEQ  1260
HKHYLDEIIE QISEFSKRVI LADANLDKVL SAYNKHRDKP IREQAENIIH LFTLTNLGAP  1320
AAFKYFDTTI DRKRYTSTKE VLDATLIHQS ITGLYETRID LSQLGGD                1367

SEQ ID NO: 68           moltype = AA  length = 1367
```

```
FEATURE                 Location/Qualifiers
REGION                  1..1367
                        note = Cas9 polypeptide
source                  1..1367
                        mol_type = protein
                        organism = synthetic construct
SEQUENCE: 68
DKKYSIGLAI GTNSVGWAVI TDEYKVPSKK FKVLGNTDRH SIKKNLIGAL LFDSGETAEA    60
TRLKRTARRR YTRRKNRICY LQEIFSNEMA KVDDSFFHRL EESFLVEEDK KHERHPIFGN   120
IVDEVAYHEK YPTIYHLRKK LVDSTDKADL RLIYLALAHM IKFRGHFLIE GDLNPDNSDV   180
DKLFIQLVQT YNQLFEENPI NASGVDAKAI LSARLSKSRR LENLIAQLPG EKKNGLFGNL   240
IALSLGLTPN FKSNFDLAED AKLQLSKDTY DDDLDNLLAQ IGDQYADLFL AAKNLSDAIL   300
LSDILRVNTE ITKAPLSASM IKRYDEHHQD LTLLKALVRQ QLPEKYKEIF FDQSKNGYAG   360
YIDGGASQEE FYKFIKPILE KMDGTEELLV KLNREDLLRK QRTFDNGSIP HQIHLGELHA   420
ILRRQEDFYP FLKDNREKIE KILTFRIPYY VGPLARGNSR FAWMTRKSEE TITPWNFEEV   480
VDKGASAQSF IERMTNFDKN LPNEKVLPKH SLLYEYFTVY NELTKVKYVT EGMRKPAFLS   540
GEQKKAIVDL LFKTNRKVTV KQLKEDYFKK IECFDSVEIS GVEDRFNASL GTYHDLLKII   600
KDKDFLDNEE NEDILEDIVL TLTLFEDREM IEERLKTYAH LFDDKVMKQL KRRRYTGWGR   660
LSRKLINGIR DKQSGKTILD FLKSDGFANR NFMQLIHDDS LTFKEDIQKA QVSGQGDSLH   720
EHIANLAGSP AIKKGILQTV KVVDELVKVM GRHKPENIVI EMARENQTTQ KGQKNSRERM   780
KRIEEGIKEL GSQILKEHPV ENTQLQNEKL YLYYLQNGRD MYVDQELDIN RLSDYDVDHI   840
VPQSFLADDS IDNKVLTRSD KNRGKSDNVP SEEVVKKMKN YWRQLLNAKL ITQRKFDNLT   900
KAERGGLSEL DKAGFIKRQL VETRQITKHV AQILDSRMNT KYDENDKLIR EVKVITLKSK   960
LVSDFRKDFQ FYKVREINNY HHAHDAYLNA VVGTALIKKY PALESEFVYG DYKVYDVRKM  1020
IAKSEQEIGK ATAKYFFYSN IMNFFKTEIT LANGEIRKAP LIETNGETGE IVWDKGRDFA  1080
TVRKVLSMPQ VNIVKKTEVQ TGGFSKESIL PKRNSDKLIA RKKDWDPKKY GGFDSPTVAY  1140
SVLVVAKVEK GKSKKLKSVK ELLGITIMER SSFEKNPIDF LEAKGYKEVK KDLIIKLPKY  1200
SLFELENGRK RMLASAGELQ KGNELALPSK YVNFLYLASH YEKLKGSPED NEQKQLFVEQ  1260
HKHYLDEIIE QISEFSKRVI LADANLDKVL SAYNKHRDKP IREQAENIIH LFTLTNLGAP  1320
AAFKYFDTTI DRKRYTSTKE VLDATLIHQS ITGLYETRID LSQLGGD               1367

SEQ ID NO: 69           moltype = DNA   length = 5355
FEATURE                 Location/Qualifiers
misc_feature            1..5355
                        note = adenosine base editor construct
source                  1..5355
                        mol_type = other DNA
                        organism = synthetic construct
SEQUENCE: 69
atggcgggaa gcaaaaaacg gcggattaag caagattctg aggtcgagtt tagccacgag    60
tattggatgc gccatgcctt gacgcttgcg aaacgtgctt gggatgaacg cgaagtccca   120
gtcggagccg tgctcgtgca caataaccga gtcattggtg agggatggaa tcgtccaatc   180
gggcgcatg accgacggc tcatgctgag atcatgcctt cagacaggg tggcttgagta   240
atgcagaact atagactcat tgatgccaca ctctacgtca ctctcgaacc gtgcgtaatg   300
tgcgcggtg caatgattca ttccagaatt ggccgtgtcg tcttcggtgc gcgggacgcg   360
aagaccggag cggctggcag cctcatggac gtgcttcacc atcctggtat gaaccaccgg   420
gtagagatca ccgaggggat tctcgcagac gagtcgcctg cccttctctc gcgattctt   480
cgcatgaggc gacaggagat taaggcccag aagaaagccc aatcatcgac tgattcgggt   540
ggcagctcgg gtggttctag tggttcagaa acaccgggca aagcgaatc cgcaaccct   600
gaatctagcg gtgggagttc tggagggtcg tcagaggtta agttagcca cgaatattgg   660
atgcgccatg ccctgacttt ggctaagcgc gctcgggacg agcgcgaagt accggtgga   720
gcggtgttag tgcttaacaa tcgggtcatt ggtgaaggct ggaatcgcgc aattggcctg   780
catgatccga cggcgcacgc tgagataatg gctctccgtc aaggaggtct agtgatgcag   840
aactacaggc ttatcgacgc gacactatat gtcacattcg agccctgcgt gatgtgtgcc   900
ggggcgatga tccactccag aatcgggcga gtcgtcttcg gcgtcaggaa gccaagacc   960
ggcgcggctg gtcgctgat ggacgtgctc cattccctg gatgaaccat cgcgttgag  1020
atcactgagg gcatactcgc cgatgagtgt gcggccctac tttgctattt cttccgaatg  1080
ccacgtcaag tattcaacgc tcagaagaag gctcagtcat ccactgacag cggtgggagc  1140
agcggcggtt catcggcag cgagactcct ggaacgtcgg aatggctaca gcccgagagc  1200
agtggcggta gttcggccgg cagtgcaag aagtacagca tcgggctggc catcgggacc  1260
aactccgtcg gctgggctgt gattaccgac gagtacaagg tgccatccaa gaagttcaag  1320
gtcctcggca acactgaccg gcacagcatt aagaagaacc tgattgggc gctgctgttc  1380
gattcggggg agactgcgga ggcgaccagg ctgaagcgga ctgcgcgccc gaggtacacc  1440
aggaggaaga atcggatctg ctacctccag gagattttct gaatagat gccaagtg  1500
gacgattcct tcttccatcg cctggaggag tcgttcctcg ttgaggagga caagaagcat  1560
gagaggcatc ccatttcgg gaatatcgtt gacgaggtgg cttaccatga gaagtacccg  1620
accatctacc atctgcggaa gaagctcgtc gattcgaccg ataaggccga cctgcggctg  1680
atctacctgg ccctcgcgca catgattaag ttcggggca atttcctcat cgagggcgac  1740
ctcaaccgg acaactcgga cgtggataag ctcttcattc agctcgtgca gacatacaac  1800
cagctcttcg aggagaatcc cattaacgcc tcgggggtcg acgctaaggc tattctctcg  1860
gctcggctgt cgaagtcgcg ccggctggag aatctcattg cccagctccc aggcgagaag  1920
aagaacggcc tcttcggcaa cctgattgcc ctgtcgctgg gctcacacc gaatttcaag  1980
tcgaacttcg acctcgccga ggacgctaag ctccagctca gcaaggatac ttacgatgat  2040
gacctcgata acctcctcgc ccagatttgg gatcagtacg ctgatcttt cctcgccgcc  2100
aagaatctca gcgatgctat tctcctgtcg gacattctcc gcgtcaacac agagattact  2160
aaggccccac tgtcggcgag catgattaag aaggtacgatg agcatcatca ggacctgaca  2220
ctgctcaagg cgctggtccg gcagcagctc ccgagaagt acaaggagat tttcttcgat  2280
cagtcaaaga atgggtacgc gggctacatt gatggcggcg cgtcccagga ggagtttac  2340
aagttcatta gcccatcct ggagaagatg acgggaccg aggagctgct ggtgaagctc  2400
```

```
aatcgggagg acctgctccg gaagcagcgc acattcgaca atggctcgat tcctcaccag   2460
attcacctgg gcgagctgca cgccattctc cgcaggcagg aggacttcta cccgttcctc   2520
aaggacaacc gcgagaagat cgagaagatc ctgaccttcc ggattccata ctacgtgggg   2580
ccgctcgcgc gggggaactc ccggttcgcg tggatgactc gcaagtccga agaaacgatt   2640
acaccgtgga atttcgagga ggtcgtcgac aagggcgcta gtgcgcagtc attcattgag   2700
aggatgacca atttcgataa gaacctgcct aacgagaagg tgctgccgaa gcattcgctg   2760
ctctacgagt acttcaccgt ttacaatgag ctgaccaagg tgaagtatgt gactgagggc   2820
atgaggaagc cagcgttcct gagcggcgag cagaagaagg ctatcgtgga cctgctcttc   2880
aagactaacc ggaaggtgac tgtgcaggag ctcaaggagg actacttcaa gaagattgaa   2940
tgcttcgatt ccgttgagat tagcggggtg gaggatggat tcaatgcttc gctcgggaca   3000
taccacgatc tcctgaagat cattaaggat aaggacttcc tcgacaacga ggagaacgag   3060
gacattctcg aagatattgt cctgaccctc accctcttcg aggatcggga gatgatcgag   3120
gagaggctca agacatacgc tcatctgttc gatgataagg tcatgaagca gctgaagcgc   3180
aggcggtaca cagggtgggg gcggctgagc cggaagctga tcaacgggat tcgggataag   3240
cagtccggga agacaattct cgacttcctc aagtccgacg ggttcgctaa ccggaacttc   3300
atgcagctca ttcatgatga ctcgctgaca ttcaaggagg atattcagaa ggcgcaggtt   3360
tcggggcagg gcgactcgct ccacgagcat attgcgaatc tggcgggctc ccccgcgatt   3420
aagaagggca ttctgcaaac cgtcaaggtg gttgatgacg tggtcaaggt catggggcgg   3480
cataagccag agaatattgt catcgagatg gcgcgggaga atcagaccac acagaagggg   3540
cagaagaact cacgggagcg gatgaagcgc atcgaggagg catcaaggag gctgggtcg   3600
cagatcctga aggagcatcc cgtggagaac actcagctgc aaaatgagaa gctgtacctc   3660
tactacctcc agaacgggag ggacatgtat gtggatcagg agctggatat taataggctg   3720
agcgattacg atgtcgacca cattgtccca cagtcgttcc tgaaggacga cagcattgac   3780
aacaaggtgc tgacccgctc ggataagaac aggggcaaga gcgataatgt tccaagcgag   3840
gaggttgtga agaagatgaa gaactactgg cggcagctcc tgaacgcgaa gctcatcaca   3900
cagcgaagt cgacaacct caccaaggct gagcgcggg gcctgagcga gctgacaag    3960
gcggggttca ttaagaggca gctggtcgag acacggcaga ttacaaagca tgttgcgcag   4020
attctcgatt cccggatgaa caccaagtac gatgagaacg ataagctgat tcgggaggtc   4080
aaggtaatta ccctgaagtc caagctggtg tccgacttca ggaaggactt ccagttctac   4140
aaggttcggg agatcaacaa ctaccaccac gcgcatgatg cctacctgaa cgccgtcgtg   4200
gggaccgctc tcatcaagaa gtacccaaag ctggagtcag agttcgtcta cggggattac   4260
aaggtttacg acgtgcggaa gatgatcgct aagagcgagc aggagattgg caaggctacc   4320
gctaagtact tcttctactc caacatcatg aacttcttca agacagagat taccctcgcg   4380
aatggcgaga tccggaagag gccccctcatc gagacaaatg gggagacagg ggagattgtc   4440
tgggataagg ggcgggattt cgcgaccgtc cggaaggtcc tgtcgatgcc ccaggttaat   4500
attgtcaaga agactgaggt ccagactggc ggcttctcaa aggagtcgat tctcccaaag   4560
aggaactccg ataagctcat tgctcggaag aaggattggg accccaagaa gtacggggga   4620
ttcgactccc ccactgttgc ttactctgtt ctggttgttg ctaaggtgga gaaggggaag   4680
tcgaagaagc tgaagagcgt gaaggagctg ctcgggatta caattatgga gaggtcatcc   4740
ttcgagaaga atcccatcga cttcctggag gccaagggct acaaggaggt gaagaaggac   4800
ctgattatta agctgcccaa gtactcgctc ttcgagctgg agaatgggcg gaagcggatg   4860
ctggcgtccg cgggggagct gcaaaagggg aacgagctgg cgctcccctc caagtatgtg   4920
aacttcctct acctggcgtc cactacgag aagctgaagg gtcccccaga ggataatgaa   4980
cagaagcagc tcttcgtcga gcagcataag cactaccctgg acgagattat cgagcagatt   5040
agcgagttct cgaagcgggt catcctgcgc gatgcgaacc tggataaggt gctcagcgcc   5100
tacaataagc accgggacaa gccgattcgg gagcaggcgg agaatattat tcacctcttc   5160
acactcacca actccggggc accagctgcg ttcaagtact tcgacactac tatcgaccgg   5220
aagcggtaca cctcgacgaa ggaggtgctc gacgccaccc tcattcacca gtcgatcaca   5280
ggcctgtacg agacacggat tgacctgtcc cagctcgggg gcgacggatc taagaagaga   5340
agaattaaac aagat                                                   5355

SEQ ID NO: 70           moltype = DNA  length = 5358
FEATURE                 Location/Qualifiers
misc_feature            1..5358
                        note = adenosine base editor construct
source                  1..5358
                        mol_type = other DNA
                        organism = synthetic construct
SEQUENCE: 70
atggcgggca gcaagaaacg ccggattaag caagattccg aagtcgagtt ctcacacgaa   60
tattggatga gacacgcgct tacactagct aaaaggcgt gggacgagcg ggaagtacct   120
gttggtgccg ttctagtgca caacaatcgg gtcatcggtg aaggttggaa taggccgatt   180
ggcagacatg atcctacagc cacgctgag atcatgcgc tgcgccaggg aggactcgtt   240
atgcagaact acagactaat tgacgatacc ctctatgca ctttggaacc atgtgtaatg   300
tgtgctgggg ctatgatcca ctccagaatt ggtagagtag tctttggcgc aagggatgct   360
aagaccggag ccgctggttc attgatggac gtcctgcacc atcccggtat gaaccatcgc   420
gttgagatta ctgagggcat tctggctgac gagtgtgccg cgctcttgtc agatttttt   480
cgaatgagga gacaggagat taaggcacag aagaaggca agtcaagtac ggatagcgga   540
ggatcatctg gtggaagtag ggctcagag acacctggagtc tgcaacacct   600
gaaagttccg gcgggtctag cggcggatct tcagaagttg agtttagtca cgaatattgc   660
atgcgtcacg ctttgaccct tgccaagcgc gcccgcgacg agcgcgaagt tcccgttgga   720
gcagttctag tgctcaacaa ccgtgttatt ggtgaaggtt ggaacagggc tattggacta   780
catgacccca ccgctcatgc tgagattatg gccttcgac aaggcgggct tgtgatgcag   840
aactacagac ttattgcgc tacctctat gttacttcg agccatgtt catgtgtgcg   900
ggagcaatga tacacagtag aatcgggcgg gtgtgttcg gggttcggaa cgcaaagact   960
ggagcggctg gtcattgat ggatgtgttg cattatccag ggatgaacca cagagttgag   1020
attacagagg gcatattagc tgacgagtgt gctgccctcc tctgctactt cttcagaatg   1080
ccaagacaag tgtttaacgc ccagaagaag gctcaatcct ccacagactc tggaggatct   1140
agtggcggtt caagtgggtc tgaaacacct gggacatccg agagtgctac tccgaatca   1200
```

```
tcaggaggtt catctggagg atctgacaag aagtatagta ttggactcgc tatcggaacc    1260
aactctgtgg ggtgggctgt tattacagat gaatataagg tgccatccaa aaagtttaaa    1320
gttctgggca atactgatag acactcaatc aagaagaatc tgataggtgc acttctgttt    1380
gatagtggag agactgccga ggcaaccaga cttaaaagga ctgcaagaag aagatatacc    1440
agaagaaaga ataggatttg ctatttgcag gaaatcttca gcaacgaatt ggccaaggtt    1500
gatgactcat ttttccatag gttggaggag agttttcttg tggaggaaga taagaagcac    1560
gaaagacacc caattttcgg gaatatagtg gacgaggtgg cttatcatga gaagtatccc    1620
actatctacc acctgagaaa gaaacttgtg gactcaaccg ataaggctga tcttaggctt    1680
atatacttgg cccttgcaca tatgatcaaa ttcaggggcc attttcttat cgaaggcgat    1740
cttaatcccg ataactcaga tgtgtgacaag ctgtttatac aacttgtgca aacctacaat    1800
caactcttcg aggagaatcc cattaacgcc tccggcgtgg atgcaaaagc catactgtca    1860
gccagactga gcaaaagtag gagactggag aatcttatag cccaactgcc cggtgaaaag    1920
aagaatgggc tcttcggaaa tctgatcgct ctttcattgg ggttgacacc caactttaag    1980
agtaactttg acttggcaga agatgcaaag ttgcagctca gtaaagacac atatgacgat    2040
gaccttgaca atctcttggc acaaataggg gatcaatacg ctgacctttt cctcgctgcc    2100
aagaacctca gcgacgctat actgttgtcc gacattctta gggttaatac cgaaattaca    2160
aaggcccctc ttagtgcaag tatgatcaaa aggtatgatg agcatcacca agaccttaca    2220
ctgctgaagg ctctggttag acagcaactc cctgaaaagt ataaggaaat attcttcgac    2280
caaagtaaga acgggtacgc cggttatatt gatgggggcg caagtcaaga agaattttac    2340
aaattcatca agccaattct tgaaaagatg gacgggactg aggaattgct ggtgaaactg    2400
aatagagagg accttcttag aaaacagagg acatttgaca atgggtccat cccacaccag    2460
attcatctgg gggaactcca cgcaatattg aggagacaag aagactttta ccattcctt     2520
aaggataata gagagaaaat cgaaaaaatc ctgactttca ggattcctta ctatgttggg    2580
ccactggcca gggggaactc aagattcgct tggatgacaa ggaagtcaga agaaaccata    2640
acccccttgga attttgaaga ggtggttgat aaggggggcat cagcccagtc tttcatagag    2700
aggatgacca actttgataa aaatcttcca aatgagaagg ttttgccaaa acatagtctt    2760
ttgtacgagt actttactgt ttataacgaa ttgaccaagg tgaagtatgt gaccgaggga    2820
atgaggaagc cagcattttt gtccggggag caaaagaaag caatcgttga tcttctcttc    2880
aagaccaaca gaaaagtgac cgtgaaacaa ctgaaggaag actacttcaa aaagatgaa     2940
tgtttcgatt cagtggaaat tagcgcttgtt gaagacagtt tcaatgcttc attgggtact    3000
taccacgacc tgttgaagat aatcaaagac aaggactttc tcgataatga ggagaacgaa    3060
gacatcttgg aagacattgt gcttacactc actttgtttg aggacaggga aatgattgag    3120
gaaagactca aaacttacgc tcatttgttt gatgataagg ttatgaaaca actaaaaaga    3180
agaaggtaca ccgctggggg aagattgagt aggaaactga tcaacggtat tagagataaa    3240
caatcccgaa agactatcct cgatttcctt aagagtgatg gctttgcaaa taggaatttt    3300
atgcagctga ttcatgacga ctcacttacc ttcaaagaag acatccaaaa agctcaggtg    3360
tctgggcaag gcgacagtct gcatgaacat atagctaact ggctgggag tcccgccatc    3420
aagaaggga tacttcaaac agttaaagtt gtggacgaat tggtgaaggt aatgggaagg    3480
cacaagcctg aaaatatagt gatagaaatg gcaagggaaa atcaaacaac ccagaaggga    3540
cagaagaaca gtagggaaag gatgaaaagg atagaagagg ggatcaaaga gcttggtagc    3600
cagatcctca aggaacatcc agtggagaat cccaacttc aaaacgagaa actctatttg     3660
tactacttgc agaacggaag agatatgtat gtggaccaag agcttgatat taacaggctg    3720
agcgattatg acgttgacca catagtgccc caatcattcc tcaaggatga ctctattgat    3780
aataaggtgc tgacaaggag tgacaagaat agagggaaat ccgacaacgt tccatccgag    3840
gaagttgtga agaagatgaa gaactactgg aggcagttgc tgaacgctaa gctcattacc    3900
cagaggaaat tcgataacct gaccaaagca gagagaggcg ggctgagcga actcgataaa    3960
gcaggtttca tcaagagaca actcgtggag actaggcaaa ttactaagca cgtggctcaa    4020
atactcgaca gcaggatgaa cacaaagtac gacgagaacg acaagctcat tagagaggtt    4080
aaggttatta ctctgaaaag taattggttg agcgatttca gaaaggattt ccaattctat    4140
aaggttagag agatcaacaa ttatcatcat gcacatgatg cctatctgaa tgctgtggtt    4200
ggtacagccc ttatcaagaa gtaccctaag ctagagagcg agtttgtgta cggagattat    4260
aaggtgtatg atgtgaggaa aatgatcgct aaaagtgagc aagagattgg aaaggctacc    4320
gccaaatact tctttattc caatattatg aatttcttca agacagaaat cacccctggct    4380
aacggcgaga taaggaagag gccgcttatc gaaactaatg gggagacagg cgaaatagtg    4440
tgggacaaag ggagggattt cgcaactgtg aggaaggttt tgagcatgcc tcaggtgaat    4500
atcgttaaga aaaccgaagt tcaaactgga gggttctcta aggaaagcat tctcccaag    4560
aggaactccg acaagctgat tgctagaaag aaagactggg accccaagaa gtatggcgga    4620
ttcgactcac ccactgtggc atatagcgtt ctcgtggtgg caaaggttga aaagggtaaa    4680
tccaaaaaac tcaaatccgt gaaggaactc ctttggcataa ctattatgga aaggagtagc    4740
tttgaaaaga atcccatcga ctttctcgaa gctcagggct ataaggaagt taagaaggac    4800
cttataatca aacttccaaa atactcccttt tttgagttgg aaaacggcag aaagagaatg    4860
ttggccagtg ccgggagct tcaaaagggc aacgaactgg ctctgcctag caaatatgtg    4920
aactttttgt atctggcatc acactacgag aaacttaaag gctctcctga ggacaacgag    4980
caaaaacagc tctttgttga acagcataag cactacctcg acgagattat tgagcagatc    5040
agcgagttct caaagagagt tattctggct gacgctaatc ttgacaaggt tttgtccgct    5100
tacaacaaac acagggataa gccaatcagg gagcaggcag aaaacataat ccatctctt    5160
accctgacaa acctcggtgc ccccgctgct ttcaagtatt ttgatactac cattgacagg    5220
aagagatata cttccactaa ggaagtgctc gacgcaaccc tcatacacca aagtatcaca    5280
ggcctctatg aaactaggat agatttgtct caacttgggg gcgatggatc taagaagaga    5340
agaattaaac aagattga                                                   5358
```

SEQ ID NO: 71           moltype = DNA   length = 5358
FEATURE                 Location/Qualifiers
misc_feature            1..5358
                        note = adenosine base editor construct
source                  1..5358
                        mol_type = other DNA
                        organism = synthetic construct
SEQUENCE: 71

```
atggcgggca gcaagaaacg ccggattaag caagattccg aagtcgagtt ctcacacgaa    60
tattggatga gacacgcgct tacactagct aaaagggcgt gggacgagcg ggaagtacct   120
gttggtgccg ttctagtgca caacaatcgg gtcatcggtg aaggttggaa taggccgatt   180
ggcagacatg atcctacagc acacgctgag atcatgcgc tgcgccaggg aggactcgtt    240
atgcagaact acagactaat tgacgctacc ctctatgtca ctttggaacc atgtgtaatg   300
tgtgctgggg ctatgatcca ctccagaatt ggtagagtag tctttggcgc aagggatgct   360
aagaccggag ccgctggttc attgatggac gtcctgcacc atcccggtat gaaccatcgc   420
gttgagatta ctgagggcat tctggctgac gagtgtgccg cgctcttgtc agattttttt   480
cgaatgagga gacaggagat taaggcacag aagaaggcac agtcaagtac ggatagcgga   540
ggatcatctg gtggaagtag cggctcagag acacctggaa catcagagtc tgcaacacct   600
gaaagttccg gcgggtctag cggcggatct tcagaagttg agtttagtca cgaatattgg   660
atgcgtcacg ctttgaccct tgccaagcgc gcccgcgacg agcgcgaagt tcccgttgga   720
gcagttctag tgctcaacaa ccgtgttatt ggtgaaggtt ggaacagggc tattggacta   780
catgacccca ccgctcatgc tgagattatg gcccttcgac aaggcgggct tgtgatgcag   840
aactacaggc ttattgacgc taccctctat gttactttcg agccatgtgt catgtgtgcg   900
ggagcaatga tacacagtag aatcgggcgg tggtgttcg gggttcggaa cgcaaagact    960
ggagcggctg ggtcattgat ggatgtgttg cattatccag gatgaaccca cagagttgag  1020
attacagagg gcatattagc tgacgagtgt gctgccctcc tctgctactt cttcagaatg  1080
ccaagacaag tgtttaacgc ccagaagaag gctcaatcct ccacagactc tggaggatct  1140
agtggcggtt caagtgggtc tgaaacacct gggacatccg agagtgctac tcccgaatca  1200
tcaggaggtt catctggagg atctgacaag aaatacagta ttggccttgc aattgggact  1260
aactctgtgg gatgggccgt gattacagac gagtacaagg tgccgagcaa gaagtttaag  1320
gtgcttggga acaccgaccg gcactcgatt aagaagaacc taataggggc acttctgttc  1380
gactccgag aaaaccgcag aggccaccgc cttaaacgca ccgcacgacg acgatacacc   1440
cggcgtaaga accggatctg ctatctacag gaaatcttca gtaatgagat ggcaaaggtg  1500
gatgacagct tttttcacag gcttgaggag tcgttcctag ttgaggagga caaaaagcac  1560
gaacgccatc ccatcttcgg gaacatcgtg gatgaggtcg cctaccacga gaagtacccg  1620
accatcctacc cctccgcaa gaaactcgtg gacagcacag acaagctgaa cctgcgactg  1680
atctacttag ccctggccca catgattaag ttccggggtc acttcctaat cgagggagac  1740
ctcaaccccg ataacagtga cgtgaacaag ctcttcatcc aacttgtgca gacctacaac  1800
cagttgttcg aggagaaccc tatcaacgcc agcggggtgg acgcgaaagc tatcctgtcc  1860
gccaggctgt cgaagtctag gcgtctggag aacctaatcg ctcagctacc gggcgaaaaa  1920
aagaatggac tgttcggcaa cctcatagcc ctgagcctgg gctgacgcc caacttcaaa   1980
agcaacttcg acctggccga ggaccaagc tccaattga gcaaggacac ctacgacgac    2040
gacttggaca acctattggc ccagataggt gaccagtatg cagacctctt ccttgcggcc  2100
aagaacttga gtgacgctat actgctcagt gacatcctga gggtgaacac tgagatcact  2160
aaggcccctc tctctgcctc aatgattaag cgttacgacg agcatcacca ggatctcacc  2220
ctgcttaagg cccttgttcg gcagcagctc cctgagaagt acaaggagat attttttgac  2280
cagtctaaga acggctacgc cggttacatt gacggtgggg caagccagga ggagttctac  2340
aagttcatca agccgatcct tgagaagatg gacggcaccg aggagctact tgtcaagttg  2400
aaccgggaag acctgctccg gaaacagcgt acattcgaca acggcagcat ccctcaccag  2460
atccacctgg gcgaactaca cgccatcctc cgacgtcagg aggacttcta tccattcttg  2520
aaagataaca gggaaaaaat cgaaaaaata cttacgtttc gaataccta ctacgtggg    2580
ccccttgctc gggaaactca cagattcgca tggatgacca ggaagtcaga ggagaccatc  2640
acaccctgga actttgagga ggtggttgac aaaggtgctt ctgcccagtc cttcattgag  2700
cggatgacta acttcgacaa gaacctgccc aacgagaagg tgctgccaaa gcacagcctg  2760
ctctacgaat actttactgt gtacaatgag ctgacgaagg tgaagtacgt gacagagggg  2820
atgcggaagc ccgcttttcct gagcggcgag caaaaaaag caatcgtgga cctactgttc  2880
aagaccaacc gaaaggtgac agtgaagcag ctcaaggagg actacttcaa aaaaatcgag  2940
tgcttcgact ctgttgagat aagcggcgtg gaggaccgat tcaacgcctc attgggaacc  3000
tatcacgact tgctcaagat cattaaggac aaggacttcc tggataatga ggagaatgag  3060
gacatcctgg aggatattgt gctgaccctt actctattcg aggacaggga gatgatcgag  3120
gagcgactca agacctacgc tcacctgttc gacgacaagg ttatgaagca attgaagcgt  3180
aggcgataca cgggggtgggg aagactctcc cgaaaactga taaacggcat cagggacaag  3240
cagtcaggga agacgatctt ggacttcctg aaatccgacg ggttcgccaa ccgcaacttc  3300
atgcagctca ttcacgacga ctcactaacg ttcaaagagg acattcagaa ggctcaagtc  3360
agtggacaag gcgactccct gcacgagcac attgcaaacc ttgcgggctc cccggcgatt  3420
aaaaaggcca ttctccaaac ggttaaggtg gtggacgagc tggtgaaggt gatgggccga  3480
cacaagcctg agaacatcgt gatcgagatg gccagggaga accagacttac ccagaaggtg  3540
cagaagaact ctcgggaacg tatgaagcgt attgagggag ggattaagga gttgggctct  3600
caaatcctca aggagcaccc tgtggagaac actcagctcc aaaacgagaa gctgtacctg  3660
tactacctgc aaaacgggcg cgatatgtac gtggatcagg agttggacat caacaggctt  3720
agcgattacg acgtggacca catcgtgcca cagtcattct aaaggacaga cagcatcgac  3780
aacaaggttc tgacgaggag cgacaagaat cgagggaaca tggccatcgt tccatccgac  3840
gaggtggtca agaaaatgaa gaactattgg cgtcagcttc tgaacgccaa gctcatcacc  3900
cagcggaaat cgacaaccct gactaaggct gagcgaggcg gactctccga gcttgacaag  3960
gctggcttca tcaagcggca gttggtcgaa acccgacaga taacgaagca cgttgcccag  4020
atacttgact cccgtatgaa caccaagtac gacgagaacg acaagctcat cagggaggtg  4080
aaggtcatta cccttaagtc caaactcgtc agcgacttct gtaaggactt ccagttctac  4140
aaggtgcgcg agatcaataa ctaccaccac gcacacgacg cctacctgaa cgcagtggtt  4200
ggaaccgcgt tgattaaaaa gtaccccaag ttggagtcgg agttcgttta cggggactac  4260
aaggtgtacg acgttcggaa gatgatcgcc aagtctgaac aggagatcgg aaagcaacc  4320
gccaagtatt tcttctatag caacatcatg aacttcttta aaaccgagat cacacttgcc  4380
aatgcggaga tccgtaagag gccgctgatc gagacaaatg gagaaggtgg cgatcgtga  4440
tgggacaagg gccgcgactt cgcaaccgtt cggaaagtct tgtccatgcc tcaagtcaac  4500
atcgtcaaga agactgaggt gcaaacaggc gggttctcga aggagtccat actgcccaag  4560
aggaactcag acaagctcat agcacgcaaa aagactgggg atccaaagaa atacggcggg  4620
ttcgactcgc cgacagtcgc atactccgtg ttagtggtga ctaaagtgga aaaggggaag  4680
tccaagaagc tcaagtccgt caaggagttg ctcgggatca ccattatgga acggtcctca  4740
```

```
ttcgagaaga atcccattga cttcctagag gcgaagggct acaaagaggt caaaaaggac    4800
ctaattatta agctccccaa gtattcactc ttcgaacttg aaaatggtcg taagcggatg    4860
ttggcaagcg ctggagagct tcagaagggg aacgagcttc cactgccttc caagtacgtg    4920
aacttcctgt acctcgcctc tcattacgag aagttgaagg gctcaccgga ggacaacgag    4980
cagaagcagt tgttcgtgga gcagcacaag cactacctcg acgagatcat tgagcagata    5040
agtgagttca gcaaacgggt gatccttgcc gacgctaacc tggacaaggt gctgagcgcc    5100
tacaacaagc acagagacaa gccgatccga gagcaagcgg agaacatcat acacctgttc    5160
accctcacga acctcggggc tcccgcagcc ttcaaatatt ttgacacgac catcgaccgt    5220
aaacgctaca ctagcacgaa ggaggtgctg gacgctaccc ttatccacca gtccatcacc    5280
ggcctgtacg agacgagaat cgacttgtcg cagctcggtg gtgacggatc taagaagaga    5340
agaattaaac aagattga                                                  5358

SEQ ID NO: 72           moltype = DNA   length = 20
FEATURE                 Location/Qualifiers
misc_feature            1..20
                        note = CRISPR spacer
source                  1..20
                        mol_type = other DNA
                        organism = synthetic construct
SEQUENCE: 72
cagatcacaa acttcaaatg                                                20

SEQ ID NO: 73           moltype = DNA   length = 20
FEATURE                 Location/Qualifiers
misc_feature            1..20
                        note = CRISPR spacer
source                  1..20
                        mol_type = other DNA
                        organism = synthetic construct
SEQUENCE: 73
agccctcctt gcgctgcaag                                                20

SEQ ID NO: 74           moltype = DNA   length = 20
FEATURE                 Location/Qualifiers
misc_feature            1..20
                        note = CRISPR spacer
source                  1..20
                        mol_type = other DNA
                        organism = synthetic construct
SEQUENCE: 74
gaaatcacgg ttgagtgtga                                                20

SEQ ID NO: 75           moltype = DNA   length = 133
FEATURE                 Location/Qualifiers
source                  1..133
                        mol_type = other DNA
                        organism = Homo sapiens
SEQUENCE: 75
gtaagtatca aggttacaag acaggtttaa ggagaccaat agaaactggg cttgtcgaga    60
cagagaagac tcttgcgttt ctgataggca cctattggtc ttactgacat ccactttgcc    120
tttctctcca cag                                                       133

SEQ ID NO: 76           moltype = DNA   length = 99
FEATURE                 Location/Qualifiers
source                  1..99
                        mol_type = other DNA
                        organism = Simian virus 40
SEQUENCE: 76
gtaagtttag tctttttgtc ttttatttca ggtcccggat ccggtggtgg tgcaaatcaa    60
agaactgctc ctcagtggat gttgccttta cttctaggc                           99
```

OPTIMIZED CRISPR-CAS NUCLEASES AND BASE EDITORS AND METHODS OF USE THEREOF

STATEMENT OF PRIORITY

This application is a divisional application of U.S. patent application Ser. No. 17/078,576, filed on Oct. 23, 2020, which claims the benefit, under 35 U.S.C. § 119(e), of U.S. Provisional Application No. 62/925,422 filed on Oct. 24, 2019, the entire contents of which is incorporated by reference herein.

STATEMENT REGARDING ELECTRONIC FILING OF A SEQUENCE LISTING

A Sequence Listing in XML format, entitled 1499-8DV ST26.xml, 250,377 bytes in size, generated on Oct. 20, 2022 and filed herewith, is hereby incorporated by reference into the specification for its disclosures.

FIELD OF THE INVENTION

This invention relates to codon optimized CRISPR-Cas nucleases and nucleic acid constructs encoding base editors comprising a CRISPR-Cas nuclease and a deaminase domain, wherein the nucleic acid constructs are optimized for expression in a plant. The invention further relates to methods of modifying nucleic acids using the nucleic acid constructs.

BACKGROUND OF THE INVENTION

Gene editing is the process of utilizing a site-directed nuclease to introduce variation at targeted genomic locations. The most widely utilized nuclease for gene editing, Cas9, can introduce mutations at a genomic region upstream of an NGG motif (e.g., PAM). These mutations generated are typically insertions or deletions of a few base pairs, but the final sequence achieved can be unpredictable. As a result, obtaining precise genomic alterations using Cas9 editing has been difficult, and for the most part, use of these tools has been for the removal of protein function. As an alternative to Cas9 gene editing, targeted base editing has recently been developed by fusing deaminase protein domains to a disabled nuclease. The most commonly used version for modifying cytosine residues, cytosine base editors (CBE), comprise an Apobec1 domain, which functions to deaminate the cytosine residues within a targeting window. In addition, the base editors can include uracil glycosylase inhibitor (UGI) domains to help facilitate the repair of the modification towards a non-cytosine base change. In mammalian systems, these modification tools have been engineered to produce a very specific cytosine to thymine (C→T) change, through multiple different base editor iterations. In contrast to mammalian systems, the use of base editor cassettes for gene modification in plants has been limited and their efficacy has been low. For example, with the exception of rice, use of CBE base editors in plants has provided low editing efficiency.

To make base editing more useful across a greater number of plant species, new base editing tools are needed.

SUMMARY OF THE INVENTION

Base editing can provide modifications of specific nucleotides within a targeting window. The type of change introduced is reliant on the type of nuclease introduced and the repair profile of the target organism. For example, cytosine base editors (CBEs) provide a base change from C→T and adenine base editors (ABEs) provide a base change from A→G. These base changes limit the type of modification that can be designed and recovered. Further, while base editing has been demonstrated in plants, the editing efficiency is low (e.g., base edits are recovered at low rates). The only plant species that has exhibited a high level of editing is rice; however, even for rice the amount of base editing recovered has been quite variable, from 0% to about 80%. In maize, base edits have been recovered at a low frequency of about 10% frequency, and for wheat the efficiency of editing is even lower at less than 2%. Currently, base editing in plants relies on the use of base editing gene cassettes employed in mammalian systems that are placed into a plant-compatible cloning vector. To enhance efficacy of base editor constructs in planta, the present invention provides base editor expression cassettes in which the components have been codon optimized to increase the efficiency of base editor activity in plants.

One aspect of the invention provides a nucleic acid construct encoding a CRISPR-Cas nuclease, wherein the CRISPR-Cas nuclease is codon optimized for expression in a plant and comprises the nucleotide sequence of any one of SEQ ID NOs:1-11 and 23-25.

A second aspect provides a nucleic acid construct encoding a CRISPR-Cas nuclease operably associated with a promoter, wherein the promoter is associated with an intron. In some embodiments, the nucleic acid construct encoding a CRISPR-Cas nuclease is operably associated with a promoter region, wherein the promoter region comprises an intron. In some embodiments, the CRISPR-Cas nuclease operably associated with a promoter/promoter region may be codon optimized for expression in a plant.

A third aspect of the invention provides a nucleic acid construct encoding a CRISPR-Cas nuclease and a deaminase domain (e.g, a base editor), wherein the CRISPR-Cas nuclease is codon optimized for expression in a plant, and optionally, the deaminase domain is codon optimized for expression in a plant. In some aspects, a nucleic acid construct of the invention encoding a base editor comprises the nucleotide sequence of any one of SEQ ID NOs: 12-22.

A fourth aspect of the invention provides a method of modifying a target nucleic acid, comprising contacting a cell or a cell free system comprising the target nucleic acid with: (a) a nucleic acid construct of the invention, or an expression cassette or vector comprising the same; and (b) a guide nucleic acid (e.g., CRISPR RNA, CRISPR DNA, crRNA, crDNA), under conditions, wherein the nucleic acid construct is expressed and forms a complex with the guide nucleic acid, the complex then hybridizing to the target nucleic acid, thereby modifying the target nucleic acid.

A fifth aspect of the invention provides a method of editing a target nucleic acid, comprising contacting a cell or a cell free system comprising the target nucleic acid with: (a) a nucleic acid construct encoding an optimized CRISPR-Cas nuclease of the invention and an adenine deaminase (e.g., a base editor), or an expression cassette or vector comprising the same; and (b) a guide nucleic acid, under conditions wherein the nucleic acid construct is expressed and the CRISPR-Cas nuclease forms a complex with the guide nucleic acid, the complex hybridizing to the target nucleic acid, wherein the adenine deaminase domain converts an adenosine (A) to a guanine (G) in the target nucleic acid, thereby editing the target nucleic acid to produce a mutation (e.g., a point mutation) in the target nucleic acid.

A sixth aspect of the invention provides a method of editing a target nucleic acid, comprising contacting a cell or a cell free system comprising the target nucleic acid with: (a) a nucleic acid construct encoding an optimized CRISPR-Cas nuclease of the invention and an cytosine deaminase (e.g., a base editor), or an expression cassette or vector comprising the same; and (b) a guide nucleic acid under conditions wherein the nucleic acid construct is expressed and the CRISPR-Cas nuclease forms a complex with the guide nucleic acid, the complex hybridizing to the target nucleic acid, wherein the cytosine deaminase domain converts a cytosine (C) to a thiamine (T) in the target nucleic acid, thereby editing the target nucleic acid to produce a (point) mutation.

The invention further provides expression cassettes and/or vectors comprising the nucleic acid constructs of the invention, and cells comprising polypeptides, fusion proteins and/or nucleic acid constructs of the invention. Additionally, the invention provides kits comprising the nucleic acid constructs of the invention and expression cassettes, vectors and/or cells comprising the same.

These and other aspects of the invention are set forth in more detail in the description of the invention below.

SEQUENCES

SEQ ID NOs:1-11 are exemplary nucleotide sequences encoding Cas9 nucleases of the invention codon optimized for use in plants.

SEQ ID NOs:12-22 and SEQ ID NOs: 69-71 are exemplary nucleotide sequences encoding base editors of the invention.

SEQ ID NOs: 23-25 are exemplary nucleotide sequences encoding Cas12a nucleases of the invention that are codon optimized for use in plants.

SEQ ID NOs:26-42 are example Cas12a amino acid sequences useful with this invention.

SEQ ID NOs:43-49 are example adenine deaminase amino acid sequences useful with this invention.

SEQ ID NOs:50-59 are example cytosine deaminase amino acid sequences useful with this invention.

SEQ ID NO:60 is an exemplary uracil-DNA glycosylase inhibitor (UGI) useful with this invention.

SEQ ID NO:61-63 are exemplary regulatory sequences encoding a promoter and intron.

SEQ ID NOs: 64-66 provide an example of a protospacer adjacent motif position for a Type V CRISPR-Cas12a nuclease.

SEQ ID NOs: 67-68 provide exemplary nucleotide sequences encoding non-natural Cas9 nucleases.

SEQ ID NOs: 69-71 provide exemplary nucleic acid constructs comprising codon optimized polynucleotides encoding base editors that include a CRISPR-Cas9 nuclease and an adenine deaminase domain.

SEQ ID NOs: 72-73 provide exemplary

DETAILED DESCRIPTION

Figure 1:
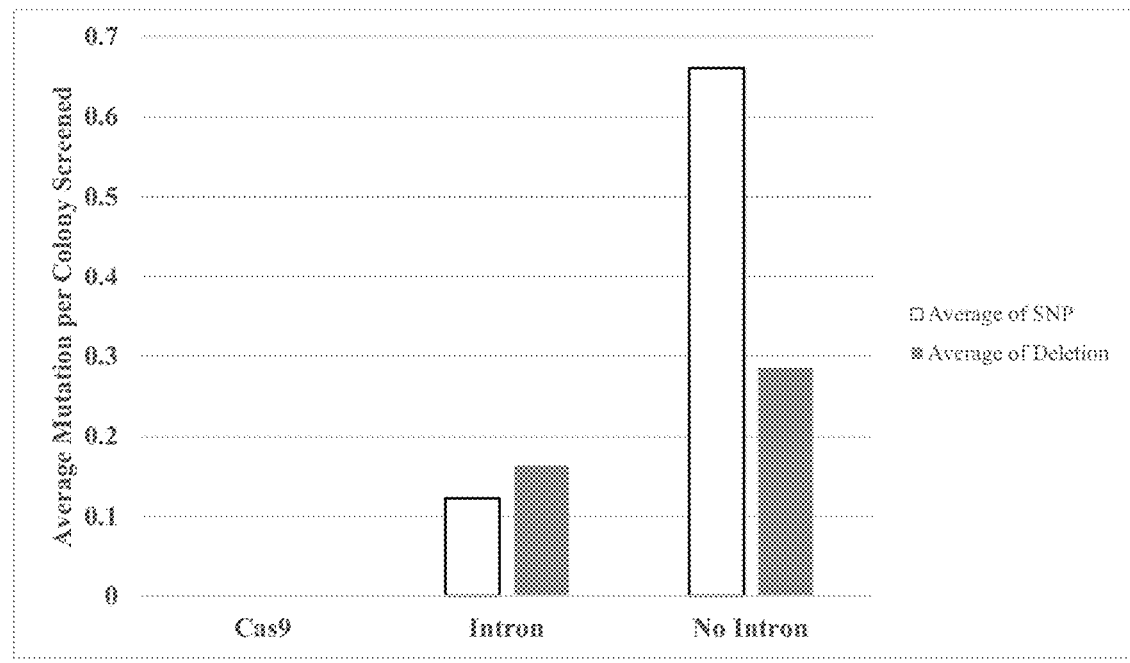
FIG. 1. Average mutation per colony screened. The number of SNPs or deletions was averaged across the total amount of colonies screened in each group.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measureable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to15 is disclosed, then 11, 12, 13, and 14 are also disclosed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "enhance," "enhancing," "improve" and "improving" (and grammatical variations thereof) describe an elevation of at least about 25%, 50%, 75%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction can result in no or essentially no (i.e., an insignificant amount, e.g., less than about 10% or even 5%) detectable activity or amount.

A "heterologous" or a "recombinant" nucleotide sequence is a nucleotide sequence not naturally associated with a host cell into which it is introduced, including non-naturally occurring multiple copies of a naturally occurring nucleotide sequence.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the reference organism. A "homologous" nucleic acid sequence is a nucleotide sequence naturally associated with a host cell into which it is introduced.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein, the term "gene" refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "mutation" refers to point mutations (e.g., missense, or nonsense, or insertions or deletions of single base pairs that result in frame shifts), insertions, deletions, and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue.

The terms "complementary" or "complementarity," as used herein, refer to the natural binding of polynucleotides under permissive salt and temperature conditions by base-pairing. For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement" as used herein can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity).

A "portion" or "fragment" of a nucleotide sequence of the invention will be understood to mean a nucleotide sequence of reduced length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid or nucleotide sequence and comprising, consisting essentially of and/or consisting of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid or nucleotide sequence. Such a nucleic acid fragment or portion according to the invention may be, where appropriate, included in a larger polynucleotide of which it is a constituent. As an example, a repeat sequence of guide nucleic acid of this invention may comprise a portion of a wild type CRISPR-Cas repeat sequence (e.g., a wild type Cas9 repeat, wild type Cas12a repeat, and the like).

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to said nucleotide sequence of the invention.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence as compared to a reference polypeptide.

As used herein, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, or more nucleotides in length, and any range therein, up to the full length of the sequence. In some embodiments, the nucleotide sequences can be substantially identical over at least about 20 nucleotides (e.g., about 20, 21, 22, 23, 24, 25, 26, 27, 28, 29, 30, 31, 32, 33, 34, 35, 36, 37, 38, 39, 40 nucleotides). In some embodiments, a substantially identical nucleotide or protein sequence performs substantially the same function as the nucleotide (or encoded protein sequence) to which it is substantially identical.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some representative embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6× SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The polynucleotide and/or recombinant nucleic acid constructs of this invention can be codon optimized for expression. In some embodiments, the polynucleotides, nucleic acid constructs, expression cassettes, and/or vectors of the invention (comprising/encoding a base editor, e.g., CRISPR-Cas nuclease, deaminase domain, linkers) are codon optimized for expression in a plant (e.g., in a particular plant species). In some embodiments, the codon optimized nucleic acid constructs, polynucleotides, expression cassettes, and/or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) identity or more to the nucleic acid constructs, polynucleotides, expression cassettes, and/or vectors that have not been codon optimized.

In any of the embodiments described herein, a polynucleotide or nucleic acid construct of the invention may be operatively associated with a variety of promoters and/or other regulatory elements for expression in a plant and/or a cell of a plant. Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron maybe referred to as a "promoter region" (e.g., Ubi1 promoter and intron).

By "operably linked" or "operably associated" as used herein in reference to polynucleotides, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," in reference to polypeptides, refers to the attachment of one polypeptide to another. A polypeptide may be linked to another polypeptide (at the N-terminus or the C-terminus) directly (e.g., via a peptide bond) or through a linker.

The term "linker" is art-recognized and refers to a chemical group, or a molecule linking two molecules or moieties, e.g., two domains of a fusion protein, such as, for example, a CRISPR-Cas nuclease polypeptide or domain (e.g., Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5 polypeptide or domain) and a polypeptide of interest (e.g., a nucleic acid-editing domain, a deaminase domain, an adenosine deaminase, a cytosine deaminase). A linker may be comprised of a single linking molecule or may comprise more than one linking molecule. In some embodiments, the linker can be an organic molecule, group, polymer, or chemical moiety such as a bivalent organic moiety. In some embodiments, the linker may be an amino acid or a peptide. In some embodiments, the linker is a peptide.

In some embodiments, a peptide linker useful with this invention may be about 4 to about 100 or more amino acids in length, for example, about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 4 to about 40, about 4 to about 50, about 4 to about 60, about 5 to about 40, about 5 to about 50, about 5 to about 60, about 9 to about 40, about 9 to about 50, about 9 to about 60, about 10 to about 40, about 10 to about 50, about 10 to about 60, or about 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length. In some embodiments, a peptide linker may be a GS linker.

A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in Genetic Engineering of Plants, T. Kosuge, C. Meredith and A. Hollaender (eds.), Plenum Press, pp. 211-227). In some embodiments, a promoter region may comprise at least one intron (e.g., SEQ ID NO:61, SEQ ID NO:62 or SEQ ID NO:63).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. Plant Cell Rep. 23:727-735 (2005); Li et al. *Gene* 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. Gene 403:132-142 (2007)) and Pdca1 is induced by salt (Li et al. *Mol Biol. Rep.* 37:1143-1154 (2010)).

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and arabidopsis (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604, 121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. *Plant Biotechnol. Reports* 9(5):297-306 (2015)), ZmSTK2_USP from maize (Wang et al. *Genome* 60(6):485-495 (2017)), LAT52 and LAT59 from tomato (Twell et al. *Development* 109(3):705-713 (1990)), Zm13 (U.S. Pat. No. 10,421,972), PLA$_2$-δ promoter from arabidopsis (U.S. Pat. No. 7,141, 424), and/or the ZmC5 promoter from maize (International PCT Publication No. WO1999/042587.

Additional examples of plant tissue-specific/tissue preferred promoters include, but are not limited to, the root hair-specific cis-elements (RHEs) (Kim et al. *The Plant Cell* 18:2958-2970 (2006)), the root-specific promoters RCc3 (Jeong et al. *Plant Physiol.* 153:185-197 (2010)) and RB7 (U.S. Pat. No. 5459252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) Nucleic Acids Res. 12:3983-4000), S-adenosyl-L-methionine synthetase (SAMS) (Vander Mijnsbrugge et al. (1996) *Plant and Cell Physiology,* 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986)*Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), petunia chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/ expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron.

Non-limiting examples of introns useful with the present invention include introns from the ADHI gene (e.g., Adh1-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdca1), the psbA gene, the atpA gene, or any combination thereof. As a non-limiting example, a nucleic acid construct of the present invention may encode a base editor comprising an optimized CRISPR-Cas nuclease (e.g., SEQ ID NOs:1-11 or 23-25) and a deaminase, wherein the nucleic acid construct further comprises a promoter comprising/associated with an intron. As a further non-limiting example, a nucleic acid construct of the present invention may encode a base editor comprising an optimized CRISPR-Cas nuclease (e.g., SEQ ID NOs:1-11 or 23-25) and a deaminase, wherein the nuclease and/or the deaminase comprises one or more introns and optionally, the nucleic acid construct further comprises a promoter comprising/associated with an intron.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a nucleic acid construct of the invention (e.g., encoding a base editor comprising a CRISPR-Cas nuclease and a deaminase domain), wherein the nucleic acid construct is operably associated with at least a control sequence (e.g., a promoter). Thus, some embodiments of the invention provide expression cassettes designed to express, for example, a nucleic acid construct of the invention (e.g., a nucleic acid construct of the invention encoding a base editor comprising a CRISPR-Cas nuclease and a deaminase domain, wherein the nucleic acid construct is optimized for expression in a plant).

An expression cassette comprising a nucleic acid construct of the invention may be chimeric, meaning that at least one of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette may also be one that is naturally occurring but has been obtained in a recombinant form useful for heterologous expression.

An expression cassette can optionally include a transcriptional and/or translational termination region (i.e., termination region) and/or an enhancer region that is functional in the selected host cell. A variety of transcriptional terminators and enhancers are known in teh art and are available for use in expression cassettes. Transcriptional terminators are responsible for the termination of transcription and correct mRNA polyadenylation. A termination region and/or the enhancer region may be native to the transcriptional initiation region, may be native to a gene encoding a CRISPR-Cas nuclease or a gene encoding a deaminase encoded by a nucleic acid construct of the invention, may be native to a host cell, or may be native to another source (e.g., foreign or heterologous to the promoter, to a gene encoding the CRISPR-Cas nuclease or a gene encoding the deaminase encoded by a nucleic acid construct of the invention, to a host cell, or any combination thereof).

An expression cassette of the invention also can include a polynucleotide encoding a selectable marker, which can be used to select a transformed host cell. As used herein, "selectable marker" means a polynucleotide sequence that when expressed imparts a distinct phenotype to the host cell expressing the marker and thus allows such transformed cells to be distinguished from those that do not have the marker. Such a polynucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

In addition to expression cassettes, the nucleic acid molecules/constructs and polynucleotide sequences described herein can be used in connection with vectors. The term "vector" refers to a composition for transferring, delivering or introducing a nucleic acid (or nucleic acids) into a cell. A vector comprises a nucleic acid construct comprising the nucleotide sequence(s) to be transferred, delivered or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, mini-circles, or Agrobacterium binary vectors in double or single stranded linear or circular form which may or may not be self transmissible or mobilizable. In some embodiments, a viral vector can include, but is not limited, to a retroviral, lentiviral, adenoviral, adeno-associated, or herpes simplex viral vector. A vector as defined herein can transform a prokaryotic or eukaryotic host either by integration into the cellular genome or exist extrachromosomally (e.g. autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid construct of this invention and/or expression cassettes comprising the same may be comprised in vectors as described herein and as known in the art.

As used herein, "contact," "contacting," "contacted," and grammatical variations thereof, refer to placing the components of a desired reaction together under conditions suitable for carrying out the desired reaction (e.g., transformation, transcriptional control, genome editing, nicking, and/or cleavage). Thus, for example, a target nucleic acid may be contacted with a nucleic acid construct of the invention encoding a base editor comprising a codon optimized CRISPR-Cas nuclease, and a guide nucleic acid, under conditions whereby the CRISPR-Cas nuclease is expressed, whereby the CRISPR-Cas nuclease forms a complex with the guide nucleic acid, and the complex hybridizes to the target nucleic acid, thereby modifying the target nucleic acid. In some embodiments, a target nucleic acid may be contacted with a nucleic acid construct of the invention encoding a base editor comprising a codon optimized CRISPR-Cas nuclease linked to a deaminase domain, and a guide nucleic acid, under conditions wherein the CRISPR-Cas nuclease and deaminase domain are expressed as a fusion protein, whereby the fusion protein forms a complex with the guide nucleic acid, and the complex hybridizes to the target nucleic acid, thereby modifying (editing) the target nucleic acid. As described herein, the target nucleic acid may be contacted with the nucleic acid constructs of the invention prior to, concurrently with, or after contact with the guide nucleic acid.

As used herein, "modifying" or "modification" in reference to a target nucleic acid includes editing (e.g., mutating), covalent modification, exchanging/substituting nucleic acids/nucleotide bases, deleting, cleaving, nicking, and/or transcriptional control of a target nucleic acid.

"Introducing," "introduce," "introduced" (and grammatical variations thereof) in the context of a polynucleotide of interest means presenting a nucleotide sequence of interest (e.g., polynucleotide, a nucleic acid construct, and/or a guide nucleic acid) to a host organism or cell of said organism (e.g., host cell; e.g., a plant cell) in such a manner that the nucleotide sequence gains access to the interior of a cell. Thus, for example, a nucleic acid construct of the invention encoding a base editor optimized for expression in a plant as described herein and guide nucleic acid may be introduced into a cell of an organism, thereby transforming the cell with the base editor and guide nucleic acid.

The term "transformation" as used herein refers to the introduction of a heterologous nucleic acid into a cell. Transformation of a cell may be stable or transient. Thus, in some embodiments, a host cell or host organism may be stably transformed with a polynucleotide/nucleic acid molecule of the invention. In some embodiments, a host cell or host organism may be transiently transformed with a nucleic acid construct of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genome of the host organism. Thus, in some embodiments, a nucleic acid construct of the invention (e.g., encoding a CRISPR-Cas nuclease codon optimized for plant expression (e.g., SEQ ID NOs:1-11, 23-25) and/or encoding a base editor comprising a codon optimized CRISPR-Cas nuclease and a deaminase domain (e.g., a fusion protein comprising the CRISPR-Cas nuclease linked to the deaminase domain) (e.g., SEQ ID NOs:12-22) may be transiently introduced into a cell with a guide nucleic acid and as such, no DNA maintained in the cell.

A nucleic acid construct of the invention can be introduced into a cell by any method known to those of skill in the art. In some embodiments of the invention, transformation of a cell comprises nuclear transformation. In other embodiments, transformation of a cell comprises plastid transformation (e.g., chloroplast transformation). In still further embodiments, the recombinant nucleic acid constuct of the invention can be introduced into a cell via conventional breeding techniques.

Procedures for transforming both eukaryotic and prokaryotic organisms are well known and routine in the art and are described throughout the literature (See, for example, Jiang et al. 2013. Nat. Biotechnol. 31:233-239; Ran et al. Nature Protocols X:2281-2:308 (2013)).

A nucleotide sequence therefore can be introduced into a host organism or its cell in any number of ways that are well known in the art. The methods of the invention do not depend on a particular method for introducing one or more nucleotide sequences into the organism, only that they gain access to the interior of at least one cell of the organism. Where more than one nucleotide sequence is to be introduced, they can be assembled as part of a single nucleic acid construct, or as separate nucleic acid constructs, and can be located on the same or different nucleic acid constructs. Accordingly, the nucleotide sequences can be introduced into the cell of interest in a single transformation event, and/or in separate transformation events, or, alternatively, where relevant, a nucleotide sequence can be incorporated into a plant, for example, as part of a breeding protocol.

Studies utilizing base editing in plants are limited. Zong et al. examined cytosine base editing (CBE) activity in rice, wheat, and maize (*Nature Biotechnol.* 35:438-440 (2017)) but found that while high base editing activity could be found in rice, the amount of activity in wheat and maize was quite low. Additionally, the only base editing architectures that have been utilized in plants are based on the base editing 1 or base editing 3 variants. In contrast, the present invention uses base editing 4 architecture, which comprises an additional UGI domain and longer linker sequence between the APOBEC1 domain and nuclease. See, e.g., Rees et al. *Nat. Rev. Genet.* 19:770-788 (2018).

In some embodiments, the present invention provides nucleic acid constructs encoding CRISPR-Cas nucleases codon optimized for expression in a plant, for example, SEQ ID NOs:1-11 and 23-25. In some embodiments, the nucleic acid constructs of the invention comprise base editors comprising a CRISPR-Cas nuclease and a deaminase domain, wherein the CRISPR-Cas nuclease, and optionally, the deaminase sequence, is/are codon optimized for expression in a plant. In some embodiments, a base editor of the invention can comprise, for example, a nucleotide sequence of any one of SEQ ID NOs:12 to 22.

In some embodiments, a nucleic acid construct encoding a CRISPR-Cas nuclease or base editor of the invention may be operably linked to at least one regulatory sequence, optionally, wherein the at least one regulatory sequence may be codon optimized for expression in a plant. In some embodiments, the at least one regulatory sequence may be, for example, a promoter, an operon, a terminator, or an enhancer. In some embodiments, the at least one regulatory sequence may be a promoter. In some embodiments, the regulatory sequence may be an intron. In some embodiments, the at least one regulatory sequence may be, for example, a promoter operably associated with an intron or a promoter region comprising an intron. In some embodiments, the at least one regulatory sequence may be, for example a ubiquitin promoter and its associated intron (e.g., *Medicago truncatula* and/or *Zea mays* and their associated introns). In some embodiments, the at least one regulatory sequence may be a terminator nucleotide sequence and/or an enhancer nucleotide sequence.

In some embodiments, the present invention provides a nucleic acid construct encoding a CRISPR-Cas nuclease (e.g., a Type I, Type II, Type III, Type IV, Type V, or Type VI CRISPR-Cas nuclease as described herein) operably associated with a promoter region, wherein the promoter region comprises an intron, optionally wherein the promoter region may be a ubiquitin promoter and intron (e.g., a *Medicago* or a maize ubiquitin promoter and intron, e.g., SEQ ID NOs:61-63). In some embodiments, the CRISPR-Cas nuclease operably associated with a promoter region comprising an intron may be codon optimized for expression in a plant.

In some embodiments, a nucleic acid construct of the invention encoding a CRISPR-Cas nuclease may further encode one or more polypeptides of interest, optionally wherein the one or more polypeptides of interest may be codon optimized for expression in a plant.

A polypeptide of interest useful with this invention can include, but is not limited to, a polypeptide or protein domain having deaminase activity, nickase activity, recombinase activity, transposase activity, methylase activity, glycosylase (DNA glycosylase) activity, glycosylase inhibitor activity (e.g., uracil-DNA glycosylase inhibitor (UGI)), demethylase activity, transcription activation activity, transcription repression activity, transcription release factor activity, histone modification activity, nuclease activity, single-strand RNA cleavage activity, double-strand RNA cleavage activity, restriction endonuclease activity (e.g., Fok1), nucleic acid binding activity, methyltransferase activity, DNA repair activity, DNA damage activity, dismutase activity, alkylation activity, depurination activity, oxidation activity, pyrimidine dimer forming activity, integrase activity, transposase activity, polymerase activity, ligase activity, helicase activity, and/or photolyase activity. In some embodiments, the polypeptide of interest is a deaminase (e.g., an adenine deaminase, a cytosine deaminase). In some embodiments, the polypeptide of interest is a Fok1 nuclease, or a uracil-DNA glycosylase inhibitor. When encoded in the polynucleotide of interest, the encoded polypeptide or protein domain may be codon optimized for expression in a plant.

In some embodiments, a nucleic acid construct of the invention encoding a base editor comprising a CRISPR-Cas nuclease and a deaminase domain (e.g., encoding a fusion protein comprising a CRISPR-Cas nuclease and a deaminase domain) may further encode a polypeptide of interest, optionally wherein the polypeptide of interest may be codon optimized for expression in a plant.

A CRISPR-Cas nuclease useful with this invention may be any CRISPR-Cas nuclease functional with a deaminase polypeptide or deaminase domain (e.g., functional with a cytosine deaminase domain and/or an adenine deaminase domain). A CRISPR-Cas nuclease can include, but is not limited to, Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5.

In some embodiments, a CRISPR-Cas nuclease useful with the invention may comprise a mutation in its nuclease active site (e.g., RuvC, HNH, e.g., RuvC site of a Cas12a nuclease domain; e.g., RuvC site and/or HNH site of a Cas9 nuclease domain). A CRISPR-Cas nuclease having a mutation in its nuclease active site, and therefore, no longer comprising nuclease activity, is commonly referred to as "dead," e.g., dCas. In some embodiments, a CRISPR-Cas nuclease domain or polypeptide having a mutation in its nuclease active site may have impaired activity or reduced activity as compared to the same CRISPR-Cas nuclease without the mutation.

A CRISPR Cas9 polypeptide or CRISPR Cas9 domain useful with this invention may be any known or later identified Cas9 nuclease. In some embodiments, a CRISPR Cas9 polypeptide can be a Cas9 polypeptide from, for example, *Streptococcus* spp. (e.g., *S. pyogenes*, *S. thermophilus*), *Lactobacillus* spp., *Bifidobacterium* spp., *Kandleria* spp., *Leuconostoc* spp., *Oenococcus* spp., *Pediococcus* spp., *Weissella* spp., and/or *Olsenella* spp. Exemplary Cas9 nucleases of the present invention include the amino acid sequence of any one of SEQ ID NOs:1-11, 67 or 68 (e.g., SEQ ID NOs:1, 2, 3, 4, 5, 6, 7, 8, 9, 10, 11 and/or 67 or 68) or a polynucleotide encoding the same.

Cas12a is a Type V Clustered Regularly Interspaced Short Palindromic Repeats (CRISPR)-Cas nuclease. Cas12a differs in several respects from the more well-known Type II CRISPR Cas9 nuclease. For example, Cas9 recognizes a G-rich protospacer-adjacent motif (PAM) that is 3' to its guide RNA (gRNA, sgRNA) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

A CRISPR Cas12a polypeptide or CRISPR Cas12a domain useful with this invention may be any known or later identified Cas12a nuclease (previously known as Cpf1) (see, e.g., U.S. Pat. No. 9,790,490, which is incorporated by reference for its disclosures of Cpf1 (Cas12a) sequences). The term "Cas12a", "Cas12a polypeptide" or "Cas12a domain" refers to an RNA-guided nuclease comprising a Cas12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as deadCas12a (e.g., dCas12a). In some embodiments, a Cas12a domain or Cas12a polypeptide having a mutation in its nuclease active site may have impaired activity.

In some embodiments, a Cas12a polypeptide/domain that may be optimized according to the present invention can include, but is not limited to, the amino acid sequence of any one of SEQ ID NOs:26-42 (e.g., SEQ ID NOs: 26, 27, 28, 29, 30, 31, 32, 33, 34, 35, 36, 37, 38, 39, 40, 41, or 42), or a polynucleotide encoding the same. In some embodiments, example optimized Cas12a polypeptides of the invention comprise the amino acid sequence of any one of SEQ ID NOs:23-25 (e.g., SEQ ID NOs:23, 24, or 25), or a polynucleotide encoding the same.

Any deaminase domain/polypeptide useful for base editing may be used with this invention. In some embodiments, the deaminase domain may be a cytosine deaminase domain or an adenine deaminase domain. A cytosine deaminase (or cytidine deaminase) useful with this invention may be any known or later identified cytosine deaminase from any organism (see, e.g., U.S. Pat. No. 10,167,457 and Thuronyi et al. Nat. Biotechnol. 37:1070-1079 (2019), each of which is incorporated by reference herein for its disclosure of cytosine deaminases). Cytosine deaminases can catalyze the hydrolytic deamination of cytidine or deoxycytidine to uridine or deoxyuridine, respectively. Thus, in some embodiments, a deaminase or deaminase domain useful with this invention may be a cytidine deaminase domain, catalyzing the hydrolytic deamination of cytosine to uracil. In some embodiments, a cytosine deaminase may be a variant of a naturally-occurring cytosine deaminase, including but not limited to a primate (e.g., a human, monkey, chimpanzee, gorilla), a dog, a cow, a rat or a mouse. Thus, in some embodiments, an cytosine deaminase useful with the invention may be about 70% to about 100% identical to a wild type cytosine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring cytosine deaminase).

In some embodiments, a cytosine deaminase useful with the invention may be an apolipoprotein B mRNA-editing complex (APOBEC) family deaminase. In some embodiments, the cytosine deaminase may be an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, an APOBEC4 deaminase, a human activation induced deaminase (hAID), an rAPOBEC1, FERNY, and/or a CDA1, optionally a pmCDA1, an atCDA1 (e.g., At2g19570), an hAID and evolved versions of the same. In some embodiments, the cytosine deaminase may be an APOBEC1 deaminase having the amino acid sequence of SEQ ID NO:50, SEQ ID NO:55 or SEQ ID NO:57. In some embodiments, the cytosine deaminase may be an APOBEC3A deaminase having the amino acid sequence of SEQ ID NO:51. In some embodiments, the cytosine deaminase may be an CDA1 deaminase, optionally a CDA1 having the amino acid sequence of SEQ ID NO:52 or SEQ ID NO:54. In some embodiments, the cytosine deaminase may be a FERNY deaminase, optionally a FERNY having the amino acid sequence of SEQ ID NO:53 or SEQ ID NO:56. In some embodiments, the cytosine deaminase may be an hAID deaminase, optionally a hAID deaminase having the amino acid sequence of SEQ ID NO:58 or SEQ ID NO:59. In some embodiments, a cytosine deaminase useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical) to the amino acid sequence of a naturally occurring cytosine deaminase (e.g., an evolved deaminase). In some embodiments, a cytosine deaminase useful with the invention may be about 70% to about 99.5% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical) to the amino acid sequence of SEQ ID NOs:50-59 (e.g., at least 80%, at least 85%, at least 90%, at least 92%, at least 95%, at least 96%, at least 97%, at least 98%, at least 99%, or at least 99.5% identical to the amino acid sequence of SEQ ID NOs:50-59). In some embodiments, a polynucleotide encoding a cytosine deaminase may be codon optimized for expression in an organism and the codon optimized polypeptide may be about 70% to 99.5% identical to the reference polynucleotide.

In some embodiments, a base editor of this invention comprising a CRISPR-Cas nuclease and a cytosine deaminase may further comprise a polypeptide of interest. In some embodiments, the polypeptide of interest may be a uracil glycosylase inhibitor (UGI) (e.g., uracil-DNA glycosylase inhibitor) polypeptide/domain. In some embodiments, a nucleic acid construct encoding an optimized CRISPR-Cas nuclease of this invention and a cytosine deaminase domain (e.g., encoding a fusion protein comprising a CRISPR-Cas nuclease and a cytosine deaminase domain) may further encode a uracil-DNA glycosylase inhibitor (UGI), optionally wherein the UGI is codon optimized for expression in a plant. In some embodiments, the invention provides a fusion protein comprising a CRISPR-Cas nuclease, a cytosine deaminase domain, and a UGI and/or one or more polynucleotides encoding the same, optionally wherein the one or more polynucleotides may be codon optimized for expression in a plant.

A "uracil glycosylase inhibitor" useful with the invention may be any protein that is capable of inhibiting a uracil-DNA glycosylase base-excision repair enzyme. In some embodiments, a UGI domain comprises a wild type UGI or a fragment thereof. In some embodiments, a UGI domain useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical and any range or value therein) to the amino acid sequence of a naturally occurring UGI domain. In some embodiments, a UGI domain may comprise the amino acid sequence of SEQ ID NO: 60 or a polypeptide having about 70% to about 99.5% identity to the amino acid sequence of SEQ ID NO:60 (e.g., at least 80%, at least 85%, at least 90%, at least 92%, at least 95%, at least 96%, at least 97%, at least 98%, at least 99%, or at least 99.5% identical to the amino acid sequence of SEQ ID NO:60). For example, in some embodiments, a UGI domain may comprise a fragment of the amino acid sequence of SEQ ID NO:60 that is 100% identical to a portion of consecutive nucleotides (e.g., 10, 15, 20, 25, 30, 35, 40, 45, 50, 55, 60, 65, 70, 75, 80 consecutive nucleotides; e.g., about 10, 15, 20, 25, 30, 35, 40, 45, to about 50, 55, 60, 65, 70, 75, 80 consecutive nucleotides) of the amino acid sequence of SEQ ID NO:60. In some embodiments, a UGI domain may be a variant of a known UGI (e.g., SEQ ID NO:60) having about 70% to about 99.5% identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% identity, and any range or value therein) to the known UGI. In some embodiments, a polynucleotide encoding a UGI may be codon optimized for expression in a plant and the codon optimized polypeptide may be about 70% to about 99.5% identical to the reference polynucleotide.

An adenine deaminase (or adenosine deaminase) useful with this invention may be any known or later identified adenine deaminase from any organism (see, e.g., U.S. Pat. No. 10,113,163, which is incorporated by reference herein for its disclosure of adenine deaminases). An adenine deaminase can catalyze the hydrolytic deamination of adenine or adenosine. In some embodiments, the adenine deaminase may catalyze the hydrolytic deamination of adenosine or deoxyadenosine to inosine or deoxyinosine, respectively. In some embodiments, the adenosine deaminase may catalyze the hydrolytic deamination of adenine or adenosine in DNA. In some embodiments, an adenine deaminase encoded by a nucleic acid construct of the invention may generate an A→G conversion in the sense (e.g., "+"; template) strand of the target nucleic acid or a T→C conversion in the antisense (e.g., "−", complementary) strand of the target nucleic acid.

In some embodiments, an adenosine deaminase may be a variant of a naturally-occurring adenine deaminase. Thus, in some embodiments, an adenosine deaminase may be about 70% to 100% identical to a wild type adenine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring adenine deaminase). In some embodiments, the deaminase or deaminase does not occur in nature and may be referred to as an engineered, mutated or evolved adenosine deaminase. Thus, for example, an engineered, mutated or evolved adenine deaminase polypeptide or an adenine deaminase domain may be about 70% to 99.9% identical to a naturally occurring adenine deaminase polypeptide/domain (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% identical, and any range or value therein, to a naturally occurring adenine deaminase polypeptide or adenine deaminase domain). In some embodiments, the adenosine deaminase may be from a bacterium, (e.g., *Escherichia coli, Staphylococcus aureus, Haemophilus influenzae, Caulobacter crescentus*, and the like). In some embodiments, a polynucleotide encoding an adenine deaminase polypeptide/domain may be codon optimized for expression in a plant.

In some embodiments, an adenine deaminase domain may be a wild type tRNA-specific adenosine deaminase domain, e.g., a tRNA-specific adenosine deaminase (TadA) and/or a mutated/evolved adenosine deaminase domain, e.g., mutated/evolved tRNA-specific adenosine deaminase domain (TadA*). In some embodiments, a TadA domain may be from *E. coli*. In some embodiments, the TadA may be modified, e.g., truncated, missing one or more N-terminal and/or C-terminal amino acids relative to a full-length TadA (e.g., 1, 2, 3, 4, 5, 6, 7, 8, 9, 10, 11, 12, 13, 14, 15, 6, 17, 18, 19, or 20 N-terminal and/or C terminal amino acid residues may be missing relative to a full length TadA. In some embodiments, a TadA polypeptide or TadA domain does not comprise an N-terminal methionine. In some embodiments, a wild type *E. coli* TadA comprises the amino acid sequence of SEQ ID NO:43. In some embodiments, a mutated/ evolved *E. coli* TadA* comprises the amino acid sequence of SEQ ID NOs:44-49 (e.g., SEQ ID NOs: 44, 45, 46, 47, 48 or 49). In some embodiments, a polynucleotide encoding a TadA/TadA* may be codon optimized for expression in a plant.

The nucleic acid constructs of the invention encoding a base editor comprising a CRISPR-Cas nuclease domain and a deaminase domain may be used in combination with a guide RNA (gRNA, CRISPR array, CRISPR RNA, crRNA), designed to function with the encoded CRISPR-Cas nuclease domain, to modify a target nucleic acid. A guide nucleic acid useful with this invention comprises a spacer sequence and a repeat sequence. The guide nucleic acid is capable of forming a complex with the CRISPR-Cas nuclease domain encoded and expressed by the nucleic acid construct of the invention and the spacer sequence is capable of hybridizing to a target nucleic acid, thereby guiding the nucleic acid construct (e.g., the CRISPR-Cas nuclease, the CRISPR-Cas nuclease and the deaminase domain (e.g., a base editor of the invention)) to the target nucleic acid, wherein the target nucleic acid may be modified (e.g., cleaved or edited) or modulated (e.g., modulating transcription) by the encoded deaminase domain and/or polypeptide of interest.

As an example, a nucleic acid construct encoding a Cas9 domain linked to a cytosine deaminase domain (e.g., fusion protein) may be used in combination with a Cas9 guide nucleic acid to modify a target nucleic acid, wherein the cytosine deaminase domain of the fusion protein deaminates a cytosine base in the target nucleic acid, thereby editing the target nucleic acid. In a further example, a nucleic acid construct encoding a Cas9 domain linked to an adenine deaminase domain (e.g., fusion protein) may be used in combination with a Cas9 guide nucleic acid to modify a target nucleic acid, wherein the adenine deaminase domain of the fusion protein deaminates an adenosine base in the target nucleic acid, thereby editing the target nucleic acid.

Likewise, a nucleic acid construct encoding a Cas12a domain (or other selected CRISPR-Cas nuclease, e.g., C2c1, C2c3, Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5) linked to a cytosine deaminase domain or adenine deaminase domain (e.g., fusion protein) may be used in combination with a Cas12a guide nucleic acid (or the guide nucleic acid for the other selected CRISPR-Cas nuclease) to modify a target nucleic acid, wherein the cytosine deaminase domain or adenine deaminase domain of the fusion protein deaminates a cytosine base in the target nucleic acid, thereby editing the target nucleic acid.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target DNA (e.g., protospacer), and at least one repeat sequence (e.g., a repeat of a Type V Cas12a CRISPR-Cas system, or a fragment or portion thereof; a repeat of a Type II Cas9 CRISPR-Cas system, or fragment thereof; a repeat of a Type V C2c1 CRISPR Cas system, or a fragment thereof; a repeat of a CRISPR-Cas system of, for example, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5, or a fragment thereof), wherein the repeat sequence may be linked to the 5' end and/or the 3' end of the spacer sequence. The design of a gRNA of this invention may be based on a Type I, Type II, Type III, Type IV, Type V, or Type VI CRISPR-Cas system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one repeat sequence-spacer sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made and not found in nature. A gRNA can be quite long and may be used as an aptamer (like in the MS2 recruitment strategy) or other RNA structures hanging off the spacer.

A "repeat sequence" as used herein, refers to, for example, any repeat sequence of a wild-type CRISPR Cas locus (e.g., a Cas9 locus, a Cas12a locus, a C2c1 locus, etc.) or a repeat sequence of a synthetic crRNA that is functional with the CRISPR-Cas nuclease encoded by the nucleic acid constructs of the invention that encode a base editor. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild-type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild-type CRISPR-Cas locus may be determined through established algorithms, such as using the CRISPRfinder offered through CRISPRdb (see, Grissa et al. Nucleic Acids Res. 35 (Web Server issue):W52-7). In some embodiments, a repeat sequence or portion thereof is linked at its 3' end to the 5' end of a spacer sequence, thereby forming a repeat-spacer sequence (e.g., guide RNA, crRNA).

In some embodiments, a repeat sequence comprises, consists essentially of, or consists of at least 10 nucleotides depending on the particular repeat and whether the guide RNA comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein; e.g., about). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100 or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% identity (e.g., at least about 90%, 91%, 92%, 93%, 94%, 95%, 96%, 97%, 98%, 99%, or more) to the same region (e.g., 5' end) of a wild type CRISPR Cas repeat nucleotide sequence. In some embodiments, a portion of a repeat sequence may comprises a pseudoknot-like structure at its 5' end (e.g., "handle").

A "spacer sequence" as used herein is a nucleotide sequence that is complementary to a target nucleic acid (e.g., target DNA) (e.g, protospacer). The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a target nucleic acid. Thus, in some embodiments, the spacer sequence can have one, two, three, four, or five mismatches as compared to the target nucleic acid, which mismatches can be contiguous or noncontiguous. In some embodiments, the spacer sequence can have 70% complementarity to a target nucleic acid. In other embodiments, the spacer nucleotide sequence can have 80% complementarity to a target nucleic acid. In still other embodiments, the spacer nucleotide sequence can have 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that is at least about 15 nucleotides to about 30 nucleotides in length. In some embodiments, the spacer is about 20 nucleotides in length. In some embodiments, the spacer is about 23 nucleotides in length.

In some embodiments, the 5' region of a spacer sequence of a guide RNA may be identical to a target DNA, while the 3' region of the spacer may be substantially complementary to the target DNA (e.g., Type V CRISPR-Cas), or the 3' region of a spacer sequence of a guide RNA may be identical to a target DNA, while the 5' region of the spacer may be substantially complementary to the target DNA (e.g., Type II CRISPR-Cas), and therefore, the overall complementarity of the spacer sequence to the target DNA may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence may be 100% complementary to the target DNA, while the remaining nucleotides in the 3' region of the spacer sequence are substantially complementary (e.g., at least about 70% complementary) to the target DNA. In some embodiments, the first 1 to 8 nucleotides (e.g., the first 1, 2, 3, 4, 5, 6, 7, 8, nucleotides, and any range therein) of the 5' end of the spacer sequence may be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA.

As a further example, in a guide for a Type II CRISPR-Cas system, the first 1, 2, 3, 4, 5, 6, 7, 8, 9, 10 nucleotides in the 3' region (i.e., seed region) of, for example, a 20 nucleotide spacer sequence may be 100% complementary to the target DNA, while the remaining nucleotides in the 5' region of the spacer sequence are substantially complementary (e.g., at least about 70% complementary) to the target DNA. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target DNA, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target DNA.

In some embodiments, a seed region of a spacer may be about 8 to about 10 nucleotides in length, about 5 to about 6 nucleotides in length, or about 6 nucleotides in length.

As used herein, a "target nucleic acid", "target DNA," "target nucleotide sequence," "target region," or a "target region in the genome" refers to a region of an organism's genome that is fully complementary (100% complementary) or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a guide RNA of this invention. A region useful for a CRISPR-Cas system, known as the protospacer adjacent motif (PAM), is located adjacent to the spacer (or target) sequence. These PAM DNA sequences are typically described by referencing their sequence and location with respect to the non-target strand of the CRISPR complex. PAM sequences can be either 3' (e.g., Type V CRISPR-Cas system) or 5' (e.g., Type II CRISPR-Cas system) to the end of the protospacer sequence. A target region (also referred to as the protospacer) may be selected from any region of at least 15 consecutive nucleotides (e.g., 15, 16, 17, 18, 19, 20, 21, 22, 23, 24, 25, 26, 27, 28, 29, 30 or more than 30 nucleotides, and the like) located adjacent to a PAM sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences (e.g., guide RNAs, CRISPR arrays, crRNAs).

In the case of Type V CRISPR-Cas (e.g., Cas12a) systems and Type II CRISPR-Cas (Cas9) systems, the protospacer sequence is flanked by (e.g., immediately adjacent to) a protospacer adjacent motif (PAM). For Type IV CRISPR-Cas systems, the PAM is located at the 5' end on the non-target strand and at the 3' end of the target strand (see below, as an example).

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR-Cas systems. Makarova et al. describes the nomenclature for all the classes, types and subtypes of CRISPR systems (*Nature Reviews Microbiology* 13:722-736 (2015)). Guide structures and PAMs are described in by R. Barrangou (*Genome Biol.* 16:247 (2015)).

Canonical Cas12a PAMs are T rich. In some embodiments, a canonical Cas12a PAM sequence may be 5'-TTN, 5'-TTTN, or 5'-TTTV. In some embodiments, canonical Cas9 (e.g., *S. pyogenes*) PAMs may be 5'-NGG-3'. In some embodiments, non-canonical PAMs may be used but may be less efficient.

Additional PAM sequences may be determined by those skilled in the art through established experimental and computational approaches. Thus, for example, experimental approaches include targeting a sequence flanked by all possible nucleotide sequences and identifying sequence members that do not undergo targeting, such as through the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

In some embodiments, the present invention provides expression cassettes and/or vectors comprising the nucleic acid constructs of the invention. In some embodiments, expression cassettes and/or vectors comprising the nucleic acid constructs of the invention and/or one or more guide nucleic acids may be provided. In some embodiments, a nucleic acid construct of the invention encoding a base editor (e.g., a construct that is codon optimized for expression in plants and comprising a CRISPR-Cas nuclease and a deaminase domain (e.g., a fusion protein)) may be comprised on the same or on a separate expression cassette or vector from that comprising the guide nucleic acid. When the nucleic acid construct encoding a base editor is comprised on a separate expression cassette or vector from that comprising the guide nucleic acid, a target nucleic acid may be contacted with (e.g., provided with) the expression cassette or vector encoding the base editor prior to, concurrently with, or after the expression cassette comprising the guide nucleic acid is provided (e.g., contacted with the target nucleic acid).

In some embodiments, the nucleic acid constructs, expression cassettes or vectors of the invention that are optimized for expression in a plant may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleic acid constructs, expression cassettes or vectors encoding the

```
5'-NNNNNNNNNNNNNNNNNNNN-3'  RNA Spacer (SEQ ID NO: 64)
   ||||||||||||||||||||
3'-AAANNNNNNNNNNNNNNNNNNNN-5'  Target strand (SEQ ID NO: 65)
   ||||
5'-TTTNNNNNNNNNNNNNNNNNNNN-3'  Non-target strand (SEQ ID NO: 66)
``` same CRISPR-Cas nuclease and/or deaminase domain but which have not been codon optimized for expression in a plant.

In some embodiments, the invention provides cells comprising one or more polynucleotides, guide nucleic acids, nucleic acid constructs, expression cassettes or vectors of the invention.

The nucleic acid constructs of the invention (e.g., a construct that is codon optimized for expression in plants and comprising a codon optimized CRISPR-Cas nuclease and/or a codon optimized CRISPR-Cas nuclease and a deaminase domain (e.g., a fusion protein)) and expression cassettes/vectors comprising the same may be used for modifying target nucleic acids and/or their expression.

In some embodiments, a nucleic acid construct of the invention may encode a codon optimized CRISPR-Cas nuclease linked to a deaminase domain (a base editor) for use in base editing a target nucleic acid in a plant, wherein the codon optimized CRISPR-Cas nuclease can be any Cas nuclease (e.g., a codon optimized Cas12a nuclease (e.g., SEQ ID NOs:23-25) or a codon optimized Cas9 nuclease (e.g., SEQ ID NOs:1-11) and the deaminase domain is a cytosine or an adenosine deaminase domain, wherein the codon optimization is for expression in a plant. In some embodiments, the nucleic acid constructs comprise promoters, introns and other regulatory sequences as described herein.

When used in combination with guide nucleic acids, the nucleic acid constructs of the invention of the invention may be used to modify a target nucleic acid. A target nucleic acid may be contacted with a nucleic acid construct of the invention prior to, concurrently with or after contacting the target nucleic acid with the guide nucleic acid. In some embodiments, the nucleic acid constructs of the invention and a guide nucleic acid may be comprised in the same expression cassette or vector and therefore, a target nucleic acid may be contacted concurrently with the nucleic acid constructs of the invention and guide nucleic acid. In some embodiments, the nucleic acid constructs of the invention and a guide nucleic acid may be in different expression cassettes or vectors and thus, a target nucleic acid may be contacted with the nucleic acid constructs of the invention prior to, concurrently with, or after contact with a guide nucleic acid.

In some embodiments, a method of modifying a target nucleic acid is provided, the method comprising contacting a cell or a cell free system comprising the target nucleic acid with (a) a nucleic acid construct encoding a codon optimized CRISPR-Cas nuclease of the invention, and/or an expression cassette or vector comprising the same, and (b) a guide nucleic acid (e.g., CRISPR RNA, CRISPR DNA, crRNA, crDNA), under conditions whereby the nucleic acid construct is expressed and produces the codon optimized CRISPR-Cas nuclease, which forms a complex with the guide nucleic acid, and wherein the complex hybridizes to the target nucleic acid, thereby modifying the target nucleic acid in the cell or cell free system. In some embodiments, the codon optimized CRISPR-Cas nuclease comprises the nucleotide sequence of any one of SEQ ID NOs:1 to 11 and/or SEQ ID NOs:23-25 or any combination thereof.

In some embodiments, a method of modifying a target nucleic acid is provided, the method comprising contacting a cell or a cell free system comprising the target nucleic acid with (a) a nucleic acid construct encoding a base editor of the invention comprising a codon optimized CRISPR-Cas nuclease and deaminase domain, and/or an expression cassette or vector comprising the same, and (b) a guide nucleic acid (e.g., CRISPR RNA, CRISPR DNA, crRNA, crDNA), under conditions whereby the nucleic acid construct is expressed to produce the base editor (e.g., the CRISPR-Cas nuclease and deaminase domain), which forms a complex with the guide nucleic acid (e.g., the codon optimized CRISPR-Cas nuclease complexes with the guide nucleic acid), and wherein the complex hybridizes to the target nucleic acid, thereby modifying the target nucleic acid in the cell or cell free system. In some embodiments, the base editor of the invention comprising a CRISPR-Cas nuclease and a deaminase domain comprises the nucleotide sequence of any one of SEQ ID NOs:12-22 or 69-71, or any combination thereof.

In some embodiments, a method of modifying a target nucleic acid in a plant is provided, the method comprising contacting a cell of the plant comprising the target nucleic acid with (a) a nucleic acid construct encoding a codon optimized CRISPR-Cas nuclease of the invention, and/or an expression cassette or vector comprising the same, and (b) a guide nucleic acid (e.g., CRISPR RNA, CRISPR DNA, crRNA, crDNA), under conditions whereby the nucleic acid construct is expressed to produce the CRISPR-Cas nuclease, which forms a complex with the guide nucleic acid, and the complex hybridizes to the target nucleic acid, thereby modifying the target nucleic acid in the plant. In some embodiments, the codon optimized CRISPR-Cas nuclease comprises the nucleotide sequence of any one of SEQ ID NOs:1 to 11 and/or SEQ ID NOs:23-25, or any combination thereof In some embodiments, a plant cell modified by the methods of this invention may be regenerated into a plant and/or a plant part.

In some embodiments, a method of modifying a target nucleic acid in a plant is provided, the method comprising contacting a cell of the plant comprising the target nucleic acid with (a) a nucleic acid construct encoding a base editor of the invention comprising a CRISPR-Cas nuclease and a deaminase domain, and/or an expression cassette or vector comprising the same, and (b) a guide nucleic acid, under conditions whereby the nucleic acid construct is expressed to produce the base editor, which forms a complex with the guide nucleic acid, wherein the complex hybridizes to the target nucleic acid, thereby modifying the target nucleic acid in the plant. In some embodiments, the base editor of the invention comprising a CRISPR-Cas nuclease and a deaminase domain comprises the nucleotide sequence of any one of SEQ ID NOs:12-22 or 69-71, or any combination thereof. In some embodiments, a plant cell modified by the methods of this invention may be regenerated into a plant and/or a plant part.

In some embodiments, a method of editing a target nucleic acid is provided, the method comprising contacting a cell or a cell free system comprising the target nucleic acid with: (a) a nucleic acid construct of the invention encoding a base editor comprising a codon optimized CRISPR-Cas nuclease and adenosine deaminase domain, and/or an expression cassette or vector comprising the same, and (b) a guide nucleic acid, under conditions whereby the nucleic acid construct is expressed to produce the base editor, which forms a complex with the guide nucleic acid, wherein the complex hybridizes to the target nucleic acid, and the adenine deaminase domain converts an adenosine (A) to a guanine (G) in the target nucleic acid, thereby editing the target nucleic acid to produce a (point) mutation in the target nucleic acid.

In some embodiments, a method of editing a target nucleic acid in a plant is provided, the method comprising contacting a cell of the plant comprising the target nucleic acid with: (a) a nucleic acid construct of the invention encoding a base editor comprising a codon optimized CRISPR-Cas nuclease and adenosine deaminase domain, and/or an expression cassette or vector comprising the same, and (b) a guide nucleic acid, under conditions whereby the nucleic acid construct is expressed to produce the base editor, which forms a complex with the guide nucleic acid, wherein the complex hybridizes to the target nucleic acid, and the adenine deaminase domain converts an adenosine (A) to a guanine (G) in the target nucleic acid, thereby editing the target nucleic acid to produce a mutation (e.g., point mutation) in the target nucleic acid in the plant. In some embodiments, a plant cell modified by the methods of this invention may be regenerated into a plant and/or a plant part.

In some embodiments, a method of editing a target nucleic acid is provided, the method comprising contacting a cell or a cell free system comprising the target nucleic acid with: (a) a nucleic acid construct of the invention encoding a base editor comprising a codon optimized CRISPR-Cas nuclease and cytosine deaminase domain, and/or an expression cassette or vector comprising the same, and (b) a guide nucleic acid, under conditions whereby the nucleic acid construct is expressed to produce the base editor, which forms a complex with the guide nucleic acid, wherein the complex hybridizes to the target nucleic acid and the cytosine deaminase domain converts a cytosine (C) to a thiamine (T) in the target nucleic acid, thereby editing the target nucleic acid to produce a (point) mutation.

In some embodiments, a method of editing a target nucleic acid is provided, the method comprising contacting a cell or a cell free system comprising the target nucleic acid with: (a) a nucleic acid construct of the invention encoding a base editor comprising the nucleotide sequence of any one of SEQ ID NOs:12-22 or 69-71, and/or an expression cassette or vector comprising the same, and (b) a guide nucleic acid, under conditions whereby the nucleic acid construct is expressed to produce the base editor, which forms a complex with the guide nucleic acid, wherein the complex hybridizes to the target nucleic acid and the cytosine deaminase domain converts a cytosine (C) to a thiamine (T) in the target nucleic acid, thereby editing the target nucleic acid to produce a (point) mutation.

In some embodiments, a method of editing a target nucleic acid in a plant is provided, the method comprising contacting a cell of the plant comprising the target nucleic acid with: (a) a nucleic acid construct of the invention encoding a base editor comprising a codon optimized CRISPR-Cas nuclease and cytosine deaminase domain, and/or an expression cassette or vector comprising the same, and (b) a guide nucleic acid, under conditions whereby the nucleic acid construct is expressed to produce the base editor, which forms a complex with the guide nucleic acid, and wherein the complex hybridizes to the target nucleic acid and the cytosine deaminase domain converts a cytosine (C) to a thiamine (T) in the target nucleic acid, thereby editing the target nucleic acid to produce a (point) mutation in the target nucleic acid in the plant. In some embodiments, a plant cell modified by the methods of this invention may be regenerated into a plant and/or plant part.

In some embodiments, a method of editing a target nucleic acid in a plant is provided, the method comprising contacting a cell of the plant comprising the target nucleic acid with: (a) a nucleic acid construct of the invention encoding a base editor comprising the nucleotide sequence of any one of SEQ ID NOs:12-22 or 69-71, and/or an expression cassette or vector comprising the same, and (b) a guide nucleic acid, under conditions whereby the nucleic acid construct is expressed to produce the base editor, which forms a complex with the guide nucleic acid, and wherein the complex hybridizes to the target nucleic acid and the cytosine deaminase domain converts a cytosine (C) to a thiamine (T) in the target nucleic acid, thereby editing the target nucleic acid to produce a (point) mutation in the target nucleic acid in the plant. In some embodiments, a plant cell modified by the methods of this invention may be regenerated into a plant and/or plant part.

A cytosine deaminase catalyzes cytosine deamination and results in a thymidine (through a uracil intermediate), causing a C to T conversion, or a G to A conversion in the complementary strand in the genome. Thus, in some embodiments, the cytosine deaminase encoded by the polynucleotide of the invention generates a C→T conversion in the sense (e.g., "+"; template) strand of the target nucleic acid or a G→A conversion in antisense (e.g., "−", complementary) strand of the target nucleic acid.

In some embodiments, the adenine deaminase encoded by the nucleic acid construct of the invention generates an A→G conversion in the sense (e.g., "+"; template) strand of the target nucleic acid or a T→C conversion in the antisense (e.g., "−", complementary) strand of the target nucleic acid.

The nucleic acid constructs of the invention encoding a base editor comprising a codon optimized CRISPR-Cas nuclease and a cytosine deaminase polypeptide, and nucleic acid constructs/expression cassettes/vectors encoding the same, may be used in combination with guide nucleic acids for modifying target nucleic acid including, but not limited to, generation of C→T or G→A mutations in a target nucleic acid including, but not limited to, a plasmid sequence; generation of C→T or G→A mutations in a coding sequence to alter an amino acid identity; generation of C→T or G→A mutations in a coding sequence to generate a stop codon; generation of C→T or G→A mutations in a coding sequence to disrupt a start codon; generation of point mutations in genomic DNA to disrupt transcription factor binding; and/or generation of point mutations in genomic DNA to disrupt splice junctions.

The nucleic acid constructs of the invention encoding a base editor comprising a codon optimized CRISPR-Cas nuclease and an adenine deaminase polypeptide, and expression cassettes and/or vectors encoding the same may be used in combination with guide nucleic acids for modifying a target nucleic acid including, but not limited to, generation of A→G or T→C mutations in a target nucleic acid including, but not limited to, a plasmid sequence; generation of A→G or T→C mutations in a coding sequence to alter an amino acid identity; generation of A→G or T→C mutations in a coding sequence to generate a stop codon; generation of A→G or T→C mutations in a coding sequence to disrupt a start codon; generation of point mutations in genomic DNA to disrupt transcription factor binding; and/or generation of point mutations in genomic DNA to disrupt splice junctions.

A target nucleic acid of any plant or plant part may be modified (e.g., mutated, e.g., base edited, cleaved, nicked, etc.) using the nucleic acid constructs of the invention (e.g., SEQ ID NOs:1-25 or 69-71). Any plant (or groupings of plants, for example, into a genus or higher order classification) may be modified using the nucleic acid constructs of this invention including an angiosperm, a gymnosperm, a monocot, a dicot, a C3, C4, CAM plant, a bryophyte, a fern and/or fern ally, a microalgae, and/or a macroalgae. A plant and/or plant part useful with this invention may be a plant and/or plant part of any plant species/variety/cultivar. The term "plant part," as used herein, includes but is not limited to, embryos, pollen, ovules, seeds, leaves, stems, shoots, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. As used herein, "shoot" refers to the above ground parts including the leaves and stems. Further, as used herein, "plant cell" refers to a structural and physiological unit of the plant, which comprises a cell wall and also may refer to a protoplast. A plant cell can be in the form of an isolated single cell or can be a cultured cell or can be a part of a higher-organized unit such as, for example, a plant tissue or a plant organ.

Non-limiting examples of plants useful with the present invention include turf grasses (e.g., bluegrass, bentgrass, ryegrass, fescue), feather reed grass, tufted hair grass, miscanthus, arundo, switchgrass, vegetable crops, including artichokes, kohlrabi, arugula, leeks, asparagus, lettuce (e.g., head, leaf, romaine), malanga, melons (e.g., muskmelon, watermelon, crenshaw, honeydew, cantaloupe), cole crops (e.g., brussels sprouts, cabbage, cauliflower, broccoli, collards, kale, chinese cabbage, bok choy), cardoni, carrots, napa, okra, onions, celery, parsley, chick peas, parsnips, chicory, peppers, potatoes, cucurbits (e.g., marrow, cucumber, zucchini, squash, pumpkin, honeydew melon, watermelon, cantaloupe), radishes, dry bulb onions, rutabaga, eggplant, salsify, escarole, shallots, endive, garlic, spinach, green onions, squash, greens, beet (sugar beet and fodder beet), sweet potatoes, chard, horseradish, tomatoes, turnips, and spices; a fruit crop such as apples, apricots, cherries, nectarines, peaches, pears, plums, prunes, cherry, quince, fig, nuts (e.g., chestnuts, pecans, pistachios, hazelnuts, pistachios, peanuts, walnuts, macadamia nuts, almonds, and the like), citrus (e.g., clementine, kumquat, orange, grapefruit, tangerine, mandarin, lemon, lime, and the like), blueberries, black raspberries, boysenberries, cranberries, currants, gooseberries, loganberries, raspberries, strawberries, blackberries, grapes (wine and table), avocados, bananas, kiwi, persimmons, pomegranate, pineapple, tropical fruits, pomes, melon, mango, papaya, and lychee, a field crop plant such as clover, alfalfa, timothy, evening primrose, meadow foam, corn/maize (field, sweet, popcorn), hops, jojoba, buckwheat, safflower, quinoa, wheat, rice, barley, rye, millet, sorghum, oats, triticale, sorghum, tobacco, kapok, a leguminous plant (beans (e.g., green and dried), lentils, peas, soybeans), an oil plant (rape, canola, mustard, poppy, olive, sunflower, coconut, castor oil plant, cocoa bean, groundnut, oil palm), duckweed, *Arabidopsis*, a fiber plant (cotton, flax, hemp, jute), *Cannabis* (e.g., *Cannabis sativa, Cannabis indica, and Cannabis ruderalis*), lauraceae (cinnamon, camphor), or a plant such as coffee, sugar cane, tea, and natural rubber plants; and/or a bedding plant such as a flowering plant, a cactus, a succulent and/or an ornamental plant (e.g., roses, tulips, violets), as well as trees such as forest trees (broad-leaved trees and evergreens, such as conifers; e.g., elm, ash, oak, maple, fir, spruce, cedar, pine, birch, cypress, eucalyptus, willow), as well as shrubs and other nursery stock. In some embodiments, the nucleic acid constructs of the invention and/or expression cassettes and/or vectors encoding the same may be used to modify maize, soybean, wheat, canola, rice, tomato, pepper, sunflower, raspberry, blackberry, black raspberry and/or cherry.

The present invention further comprises a kit or kits to carry out the methods of this invention. A kit of this invention can comprise reagents, buffers, and apparatus for mixing, measuring, sorting, labeling, etc., as well as instructions and the like as would be appropriate for modifying a target nucleic acid.

In some embodiments, the invention provides a kit comprising one or more nucleic acid constructs of the invention (e.g., SEQ ID NOs:1-25 or 69-71), and/or expression cassettes and/or vectors comprising the same, with optional instructions for the use thereof. In some embodiments, a kit may further comprise a CRISPR-Cas guide nucleic acid (corresponding to the CRISPR-Cas nuclease encoded by the polynucleotide of the invention) and/or expression cassette and/or vector comprising the same. In some embodiments, the guide nucleic acid may be provided on the same expression cassette and/or vector as a nucleic acid construct of the invention. In some embodiments, the guide nucleic acid may be provided on a separate expression cassette or vector from that comprising the nucleic acid construct of the invention.

Accordingly, in some embodiments, kits are provided comprising a nucleic acid construct comprising (a) a polynucleotide encoding a base editor as provided herein and (b) a promoter that drives expression of the polynucleotide of (a). In some embodiments, the kit may further comprise a nucleic acid construct encoding a guide nucleic acid, wherein the construct comprises a cloning site for cloning of a nucleic acid sequence identical or complementary to a target nucleic acid sequence into backbone of the guide nucleic acid.

In some embodiments, the nucleic acid construct of the invention encoding the base editor may be an mRNA that may encode one or more introns within the encoded base editor. In some embodiments, the nucleic acid construct of the invention encoding a base editor, and/or an expression cassette and/or vector comprising the same, may further encode one or more selectable markers useful for identifying transformants (e.g., a nucleic acid encoding an antibiotic resistance gene, herbicide resistance gene, and the like).

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1

Polynucleotides encoding a base editor that comprises a CRISPR-Cas nuclease and either a cytosine deaminase or an adenine deaminase were generated (e.g., SEQ ID NOs:12 to 22). The polynucleotides that were generated are codon optimized for expression in soybean or corn.

In maize, six different optimized polynucleotides encoding base editors that include a CRISPR-Cas9 nuclease and a cytosine deaminase domain are provided, and in soybean, five different optimized polynucleotides encoding base editors are provided. The optimizations were placed behind a plant-specific promoter and transformed into plants via agrobacterium mediated transformation protocols.

TABLE 1

Listing of the optimized base editors

| Coding sequence optimized version | Plant Type | SEQ ID NO: | Cas 9 SEQ ID NO |
|---|---|---|---|
| Mon_GS_V1 | Monocot | 12 | 1 |
| Mon_GS_V2 | Monocot | 13 | 2 |
| Mon-GS_V3 | Monocot | 14 | 3 |
| Mon_BY_V1 | Monocot | 15 | 4 |
| Mon_BY_V2 | Monocot | 16 | 5 |
| Mon_BY_V3 | Monocot | 17 | 6 |
| Di_GS_V1 | Dicot | 18 | 7 |
| Di_GS_V2 | Dicot | 19 | 8 |
| Di_GS_V3 | Dicot | 20 | 9 |
| Di_BY_V1 | Dicot | 21 | 10 |
| Di_BY_V2 | Dicot | 22 | 11 |

To examine the amount of base editing achievable with different optimizations, target regions were chosen that contained cytosine residues within a known targeting region (13-17 bp upstream of the PAM sequence). Specifically, the target nucleic acids that were chosen for maize are in the genes CenH3 and glossy2 (g12). In soybean, the target nucleic acid that was chosen is in the Mir1509 gene.

TABLE 2

Guide nucleic acids

| Guide # | Target | Protospacer |
|---|---|---|
| PWg090001 | g12 | CAGATCACAAACTTCAAATG |
| PWg090002 | ZmCENH3 | AGCCCTCCTTGCGCTGCAAG |
| PWg090005 | MIR1509 | GAAATCACGGTTGAGTGTGA |

The constructs comprising the codon optimized polynucleotides and the guides comprising the spacers targeting the target nucleic acids were introduced into soybean and maize plants using Agrobacterium transformation methods as known in the art.

Following transformation and regeneration of the corn and soybean plantlets, leaf tissues were sampled from each plant and editing efficiency was measured via amplicon sequencing followed by next generation sequencing. Bioinformatic analysis of the sequencing results examined the genetic region targeted by the nuclease to determine if the targeted cytosine residues had been converted to thymine residues. Plasmid sequencing was performed using the PlexWell service from seqWell.

When the codon optimizations were introduced to plants through *Agrobacterium* transformation, the amount of base editing that resulted differed between the different targets and optimizations. Notably, at the CenH3 target, which was previously reported to have a 10% editing efficiency, showed an overall editing efficiency of over 25%. Editing efficiency is measured as the number of plants showing at least 10% of reads with a single edit divided by the total number of plants exposed to the editing reagent (Table 3). At the g12 target in corn, overall editing efficiency was over 60% with four of six optimizations obtaining over 80% editing efficiency.

TABLE 3

Editing efficiency of the plant optimized base editors in maize and soybean. The optimization column includes entries for 'Cas9', which is a baseline, unoptimized version of the Cas9 protein.

| Crop | Target | Construct | Optimization | n.Total | Edit.BE | Edit.Efficiency |
|---|---|---|---|---|---|---|
| Corn | g12 | pWISE27 | GS-V1 | 94 | 79 | 84% |
| Corn | g12 | pWISE30 | GS-V2 | 63 | 47 | 75% |
| Corn | g12 | pWISE33 | GS-V3 | 75 | 45 | 60% |
| Corn | g12 | pWISE36 | Cas9 | 67 | 0 | 0% |
| Corn | g12 | pWISE179 | BY-V1 | 21 | 17 | 81% |
| Corn | g12 | pWISE180 | BY-V2 | 91 | 77 | 85% |
| Corn | g12 | pWISE181 | BY-V3 | 41 | 34 | 83% |
| Corn | ZmCenH3 | pWISE28 | GS-V1 | 118 | 46 | 39% |
| Corn | ZmCenH3 | pWISE34 | GS-V3 | 46 | 12 | 26% |
| Corn | ZmCenH3 | pWISE189 | BY-V1 | 24 | 12 | 50% |
| Corn | ZmCenH3 | pWISE190 | BY-V2 | 90 | 33 | 37% |
| Corn | ZmCenH3 | pWISE191 | BY-V3 | 6 | 4 | 67% |
| Corn | ZmCENH3 | pWISE28 | GS-V1 | 118 | 46 | 39% |
| Corn | ZmCENH3 | pWISE31 | GS-V2 | 49 | 23 | 57% |
| Corn | ZmCENH3 | pWISE37 | Cas9 | 5 | 1 | 20% |
| Soy | mir1509 | pWISE39 | GS-V1 | 156 | 0 | 0% |
| Soy | mir1509 | pWISE41 | GS-V2 | 19 | 0 | 0% |
| Soy | mir1509 | pWISE45 | Cas9 | 232 | 0 | 0% |
| Soy | mir1509 | pWISE182 | BY-V1 | 12 | 10 | 83% |
| Soy | mir1509 | pWISE183 | BY-V2 | 13 | 6 | 46% |

Example 2

In Example 1, different promoters were used to drive the base editing cassettes. As indicated in Table 3, in soy, the ubiquitin2 promoter, containing the native intron from the ubiquitin2 gene, from *Medicago truncatula* was used to drive cassette expression. In the case of GS-V1, GS-V2 and unoptimized Cas9, no edits were obtained. For BY-V1 and BY-V2, edits were obtained, however, the number of edits was unsatisfactory.

A third set of constructs were tested which comprised a tandem viral promoter driving the base editing cassette. The viral promoter has known leaky expression in prokaryotic systems. Complete plasmid sequencing of the vectors recovered after *Agrobacterium* and *E. coli* propagations consistently revealed C→T base changes. Indels could also be observed in some of the vectors with this leaky prokaryotic expression. These changes were found only in the viral promoter constructs lacking introns in the coding sequence of the cytosine base editor. It is interpreted that leaky expression in the prokaryotic system is leading to off-site editing of the plasmids and very likely the prokaryotic genome. This mutational activity is likely leading to construct instability in the prokaryotic systems.

Thus, a fourth set of constructs were tested utilizing the same MtUbq2 promoter but with an addition of an intron. The data from these tests are shown in Table 4.

TABLE 4

Editing efficiency in soy when a promoter region comprising an intron is used

| Crop | Target  | Construct | Optimization   | n.Total | Edit.BE | Edit.Efficiency |
|------|---------|-----------|----------------|---------|---------|-----------------|
| Soy  | mir1509 | pWISE652  | GS-V1 + Intron | 30      | 2       | 7%              |
| Soy  | mir1509 | pWISE653  | GS-V2 + Intron | 30      | 10      | 33%             |
| Soy  | mir1509 | pWISE655  | BY-V1 + Intron | 50      | 26      | 52%             |

In the case of GS-V1, while the editing efficiency remained low at 7%, the same construct without an intron did not make any edits. For GS-V2, an editing efficiency of 33% was achieved. For BY-V1, while the editing efficiency decreased from 83% to 52%, there was a 250% increase in the number of edits made, indicating a much better editing system.

Example 3

As a further means of improving editing efficiency and to prevent leaky expression in the prokaryotic system, constructs can be made utilizing an additional intron in either the APOBEC/deaminase domain or the UGI domain.

The nucleic acid constructs of the invention provide precision modification of plants through base editing. Prior to this work, the ability to confer specific base changes was limited by the low efficiency of the editing reagent. As a result, large quantities of starting material were required to generate plants with a desired mutation/genotype. However, the nucleic acid constructs provided by the present invention, now provide base editing at consistently higher levels than previously achievable.

Example 4

When assembling constructs containing a cytosine deaminase domain, Apobec1 and Apobec3a (A3A), instability was observed in the resulting clones in the form of mutant sequences. The most prominent change observed were C>T changes in the plasmid sequence. Also observed were large deletions in the plasmid, and in particular, deletions that disrupted the deaminase itself. The prevalence of mutations in the deaminase suggests a selection for such mutations and therefore likelihood that the deaminase may be cytotoxic in the bacteria.

Introns for Improving Stability

The stability of the base editor constructs designed for use with Cas9 was improved by utilizing a promoter, the *Medicago* ubiquitin 2 promoter (MtUbq2, SEQ ID NO:63), which contains an intron at the 3' end following the promoter and 5' UTR.

The *Medicago* ubiquitin intron, which cannot be excised by prokaryotes, prevents the downstream deaminase from being expressed, and therefore, reduces or prevents construct instability. Constructs that utilized the MtUbq2 promoter to drive expression of a cytosine base editor (APOBE1) (see, e.g., SEQ ID NOs:12-22), as well as those that utilize a constitutive tandem viral promoter, were transformed into *E. coli* and then sequenced by next generation sequencing. The resulting sequence was aligned to the reference sequence and the number of SNPs or deletions was tabulated for each construct. A total of 10 colonies for a standard Cas9 construct, 49 colonies having the base editor driven by MtUbq2 containing an intron, and 56 colonies having the base editor without an intron were screened. As seen in Table 5 and FIG. 1, the number of mutations observed is lower when an intron is present proceeding the editor.

TABLE 5

Sum of SNP and Deletions in base editor constructs when compared to nuclease vector control.

| Editor                              | Sum of SNP | Sum of Deletion | Colonies Counted |
|-------------------------------------|------------|-----------------|------------------|
| Cas9 Nuclease                       | 0          | 0               | 10               |
| Cytosine Base Editor with Intron    | 6          | 8               | 49               |
| Cytosine Base Editor without Intron | 37         | 16              | 56               |

Cas12a Cytosine Base Editor Comprising an Intron in an A3A Deaminase (APOBEC3A)

The ability to assemble plasmids that match the originally intended sequence (i.e., a base editor construct of the invention, for example, but not limited to, SEQ ID NOs:12-22, that have not been edited by the cytosine deaminase in the construct) and that contain base editors is greatly impaired by instability caused by the deaminase domain. To assist with the assembly of a cytosine base editor for testing in a human cell system, a human chimeric intron (GTAAGTATCAAGGTTACAAGACAGGTTTAAGGAGAC-CAATAGAAACTGG GCTTGTCGAGACAGAGAA-GACTCTTGCGTTTCTGATAGGCACCTATTGGTCTTAC TGACATCCACTTTGCCTTTCTCTCCACAG) (SEQ ID NO:75) comprising the 5'-donor site from the first intron of the human β-globin gene and the branch and 3'-acceptor site from the intron that is between the leader and the body of an immunoglobulin gene heavy chain variable region (see, e.g., Younis et al. *Mol. Cell. Biol.* 30:1718-1728 (2010)) was placed into the active site of the human A3A deaminase. Specifically, the intron was placed 152 bases after the start of the intron coding sequence, which causes a premature stop codon and prevents further translation of the editor unless the intron sequence is removed.

When the assembly of the full base editor construct containing the A3A deaminase was performed, the ability to recover the desired clones was assessed. In this case, the assembly places the editor into a full transformation backbone, so that all of the components are put together at once. A fragment that contained A3A and a fragment that contained A3A with an intron were used. It was determined that when the intron was included it was much more likely to contain the originally designed sequence. Specifically, in this experiment, the deaminase was assembled with or without the intron as described and fused to a dCas12a enzyme (i.e., no nuclease activity) to create a Cas12a cytosine base editor via golden gate assembly. Following assembly, reactions were transformed into *E. coli* cells and the resulting clones sequenced by next generation sequencing. Of 6 constructs tested, when the intron was not present, only one (1/6) clone was detected through screening that had a 100% match with the intended sequence, whereas, when the intron was present, all of the clones (6/) had a 100% match with the intended sequence. The overall success rate was 20% when an intron was included in contrast to only 2% without an intron (Table 6).

TABLE 6

Summary of cloning results for the assembly of a cytosine deaminase vector

|  | Number of Colonies Screened | Correct Colonies (100% match to the expected sequence) | Success rate |
| --- | --- | --- | --- |
| A3A + intron | 90 | 18 | 20% |
| A3A | 176 | 3 | 2% |

Exemplary mutations identified among the potential clones of cytosine base editor assembly reactions are shown in Table 7.

TABLE 7

Example mutations found by sequencing potential clones of cytosine base editor assembly reactions

| Colony Name | UGI Region | A3A Region |
| --- | --- | --- |
| 1720_1-5 | correct | T missing in A3A |
| 1720_2-8 | correct | C missing in A3A |
| 1720_3-4 | no UGI | Linker missing |
| 1720_3-8 | Correct | A missing in A3A |
| 1720_6-8 | correct | C to G point mutation |
| 1720_7-8 | correct | No A3A |
| 1716_2-4 | correct | G missing in A3A |
| 1716_3-4 | correct | wrong UGI, missing linker, G missing in A3A |
| 1716_10-1 | correct | extra A in A3A |
| 1716_10-2 | correct | 2 sites incorrect |
| 1716_10-3 | correct | C missing in A3A |
| 1716_11-8 | correct | C missing in A3A |

Base Editing Using a Base Editor Construct Comprising an Intron

Figure 2:
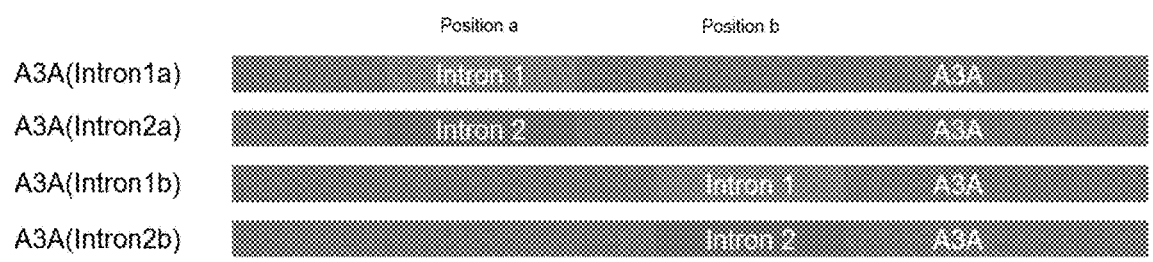
FIG. 2. Graphical representation of the architecture of the intron placement in the Apobec3A domain. Intron 1—Beta-globlin/immunoglobin chimeric intron; Intron 2—SV40 intron FIG. 3. Comparison of base editing activity at the RNF2 locus in human cells. Apobec1 and evoCDA1 deaminase constructs do not contain an intron and the A3A constructs contain either the β-globulin/immunoglobulin chimeric intron (intron 1), or the SV40 intron (Intron 2). Y axis is % sequence reads with C>T conversions. C3, C6 and C12 are the positions of each of the cytosines that are edited in at the RNF2 locus.

Two different introns, the human chimeric intron discussed previously and the SV40 intron (Xu et al, J Cell Mol Med. 22(4):2231-2239 (2018) (GTAAGTTTAGTCTTTTTGTCT TTTATTTCAGGTCCCGGATCCGGTGGTGGTGCAAATCAAAGAACTGCTCCTCAGT GGATGTTGCCTTTACTTCTAGGC) (SEQ ID NO:76), were introduced into the A3A deaminase and fused to a deactivated Cas9 protein. The introns were placed in two different regions of the deaminase domain (FIG. 2). Specifically, the intron was placed within the motif (A/C)AG [Intron]G(G/T), in order to maintain the canonical intron splicing sequence context. It is expected that other sites with this motif would also allow for efficient intron splicing.

Each base editor construct was compared against a base editor construct with the apobec1- or evoCDA1-deaminase at four loci in the human 293T cells, the RNF2 locus, the FANCF1 locus, AAVS1b locus and the AAVS1c locus. The results are shown in FIGS. 3-6.

Figure 3:
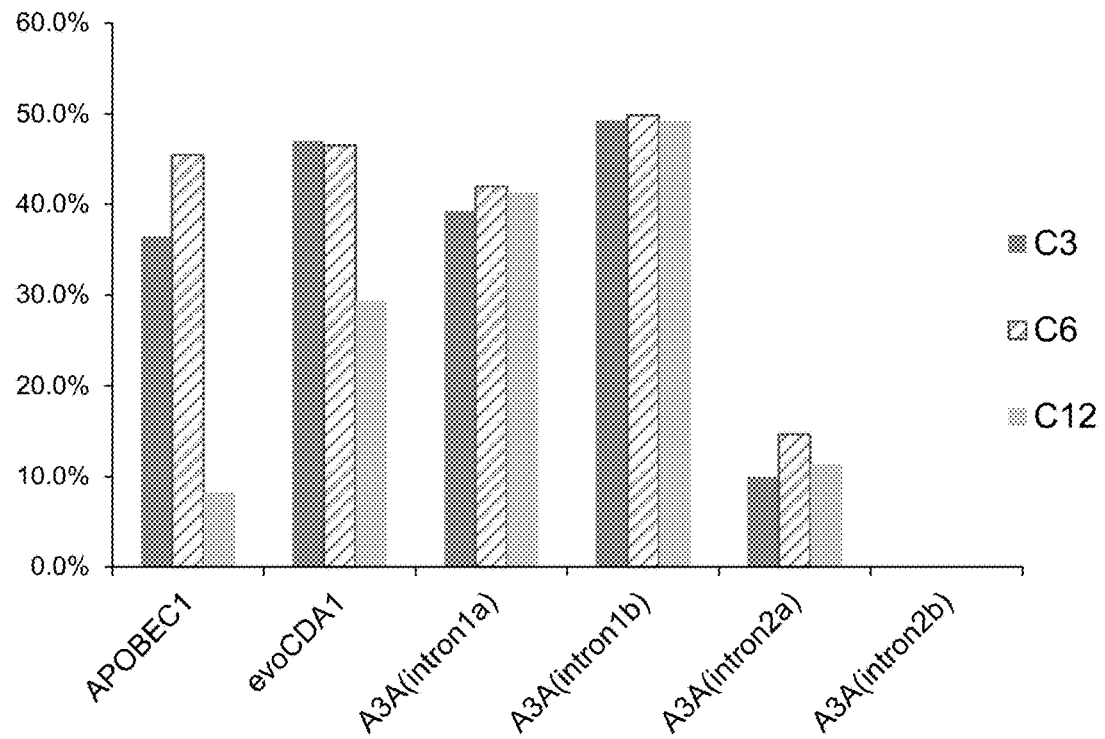

In FIG. 3, the base editing activity is shown using constructs with and without the introns. The editing is at the RNF2 locus in the human cells. The Apobec1 and evoCDA1 deaminase constructs do not contain an intron and the A3A constructs contain either the β-globulin/immunoglobulin chimeric intron (intron 1), or the SV40 intron (Intron 2).

Figure 4:
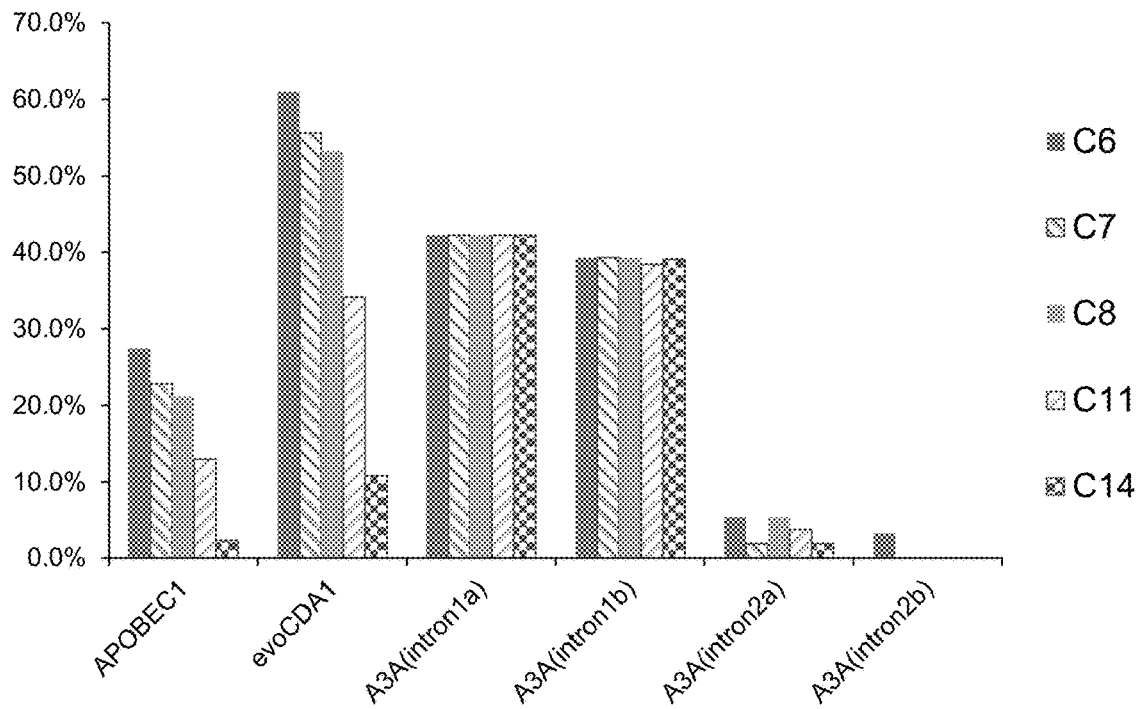
FIG. 4. Comparison of base editing activity with and without introns at the FANCF1 locus in human cells. Apobec1 and evoCDA1 deaminase constructs do not contain an intron, A3A constructs contain either the β-globulin/immunoglobulin chimeric intron (intron 1), or the SV40 intron (Intron 2). Y axis is % sequence reads with C>T conversions. C6, C7, C8, C11, and C14 are the cytosine positions at the FANCF1 locus.
Figure 5:
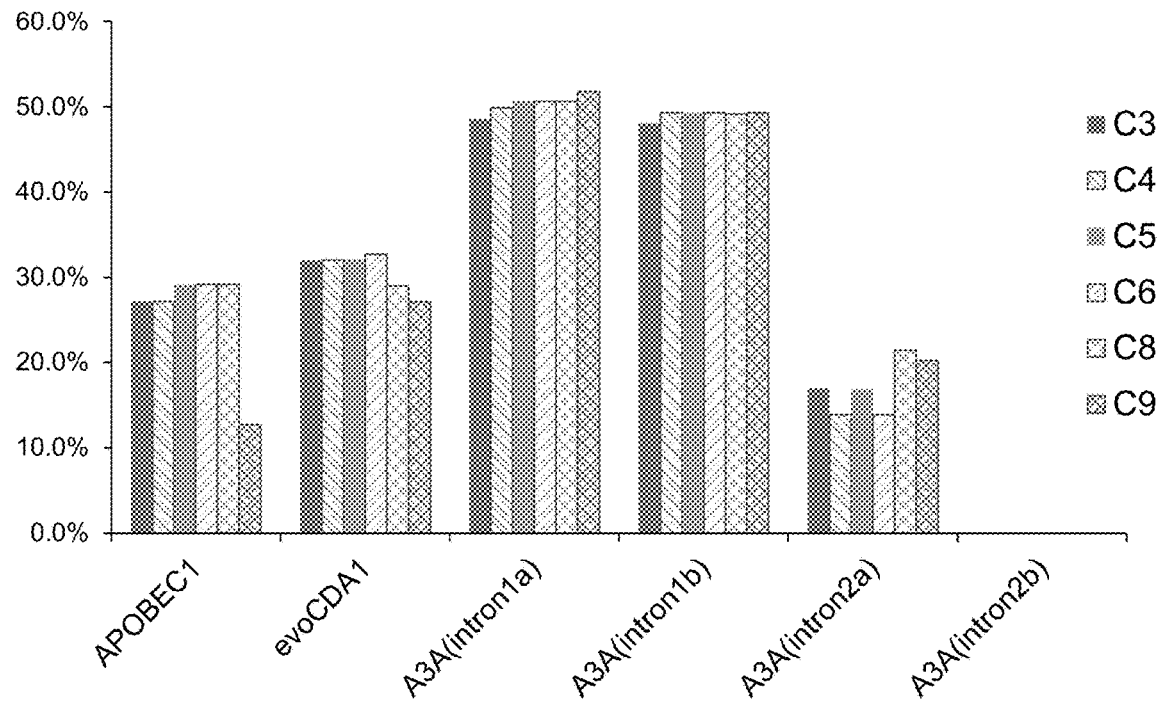
FIG. 5. Comparison of base editing activity with and without introns at the AAVS1b locus in human cells. Apobec1 and evoCDA1 deaminase constructs do not contain an intron and the A3A constructs contain either the β-globulin/immunoglobulin chimeric intron (intron 1), or the SV40 intron (Intron 2). Y axis is % sequence reads with C>T conversions. C3, C4, C5, C6, C8 and C9 are the positions of each of the cytosines that are edited in the AAVS1b locus.
Figure 6:
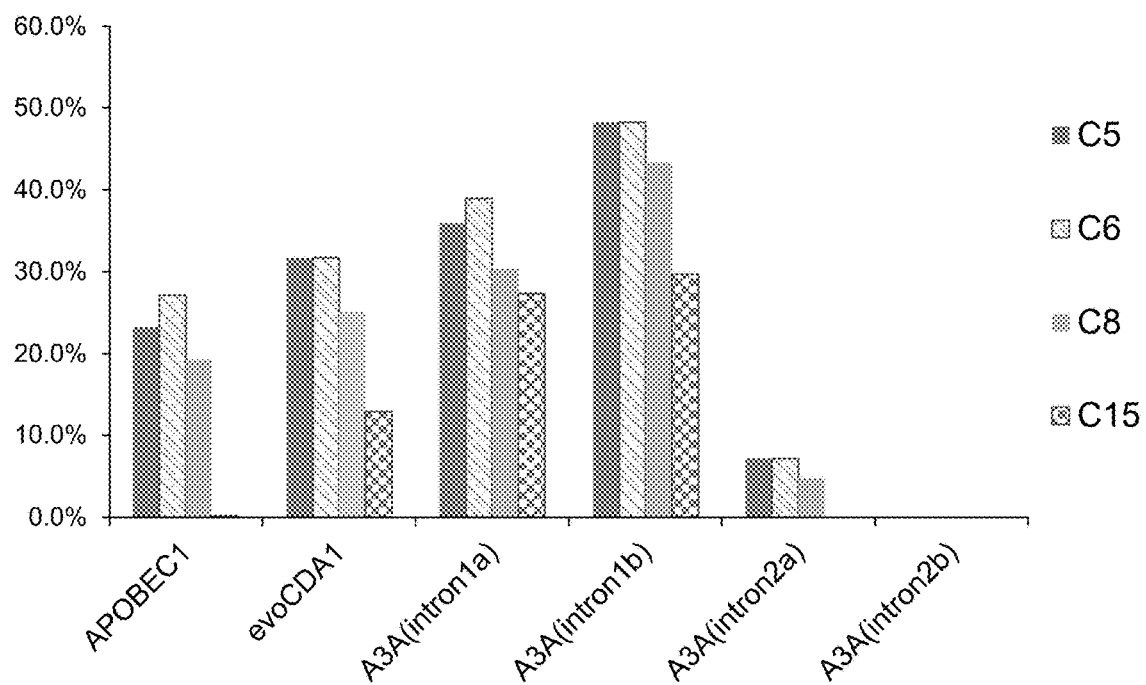
FIG. 6 Comparison of base editing activity at the AAVS1c locus in human cells. Apobec1 and evoCDA1 deaminase constructs do not contain an intron and the A3A constructs contain either the β-globulin/immunoglobulin chimeric intron (intron 1), or the SV40 intron (Intron 2). Y axis is % sequence reads with C>T conversions. C5, C6 C8 and C15 are the positions of each of the cytosines that are edited in the AAVS1c locus.

FIG. 4 shows a comparison of base editing activity at the FANCF1 locus in human cells for Apobec1 and evoCDA1 deaminase constructs that do not contain an intron, and A3A constructs that contain either the β-globulin/immunoglobulin chimeric intron (intron 1), or the SV40 intron (Intron 2). FIG. 8 compares base editing activity at the AAVS1b locus in human cells for Apobec1 and evoCDA1 deaminase constructs that do not contain an intron, and A3A constructs that contain either the β-globulin/immunoglobulin chimeric intron (intron 1), or the SV40 intron (Intron 2). In FIG. 9 base editing activity at the AAVS1c locus in human cells is compared for Apobec1 and evoCDA1 deaminase constructs that do not contain an intron, and A3A constructs that contain either the β-globulin/immunoglobulin chimeric intron (intron 1), or the SV40 intron (Intron 2). As shown in each of FIGS. 3-6, the chimeric intron resulted in base editing rates similar to editing rates without an intron, demonstrating that the presence of the intron is not preventing deaminase activity but with the advantage that constructs comprising intron as described herein can be produced without generating mutations in the vector sequence.

Example 5

Adenine base editors were constructed by placing the TadA deaminase and the variant TadA* directly 5' of a nickase variant of Cas9. The TadA and TadA* are separated by a protein linker, and there is an additional linker between the deaminase proteins and the start of nCas9. Similar to the cytosine base editors, the monocot vectors utilize the *Zea mays* Ubiquitin 1 promoter, and the dicot vectors utilize the *Medicago truncatula* Ubiquitin 2 promoter. These editor sequences were then codon optimized via proprietary algorithms for either corn and soy and the predicted sequences synthesized via solid state synthesis.

Nucleic acid constructs encoding an adenosine base editor that comprises a CRISPR-Cas nuclease and an adenine deaminase were generated (e.g., SEQ ID NOs:69-71). The nucleic acid constructs that were generated were codon optimized for expression in soybean (dicot, Di) or corn (monocot, Mon).

The constructs for optimized adenosine base editors as described herein are provided in Table 8.

TABLE 8

Optimized base editors

| Coding sequence optimized version | Plant Type |
| --- | --- |
| Mon_BY_V1_ABE (SEQ ID NO: 69) | Monocot |
| Di_BY_V1_ABE (SEQ ID NO: 70) | Dicot |
| Di_BY_V2_ABE (SEQ ID NO: 71) | Dicot |

TABLE 9

Editing efficiency of the base editors in corn and soy

| Target | Codon Optimization | Edited Plants | Total Samples | Editing Efficiency* |
| --- | --- | --- | --- | --- |
| Corn Target 2 (Locus1) | Mon_BY_V1_ABE | 6 | 101 | 5.9% |

TABLE 9-continued

Editing efficiency of the base editors in corn and soy

| Target | Codon Optimization | Edited Plants | Total Samples | Editing Efficiency* |
|---|---|---|---|---|
| Corn Target 2 (Locus2) | Mon_BY_V1_ABE | 18 | 101 | 17.8% |
| Soy Target 2 | Di_BY_V2_ABE | 1 | 46 | 2% |

*Editing over 10% of reads.

Editing in dicots with the V1 ABE was below the 10% cutoff used for higher-activity tools, however, activity was detected. Using a lower threshold of activity of 1%, the editing efficiency is shown in Table 10.

TABLE 10

Editing efficiency of the tested base editors in soy

| Target | Codon Optimization | Edited Plants | Total Samples | Editing Efficiency* |
|---|---|---|---|---|
| Soy Target 1 | Di_BY_V1_ABE | 11 | 235 | 4.6% |
| Soy Target 2 | Di_BY_V1_ABE | 31 | 235 | 13.2% |
| Soy Target 1 | Di_BY_V2_ABE | 0 | 46 | 0% |

*Editing over 1% of reads.

The foregoing is illustrative of the present invention, and is not to be construed as limiting thereof. The invention is defined by the following claims, with equivalents of the claims to be included therein.

That which is claimed is:

1. A method of increasing the stability of a base editor in a prokaryotic cell, the method comprising:
   (a) providing a base editor comprising a deaminase domain and a CRISPR-Cas nuclease operably associated with a promoter region, wherein the promoter region comprises an intron; and
   (b) introducing the base editor into a prokaryote, wherein the number of mutations in the base editor is reduced when compared to an identical base editor comprising a promoter region that does not comprise an intron, thereby increasing the stability of the base editor.

2. The method of claim 1, wherein the intron is located 3' of the promoter region of the CRISPR-Cas nuclease.

3. The method of claim 1, wherein the promoter region is from an ADHI gene, a ubiquitin gene (Ubi), a RuBisCO small subunit (rbcS) gene, a RuBisCO large subunit (rbcL) gene, an actin gene, a pyruvate dehydrogenase kinase gene (pdk), a nitrate reductase gene (nr), a duplicated carbonic anhydrase gene 1 (Tdca1), a psbA gene, or an atpA gene.

4. The method of claim 1, wherein the promoter region is from a ubiquitin gene.

5. The method of claim 1, wherein the intron is an intron associated with a ubiquitin promoter.

6. The method of claim 1, wherein CRISPR-Cas nuclease is a Cas9 nuclease or a Cas12a nuclease.

7. The method of claim 1, wherein the deaminase domain is a cytosine deaminase domain or an adenine deaminase domain.

8. The method of claim 1, wherein the prokaryote cell is an *Agrobacterium* cell or *Escherichia coli* cell.

\* \* \* \* \*

UNITED STATES PATENT AND TRADEMARK OFFICE
CERTIFICATE OF CORRECTION

PATENT NO. : 11,913,005 B2  
APPLICATION NO. : 18/048236  
DATED : February 27, 2024  
INVENTOR(S) : Nathaniel Graham Page 1 of 1

It is certified that error appears in the above-identified patent and that said Letters Patent is hereby corrected as shown below:

In the Specification

Column 1, Line 17: Please correct "1499-8DV" to read --1499-8DV_--

Column 18, Line 23: Please correct "X:2281-2:308" to read --8:2281-2308--

Column 20, Line 6: Please remove the paragraph break before "Csm6,"

Column 38, Lines 43-48: Please correct "(GTAAGTAT-CAAGGTTACAAGACAGGTTTAAGGAGAC-CAATAGAAACTGG GCTTGTCGAGACAGAGAA-GACTCTTGCGTTTCTGATAGGCACCTATTGGTCTTAC TGACATCCACTTTGCCTTTCTCTCCACAG) (SEQ ID NO:75)" to read --(GTAAGTATCAAGGTTACAAGACAGGTTTAAGGAGACCAATAGAAACTGG GCTTGTCGAGACAGAGAAGACTCTTGCGTTTCTGATAGGCACCTATTGGTCTTAC TGACATCCACTTTGCCTTTCTCTCCACAG) (SEQ ID N0:75)--

Column 39, Lines 49-52: Please correct "22(4):2231-2239 (2018) (GTAAGTT-TAGTCTTTTTGTCT TTTATTTCAGGTCCCG-GATCCGGTGGTGGTGCAAAT-CAAAGAACTGCTCCTCAGT GGATGTTGCCTTTACTTCTAGGC) (SEQ ID NO:76)" to read --22(4):2231-2239 (2018) (GTAAGTTTAGTCTTTTTGTCTTTTATTTCAGGTCCCGGATCCGGTGGTGGTGCAAATCAAA GAACTGCTCCTCAGTGGATGTTGCCTTTACTTCTAGGC) (SEQ ID NO: 76)--

Signed and Sealed this  
Fifth Day of November, 2024

Katherine Kelly Vidal  
*Director of the United States Patent and Trademark Office*